United States Patent
Sato et al.

(10) Patent No.: US 10,487,072 B2
(45) Date of Patent: Nov. 26, 2019

(54) SUBSTITUTED IMIDAZOLES AS MELANOCORTIN RECEPTOR AGONISTS

(71) Applicant: MITSUBISHI TANABE PHARMA CORPORATION, Osaka-shi, Osaka (JP)

(72) Inventors: Atsushi Sato, Osaka (JP); Ritsuo Imashiro, Osaka (JP); Hidekazu Tsujishima, Osaka (JP); Kouichi Tanimoto, Osaka (JP); Yasuo Yamamoto, Osaka (JP); Tetsu Nakane, Osaka (JP); Chihiro Toshikawa, Osaka (JP)

(73) Assignee: MITSUBISHI TANABE PHARMA CORPORATION, Osaka-shi (JP)

( * ) Notice: Subject to any disclaimer, the term of this patent is extended or adjusted under 35 U.S.C. 154(b) by 0 days.

(21) Appl. No.: 15/779,435

(22) PCT Filed: Nov. 25, 2016

(86) PCT No.: PCT/JP2016/085017
§ 371 (c)(1),
(2) Date: May 25, 2018

(87) PCT Pub. No.: WO2017/090743
PCT Pub. Date: Jun. 1, 2017

(65) Prior Publication Data
US 2018/0258076 A1     Sep. 13, 2018

(30) Foreign Application Priority Data
Nov. 27, 2015  (JP) ................. 2015-231745

(51) Int. Cl.
| | | |
|---|---|---|
| A61K 31/4168 | (2006.01) | |
| C07D 233/88 | (2006.01) | |
| C07D 403/12 | (2006.01) | |
| C07D 401/14 | (2006.01) | |
| C07D 413/14 | (2006.01) | |
| A61K 31/454 | (2006.01) | |
| A61K 31/4725 | (2006.01) | |
| A61K 31/5377 | (2006.01) | |
| A61K 31/541 | (2006.01) | |
| C07D 403/14 | (2006.01) | |
| C07D 417/14 | (2006.01) | |
| A61P 17/06 | (2006.01) | |
| A61P 37/02 | (2006.01) | |
| A61P 13/12 | (2006.01) | |
| A61P 29/00 | (2006.01) | |
| A61P 35/00 | (2006.01) | |

(52) U.S. Cl.
CPC .......... *C07D 403/12* (2013.01); *A61K 31/454* (2013.01); *A61K 31/4725* (2013.01); *A61K 31/5377* (2013.01); *A61K 31/541* (2013.01); *A61P 13/12* (2018.01); *A61P 17/06* (2018.01); *A61P 29/00* (2018.01); *A61P 35/00* (2018.01); *A61P 37/02* (2018.01); *C07D 401/14* (2013.01); *C07D 403/14* (2013.01); *C07D 413/14* (2013.01); *C07D 417/14* (2013.01)

(58) Field of Classification Search
CPC .......................... A61K 31/4168; C07D 233/88
USPC ........................................ 514/398; 568/332.5
See application file for complete search history.

(56) References Cited

U.S. PATENT DOCUMENTS
2017/0190697 A1   7/2017 Yamamoto et al.

FOREIGN PATENT DOCUMENTS

| | | |
|---|---|---|
| JP | 2006-521359 A | 9/2006 |
| JP | 2009-504671 A | 2/2009 |
| JP | 2009-543774 A | 12/2009 |
| JP | 2012-502887 A | 2/2012 |
| WO | WO 2004/087159 A1 | 10/2004 |
| WO | WO 2007/021990 A2 | 2/2007 |
| WO | WO 2008/007930 A1 | 1/2008 |
| WO | WO 2010/028862 A1 | 3/2010 |

(Continued)

OTHER PUBLICATIONS

Jordan, V. C. Nature Reviews: Drug Discovery, 2, 2003, 205.*

(Continued)

*Primary Examiner* — Douglas M Willis
(74) *Attorney, Agent, or Firm* — Birch, Stewart, Kolasch & Birch, LLP

(57) ABSTRACT

The present invention relates to a novel imidazole compound or a pharmaceutically acceptable salt thereof having a melanocortin receptor agonistic activity, and medical use thereof. The present invention relates to an imidazole compound represented by general formula [I]

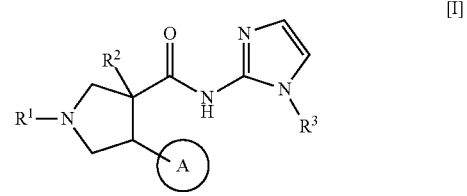

[wherein: Ring A represents an optionally substituted aryl group or the like; R¹ represents a hydrogen atom, an optionally substituted alkyl group, or the like; R² represents a hydrogen atom, a halogen atom, or the like; and R³ represents an optionally substituted alkyl group] or a pharmaceutically acceptable salt thereof.

17 Claims, No Drawings

(56) References Cited

FOREIGN PATENT DOCUMENTS

WO  WO 2015/182723 A1  12/2015
WO  WO 17/090743  *  6/2017

OTHER PUBLICATIONS

Hackam, et al. JAMA, 296(14), 2006, 1731-1732.*
Catania et al., "Targeting Melanocortin Receptors as a Novel Strategy to Control Inflammation," Pharmacol. Rev. (2004), vol. 56, No. 1, pp. 1-29.
Ceriani et al., "The Neuropeptide Alpha-Melanocyte-Stimulating Hormone Inhibits Experimental Arthritis in Rats," Neuroimmunomodulation (1994), vol. 1, pp. 28-32.
Hadley, M. E. and C. Haskell-Luevano, "The Proopiomelanocortin System," Annals of the New York Academy of Science (1999), vol. 885, pp. 1-21.
International Preliminary Report on Patentability dated May 29, 2018, in PCT International Application No. PCT/JP2016/085017.
International Search Report dated Feb. 7, 2017, in PCT International Application No. PCT/JP2016/085017.
Slominski et al., "Corticotropin Releasing Hormone and Proopiomelanocortin Involvement in the Cutaneous Response to Stress," Physiological Reviews (Jul. 2000), vol. 80, No. 3, pp. 979-1020.
Suzuki et al., "Binding of Melanotropic Hormones to the Melanocortin Receptor MC1R on Human Melanocytes Stimulates Proliferation and Melanogenesis," Endocrinology (1996), vol. 137, No. 5, pp. 1627-1633.
Written Opinion of the International Searching Authority dated Feb. 7, 2017, in PCT International Application No. PCT/JP2016/085017.
Extended European Search Report, dated May 16, 2019, for European Application No. 16868686.3.

* cited by examiner

SUBSTITUTED IMIDAZOLES AS MELANOCORTIN RECEPTOR AGONISTS

TECHNICAL FIELD

The present invention relates to a novel imidazole compound having a melanocortin receptor (MCR) agonistic activity (agonist activity).

BACKGROUND ART

α-Melanocyte stimulation hormone (α-MSH) is a hormone derived from pro-opiomelanocortin (POMC) (Nonpatent Document 1), and referred to as a melanocortin peptide along with β-MSH, γ-MSH, and adrenocorticotropic hormone (ACTH). α-MSH is known to exhibit an inhibitory action on the production of inflammation- or fibrosis related mediators associated with various pathogenesis, and exhibit efficacies in autoimmune disease models such as colitis, uveoretinitis, and arthritis (Nonpatent Document 2). Also, α-MSH analogs have been developed for use in the treatment of protoporphyria, acute renal failure, or postoperative pain.

Melanocortin receptors (MCRs), which are receptors for α-MSH, are seven-transmembrane G-protein-coupled receptors (GPCRs), and the activation thereof increases the intracellular cyclic AMP (cAMP) (Nonpatent Document 3). There are five subtypes of MCRs, i.e., MC1R to MC5R.

MC1R is a receptor which is mainly activated by α-MSH, and expressed in melanocytes, immune and inflammatory cells, fibroblasts, keratinocytes, endothelial cells, glial cells, and the like. Thus, the activation of MC1R is known to increase the cAMP level in MC1R-expressing cells, and produce effects such as melanogenesis in a skin and homeostasis against external stimuli (Nonpatent Document 4), anti-inflammatory effects, and inhibitory effects on tissue fibrosis (Nonpatent Document 5). MC2R is a receptor which poorly responds to α-MSH and activated mainly by ACTH, and highly expressed in adrenal cortex. The activation of MC2R is known to produce steroidogenesis effects. MC3R is a receptor which is activated mainly by γ-MSH and ACTH, and expressed in central nerves, macrophage, and the like. The activation of MC3R is known to produce effects such as regulation of autonomic function and anti-inflammatory effects. MC4R is a receptor which is activated mainly by α-MSH and ACTH, and expressed in central nerves and the like. Thus, the activation of MC4R is known to produce effects such as feeding suppression and enhancement of erectile function. MC5R is a receptor activated mainly by α-MSH, and expressed in exocrine glands, lymphocytes, and the like. The activation of MC5R is known to produce effects such as exocrine fluid regulation and immune function regulation. Thus, the activation of these melanocortin receptors (MCRs) is expected to produce effects such as immune regulation, anti-inflammation, and suppression of tissue fibrosis through the formation of cAMP.

Meanwhile, documents such as Patent Document 1 and Patent Document 2 are known to disclose a pyrrolidine compound having a carbamoyl group at the position 3 of pyrrolidine. The compound disclosed in Patent Document 1 also has an alkyl group, an aryl group, or a heteroaryl group as a substituent at the position 2 of pyrrolidine and binds to HDM2 to exhibit anticancer effects. However, Patent Document 1 does not disclose a pyrrolidine compound having substituents at the position 1, position 3, and position 4 like the compound of the present invention.

Also, the compound disclosed in Patent Document 2 is a compound wherein the carbamoyl group at the position 3 of pyrrolidine is substituted with a pyrrolidinyl group. However, Patent Document 2 does not disclose a compound wherein the carbamoyl group at the position 3 of pyrrolidine is substituted with an imidazolyl group like the compound of the present invention.

CITATION LIST

Patent Document

Patent Document 1: WO 2010/028862 pamphlet
Patent Document 2: WO 2008/007930 pamphlet

Nonpatent Document

Nonpatent Document 1: *Annals of the New York Academy of Science*, 1999; 885: p. 1-21
Nonpatent Document 2: *Pharmacological Review*, 2004; 56: p. 1-29
Nonpatent Document 3: *Endocrinology*, 1996; 137: p. 1627-1633
Nonpatent Document 4: *Physiological Reviews*, 2000; 80: p. 979-1020
Nonpatent Document 5: *Neuroimmunomodulation*, 1994; 1: p. 28-32

SUMMARY OF THE INVENTION

Problems to be Solved by Invention

The present invention relates to a novel imidazole compound or a pharmaceutically acceptable salt thereof having a melanocortin receptor (MCR) agonistic activity, especially a melanocortin receptor 1 (MC1R) agonistic activity (agonist activity). The compound of the present invention is therefore useful for preventing, treating, or improving the prognosis of various diseases or symptoms associated with the activation of MCR, especially MC1R.

Means to Solve Problems

The present invention relates to an imidazole compound represented by general formula [I]

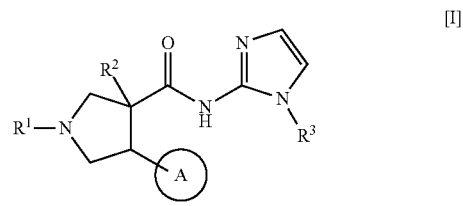

[wherein:
Ring A represents an optionally substituted aryl group or an optionally substituted heteroaryl group;
$R^1$ represents a hydrogen atom, an optionally substituted alkyl group, an optionally substituted cycloalkyl group, an optionally substituted aryl group, an optionally substituted heteroaryl group, an optionally substituted aliphatic heterocyclic group, or an optionally substituted alkanoyl group;
$R^2$ represents a hydrogen atom, a halogen atom, an optionally substituted alkyl group, or an optionally substituted alkoxy group; and $R^3$ represents an optionally substituted alkyl group], or a pharmaceutically acceptable salt thereof.

The present invention also relates to a method for preventing, treating, or improving the prognosis of various diseases or symptoms associated with the activation of MCR (especially MC1R) which comprises administering an effective amount of the compound represented by the above general formula [I] or a pharmaceutically acceptable salt thereof to a patient. The present invention also relates to a pharmaceutical composition comprising the above compound [I] or a pharmaceutically acceptable salt thereof as an active ingredient, and use of the compound [I] or a pharmaceutically acceptable salt thereof in the manufacture of the composition. The present invention also relates to the compound [I] or a pharmaceutically acceptable salt thereof, or a pharmaceutical composition comprising said compound or salt as an active ingredient for use in the prevention, treatment, or improved prognosis of various diseases or symptoms associated with MCR (especially MC1R). The present invention also relates to a method for producing the above compound [I] or a pharmaceutically acceptable salt thereof.

Effect of Invention

The compound of the present invention exhibits a melanocortin receptor (MCR) agonistic activity (agonist activity), especially MC1R agonistic activity. Thus, the compound of the present invention is useful for the prevention, treatment, or improved prognosis of various diseases or symptoms associated with the activation of MCR, especially the activation of MC1R.

MODE FOR CARRYING OUT THE INVENTION

The definitions of the groups as used herein may be combined with each other as needed, unless otherwise specified.

The term of "alkyl" as used herein refers to a straight or branched saturated hydrocarbon chain group having 1 to 6 carbon atom(s) ($C_{1-6}$). Specific examples thereof include methyl, ethyl, n-propyl, i-propyl, n-butyl, t-butyl, 2-methyl-n-butyl, i-amyl (3-methyl-n-butyl), and 2-methyl-n-pentyl.

The term of "alkenyl" refers to a straight or branched hydrocarbon chain group having 2 to 6 carbon atoms ($C_{2-6}$) and having at least one carbon-carbon double bond. Especially, examples of the "alkenyl" include a group having 2 to 4 carbon atoms ($C_{2-4}$). Specific examples thereof include vinyl, propenyl, and butenyl.

The term of "cycloalkyl" refers to a monocyclic saturated hydrocarbon group having 3 to 7 carbon atoms ($C_{3-7}$), and specific examples thereof include cyclopropyl, cyclobutyl, cyclopentyl, cyclohexyl, and cycloheptyl.

The term of "cycloalkenyl" refers to a cyclic group having 3 to 7 ($C_{3-7}$) carbon atoms and having at least one carbon-carbon double bond. Specific examples thereof include cyclopropenyl, cyclobutenyl, cyclopentenyl, and cyclohexenyl.

The term of "alkoxy" refers to a monovalent group in which the above alkyl binds to an oxygen atom, and examples thereof include a straight or branched alkyl-O— having 1 to 6 carbon atom(s) ($C_{1-6}$), and preferable examples thereof include alkyl-O— having 1 to 4 carbon atom(s) ($C_{1-4}$). Specific examples thereof include methoxy, ethoxy, n-propoxy, i-propoxy, n-butoxy, t-butoxy, 2-methyl-n-propoxy, and 3-methyl-n-butoxy.

The term of "alkanoyl" refers to a group in which the above alkyl bonds to a carbonyl (C=O), and examples thereof include straight or branched alkyl-C(=O)— having 1 to 6 carbon atom(s) ($C_{1-6}$), and preferable examples thereof include alkyl-C(=O)— having 1 to 4 carbon atom(s) ($C_{1-4}$). Specific examples thereof include acetyl, propionyl, and butyryl.

Examples of the term of "halogen" or "halo" include a fluorine atom, a chlorine atom, a bromine atom, or an iodine atom. Especially, "halogen" or "halo" may be a fluorine atom and a chlorine atom.

The term of "haloalkyl" refers to alkyl substituted with 1 to 3 halogen atoms, and specific examples thereof include difluoromethyl, trifluoromethyl, 1-fluoromethyl, and 2-fluoroethyl.

Examples of the term of "aryl" include a 6 to 10 membered aromatic hydrocarbon cyclic group. Preferable examples thereof include a monocyclic or bicyclic aryl, and specific examples thereof include phenyl and naphthyl, and especially preferable examples include phenyl.

The term of "heteroaryl" refers to a 5 to 10 membered monocyclic or bicyclic group comprising 1 to 4 heteroatoms independently selected from the group consisting of a sulfur atom, an oxygen atom, and a nitrogen atom. Preferable examples thereof include a 5 to 6 membered monocyclic heteroaryl comprising at least one nitrogen atom and further optionally comprising 1 to 3 heteroatoms independently selected from the group consisting of a sulfur atom, an oxygen atom, and a nitrogen atom. Also, other preferable examples thereof include a 10 membered bicyclic heteroaryl group comprising one nitrogen atom and further optionally comprising 1 to 3 heteroatoms independently selected from the group consisting of a sulfur atom, an oxygen atom, and a nitrogen atom. Specific examples thereof include pyrrolyl, furanyl, thienyl, imidazolyl, pyrazolyl, oxazolyl, isoxazolyl, thiazolyl, triazolyl, tetrazolyl, oxadiazolyl, pyridinyl, pyrazinyl, pyrimidinyl, pyridazinyl, thiazinyl, triazinyl, indolyl, quinolyl, isoquinolyl, isoindolyl, and benzimidazolyl, and preferable examples thereof include oxazolyl, oxadiazolyl, pyridyl, tetrazolyl, and isoquinolyl.

Examples of the term of "optionally partially hydrogenated heteroaryl" include the above heteroaryl in which a part of the ring is hydrogenated, and specific examples thereof include tetrahydroisoquinolyl.

The term of "aliphatic heterocyclic" refers to a 4 to 8 membered saturated cyclic group comprising 1 to 3 heteroatoms independently selected from the group consisting of an oxygen atom, a sulfur atom, and a nitrogen atom. Preferable examples thereof include a 4 to 7 membered monocyclic aliphatic heterocyclic comprising at least one nitrogen atom and further optionally comprising one heteroatom selected from the group consisting of an oxygen atom, a sulfur atom, and a nitrogen atom. More preferable examples thereof include a 5 to 6 membered monocyclic aliphatic heterocyclic comprising at least one nitrogen atom and further optionally comprising one heteroatom selected from the group consisting of an oxygen atom, a sulfur atom, and a nitrogen atom. Specific examples thereof include azetidinyl, pyrrolidinyl, tetrahydrofuranyl, imidazolidinyl, thiazolidinyl, isothiazolidinyl, piperidinyl, piperazinyl, morpholinyl, thiomorpholinyl, tetrahydropyranyl, homopiperazinyl, homomorpholinyl, 3-azabicyclo[3.1.0]hexyl, and octahydropyrrolo[3,4-c]pyrrolyl. Preferable examples thereof include azetidinyl, pyrrolidinyl, imidazolidinyl, thiazolidinyl, piperidinyl, morpholinyl, thiomorpholinyl, piperazinyl, and 3-azabicyclo[3.1.0]hexyl. More preferable examples thereof include pyrrolidinyl, piperidinyl, morpholinyl, thiazolidinyl, and imidazolidinyl. Also, other preferable examples thereof include piperidinyl, piperazinyl, morpholinyl, and thiomorpholinyl.

In a preferable embodiment, the present invention includes the compound represented by the above general formula [I], wherein the substituent of the optionally substituted aryl group and the optionally substituted heteroaryl group represented by Ring A is 1 to 3 groups each independently selected from the group consisting of a halogen atom and an alkoxy group;

wherein said aryl moiety in the optionally substituted aryl group represented by Ring A is a 6 to 10 membered monocyclic or bicyclic aryl;

said heteroaryl moiety in the optionally substituted heteroaryl group represented by Ring A is a 5 to 10 membered monocyclic or bicyclic heteroaryl comprising 1 to 4 heteroatoms independently selected from the group consisting of a sulfur atom, an oxygen atom, and a nitrogen atom;

the substituent of the (1) optionally substituted alkyl group represented by $R^1$ is 1 to 3 groups independently selected from the group consisting of a halogen atom, a hydroxy group, a cyano group, an optionally substituted alkoxy group, an alkanoyl group, an optionally substituted aryl group, an optionally partially hydrogenated and optionally substituted heteroaryl group, an optionally substituted aliphatic heterocyclic group, an optionally substituted amino group, an optionally substituted carbamoyl group, and an optionally substituted sulfonyl group;

the substituent of the (2) optionally substituted cycloalkyl group, (3) optionally substituted aryl group, (4) optionally substituted heteroaryl group, (5) optionally substituted aliphatic heterocyclic group, and (6) optionally substituted alkanoyl group represented by $R^1$ is 1 to 3 groups each independently selected from the group consisting of a halogen atom, a hydroxy group, a cyano group, an optionally substituted alkyl group, an optionally substituted alkoxy group, an alkanoyl group, an optionally substituted aryl group, an optionally partially hydrogenated and optionally substituted heteroaryl group, an optionally substituted aliphatic heterocyclic group, an optionally substituted amino group, an optionally substituted carbamoyl group, and an optionally substituted sulfonyl group;

wherein said aryl moiety in the optionally substituted aryl group represented by $R^1$ is a 6 to 10 membered monocyclic or bicyclic aryl;

said heteroaryl moiety in the optionally substituted heteroaryl group represented by $R^1$ is a 5 to 10 membered monocyclic or bicyclic heteroaryl comprising 1 to 4 heteroatoms independently selected from the group consisting of a sulfur atom, an oxygen atom, and a nitrogen atom;

said aliphatic heterocyclic moiety in the optionally substituted aliphatic heterocyclic group represented by $R^1$ is a 4 to 8 membered monocyclic aliphatic heterocyclic group comprising 1 to 3 heteroatoms independently selected from the group consisting of a sulfur atom, an oxygen atom, and a nitrogen atom;

said aryl moiety in the optionally substituted aryl group in the substituent of $R^1$ is a 6 to 10 membered monocyclic or bicyclic aryl;

said heteroaryl moiety in the optionally partially hydrogenated and optionally substituted heteroaryl group in the substituent of $R^1$ is a 5 to 10 membered monocyclic or bicyclic heteroaryl comprising 1 to 4 heteroatoms independently selected from the group consisting of a sulfur atom, an oxygen atom, and a nitrogen atom;

said aliphatic heterocyclic moiety in the optionally substituted aliphatic heterocyclic group in the substituent of $R^1$ is a 4 to 8 membered monocyclic aliphatic heterocyclic group comprising 1 to 3 heteroatoms independently selected from the group consisting of a sulfur atom, an oxygen atom, and a nitrogen atom;

$R^2$ represents a hydrogen atom, a halogen atom, an alkyl group, a haloalkyl group, or an alkoxy group;

$R^3$ represents a group of the following formula [II]

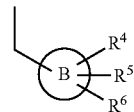

[II]

[wherein:

Ring B represents an aryl group, a cycloalkyl group, or a heteroaryl group;

wherein said aryl moiety in the aryl group represented by Ring B is a 6 to 10 membered monocyclic or bicyclic aryl;

said heteroaryl moiety in the heteroaryl group represented by Ring B is a 5 to 10 membered monocyclic or bicyclic heteroaryl comprising 1 to 4 heteroatoms independently selected from the group consisting of a sulfur atom, an oxygen atom, and a nitrogen atom;

$R^4$, $R^5$, and $R^6$ represent each a group independently selected from the group consisting of a hydrogen atom; a halogen atom; an optionally substituted alkyl group; an optionally substituted cycloalkyl group; an optionally substituted heteroaryl group; an optionally substituted aliphatic heterocyclic group; and an amino group optionally substituted with 1 to 2 groups independently selected from the group consisting of an optionally substituted alkyl group;

wherein the substituent of the (1) optionally substituted alkyl group represented by $R^4$, $R^5$, or $R^6$ is 1 to 2 groups independently selected from the group consisting of a hydroxy group; a halogen atom; an oxo group; a cyano group; an optionally substituted heteroaryl group; a carboxyl group; an alkoxycarbonyl group; an optionally substituted carbamoyl group; an alkylsulfonyl group; an alkylsulfonylamino group; an alkylsulfonylaminocarbonyl group; and an optionally substituted aminosulfonylaminocarbonyl group;

the substituent of the (2) optionally substituted cycloalkyl group, (3) optionally substituted heteroaryl group, and (4) optionally substituted aliphatic heterocyclic group represented by $R^4$, $R^5$, or $R^6$ is 1 to 2 groups each independently selected from the group consisting of a hydroxy group; a halogen atom; an oxo group; a cyano group; an alkyl group; an optionally substituted heteroaryl group; a carboxyl group; an alkoxycarbonyl group; an optionally substituted carbamoyl group; an alkylsulfonyl group; an alkylsulfonylamino group; an alkylsulfonylaminocarbonyl group; and an optionally substituted aminosulfonylaminocarbonyl group;

wherein said heteroaryl moiety in the optionally substituted heteroaryl group represented by $R^4$, $R^5$, or $R^6$ is a 5 to 10 membered monocyclic or bicyclic heteroaryl comprising 1 to 4 heteroatoms independently selected from the group consisting of a sulfur atom, an oxygen atom, and a nitrogen atom;

said aliphatic heterocyclic moiety in the optionally substituted aliphatic heterocyclic group represented by $R^4$, $R^5$, or $R^6$ is a 4 to 8 membered monocyclic aliphatic heterocyclic group comprising 1 to 3 heteroatoms independently selected from the group consisting of a sulfur atom, an oxygen atom, and a nitrogen atom; and said heteroaryl moiety in the optionally substituted heteroaryl group in the substituent of the group represented by $R^4$, $R^5$, or $R^6$ is a 5 to 10 membered monocyclic or bicyclic heteroaryl comprising 1 to 4 heteroatoms independently selected from the group consisting of a sulfur atom, an oxygen atom, and a nitrogen atom]

or a pharmaceutically acceptable salt thereof.

In a more preferable embodiment, the present invention includes the compound represented by the above general formula [I], wherein the substituent of the optionally substituted aryl group and the optionally substituted heteroaryl group represented by Ring A is 1 to 3 groups each independently selected from the group consisting of a halogen atom and an alkoxy group;

wherein said aryl moiety in the optionally substituted aryl group represented by Ring A is a 6 to 10 membered monocyclic or bicyclic aryl;

said heteroaryl moiety in the optionally substituted heteroaryl group represented by Ring A is a 5 to 10 membered monocyclic or bicyclic heteroaryl comprising 1 to 4 heteroatoms independently selected from the group consisting of a sulfur atom, an oxygen atom, and a nitrogen atom;

the substituent of the (1) optionally substituted alkyl group represented by $R^1$ is 1 to 3 groups independently selected from the group consisting of a halogen atom; a hydroxy group; a cyano group; an alkoxy group optionally substituted with an aryl group; an alkanoyl group; an aryl group optionally substituted with a group selected from the group consisting of an alkylsulfonyl group and an aminosulfonyl group; an optionally partially hydrogenated heteroaryl group optionally substituted with 1 to 2 groups independently selected from the group consisting of an oxo group and a hydroxy group; an aliphatic heterocyclic group optionally substituted with 1 to 2 oxo groups; an amino group optionally substituted with 1 to 2 groups independently selected from the group consisting of an alkyl group, a heteroaryl group, an alkoxycarbonyl group, an alkylsulfonyl group, and an aminosulfonyl group; a carbamoyl group optionally substituted with 1 to 2 alkyl groups; and a sulfonyl group optionally substituted with a group selected from the group consisting of an aliphatic heterocyclic group optionally substituted with a hydroxy group and an amino group optionally substituted with 1 to 2 alkyl groups;

the substituent of the (2) optionally substituted cycloalkyl group, (3) optionally substituted aryl group, (4) optionally substituted heteroaryl group, (5) optionally substituted aliphatic heterocyclic group, and (6) optionally substituted alkanoyl group represented by $R^1$ is 1 to 3 groups each independently selected from the group consisting of a halogen atom; a hydroxy group; a cyano group; an alkyl group optionally substituted with 1 to 2 groups independently selected from the group consisting of a halogen atom, a hydroxy group, and a cyano group; an alkoxy group optionally substituted with an aryl group; an alkanoyl group; an aryl group optionally substituted with a group selected from the group consisting of an alkylsulfonyl group and an aminosulfonyl group; an optionally partially hydrogenated heteroaryl group optionally substituted with 1 to 2 groups independently selected from the group consisting of a hydroxy group and an oxo group; an aliphatic heterocyclic group optionally substituted with 1 to 2 oxo groups; an amino group optionally substituted with 1 to 2 groups independently selected from the group consisting of an alkyl group, a heteroaryl group, an alkoxycarbonyl group, an alkylsulfonyl group, and an aminosulfonyl group; a carbamoyl group optionally substituted with 1 to 2 alkyl groups; and a sulfonyl group optionally substituted with a group selected from the group consisting of an aliphatic heterocyclic group optionally substituted with a hydroxy group and an amino group optionally substituted with 1 to 2 alkyl groups;

wherein said aryl moiety in the optionally substituted aryl group represented by $R^1$ is a 6 to 10 membered monocyclic or bicyclic aryl;

said heteroaryl moiety in the optionally substituted heteroaryl group represented by $R^1$ is a 5 to 10 membered monocyclic or bicyclic heteroaryl comprising 1 to 4 heteroatoms independently selected from the group consisting of a sulfur atom, an oxygen atom, and a nitrogen atom;

said aliphatic heterocyclic moiety in the optionally substituted aliphatic heterocyclic group represented by $R^1$ is a 4 to 8 membered monocyclic aliphatic heterocyclic group comprising 1 to 2 heteroatoms independently selected from the group consisting of a sulfur atom, an oxygen atom, and a nitrogen atom;

said aryl moiety in the optionally substituted aryl group in the substituent of the group represented by $R^1$ is a 6 to 10 membered monocyclic or bicyclic aryl;

said heteroaryl moiety in the optionally partially hydrogenated and optionally substituted heteroaryl group in the substituent of the group represented by $R^1$ is a 5 to 10 membered monocyclic or bicyclic heteroaryl comprising 1 to 4 heteroatoms independently selected from the group consisting of a sulfur atom, an oxygen atom, and a nitrogen atom;

said aliphatic heterocyclic moiety in the optionally substituted aliphatic heterocyclic group in the substituent of the group represented by $R^1$ is a 4 to 8 membered monocyclic aliphatic heterocyclic group comprising 1 to 2 heteroatoms independently selected from the group consisting of a sulfur atom, an oxygen atom, and a nitrogen atom;

$R^2$ represents a hydrogen atom, a halogen atom, an alkyl group, a haloalkyl group, or an alkoxy group;

Ring B represents an aryl group, a cycloalkyl group, or a heteroaryl group;

$R^4$, $R^5$, and $R^6$ represent each a group independently selected from the group consisting of a hydrogen atom; a halogen atom; an optionally substituted alkyl group; an optionally substituted cycloalkyl group; an optionally substituted heteroaryl group; an optionally substituted aliphatic heterocyclic group; and an amino group optionally substituted with 1 to 2 groups independently selected from the group consisting of an alkyl group optionally substituted with a carboxyl group;

wherein the substituent of the (1) optionally substituted alkyl group represented by $R^4$, $R^5$, or $R^6$ is 1 to 2 groups independently selected from the group consisting of a hydroxy group; a halogen atom; an oxo group; a cyano group; a heteroaryl group optionally substituted with a group selected from the group consisting of a hydroxy group and an oxo group; a carboxyl group; an alkoxycarbonyl group; a carbamoyl group optionally substituted with 1 to 2 alkyl groups; an alkylsulfonyl group; an alkylsulfonylamino group; an alkylsulfonylaminocarbonyl group; and an aminosulfonylaminocarbonyl group optionally substituted with 1 to 2 alkyl groups;

the substituent of the (2) optionally substituted cycloalkyl group, (3) optionally substituted heteroaryl group, and (4) optionally substituted aliphatic heterocyclic group represented by $R^4$, $R^5$, or $R^6$ is 1 to 2 groups each independently selected from the group consisting of a hydroxy group; a halogen atom; an oxo group; a cyano group; an alkyl group; a heteroaryl group optionally substituted with a group selected from the group consisting of a hydroxy group and an oxo group; a carboxyl group; an alkoxycarbonyl group;

a carbamoyl group optionally substituted with 1 to 2 alkyl groups; an alkylsulfonyl group; an alkylsulfonylamino group; an alkylsulfonylaminocarbonyl group; and an aminosulfonylaminocarbonyl group optionally substituted with 1 to 2 alkyl groups, wherein said heteroaryl moiety in the optionally substituted heteroaryl group represented by $R^4$, $R^5$, or $R^6$ is a 5 to 10 membered monocyclic or bicyclic heteroaryl comprising 1 to 4 heteroatoms independently selected from the group consisting of a sulfur atom, an oxygen atom, and a nitrogen atom;

said aliphatic heterocyclic moiety in the optionally substituted aliphatic heterocyclic group represented by $R^4$, $R^5$, or $R^6$ is a 4 to 8 membered monocyclic aliphatic heterocyclic group comprising 1 to 2 heteroatoms independently selected from the group consisting of a sulfur atom, an oxygen atom, and a nitrogen atom; and said heteroaryl moiety in the optionally substituted heteroaryl group in the substituent of the group represented by $R^4$, $R^5$, or $R^6$ is a 5 to 10 membered monocyclic or bicyclic heteroaryl comprising 1 to 4 heteroatoms independently selected from the group consisting of a sulfur atom, an oxygen atom, and a nitrogen atom, or a pharmaceutically acceptable salt thereof.

In a still more preferable embodiment, the present invention includes the compound represented by the above general formula [I], wherein said aryl moiety in the optionally substituted aryl group represented by Ring A is phenyl or naphthyl;

said heteroaryl moiety in the optionally substituted heteroaryl group represented by Ring A is pyrrolyl, furanyl, thienyl, imidazolyl, pyrazolyl, oxazolyl, isoxazolyl, thiazolyl, triazolyl, tetrazolyl, oxadiazolyl, pyridyl, pyrazinyl, pyrimidinyl, pyridazinyl, thiazinyl, triazinyl, indolyl, quinolyl, isoquinolyl, isoindolyl, or benzimidazolyl;

said aryl moiety in the optionally substituted aryl group represented by $R^1$ is phenyl or naphthyl;

said heteroaryl moiety in the optionally substituted heteroaryl group represented by $R^1$ is pyrrolyl, furanyl, thienyl, imidazolyl, pyrazolyl, oxazolyl, isoxazolyl, thiazolyl, triazolyl, tetrazolyl, oxadiazolyl, pyridyl, pyrazinyl, pyrimidinyl, pyridazinyl, thiazinyl, triazinyl, indolyl, quinolyl, isoquinolyl, isoindolyl, or benzimidazolyl;

said aliphatic heterocyclic moiety in the optionally substituted aliphatic heterocyclic group represented by $R^1$ is azetidinyl, pyrrolidinyl, tetrahydrofuranyl, imidazolinyl, thiazolidinyl, isothiazolidinyl, piperidinyl, piperazinyl, morpholinyl, thiomorpholinyl, tetrahydropyranyl, homopiperazinyl, homomorpholinyl, 3-azabicyclo[3.1.0]hexyl, or octahydropyrrolo[3,4-c]pyrrolyl;

said aryl moiety in the optionally substituted aryl group in the substituent of the group represented by $R^1$ is phenyl or naphthyl;

said heteroaryl moiety in the optionally partially hydrogenated and optionally substituted heteroaryl group in the substituent of the group represented by $R^1$ is pyrrolyl, furanyl, thienyl, imidazolyl, pyrazolyl, oxazolyl, isoxazolyl, thiazolyl, triazolyl, tetrazolyl, oxadiazolyl, pyridyl, pyrazinyl, pyrimidinyl, pyridazinyl, thiazinyl, triazinyl, indolyl, quinolyl, isoquinolyl, isoindolyl, or benzimidazolyl;

said aliphatic heterocyclic moiety in the optionally substituted aliphatic heterocyclic group in the substituent of the group represented by $R^1$ is azetidinyl, pyrrolidinyl, tetrahydrofuranyl, imidazolinyl, thiazolidinyl, isothiazolidinyl, piperidinyl, piperazinyl, morpholinyl, thiomorpholinyl, tetrahydropyranyl, homopiperazinyl, homomorpholinyl, 3-azabicyclo[3.1.0]hexyl, or octahydropyrrolo[3,4-c]pyrrolyl;

the aryl group represented by Ring B is phenyl or naphthyl;

the heteroaryl group represented by Ring B is pyrrolyl, furanyl, thienyl, imidazolyl, pyrazolyl, oxazolyl, isoxazolyl, thiazolyl, triazolyl, tetrazolyl, oxadiazolyl, pyridyl, pyrazinyl, pyrimidinyl, pyridazinyl, thiazinyl, triazinyl, indolyl, quinolyl, isoquinolyl, isoindolyl, or benzimidazolyl;

said heteroaryl moiety in the optionally substituted heteroaryl group represented by $R^4$, $R^5$, or $R^6$ is pyrrolyl, furanyl, thienyl, imidazolyl, pyrazolyl, oxazolyl, isoxazolyl, thiazolyl, triazolyl, tetrazolyl, oxadiazolyl, pyridyl, pyrazinyl, pyrimidinyl, pyridazinyl, thiazinyl, triazinyl, indolyl, quinolyl, isoquinolyl, isoindolyl, or benzimidazolyl;

said aliphatic heterocyclic moiety in the optionally substituted aliphatic heterocyclic group represented by $R^4$, $R^5$, or $R^6$ is azetidinyl, pyrrolidinyl, tetrahydrofuranyl, imidazolinyl, thiazolidinyl, isothiazolidinyl, piperidinyl, piperazinyl, morpholinyl, thiomorpholinyl, tetrahydropyranyl, homopiperazinyl, homomorpholinyl, 3-azabicyclo[3.1.0]hexyl, or octahydropyrrolo[3,4-c]pyrrolyl; and said heteroaryl moiety in the optionally substituted heteroaryl group in the substituent of the group represented by $R^4$, $R^5$, or $R^6$ is pyrrolyl, furanyl, thienyl, imidazolyl, pyrazolyl, oxazolyl, isoxazolyl, thiazolyl, triazolyl, tetrazolyl, oxadiazolyl, pyridyl, pyrazinyl, pyrimidinyl, pyridazinyl, thiazinyl, triazinyl, indolyl, quinolyl, isoquinolyl, isoindolyl, or benzimidazolyl, or a pharmaceutically acceptable salt thereof.

In other more preferable embodiment, the present invention includes the compound in the above each embodiment, wherein:

$R^4$ represents a group selected from the group consisting of an optionally substituted alkyl group; an optionally substituted cycloalkyl group; an optionally substituted heteroaryl group; an optionally substituted aliphatic heterocyclic group; and an amino group optionally substituted with 1 to 2 groups independently selected from the group consisting of an optionally substituted alkyl group; and $R^5$ and $R^6$ represent each a group independently selected from the group consisting of a hydrogen atom, a halogen atom, an alkyl group, a haloalkyl group, and a cycloalkyl group, or a pharmaceutically acceptable salt thereof.

In another preferable embodiment, the present invention includes the compound represented by the above general formula [I], wherein the substituent of the optionally substituted aryl group and the optionally substituted heteroaryl group represented by Ring A is 1 to 3 groups each independently selected from the group consisting of a halogen atom and an alkoxy group;

wherein said aryl moiety in the optionally substituted aryl group represented by Ring A is a 6 to 10 membered monocyclic or bicyclic aryl;

said heteroaryl moiety in the optionally substituted heteroaryl group represented by Ring A is a 5 to 10 membered monocyclic or bicyclic heteroaryl comprising 1 to 4 heteroatoms independently selected from the group consisting of a sulfur atom, an oxygen atom, and a nitrogen atom;

the substituent of the (1) optionally substituted alkyl group represented by $R^1$ is 1 to 3 groups independently selected from the group consisting of a halogen atom, a hydroxy group, a cyano group, an optionally substituted alkoxy group, an alkanoyl group, an optionally substituted aryl group, an optionally partially hydrogenated and optionally substituted heteroaryl group, an optionally substituted aliphatic heterocyclic group, an optionally substituted amino group, an optionally substituted carbamoyl group, and an optionally substituted sulfonyl group;

the substituent of the (2) optionally substituted cycloalkyl group, (3) optionally substituted aryl group, (4) optionally substituted heteroaryl group, (5) optionally substituted aliphatic heterocyclic group, and (6) optionally substituted alkanoyl group represented by $R^1$ is 1 to 3 groups each independently selected from the group consisting of a halogen atom, a hydroxy group, a cyano group, an optionally substituted alkyl group, an optionally substituted alkoxy group, an alkanoyl group, an optionally substituted aryl group, an optionally partially hydrogenated and optionally substituted heteroaryl group, an optionally substituted aliphatic heterocyclic group, an optionally substituted amino group, an optionally substituted carbamoyl group, and an optionally substituted sulfonyl group;

wherein said aryl moiety in the optionally substituted aryl group represented by $R^1$ is a 6 to 10 membered monocyclic or bicyclic aryl;

said heteroaryl moiety in the optionally substituted heteroaryl group represented by $R^1$ is a 5 to 10 membered monocyclic or bicyclic heteroaryl comprising 1 to 4 heteroatoms independently selected from the group consisting of a sulfur atom, an oxygen atom, and a nitrogen atom;

said aliphatic heterocyclic moiety in the optionally substituted aliphatic heterocyclic group represented by $R^1$ is a 4 to 8 membered monocyclic aliphatic heterocyclic group comprising 1 to 3 heteroatoms independently selected from the group consisting of a sulfur atom, an oxygen atom, and a nitrogen atom;

said aryl moiety in the optionally substituted aryl group in the substituent of the group represented by $R^1$ is a 6 to 10 membered monocyclic or bicyclic aryl;

said heteroaryl moiety in the optionally partially hydrogenated and optionally substituted heteroaryl group in the substituent of the group represented by $R^1$ is a 5 to 10 membered monocyclic or bicyclic heteroaryl comprising 1 to 4 heteroatoms independently selected from the group consisting of a sulfur atom, an oxygen atom, and a nitrogen atom;

said aliphatic heterocyclic moiety in the optionally substituted aliphatic heterocyclic group in the substituent of the group represented by $R^1$ is a 4 to 8 membered monocyclic aliphatic heterocyclic group comprising 1 to 3 heteroatoms independently selected from the group consisting of a sulfur atom, an oxygen atom, and a nitrogen atom;

$R^2$ represents a hydrogen atom, a halogen atom, an alkyl group, a haloalkyl group, or an alkoxy group;

$R^3$ represents a group of the following formula [II]

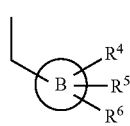

[wherein:

Ring B represents an aryl group, a cycloalkyl group, or a heteroaryl group;

wherein said aryl moiety in the aryl group represented by Ring B is a 6 to 10 membered monocyclic or bicyclic aryl;

said heteroaryl moiety in the heteroaryl group represented by Ring B is a 5 to 10 membered monocyclic or bicyclic heteroaryl comprising 1 to 4 heteroatoms independently selected from the group consisting of a sulfur atom, an oxygen atom, and a nitrogen atom;

$R^4$ represents a group selected from the group consisting of an optionally substituted alkyl group; an optionally substituted cycloalkyl group; an optionally substituted heteroaryl group; an optionally substituted aliphatic heterocyclic group; and an amino group optionally substituted with 1 to 2 groups independently selected from the group consisting of an optionally substituted alkyl group;

wherein the substituent of the (1) optionally substituted alkyl group represented by $R^4$ is 1 to 2 groups independently selected from the group consisting of a hydroxy group; a halogen atom; an oxo group; a cyano group; an optionally substituted heteroaryl group; a carboxyl group; an alkoxycarbonyl group; a carbamoyl group optionally substituted with 1 to 2 alkyl groups; an alkylsulfonyl group; an alkylsulfonylamino group; an alkylsulfonylaminocarbonyl group; and an optionally substituted aminosulfonylaminocarbonyl group;

the substituent of the (2) optionally substituted cycloalkyl group, (3) optionally substituted heteroaryl group, and (4) optionally substituted aliphatic heterocyclic group represented by $R^4$ is 1 to 2 groups each independently selected from the group consisting of a hydroxy group; a halogen atom; an oxo group; a cyano group; an alkyl group; an optionally substituted heteroaryl group; a carboxyl group; an alkoxycarbonyl group; a carbamoyl group optionally substituted with 1 to 2 alkyl groups; an alkylsulfonyl group; an alkylsulfonylamino group; an alkylsulfonylaminocarbonyl group; and an optionally substituted aminosulfonylaminocarbonyl group;

wherein said heteroaryl moiety in the optionally substituted heteroaryl group represented by $R^4$ is a 5 to 10 membered monocyclic or bicyclic heteroaryl comprising 1 to 4 heteroatoms independently selected from the group consisting of a sulfur atom, an oxygen atom, and a nitrogen atom;

said aliphatic heterocyclic moiety in the optionally substituted aliphatic heterocyclic group represented by $R^4$ is a 4 to 8 membered monocyclic aliphatic heterocyclic group comprising 1 to 3 heteroatoms independently selected from the group consisting of a sulfur atom, an oxygen atom, and a nitrogen atom;

said heteroaryl moiety in the optionally substituted heteroaryl group in the substituent of the group represented by $R^4$ is a 5 to 10 membered monocyclic or bicyclic heteroaryl comprising 1 to 4 heteroatoms independently selected from the group consisting of a sulfur atom, an oxygen atom, and a nitrogen atom;

$R^5$ and $R^6$ represent each a group independently selected from the group consisting of a hydrogen atom, a halogen atom, an alkyl group, a haloalkyl group, and a cycloalkyl group]

or a pharmaceutically acceptable salt thereof.

In a still more preferable embodiment, the present invention includes the compound represented by the above general formula [I], wherein the substituent of the optionally substituted aryl group and the optionally substituted heteroaryl group represented by Ring A is 1 to 3 groups each independently selected from the group consisting of a halogen atom and an alkoxy group;

wherein said aryl moiety in the optionally substituted aryl group represented by Ring A is a 6 to 10 membered monocyclic or bicyclic aryl;

said heteroaryl moiety in the optionally substituted heteroaryl group represented by Ring A is a 5 to 10 membered monocyclic or bicyclic heteroaryl comprising 1 to 4 heteroatoms independently selected from the group consisting of a sulfur atom, an oxygen atom, and a nitrogen atom;

the substituent of the (1) optionally substituted alkyl group represented by $R^1$ is 1 to 3 groups independently selected from the group consisting of a halogen atom; a hydroxy group; a cyano group; an alkoxy group optionally substituted with an aryl group; an alkanoyl group; an aryl group optionally substituted with a group selected from the group consisting of an alkylsulfonyl group and an aminosulfonyl group; an optionally partially hydrogenated heteroaryl group optionally substituted with 1 to 2 groups independently selected from the group consisting of an oxo group and a hydroxy group; an aliphatic heterocyclic group optionally substituted with 1 to 2 oxo groups; an amino group optionally substituted with 1 to 2 groups independently selected from the group consisting of an alkyl group, a heteroaryl group, an alkoxycarbonyl group, an alkylsulfonyl group, and an aminosulfonyl group; a carbamoyl group optionally substituted with 1 to 2 alkyl groups; and a sulfonyl group optionally substituted with a group selected from the group consisting of an aliphatic heterocyclic group optionally substituted with a hydroxy group and an amino group optionally substituted with 1 to 2 alkyl groups;

the substituent of the (2) optionally substituted cycloalkyl group, (3) optionally substituted aryl group, (4) optionally substituted heteroaryl group, (5) optionally substituted aliphatic heterocyclic group, and (6) optionally substituted alkanoyl group represented by $R^1$ is 1 to 3 groups each independently selected from the group consisting of a halogen atom; a hydroxy group; a cyano group; an alkyl group optionally substituted with 1 to 2 groups independently selected from the group consisting of a halogen atom, a hydroxy group, and a cyano group; an alkoxy group optionally substituted with an aryl group; an alkanoyl group; an aryl group optionally substituted with a group selected from the group consisting of an alkylsulfonyl group and an aminosulfonyl group; an optionally partially hydrogenated heteroaryl group optionally substituted with 1 to 2 groups independently selected from the group consisting of a hydroxy group and an oxo group; an aliphatic heterocyclic group optionally substituted with 1 to 2 oxo groups; an amino group optionally substituted with 1 to 2 groups independently selected from the group consisting of an alkyl group, a heteroaryl group, an alkoxycarbonyl group, an alkylsulfonyl group, and an aminosulfonyl group; a carbamoyl group optionally substituted with 1 to 2 alkyl groups; and a sulfonyl group optionally substituted with a group selected from the group consisting of an aliphatic heterocyclic group optionally substituted with a hydroxy group and an amino group optionally substituted with 1 to 2 alkyl groups, wherein said aryl moiety in the optionally substituted aryl group represented by $R^1$ is a 6 to 10 membered monocyclic or bicyclic aryl;

said heteroaryl moiety in the optionally substituted heteroaryl group represented by $R^1$ is a 5 to 10 membered monocyclic or bicyclic heteroaryl comprising 1 to 4 heteroatoms independently selected from the group consisting of a sulfur atom, an oxygen atom, and a nitrogen atom;

said aliphatic heterocyclic moiety in the optionally substituted aliphatic heterocyclic group represented by $R^1$ is a 4 to 8 membered monocyclic aliphatic heterocyclic group comprising 1 to 2 heteroatoms independently selected from the group consisting of a sulfur atom, an oxygen atom, and a nitrogen atom;

said aryl moiety in the optionally substituted aryl group in the substituent of the group represented by $R^1$ is a 6 to 10 membered monocyclic or bicyclic aryl;

said heteroaryl moiety in the optionally partially hydrogenated and optionally substituted heteroaryl group in the substituent of the group represented by $R^1$ is a 5 to 10 membered monocyclic or bicyclic heteroaryl comprising 1 to 4 heteroatoms independently selected from the group consisting of a sulfur atom, an oxygen atom, and a nitrogen atom;

said aliphatic heterocyclic moiety in the optionally substituted aliphatic heterocyclic group in the substituent of the group represented by $R^1$ is a 4 to 8 membered monocyclic aliphatic heterocyclic group comprising 1 to 2 heteroatoms independently selected from the group consisting of a sulfur atom, an oxygen atom, and a nitrogen atom;

$R^2$ represents a hydrogen atom, a halogen atom, an alkyl group, a haloalkyl group, or an alkoxy group;

$R^3$ represents a group of the above formula [II];

Ring B represents an aryl group, a cycloalkyl group, or a heteroaryl group;

$R^4$ represents a group selected from the group consisting of an optionally substituted alkyl group; an optionally substituted cycloalkyl group; an optionally substituted heteroaryl group; an optionally substituted aliphatic heterocyclic group; and an amino group optionally substituted with 1 to 2 groups independently selected from the group consisting of an alkyl group optionally substituted with a carboxyl group;

wherein the substituent of the (1) optionally substituted alkyl group represented by $R^4$ is 1 to 2 groups independently selected from the group consisting of a hydroxy group; a halogen atom; an oxo group; a cyano group; a heteroaryl group optionally substituted with a group selected from the group consisting of a hydroxy group and an oxo group; a carboxyl group; an alkoxycarbonyl group; a carbamoyl group optionally substituted with 1 to 2 alkyl groups; an alkylsulfonyl group; an alkylsulfonylamino group; an alkylsulfonylaminocarbonyl group; and an aminosulfonylaminocarbonyl group optionally substituted with 1 to 2 alkyl groups;

the substituent of the (2) optionally substituted cycloalkyl group, (3) optionally substituted heteroaryl group, and (4) optionally substituted aliphatic heterocyclic group represented by $R^4$ is 1 to 2 groups each independently selected from the group consisting of a hydroxy group; a halogen atom; an oxo group; a cyano group; an alkyl group; a heteroaryl group optionally substituted with a group selected from the group consisting of a hydroxy group and an oxo group; a carboxyl group; an alkoxycarbonyl group; a carbamoyl group optionally substituted with 1 to 2 alkyl groups; an alkylsulfonyl group; an alkylsulfonylamino group; an alkylsulfonylaminocarbonyl group; and an aminosulfonylaminocarbonyl group optionally substituted with 1 to 2 alkyl groups;

wherein said heteroaryl moiety in the optionally substituted heteroaryl group represented by $R^4$ is a 5 to 10 membered monocyclic or bicyclic heteroaryl comprising 1 to 4 heteroatoms independently selected from the group consisting of a sulfur atom, an oxygen atom, and a nitrogen atom;

said aliphatic heterocyclic moiety in the optionally substituted aliphatic heterocyclic group represented by $R^4$ is a 4 to 8 membered monocyclic aliphatic heterocyclic group comprising 1 to 2 heteroatoms independently selected from the group consisting of a sulfur atom, an oxygen atom, and a nitrogen atom;

said heteroaryl moiety in the optionally substituted heteroaryl group in the substituent of the group represented by $R^4$ is a 5 to 10 membered monocyclic or bicyclic heteroaryl comprising 1 to 4 heteroatoms independently selected from the group consisting of a sulfur atom, an oxygen atom, and a nitrogen atom; and $R^5$ and $R^6$ represent each a group independently selected from the group consisting of a hydrogen atom, a halogen atom, an alkyl group, a haloalkyl group, and a cycloalkyl group, or a pharmaceutically acceptable salt thereof.

In a still more preferable embodiment, the present invention includes the compound represented by the above general formula [I], wherein said aryl moiety in the optionally substituted aryl group represented by Ring A is phenyl or naphthyl;

said heteroaryl moiety in the optionally substituted heteroaryl group represented by Ring A is pyrrolyl, furanyl, thienyl, imidazolyl, pyrazolyl, oxazolyl, isoxazolyl, thiazolyl, triazolyl, tetrazolyl, oxadiazolyl, pyridyl, pyrazinyl, pyrimidinyl, pyridazinyl, thiazinyl, triazinyl, indolyl, quinolyl, isoquinolyl, isoindolyl, or benzimidazolyl;

said aryl moiety in the optionally substituted aryl group represented by $R^1$ is phenyl or naphthyl;

said heteroaryl moiety in the optionally substituted heteroaryl group represented by $R^1$ is pyrrolyl, furanyl, thienyl, imidazolyl, pyrazolyl, oxazolyl, isoxazolyl, thiazolyl, triazolyl, tetrazolyl, oxadiazolyl, pyridyl, pyrazinyl, pyrimidinyl, pyridazinyl, thiazinyl, triazinyl, indolyl, quinolyl, isoquinolyl, isoindolyl, or benzimidazolyl;

said aliphatic heterocyclic moiety in the optionally substituted aliphatic heterocyclic group represented by $R^1$ is azetidinyl, pyrrolidinyl, tetrahydrofuranyl, imidazolinyl, thiazolidinyl, isothiazolidinyl, piperidinyl, piperazinyl, morpholinyl, thiomorpholinyl, tetrahydropyranyl, homopiperazinyl, homomorpholinyl, 3-azabicyclo[3.1.0]hexyl, or octahydropyrrolo[3,4-c]pyrrolyl;

said aryl moiety in the optionally substituted aryl group in the substituent of the group represented by $R^1$ is phenyl or naphthyl;

said heteroaryl moiety in the optionally partially hydrogenated and optionally substituted heteroaryl group in the substituent of the group represented by $R^1$ is pyrrolyl, furanyl, thienyl, imidazolyl, pyrazolyl, oxazolyl, isoxazolyl, thiazolyl, triazolyl, tetrazolyl, oxadiazolyl, pyridyl, pyrazinyl, pyrimidinyl, pyridazinyl, thiazinyl, triazinyl, indolyl, quinolyl, isoquinolyl, isoindolyl, or benzimidazolyl;

said aliphatic heterocyclic moiety in the optionally substituted aliphatic heterocyclic group in the substituent of the group represented by $R^1$ is azetidinyl, pyrrolidinyl, tetrahydrofuranyl, imidazolinyl, thiazolidinyl, isothiazolidinyl, piperidinyl, piperazinyl, morpholinyl, thiomorpholinyl, tetrahydropyranyl, homopiperazinyl, homomorpholinyl, 3-azabicyclo[3.1.0]hexyl, or octahydropyrrolo[3,4-c]pyrrolyl;

the aryl group represented by Ring B is phenyl or naphthyl;

the heteroaryl group represented by Ring B is pyrrolyl, furanyl, thienyl, imidazolyl, pyrazolyl, oxazolyl, isoxazolyl, thiazolyl, triazolyl, tetrazolyl, oxadiazolyl, pyridyl, pyrazinyl, pyrimidinyl, pyridazinyl, thiazinyl, triazinyl, indolyl, quinolyl, isoquinolyl, isoindolyl, or benzimidazolyl;

wherein said heteroaryl moiety in the optionally substituted heteroaryl group represented by $R^4$ is pyrrolyl, furanyl, thienyl, imidazolyl, pyrazolyl, oxazolyl, isoxazolyl, thiazolyl, triazolyl, tetrazolyl, oxadiazolyl, pyridyl, pyrazinyl, pyrimidinyl, pyridazinyl, thiazinyl, triazinyl, indolyl, quinolyl, isoquinolyl, isoindolyl, or benzimidazolyl;

said aliphatic heterocyclic moiety in the optionally substituted aliphatic heterocyclic group represented by $R^4$ is azetidinyl, pyrrolidinyl, tetrahydrofuranyl, imidazolinyl, thiazolidinyl, isothiazolidinyl, piperidinyl, piperazinyl, morpholinyl, thiomorpholinyl, tetrahydropyranyl, homopiperazinyl, homomorpholinyl, 3-azabicyclo[3.1.0]hexyl, or octahydropyrrolo[3,4-c]pyrrolyl; and said heteroaryl moiety in the optionally substituted heteroaryl group in the substituent of the group represented by $R^4$ is pyrrolyl, furanyl, thienyl, imidazolyl, pyrazolyl, oxazolyl, isoxazolyl, thiazolyl, triazolyl, tetrazolyl, oxadiazolyl, pyridyl, pyrazinyl, pyrimidinyl, pyridazinyl, thiazinyl, triazinyl, indolyl, quinolyl, isoquinolyl, isoindolyl, or benzimidazolyl, or a pharmaceutically acceptable salt thereof.

In a still more preferable embodiment, the present invention includes the compound represented by the above general formula [I], wherein the substituent of the optionally substituted aryl group and the optionally substituted heteroaryl group represented by Ring A is 1 to 3 groups each independently selected from the group consisting of a halogen atom and an alkoxy group;

wherein said aryl moiety in the optionally substituted aryl group represented by Ring A is a 6 to 10 membered monocyclic or bicyclic aryl;

said heteroaryl moiety in the optionally substituted heteroaryl group represented by Ring A is a 5 to 10 membered monocyclic or bicyclic heteroaryl comprising 1 to 4 heteroatoms independently selected from the group consisting of a sulfur atom, an oxygen atom, and a nitrogen atom;

the substituent of the (1) optionally substituted alkyl group represented by $R^1$ is 1 to 3 groups independently selected from the group consisting of a halogen atom; a hydroxy group; a cyano group; an alkoxy group optionally substituted with an aryl group; an alkanoyl group; an aryl group optionally substituted with a group selected from the group consisting of an alkylsulfonyl group and an aminosulfonyl group; an optionally partially hydrogenated heteroaryl group optionally substituted with 1 to 2 groups independently selected from the group consisting of an oxo group and a hydroxy group; an aliphatic heterocyclic group optionally substituted with 1 to 2 oxo groups; an amino group optionally substituted with 1 to 2 groups independently selected from the group consisting of an alkyl group, a heteroaryl group, an alkoxycarbonyl group, an alkylsulfonyl group, and an aminosulfonyl group; a carbamoyl group optionally substituted with 1 to 2 alkyl groups; and a sulfonyl group optionally substituted with a group selected from the group consisting of an aliphatic heterocyclic group optionally substituted with a hydroxy group and an amino group optionally substituted with 1 to 2 alkyl groups;

the substituent of the (2) optionally substituted cycloalkyl group, (3) optionally substituted aryl group, (4) optionally substituted heteroaryl group, (5) optionally substituted aliphatic heterocyclic group, and (6) optionally substituted alkanoyl group represented by $R^1$ is 1 to 3 groups each independently selected from the group consisting of a halogen atom; a hydroxy group; a cyano group; an alkyl group optionally substituted with 1 to 2 groups independently selected from the group consisting of a halogen atom, a hydroxy group, and a cyano group; an alkoxy group optionally substituted with an aryl group; an alkanoyl group; an aryl group optionally substituted with a group selected from the group consisting of an alkylsulfonyl group and an aminosulfonyl group; an optionally partially hydrogenated heteroaryl group optionally substituted with 1 to 2 groups independently selected from the group consisting of a hydroxy group and an oxo group; an aliphatic heterocyclic group optionally substituted with 1 to 2 oxo groups; an amino group optionally substituted with 1 to 2 groups independently selected from the group consisting of an alkyl group, a heteroaryl group, an alkoxycarbonyl group, an alkylsulfonyl group, and an aminosulfonyl group; a carbamoyl group optionally substituted with 1 to 2 alkyl groups; and a sulfonyl group optionally substituted with a group selected from the group consisting of an aliphatic heterocyclic group optionally substituted with a hydroxy group and an amino group optionally substituted with 1 to 2 alkyl groups, wherein said aryl moiety in the optionally substituted aryl group represented by $R^1$ is a 6 to 10 membered monocyclic or bicyclic aryl;

said heteroaryl moiety in the optionally substituted heteroaryl group represented by $R^1$ is a 5 to 10 membered monocyclic or bicyclic heteroaryl comprising 1 to 4 heteroatoms independently selected from the group consisting of a sulfur atom, an oxygen atom, and a nitrogen atom;

said aliphatic heterocyclic moiety in the optionally substituted aliphatic heterocyclic group represented by $R^1$ is a 4 to 8 membered monocyclic aliphatic heterocyclic group comprising 1 to 2 heteroatoms independently selected from the group consisting of a sulfur atom, an oxygen atom, and a nitrogen atom;

said aryl moiety in the optionally substituted aryl group in the substituent of the group represented by $R^1$ is a 6 to 10 membered monocyclic or bicyclic aryl;

said heteroaryl moiety in the optionally partially hydrogenated and optionally substituted heteroaryl group in the substituent of the group represented by $R^1$ is a 5 to 10 membered monocyclic or bicyclic heteroaryl comprising 1 to 4 heteroatoms independently selected from the group consisting of a sulfur atom, an oxygen atom, and a nitrogen atom;

said aliphatic heterocyclic moiety in the optionally substituted aliphatic heterocyclic group in the substituent of the group represented by $R^1$ is a 4 to 8 membered monocyclic aliphatic heterocyclic group comprising 1 to 2 heteroatoms independently selected from the group consisting of a sulfur atom, an oxygen atom, and a nitrogen atom;

$R^2$ represents a hydrogen atom, a halogen atom, an alkyl group, a haloalkyl group, or an alkoxy group;

$R^3$ represents a group of the above formula [II];

Ring B represents an aryl group, a cycloalkyl group, or a heteroaryl group, wherein said aryl moiety in the aryl group represented by Ring B is a 6 to 10 membered monocyclic or bicyclic aryl;

said heteroaryl moiety in the heteroaryl group represented by Ring B is a 5 to 10 membered monocyclic or bicyclic heteroaryl comprising 1 to 4 heteroatoms independently selected from the group consisting of a sulfur atom, an oxygen atom, and a nitrogen atom;

$R^4$ represents a group selected from the group consisting of an alkyl group optionally substituted with a carboxyl group; a cycloalkyl group optionally substituted with a carboxyl group; a heteroaryl group optionally substituted with a carboxyl group; an aliphatic heterocyclic group optionally substituted with a carboxyl group; and an amino group optionally substituted with 1 to 2 groups independently selected from the group consisting of an alkyl group optionally substituted with a carboxyl group;

wherein said heteroaryl moiety in the optionally substituted heteroaryl group represented by $R^4$ is a 5 to 10 membered monocyclic or bicyclic heteroaryl comprising 1 to 4 heteroatoms independently selected from the group consisting of a sulfur atom, an oxygen atom, and a nitrogen atom;

said aliphatic heterocyclic moiety in the optionally substituted aliphatic heterocyclic group represented by $R^4$ is a 4 to 8 membered monocyclic aliphatic heterocyclic comprising 1 to 2 heteroatoms independently selected from the group consisting of a sulfur atom, an oxygen atom, and a nitrogen atom; and $R^5$ and $R^6$ represent each a group independently selected from the group consisting of a hydrogen atom, a halogen atom, an alkyl group, a haloalkyl group, and a cycloalkyl group, or a pharmaceutically acceptable salt thereof.

In a still more preferable embodiment, the present invention includes the compound in the above embodiment, wherein said aryl moiety in the optionally substituted aryl group represented by Ring A is phenyl or naphthyl;

said heteroaryl moiety in the optionally substituted heteroaryl group represented by Ring A is pyrrolyl, furanyl, thienyl, imidazolyl, pyrazolyl, oxazolyl, isoxazolyl, thiazolyl, triazolyl, tetrazolyl, oxadiazolyl, pyridyl, pyrazinyl, pyrimidinyl, pyridazinyl, thiazinyl, triazinyl, indolyl, quinolyl, isoquinolyl, isoindolyl, or benzimidazolyl;

said aryl moiety in the optionally substituted aryl group represented by $R^1$ is phenyl or naphthyl;

said heteroaryl moiety in the optionally substituted heteroaryl group represented by $R^1$ is pyrrolyl, furanyl, thienyl, imidazolyl, pyrazolyl, oxazolyl, isoxazolyl, thiazolyl, triazolyl, tetrazolyl, oxadiazolyl, pyridyl, pyrazinyl, pyrimidinyl, pyridazinyl, thiazinyl, triazinyl, indolyl, quinolyl, isoquinolyl, isoindolyl, or benzimidazolyl;

said aliphatic heterocyclic moiety in the optionally substituted aliphatic heterocyclic group represented by $R^1$ is azetidinyl, pyrrolidinyl, tetrahydrofuranyl, imidazolinyl, thiazolidinyl, isothiazolidinyl, piperidinyl, piperazinyl, morpholinyl, thiomorpholinyl, tetrahydropyranyl, homopiperazinyl, homomorpholinyl, 3-azabicyclo[3.1.0]hexyl, or octahydropyrrolo[3,4-c]pyrrolyl;

said aryl moiety in the optionally substituted aryl group in the substituent of the group represented by $R^1$ is phenyl or naphthyl;

said heteroaryl moiety in the optionally partially hydrogenated and optionally substituted heteroaryl group in the substituent of the group represented by $R^1$ is pyrrolyl, furanyl, thienyl, imidazolyl, pyrazolyl, oxazolyl, isoxazolyl, thiazolyl, triazolyl, tetrazolyl, oxadiazolyl, pyridyl, pyrazinyl, pyrimidinyl, pyridazinyl, thiazinyl, triazinyl, indolyl, quinolyl, isoquinolyl, isoindolyl, or benzimidazolyl;

said aliphatic heterocyclic moiety in the optionally substituted aliphatic heterocyclic group in the substituent of the group represented by $R^1$ is azetidinyl, pyrrolidinyl, tetrahydrofuranyl, imidazolinyl, thiazolidinyl, isothiazolidinyl, piperidinyl, piperazinyl, morpholinyl, thiomorpholinyl, tetrahydropyranyl, homopiperazinyl, homomorpholinyl, 3-azabicyclo[3.1.0]hexyl, or octahydropyrrolo[3,4-c]pyrrolyl;

the aryl group represented by Ring B is phenyl or naphthyl;

the heteroaryl group represented by Ring B is pyrrolyl, furanyl, thienyl, imidazolyl, pyrazolyl, oxazolyl, isoxazolyl, thiazolyl, triazolyl, tetrazolyl, oxadiazolyl, pyridyl, pyrazinyl, pyrimidinyl, pyridazinyl, thiazinyl, triazinyl, indolyl, quinolyl, isoquinolyl, isoindolyl, or benzimidazolyl;

said heteroaryl moiety in the optionally substituted heteroaryl group represented by $R^4$ is pyrrolyl, furanyl, thienyl, imidazolyl, pyrazolyl, oxazolyl, isoxazolyl, thiazolyl, triazolyl, tetrazolyl, oxadiazolyl, pyridyl, pyrazinyl, pyrimidinyl, pyridazinyl, thiazinyl, triazinyl, indolyl, quinolyl, isoquinolyl, isoindolyl, or benzimidazolyl; and said aliphatic heterocyclic moiety in the optionally substituted aliphatic heterocyclic group represented by $R^4$ is azetidinyl, pyrrolidinyl, tetrahydrofuranyl, imidazolinyl, thiazolidinyl, isothiazolidinyl, piperidinyl, piperazinyl, morpholinyl, thiomorpholinyl, tetrahydropyranyl, homopiperazinyl, homomorpholinyl, 3-azabicyclo[3.1.0]hexyl, or octahydropyrrolo[3,4-c]pyrrolyl, or a pharmaceutically acceptable salt thereof.

In a still more preferable embodiment, the present invention includes the compound represented by the above general formula [I], wherein $R^4$ represents an aliphatic heterocyclic group substituted with a carboxyl group, wherein said aliphatic heterocyclic moiety is selected from azetidinyl, pyrrolidinyl, tetrahydrofuranyl, imidazolinyl, thiazolidinyl, isothiazolidinyl, piperidinyl, piperazinyl, morpholinyl, thiomorpholinyl, tetrahydropyranyl, homopiperazinyl, homomorpholinyl, 3-azabicyclo[3.1.0]hexyl, or octahydropyrrolo[3,4-c]pyrrolyl, or a pharmaceutically acceptable salt thereof.

In another preferable embodiment, the present invention includes the compound represented by the above general formula [I], wherein Ring A represents (1) a 6 membered monocyclic aryl group optionally substituted with 1 to 2 groups independently selected from the group consisting of a halogen atom and an alkoxy group, or (2) a 5 to 6 membered monocyclic heteroaryl group optionally substituted with 1 to 2 groups independently selected from the group consisting of a halogen atom, wherein said heteroaryl moiety comprises one nitrogen atom and further optionally comprises 1 to 3 heteroatoms independently selected from the group consisting of a sulfur atom, an oxygen atom, and a nitrogen atom;

$R^1$ represents (1) an alkyl group optionally substituted with 1 to 2 groups independently selected from the group consisting of a halogen atom; a hydroxy group; a cyano group; an alkoxy group optionally substituted with a 6 membered monocyclic aryl group; a 6 membered monocyclic aryl group optionally substituted with a group selected from the group consisting of an alkylsulfonyl group and an aminosulfonyl group; a 5 to 6 membered monocyclic heteroaryl group optionally substituted with 1 to 2 groups independently selected from the group consisting of an oxo group and a hydroxy group, wherein said heteroaryl moiety comprises one nitrogen atom and further optionally comprises 1 to 3 heteroatoms independently selected from the group consisting of a sulfur atom, an oxygen atom, and a nitrogen atom; an optionally partially hydrogenated 10 membered bicyclic heteroaryl group comprising one nitrogen atom and further optionally comprising 1 to 3 heteroatoms independently selected from the group consisting of a sulfur atom, an oxygen atom, and a nitrogen atom; a 4 to 7 membered monocyclic aliphatic heterocyclic group optionally substituted with 1 to 2 oxo groups, wherein said aliphatic heterocyclic moiety comprises one nitrogen atom and further optionally comprises one heteroatom independently selected from the group consisting of a sulfur atom, an oxygen atom, and a nitrogen atom; an amino group optionally substituted with 1 to 2 groups independently selected from the group consisting of an alkyl group, a 5 to 6 membered monocyclic heteroaryl group comprising one nitrogen atom and further optionally comprising 1 to 3 heteroatoms independently selected from the group consisting of a sulfur atom, an oxygen atom, and a nitrogen atom, an alkoxycarbonyl group, an alkylsulfonyl group, and an aminosulfonyl group; a carbamoyl group optionally substituted with 1 to 2 alkyl groups; and a sulfonyl group optionally substituted with a group selected from the group consisting of a 4 to 7 membered monocyclic aliphatic heterocyclic group optionally substituted with a hydroxy group comprising one nitrogen atom and further optionally comprising one heteroatom independently selected from the group consisting of a sulfur atom, an oxygen atom, and a nitrogen atom, and an amino group optionally substituted with 1 to 2 alkyl groups, (2) a cycloalkyl group, (3) a 5 to 6 membered monocyclic heteroaryl group comprising one nitrogen atom and further optionally comprising 1 to 3 heteroatoms independently selected from the group consisting of a sulfur atom, an oxygen atom, and a nitrogen atom optionally substituted with an alkyl group, (4) a 4 to 7 membered monocyclic aliphatic heterocyclic group comprising one nitrogen atom and further optionally comprising one heteroatom independently selected from the group consisting of a sulfur atom, an oxygen atom, and a nitrogen atom optionally substituted with 1 to 2 groups independently selected from the group consisting of an alkyl group optionally substituted with 1 to 2 groups independently selected from the group consisting of a halogen atom, a hydroxy group, and a cyano group, and an alkanoyl group, or (5) an alkanoyl group optionally substituted with an optionally partially hydrogenated 10 membered bicyclic heteroaryl group comprising one nitrogen atom and further optionally comprising 1 to 3 heteroatoms independently selected from the group consisting of a sulfur atom, an oxygen atom, and a nitrogen atom;

$R^2$ represents a hydrogen atom, a halogen atom, an alkyl group, a haloalkyl group, or an alkoxy group;

$R^3$ represents a group of the above formula [II];

Ring B represents a 6 membered monocyclic aryl group, a cycloalkyl group, or a 5 to 6 membered monocyclic heteroaryl group comprising one nitrogen atom and further optionally comprising 1 to 3 heteroatoms independently selected from the group consisting of a sulfur atom, an oxygen atom, and a nitrogen atom;

$R^4$ represents (1) an alkyl group, (2) a cycloalkyl group optionally substituted with a carboxyl group, (3) a 5 to 6 membered monocyclic heteroaryl group optionally substituted with a 5 to 6 membered monocyclic heteroaryl group comprising one nitrogen atom and further optionally comprising 1 to 3 heteroatoms independently selected from the group consisting of a sulfur atom, an oxygen atom, and a nitrogen atom optionally substituted with an oxo group, wherein said heteroaryl moiety comprises one nitrogen atom and further optionally comprises 1 to 3 heteroatoms independently selected from the group consisting of a sulfur atom, an oxygen atom, and a nitrogen atom;

(4) a 4 to 7 membered monocyclic aliphatic heterocyclic group optionally substituted with 1 to 2 groups independently selected from the group consisting of a hydroxy group; a halogen atom; an oxo group; a cyano group; an alkyl group; a 5 to 6 membered monocyclic heteroaryl group comprising one nitrogen atom and further optionally comprising 1 to 3 heteroatoms independently selected from the group consisting of a sulfur atom, an oxygen atom, and a nitrogen atom optionally substituted with a group selected from the group consisting of a hydroxy group and an oxo group; a carboxyl group; an alkoxycarbonyl group; a carbamoyl group optionally substituted with 1 to 2 alkyl groups; an alkylsulfonyl group; an alkylsulfonylamino group; an alkylsulfonylaminocarbonyl group; and an aminosulfonylaminocarbonyl group optionally substituted with 1 to 2 alkyl groups, wherein said aliphatic heterocyclic moiety comprises one nitrogen atom and further optionally comprising one heteroatom independently selected from the group consisting of a sulfur atom, an oxygen atom, and a nitrogen atom; or (5) an amino group optionally substituted with 1 to 2 groups independently selected from the group consisting of an alkyl group optionally substituted with a carboxyl group; and $R^5$ and $R^6$ are each a group independently selected from the group consisting of a hydrogen atom, a halogen atom, an alkyl group, a haloalkyl group, and a cycloalkyl group, or a pharmaceutically acceptable salt thereof.

In a more preferable embodiment, the present invention includes the compound represented by the above general formula [I], wherein Ring A represents (1) a phenyl group optionally substituted with 1 to 2 groups independently selected from the group consisting of a halogen atom and an alkoxy group, or (2) a heteroaryl group optionally substituted with 1 to 2 groups independently selected from the group consisting of a halogen atom, wherein said heteroaryl moiety is selected from the group consisting of pyrrolyl, imidazolyl, pyrazolyl, oxazolyl, isoxazolyl, thiazolyl, triazolyl, tetrazolyl, oxadiazolyl, pyridyl, pyrazinyl, pyrimidinyl, pyridazinyl, thiazinyl, and triazinyl;

$R^1$ represents (1) an alkyl group optionally substituted with 1 to 2 groups independently selected from the group consisting of a halogen atom; a hydroxy group; a cyano group; an alkoxy group optionally substituted with a phenyl group; a phenyl group optionally substituted with a group selected from the group consisting of an alkylsulfonyl group and an aminosulfonyl group; a heteroaryl group optionally substituted with 1 to 2 groups independently selected from the group consisting of an oxo group and a hydroxy group, wherein said heteroaryl moiety is selected from the group consisting of pyrrolyl, imidazolyl, pyrazolyl, oxazolyl, isoxazolyl, thiazolyl, triazolyl, tetrazolyl, oxadiazolyl, pyridyl, pyrazinyl, pyrimidinyl, pyridazinyl, thiazinyl, and triazinyl; an optionally partially hydrogenated heteroaryl group, wherein said heteroaryl moiety is quinolyl or isoquinolyl; an aliphatic heterocyclic group optionally substituted with 1 to 2 oxo groups, wherein said aliphatic heterocyclic moiety is selected from the group consisting of azetidinyl, pyrrolidinyl, imidazolinyl, thiazolidinyl, isothiazolidinyl, piperidinyl, piperazinyl, morpholinyl, thiomorpholinyl, homopiperazinyl, and homomorpholinyl; an amino group optionally substituted with 1 to 2 groups independently selected from the group consisting of an alkyl group, a heteroaryl group, an alkoxycarbonyl group, an alkylsulfonyl group, and an aminosulfonyl group, wherein said heteroaryl moiety in the heteroaryl group in the substituent is a group selected from the group consisting of pyrrolyl, imidazolyl, pyrazolyl, oxazolyl, isoxazolyl, thiazolyl, triazolyl, tetrazolyl, oxadiazolyl, pyridyl, pyrazinyl, pyrimidinyl, pyridazinyl, thiazinyl, and triazinyl; a carbamoyl group optionally substituted with 1 to 2 alkyl groups; and a sulfonyl group optionally substituted with a group selected from the group consisting of an aliphatic heterocyclic group optionally substituted with a hydroxy group and an amino group optionally substituted with 1 to 2 alkyl groups, wherein said aliphatic heterocyclic moiety in the aliphatic heterocyclic group in the substituent is a group selected from the group consisting of azetidinyl, pyrrolidinyl, imidazolinyl, thiazolidinyl, isothiazolidinyl, piperidinyl, piperazinyl, morpholinyl, thiomorpholinyl, homopiperazinyl, and homomorpholinyl, (2) a cycloalkyl group, (3) a heteroaryl group optionally substituted with an alkyl group, wherein said heteroaryl moiety is selected from the group consisting of pyrrolyl, imidazolyl, pyrazolyl, oxazolyl, isoxazolyl, thiazolyl, triazolyl, tetrazolyl, oxadiazolyl, pyridyl, pyrazinyl, pyrimidinyl, pyridazinyl, thiazinyl, and triazinyl, (4) an aliphatic heterocyclic group optionally substituted with 1 to 2 groups independently selected from the group consisting of an alkyl group optionally substituted with 1 to 2 groups independently selected from the group consisting of a halogen atom, a hydroxy group, and a cyano group, and an alkanoyl group, wherein said aliphatic heterocyclic moiety is selected from the group consisting of azetidinyl, pyrrolidinyl, imidazolinyl, thiazolidinyl, isothiazolidinyl, piperidinyl, piperazinyl, morpholinyl, thiomorpholinyl, homopiperazinyl, and homomorpholinyl, or (5) an alkanoyl group optionally substituted with an optionally partially hydrogenated heteroaryl group, wherein said heteroaryl moiety in the heteroaryl group in the substituent is a group of quinolyl or isoquinolyl;

$R^2$ represents a hydrogen atom, a halogen atom, an alkyl group, a haloalkyl group, or an alkoxy group;

$R^3$ represents a group of the above formula [II];

Ring B represents a phenyl group, a cycloalkyl group, or a heteroaryl group, wherein said heteroaryl moiety is selected from the group consisting of pyrrolyl, imidazolyl, pyrazolyl, oxazolyl, isoxazolyl, thiazolyl, triazolyl, tetrazolyl, oxadiazolyl, pyridyl, pyrazinyl, pyrimidinyl, pyridazinyl, thiazinyl, and triazinyl;

$R^4$ represents (1) an alkyl group, (2) a cycloalkyl group optionally substituted with a carboxyl group, (3) a heteroaryl group optionally substituted with a heteroaryl group optionally substituted with an oxo group, wherein said heteroaryl moiety is selected from the group consisting of pyrrolyl, imidazolyl, pyrazolyl, oxazolyl, isoxazolyl, thiazolyl, triazolyl, tetrazolyl, oxadiazolyl, pyridyl, pyrazinyl, pyrimidinyl, pyridazinyl, thiazinyl, and triazinyl, and wherein said heteroaryl moiety in the heteroaryl group in the substituent is a group selected from the group consisting of pyrrolyl, imidazolyl, pyrazolyl, oxazolyl, isoxazolyl, thiazolyl, triazolyl, tetrazolyl, oxadiazolyl, pyridyl, pyrazinyl, pyrimidinyl, pyridazinyl, thiazinyl, and triazinyl, (4) an aliphatic heterocyclic group optionally substituted with 1 to 2 groups independently selected from the group consisting of a hydroxy group; a halogen atom; an oxo group; a cyano group; an alkyl group; a heteroaryl group optionally substituted with a group selected from the group consisting of a hydroxy group and an oxo group, wherein said heteroaryl moiety is selected from the group consisting of pyrrolyl, imidazolyl, pyrazolyl, oxazolyl, isoxazolyl, thiazolyl, triazolyl, tetrazolyl, oxadiazolyl, pyridyl, pyrazinyl, pyrimidinyl, pyridazinyl, thiazinyl, and triazinyl; a carboxyl group; an alkoxycarbonyl group; a carbamoyl group optionally substituted with 1 to 2 alkyl groups; an alkylsulfonyl group; an alkylsulfonylamino group; an alkylsulfonylaminocarbonyl group; and an aminosulfonylaminocarbonyl group optionally substituted with 1 to 2 alkyl groups, wherein said aliphatic heterocyclic moiety is selected from the group consisting of azetidinyl, pyrrolidinyl, imidazolinyl, thiazolidinyl, isothiazolidinyl, piperidinyl, piperazinyl, morpholinyl, thiomorpholinyl, homopiperazinyl, and homomorpholinyl; or (5) an amino group optionally substituted with 1 to 2 groups independently selected from the group consisting of an alkyl group optionally substituted with a carboxyl group; and $R^5$ and $R^6$ are each a group independently selected from the group consisting of a hydrogen atom, a halogen atom, an alkyl group, a haloalkyl group, and a cycloalkyl group, or a pharmaceutically acceptable salt thereof.

In a more preferable embodiment, the present invention includes the compound in the above embodiment, wherein Ring A represents
(1) a 6 membered monocyclic aryl group optionally substituted with 1 to 2 groups independently selected from the group consisting of a halogen atom and an alkoxy group, or
(2) a 5 to 6 membered monocyclic heteroaryl group comprising one nitrogen atom optionally substituted with 1 to 2 groups independently selected from the group consisting of a halogen atom;

$R^1$ represents
(1) an alkyl group optionally substituted with 1 to 2 groups independently selected from the group consisting of a halogen atom; a hydroxy group; a cyano group; an alkoxy group optionally substituted with a 6 membered monocyclic aryl group; a 6 membered monocyclic aryl group optionally substituted with a group selected from the group consisting of an alkylsulfonyl group and an aminosulfonyl group; a 5 to 6 membered monocyclic heteroaryl group optionally substituted with 1 to 2 groups independently selected from the group consisting of an oxo group and a hydroxy group, wherein said heteroaryl moiety comprises one nitrogen atom and further optionally comprises 1 to 2 heteroatoms independently selected from the group consisting of a sulfur atom, an oxygen atom, and a nitrogen atom; an optionally partially hydrogenated 10 membered bicyclic heteroaryl group comprising one nitrogen atom; a 4 to 7 membered monocyclic aliphatic heterocyclic group optionally substituted with 1 to 2 oxo groups, wherein said aliphatic heterocyclic moiety comprises one nitrogen atom and further optionally comprises one heteroatom independently selected from the group consisting of a sulfur atom, an oxygen atom, and a nitrogen atom; an amino group optionally substituted with 1 to 2 groups independently selected from the group consisting of an alkyl group, a 5 to 6 membered monocyclic heteroaryl group comprising one nitrogen atom, an alkoxycarbonyl group, an alkylsulfonyl group, and an aminosulfonyl group; a carbamoyl group optionally substituted with 1 to 2 alkyl groups; and a sulfonyl group optionally substituted with a group selected from the group consisting of a 4 to 7 membered monocyclic aliphatic heterocyclic group comprising one nitrogen atom optionally substituted with a hydroxy group, and an amino group optionally substituted with 1 to 2 alkyl groups,
(2) a cycloalkyl group,
(3) a 5 to 6 membered monocyclic heteroaryl group comprising one nitrogen atom optionally substituted with an alkyl group,
(4) a 4 to 7 membered monocyclic aliphatic heterocyclic group comprising one nitrogen atom optionally substituted with 1 to 2 groups independently selected from the group consisting of an alkyl group optionally substituted with 1 to 2 groups independently selected from the group consisting of a halogen atom, a hydroxy group, and a cyano group, and an alkanoyl group, or (5) an alkanoyl group optionally substituted with an optionally partially hydrogenated 10 membered bicyclic heteroaryl group comprising one nitrogen atom;

$R^2$ represents a hydrogen atom, a halogen atom, an alkyl group, a haloalkyl group, or an alkoxy group;

$R^3$ represents a group of the above formula [II];

Ring B represents a 6 membered monocyclic aryl group, a cycloalkyl group, or a 5 to 6 membered monocyclic heteroaryl group comprising one nitrogen atom;

$R^4$ represents
(1) an alkyl group,
(2) a cycloalkyl group optionally substituted with a carboxyl group,
(3) a 5 to 6 membered monocyclic heteroaryl group comprising one nitrogen atom optionally substituted with a 5 to 6 membered monocyclic heteroaryl group comprising one nitrogen atom and further optionally comprising 1 to 2 heteroatoms independently selected from the group consisting of a sulfur atom, an oxygen atom, and a nitrogen atom optionally substituted with an oxo group;
(4) a 4 to 7 membered monocyclic aliphatic heterocyclic group optionally substituted with 1 to 2 groups independently selected from the group consisting of a hydroxy group; a halogen atom; an oxo group; a cyano group; an alkyl group; a 5 to 6 membered monocyclic heteroaryl group comprising one nitrogen atom and further optionally comprising 1 to 3 heteroatoms independently selected from the group consisting of a sulfur atom, an oxygen atom, and a nitrogen atom optionally substituted with a group selected from the group consisting of a hydroxy group and an oxo group; a carboxyl group; an alkoxycarbonyl group; a carbamoyl group optionally substituted with 1 to 2 alkyl groups; an alkylsulfonyl group; an alkylsulfonylamino group; an alkylsulfonylaminocarbonyl group; and an aminosulfonylaminocarbonyl group optionally substituted with 1 to 2 alkyl groups, wherein said aliphatic heterocyclic moiety comprises one nitrogen atom and further optionally comprises one heteroatom independently selected from the group consisting of a sulfur atom, an oxygen atom, and a nitrogen atom; or
(5) an amino group optionally substituted with 1 to 2 groups independently selected from the group consisting of an alkyl group optionally substituted with a carboxyl group; and $R^5$ and $R^6$ are each a group independently selected from the group consisting of a hydrogen atom, a halogen atom, an alkyl group, a haloalkyl group, and a cycloalkyl group, or a pharmaceutically acceptable salt thereof.

In a more preferable embodiment, the present invention includes the compound in the above embodiment, wherein Ring A represents
(1) a phenyl group optionally substituted with 1 to 2 groups independently selected from the group consisting of a halogen atom and an alkoxy group, or
(2) a heteroaryl group optionally substituted with 1 to 2 groups independently selected from the group consisting of a halogen atom, wherein said heteroaryl moiety is selected from the group consisting of pyrrolyl and pyridyl;

$R^1$ represents
(1) an alkyl group optionally substituted with 1 to 2 groups independently selected from the group consisting of a halogen atom; a hydroxy group; a cyano group; an alkoxy group optionally substituted with a phenyl group; a phenyl group optionally substituted with a group selected from the group consisting of an alkylsulfonyl group and an aminosulfonyl group; a heteroaryl group optionally substituted with 1 to 2 groups independently selected from the group consisting of an oxo group and a hydroxy group, wherein said heteroaryl moiety is selected from the group consisting of pyrrolyl, imidazolyl, pyrazolyl, oxazolyl, isoxazolyl, thiazolyl, triazolyl, oxadiazolyl, pyridyl, pyrazinyl, pyrimidinyl, pyridazinyl, thiazinyl, and triazinyl; an optionally partially hydrogenated heteroaryl group, wherein said heteroaryl moiety is quinolyl or isoquinolyl; an aliphatic heterocyclic group optionally substituted with 1 to 2 oxo groups, wherein said aliphatic heterocyclic moiety is selected from the group consisting of azetidinyl, pyrrolidinyl, imidazolinyl, thiazolidinyl, isothiazolidinyl, piperidinyl, piperazinyl, morpholinyl, thiomorpholinyl, homopiperazinyl, and homomorpholinyl; an amino group optionally substituted with 1 to 2 groups independently selected from the group consisting of an alkyl group, a heteroaryl group, an alkoxycarbonyl group, an alkylsulfonyl group, and an aminosulfonyl group, wherein said heteroaryl moiety in the heteroaryl group in the substituent is pyrrolyl or pyridyl; a carbamoyl group optionally substituted with 1 to 2 alkyl groups; and a sulfonyl group optionally substituted with a group selected from the group consisting of an aliphatic heterocyclic group optionally substituted with a hydroxy group and an amino group optionally substituted with 1 to 2 alkyl groups, wherein said aliphatic heterocyclic moiety in the aliphatic heterocyclic group in the substituent is selected from the group consisting of azetidinyl, pyrrolidinyl, and piperidinyl,
(2) a cycloalkyl group,
(3) a heteroaryl group optionally substituted with an alkyl group, wherein said heteroaryl moiety is pyrrolyl or pyridyl,
(4) an aliphatic heterocyclic group optionally substituted with 1 to 2 groups independently selected from the group consisting of an alkyl group optionally substituted with 1 to 2 groups independently selected from the group consisting of a halogen atom, a hydroxy group, and a cyano group, and an alkanoyl group, wherein said aliphatic heterocyclic moiety is selected from the group consisting of azetidinyl, pyrrolidinyl, and piperidinyl, or
(5) an alkanoyl group optionally substituted with an optionally partially hydrogenated heteroaryl group, wherein said heteroaryl moiety in the heteroaryl group in the substituent is quinolyl or isoquinolyl;
$R^2$ represents a hydrogen atom, a halogen atom, an alkyl group, a haloalkyl group, or an alkoxy group;
$R^3$ represents a group of the above formula [II];
Ring B represents a phenyl group, a cycloalkyl group, or a heteroaryl group, wherein said heteroaryl moiety is pyrrolyl or pyridyl;
$R^4$ represents
(1) an alkyl group,
(2) a cycloalkyl group optionally substituted with a carboxyl group,
(3) a heteroaryl group optionally substituted with a heteroaryl group optionally substituted with an oxo group, wherein said heteroaryl moiety is pyrrolyl or pyridyl, and said heteroaryl moiety in the heteroaryl group in the substituent is selected from the group consisting of pyrrolyl, imidazolyl, pyrazolyl, oxazolyl, isoxazolyl, thiazolyl, triazolyl, oxadiazolyl, pyridyl, pyrazinyl, pyrimidinyl, pyridazinyl, thiazinyl, and triazinyl,
(4) an aliphatic heterocyclic group optionally substituted with 1 to 2 groups independently selected from the group consisting of a hydroxy group; a halogen atom; an oxo group; a cyano group; an alkyl group; a heteroaryl group optionally substituted with a group selected from the group consisting of a hydroxy group and an oxo group, wherein said heteroaryl moiety is selected from the group consisting of pyrrolyl, imidazolyl, pyrazolyl, oxazolyl, isoxazolyl, thiazolyl, triazolyl, tetrazolyl, oxadiazolyl, pyridyl, pyrazinyl, pyrimidinyl, pyridazinyl, thiazinyl, and triazinyl; a carboxyl group; an alkoxycarbonyl group; a carbamoyl group optionally substituted with 1 to 2 alkyl groups; an alkylsulfonyl group; an alkylsulfonylamino group; an alkylsulfonylaminocarbonyl group; and an aminosulfonylaminocarbonyl group optionally substituted with 1 to 2 alkyl groups, wherein said aliphatic heterocyclic moiety is selected from the group consisting of azetidinyl, pyrrolidinyl, imidazolinyl, thiazolidinyl, isothiazolidinyl, piperidinyl, piperazinyl, morpholinyl, thiomorpholinyl, homopiperazinyl, and homomorpholinyl, or
(5) an amino group optionally substituted with 1 to 2 groups independently selected from the group consisting of an alkyl group optionally substituted with a carboxyl group; and
$R^5$ and $R^6$ are each a group independently selected from the group consisting of a hydrogen atom, a halogen atom, an alkyl group, a haloalkyl group, and a cycloalkyl group,
or a pharmaceutically acceptable salt thereof.

In another preferable embodiment, the present invention includes the compound represented by the above general formula [I], wherein
Ring A represents
(1) a phenyl group optionally substituted with 1 to 2 groups independently selected from the group consisting of a halogen atom and an alkoxy group, or
(2) a pyridyl group optionally substituted with 1 to 2 groups independently selected from the group consisting of a halogen atom;
$R^1$ represents
(1) an alkyl group optionally substituted with 1 to 2 groups independently selected from the group consisting of a halogen atom; a hydroxy group; a cyano group; an alkoxy group optionally substituted with a phenyl group; a phenyl group optionally substituted with a group selected from the group consisting of an alkylsulfonyl group and an aminosulfonyl group; a heteroaryl group optionally substituted with 1 to 2 groups independently selected from the group consisting of an oxo group and a hydroxy group, wherein said heteroaryl is selected from oxazolyl, oxadiazolyl, triazolyl, and pyridyl; a tetrahydroisoquinolyl group; an aliphatic heterocyclic group optionally substituted with 1 to 2 oxo groups, wherein said aliphatic heterocyclic moiety is selected from piperidinyl, morpholinyl, thiazolidinyl, and imidazolidinyl; an amino group optionally substituted with 1 to 2 groups independently selected from the group consisting of an alkyl group, a pyridyl group, an alkoxycarbonyl group, an alkylsulfonyl group, and an aminosulfonyl group; a carbamoyl group optionally substituted with 1 to 2 alkyl groups; and a sulfonyl group optionally substituted with a group selected from the group consisting of a pyrrolidinyl group optionally substituted with a hydroxy group and an amino group optionally substituted with 1 to 2 alkyl groups,
(2) a cycloalkyl group,
(3) a pyridyl group optionally substituted with an alkyl group,
(4) a piperidinyl group optionally substituted with 1 to 2 groups independently selected from the group consisting of an alkyl group optionally substituted with 1 to 2 groups independently selected from the group consisting of a halogen atom, a hydroxy group, and a cyano group, and an alkanoyl group, or
(5) an alkanoyl group optionally substituted with a tetrahydroisoquinolyl group;
$R^2$ represents a hydrogen atom, a halogen atom, an alkyl group, a haloalkyl group, or an alkoxy group;
$R^3$ represents a group of the above formula [II];

Ring B represents a phenyl group, a cycloalkyl group, or a pyridyl group, $R^4$ represents
(1) an alkyl group,
(2) a cycloalkyl group optionally substituted with a carboxyl group,
(3) a pyridyl group optionally substituted with an oxadiazolyl group optionally substituted with an oxo group,
(4) an aliphatic heterocyclic group optionally substituted with 1 to 2 groups independently selected from the group consisting of a hydroxy group; a halogen atom; an oxo group; a cyano group; an alkyl group; a heteroaryl group optionally substituted with a group selected from the group consisting of a hydroxy group and an oxo group, wherein said heteroaryl moiety is selected from oxazolyl, oxadiazolyl, and tetrazolyl; a carboxyl group; an alkoxycarbonyl group; a carbamoyl group optionally substituted with 1 to 2 alkyl groups; an alkylsulfonyl group; an alkylsulfonylamino group; an alkylsulfonylaminocarbonyl group; and an aminosulfonylaminocarbonyl group optionally substituted with 1 to 2 alkyl groups, wherein said aliphatic heterocyclic moiety is selected from piperidinyl, piperazinyl, morpholinyl, and thiomorpholinyl, or
(5) an amino group optionally substituted with 1 to 2 groups independently selected from the group consisting of an alkyl group optionally substituted with a carboxyl group; and $R^5$ and $R^6$ are each a group independently selected from the group consisting of a hydrogen atom, a halogen atom, an alkyl group, a haloalkyl group, and a cycloalkyl group, or a pharmaceutically acceptable salt thereof.

In another preferable embodiment, the present invention includes the compound represented by the above general formula [I], wherein Ring A represents
(1) a 6 membered monocyclic aryl group optionally substituted with 1 to 2 groups independently selected from the group consisting of a halogen atom and an alkoxy group;

$R^1$ represents
(1) an alkyl group optionally substituted with 1 to 2 groups independently selected from the group consisting of a sulfonyl group optionally substituted with an aliphatic heterocyclic group, and an alkoxy group, or
(2) a cycloalkyl group,
wherein said aliphatic heterocyclic moiety of the aliphatic heterocyclic group in the substituent of the group represented by $R^1$ is a 4 to 7 membered monocyclic aliphatic heterocyclic group comprising one nitrogen atom and further optionally comprising one heteroatom independently selected from the group consisting of a sulfur atom, an oxygen atom, and a nitrogen atom;

$R^2$ represents a halogen atom;
$R^3$ represents a group of the above formula [II];
Ring B represents a 6 membered monocyclic aryl group;
$R^4$ represents an aliphatic heterocyclic group optionally substituted with a carboxyl group,
wherein said aliphatic heterocyclic moiety is a 4 to 7 membered monocyclic aliphatic heterocyclic group comprising one nitrogen atom and further optionally comprising one heteroatom independently selected from the group consisting of a sulfur atom, an oxygen atom, and a nitrogen atom; and $R^5$ and $R^6$ represent each a group independently selected from the group consisting of a hydrogen atom, an alkyl group, and a haloalkyl group,
or a pharmaceutically acceptable salt thereof.

In a more preferable embodiment, the present invention includes the compound in the above embodiment, wherein Ring A represents
(1) a phenyl group optionally substituted with 1 to 2 groups independently selected from the group consisting of a halogen atom and an alkoxy group;

$R^1$ represents
(1) an alkyl group optionally substituted with 1 to 2 groups independently selected from the group consisting of a sulfonyl group optionally substituted with an aliphatic heterocyclic group, and an alkoxy group, or
(2) a cycloalkyl group,
wherein said aliphatic heterocyclic moiety of the aliphatic heterocyclic group in the substituent of the group represented by $R^1$ is a group selected from the group consisting of azetidinyl, pyrrolidinyl, imidazolinyl, thiazolidinyl, isothiazolidinyl, piperidinyl, piperazinyl, morpholinyl, thiomorpholinyl, homopiperazinyl, and homomorpholinyl;

$R^2$ represents a halogen atom;
$R^3$ represents a group of the above formula [II];
Ring B represents a phenyl group;
$R^4$ represents an aliphatic heterocyclic group optionally substituted with a carboxyl group,
wherein said aliphatic heterocyclic moiety is a group selected from the group consisting of azetidinyl, pyrrolidinyl, imidazolinyl, thiazolidinyl, isothiazolidinyl, piperidinyl, piperazinyl, morpholinyl, thiomorpholinyl, homopiperazinyl, and homomorpholinyl; and $R^5$ and $R^6$ represent each a group independently selected from the group consisting of a hydrogen atom, an alkyl group, and a haloalkyl group,
or a pharmaceutically acceptable salt thereof.

In another preferable embodiment, the present invention includes the compound represented by the above general formula [I], wherein Ring A represents
(1) a phenyl group optionally substituted with 1 to 2 groups independently selected from the group consisting of a halogen atom and an alkoxy group;

$R^1$ represents
(1) an alkyl group optionally substituted with a group selected from the group consisting of a sulfonyl group optionally substituted with a pyrrolidinyl group, and an alkoxy group, or
(2) a cycloalkyl group;

$R^2$ represents a halogen atom;
$R^3$ represents a group of the above formula [II];
Ring B represents a phenyl group;
$R^4$ represents a piperidinyl group optionally substituted with a carboxyl group; and $R^5$ and $R^6$ represent each a group independently selected from the group consisting of a hydrogen atom, an alkyl group, and a haloalkyl group,
or a pharmaceutically acceptable salt thereof.

In another preferable embodiment, the present invention includes a compound selected from the group consisting of
1-(2-{[2-({[(3R,4R)-4-(2,4-difluorophenyl)-3-fluoro-1-(4-methoxy-4-methylpentyl)pyrrolidin-3-yl]carbonyl}amino)-1H-imidazol-1-yl]methyl}-5-methylphenyl)piperidine-4-carboxylic acid (Example 13);
1-[2-{[2-({[(3R,4R)-4-(2,4-difluorophenyl)-3-fluoro--(pentan-3-yl)pyrrolidin-3-yl]carbonyl}amino)-1H-imidazol-yl]methyl}-5-(trifluoromethyl)phenyl]piperidine-4-carboxylic acid (Example 14);
1-[2-{[2-({[(3R,4R)-1-cyclopentyl-4-(2,4-difluorophenyl)-3-fluoropyrrolidin-3-yl]carbonyl}amino)-1H-imidazol-1-yl]methyl}-5-(trifluoromethyl)phenyl]piperidin-4-carboxylic acid (Example 16);

1-[2-{[2-({[(3R,4R)-4-(2,4-difluorophenyl)-3-fluoro-1-(4-methoxy-4-methylpentyl)pyrrolidin-3-yl]carbonyl}amino)-1H-imidazol-1-yl]methyl}-5-(trifluoromethyl)phenyl]piperidine-4-carboxylic acid (Example 19);

1-[2-({2-[({(3R,4R)-4-(2,4-difluorophenyl)-3-fluoro-1-[3-(pyrrolidin-1-ylsulfonyl)propyl]pyrrolidin-3-yl}carbonyl)amino]-1H-imidazol-1-yl}methyl)-5-(trifluoromethyl)phenyl]piperidine-4-carboxylic acid (Example 26);

1-[2-{[2-({[(3R,4R)-1-tert-butyl-4-(2,4-difluorophenyl)-3-fluoropyrrolidin-3-yl]carbonyl}amino)-1H-imidazol-1-yl]methyl}-5-(trifluoromethyl)phenyl]piperidin-4-carboxylic acid (Example 36);

1-[2-{[2-({[(3R,4R)-1-tert-butyl-3-fluoro-4-(4-fluorophenyl)pyrrolidin-3-yl]carbonyl}amino)-1H-imidazol-1-yl]methyl}-5-(trifluoromethyl)phenyl]piperidine-4-carboxylic acid (Example 43);

1-[2-{[2-({[(3R,4R)-1-tert-butyl-3-fluoro-4-(4-fluorophenyl)pyrrolidin-3-yl]carbonyl}amino)-1H-imidazol-1-yl]methyl}-5-(propan-2-yl)phenyl]piperidine-4-carboxylic acid (Example 49);

1-[2-{[2-({[(3R,4R)-1-tert-butyl-3-fluoro-4-(4-methoxyphenyl)pyrrolidin-3-yl]carbonyl}amino)-1H-imidazol-1-yl]methyl}-5-(trifluoromethyl)phenyl]piperidine-4-carboxylic acid (Example 52); and 1-[2-{[2-({[(3R,4R)-1-tert-butyl-3-fluoro-4-(4-methoxyphenyl)pyrrolidin-3-yl]carbonyl}amino)-1H-imidazol-1-yl]methyl}-5-(propan-2-yl)phenyl]piperidine-4-carboxylic acid (Example 54)

or a pharmaceutically acceptable salt thereof.

When the compound [I] of the present invention has an asymmetric carbon atom in the molecule, it may exist as more than one stereoisomers (i.e., diastereomers or optical isomers) on the basis of said asymmetric carbon atom. The present invention includes both any one of these stereoisomers and a mixture thereof. To indicate that the compound [I] of the present invention is a mixture of more than one stereoisomers, the bond causing a stereoisomer may be represented by the following wavy line.

Also, the compound [I] of the present invention may include cis- and trans-isomer as geometric isomers, and may further include isomers on the basis of axial chirality when it has axial chirality in the molecule. The present invention includes both any one of these isomers and a mixture thereof.

The compound [I] of the present invention includes compounds labeled with an isotope (for example, $^2$H, $^3$H, $^{13}$C, $^{14}$C, $^{15}$N, $^{18}$F, $^{32}$P, $^{35}$S, or $^{125}$I) or the like, and deuterated products.

The compound [I] of the present invention or a pharmaceutically acceptable salt thereof has an especially excellent MC1R agonistic activity. The target compound of the present invention and a pharmaceutical composition comprising the same as an active ingredient are useful for treating or preventing various autoimmune diseases, inflammation-related diseases, and fibrosis-related diseases of which a pathological condition are expected to be improved by an MC1R agonistic activity, or useful for improving the prognosis of these diseases. Examples of these diseases include rheumatoid arthritis, gouty arthritis, osteoarthritis, inflammatory bowel disease, systemic sclerosis, psoriasis, fibrosis, protoporphyria (for example, erythropoietic protoporphyria), systemic lupus erythematosus, melanoma, skin cancer, vitiligo, alopecia, poliosis, pain, ischemia/reperfusion injury, cerebral inflammatory disease, hepatitis, sepsis/septic shock, nephritis, transplantation, HIV disease exacerbation, vasculitis, uveitis, retinitis pigmentosa, age-related macular degeneration, microbial infection, celiac disease, nephrotic syndrome, and melanoma invasion.

Specifically, the target compound of the present invention and a pharmaceutical composition comprising the same as an active ingredient are useful for treating or preventing systemic sclerosis, psoriasis, protoporphyria, melanoma, skin cancer, vitiligo, alopecia, poliosis, retinitis pigmentosa, age-related macular degeneration, nephrotic syndrome, or the like, or useful for improving the prognosis of these diseases. Especially specifically, the target compound of the present invention and a pharmaceutical composition comprising the same as an active ingredient are useful for treating or preventing systemic sclerosis, protoporphyria, melanoma, vitiligo, retinitis pigmentosa, age-related macular degeneration, nephrotic syndrome, or the like, or useful for improving the prognosis of these diseases.

As described above, the compound [I] of the present invention or a pharmaceutically acceptable salt thereof has an excellent agonistic activity against MC1R, and each compound described in the Examples of the present description was assayed according to the assay method in Experimental Example 1 described below to study the agonistic activity against human MC1R, and as a result, showed an $EC_{50}$ value of 100 nM or less. Also, the compound [I] of the present invention or a pharmaceutically acceptable salt thereof showed drug efficacy in a LPS-induced rat blood TNF-α production model (according to the method described in Cytokine, 2010; 49: p. 319-324). Further, the compound [I] of the present invention includes compounds having high selectivity for MC1R. For example, the compound described in Example 32 of the present description (chemical name: 1-(2-{[2-({[(3S,4R)-4-(2,4-difluorophenyl)-1-{2-[(3R)-1,2,3,4-tetrahydroisoquinolin-3-yl]ethyl}pyrrolidin-3-yl]carbonyl}amino)-1H-imidazol-1-yl]methyl}-5-methylphenyl)piperidine-4-carboxylic acid tetrahydrochloride) is one of the compounds having high selectivity for MC1R showing the ratio of about 1:200 of the $EC_{50}$ value (2.8 nM) for human MC1R agonistic activity to the $EC_{50}$ value (557 nM) for human MC4R agonistic activity.

The compound [I] of the present invention may be used in a medical use in the free form or in the form of a pharmaceutically acceptable salt. Examples of the pharmaceutically acceptable salt include inorganic acid salts such as hydrochloride, sulfate, phosphate, or hydrobromide; and organic acid salts such as acetate, fumarate, oxalate, citrate, methanesulfonate, benzenesulfonate, tosylate, and maleate.

The compound [I] of the present invention or a pharmaceutically acceptable salt thereof also includes all of an intramolecular salt or an adduct thereof, a solvate or a hydrate thereof, a cocrystal thereof, and the like.

One or more of the compound represented by formula [I] of the present invention or a pharmaceutically acceptable salt thereof may be directly administered to a patient, but preferably the compound represented by formula [I] of the present invention or a pharmaceutically acceptable salt thereof may be mixed with a pharmacologically and pharmaceutically acceptable additive(s) to be provided as a formulation in a form well known to those skilled in the art.

Examples of the pharmacologically and pharmaceutically acceptable additive(s) include appropriate excipients, disintegrants, binders, lubricants, coating agents, colorants, diluents, bases, and isotonic agents usually used in the manufacture of a medicine.

After the compound of the present invention is mixed with the above additive(s) to be prepared into an appropriate dosage form (for example, a powder, an injection, a tablet, a capsule, or a topical agent for external use), it may be administered to a patient (a human or an animal) by an appropriate administration method (for example, intravenous administration, oral administration, transdermal administration, or topical administration) depending on the dosage form.

The dose may depend on the age, body weight, general health condition, sex, diet, administration time, administration method, excretion rate, combination of drugs, and the severity of the disease condition of a patient treated at the time of administration, and may be determined in view of them or other factors. The compound of the present invention or a pharmaceutically acceptable salt thereof has low toxicity and can be used safely. The daily dose thereof may vary depending on the condition or body weight of a patient, the type of the compound, the administration route, and the like. For example, in the case of parenteral administration, the compound of the present invention or a pharmaceutically acceptable salt thereof is administered subcutaneously, intravenously, intramuscularly, or intrarectally at a dose of about 0.0001 to 1,000 mg/person/day, preferably about 0.001 to 1,000 mg/person/day, and especially preferably about 0.01 to 500 mg/person/day, or in the case of oral administration, the compound of the present invention or a pharmaceutically acceptable salt thereof is administered at a dose of about 0.0001 to 1,000 mg/person/day, and preferably about 0.01 to 500 mg/person/day.

The compound of the present invention or a pharmaceutically acceptable salt thereof may be prepared, for example, as follows. Note that each of the abbreviations as used herein indicates the following meaning.

Me: Methyl
Et: Ethyl

Synthesis Method A-1

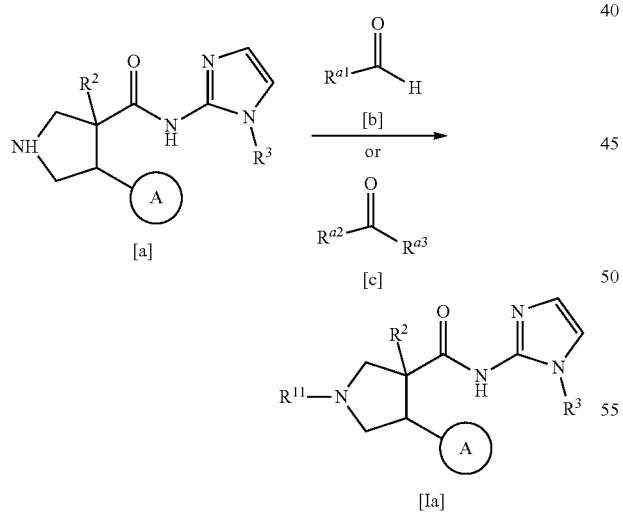

Among the target compound [I] of the present invention, the compound wherein $R^1$ represents an optionally substituted alkyl group, an optionally substituted cycloalkyl group, or an optionally substituted aliphatic heterocyclic group represented by general formula [Ia] (wherein $R^{11}$ represents an optionally substituted alkyl group, an optionally substituted cycloalkyl group, or an optionally substituted aliphatic heterocyclic group, and the other symbols are the same as defined above) may be prepared, for example, as follows.

The compound represented by general formula [a] (wherein the symbols are the same as defined above) or a salt thereof is subjected to a reductive amination reaction with the compound represented by general formula [b] (wherein $R^{a1}$ represents an optionally substituted alkyl group) or the compound represented by general formula [c] (wherein $R^{a2}$ and $R^{a3}$ represent each independently an optionally substituted alkyl group, or $R^{a2}$ and $R^{a3}$ are combined with each other at their terminals with the carbon atom to which $R^{a2}$ and $R^{a3}$ are attached to form an optionally substituted cycloalkyl group or an optionally substituted aliphatic heterocyclic group), and if desired, the product is converted into a pharmaceutically acceptable salt to obtain the target compound [Ia] or a pharmaceutically acceptable salt thereof.

Examples of the salt of the compound [a] include a salt with an inorganic acid such as hydrochloric acid and a salt with a carboxylic acid such as acetic acid.

The reductive amination reaction of the compound [a] or a salt thereof with the compound [b] or the compound [c] may be carried out according to a conventional method in an appropriate solvent, and for example, in the presence of a reducing agent and an acid. Any solvent may be used as long as it does not interfere with the reaction, and examples thereof include halogenated aliphatic hydrocarbons such as methylene chloride, alcohols such as methanol, ethers such as tetrahydrofuran, aromatic hydrocarbons such as toluene, and mixed solvents thereof. Examples of the reducing agent include sodium triacetoxyborohydride, sodium borohydride, hydrogen, and palladium catalysts (for example, an activated carbon-supported palladium catalyst). Examples of the acid include acetic acid. The amounts of the compound [b] and the compound [c] to be used may be 0.1 to 10 molar equivalents, preferably 1 to 5 molar equivalent(s), relative to the compound [a]. The amount of the reducing agent to be used may be 1 to 10 molar equivalent(s), preferably 1 to 3 molar equivalent(s), relative to the compound [a]. The amount of the acid to be used may be 1 to 10 molar equivalent(s), preferably 1 to 3 molar equivalent(s), relative to the compound [a]. The reaction may be carried out at −10 to 100° C., preferably 10 to 50° C.

Synthesis Method A-2

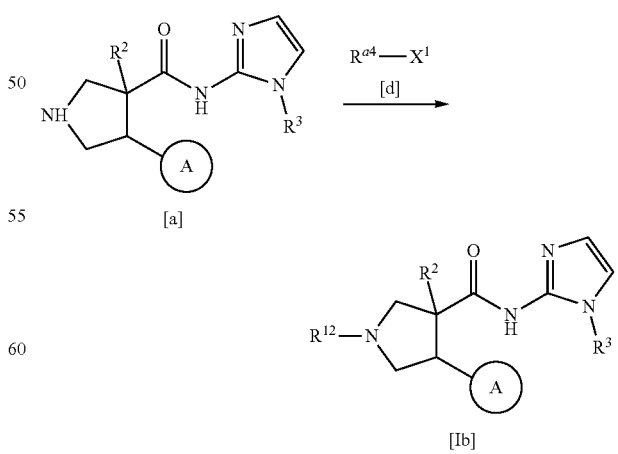

Among the target compound [I], the compound wherein $R^1$ represents an optionally substituted alkyl group represented by general formula [Ib] (wherein $R^{12}$ represents an optionally substituted alkyl group, and the other symbols are the same as defined above) may also be prepared, for example, as follows.

The compound [a] or a salt thereof is reacted with the compound represented by general formula [d] (wherein $R^{a4}$ represents an optionally substituted alkyl group, and $X^1$ represents a leaving group), and if desired, the product is converted into a pharmaceutically acceptable salt to obtain the target compound [Ib].

Examples of the leaving group represented by $X^1$ include a halogen atom (for example, a fluorine atom, a chlorine atom, a bromine atom, or an iodine atom), a methylsulfonyloxy group, and a p-toluenesulfonyloxy group. Especially, preferable examples of the leaving group include a halogen atom.

The reaction of the compound [a] or a salt thereof with the compound [d] may be carried out, for example, in an appropriate solvent and in the presence of a base. Any solvent may be used as long as it does not interfere with the reaction, and examples thereof include nitriles such as acetonitrile, halogenated aliphatic hydrocarbons such as methylene chloride, ethers such as tetrahydrofuran, aromatic hydrocarbons such as toluene, amides such as N,N-dimethylformamide and dimethylsulfoxide, and mixed solvents thereof. Examples of the base include amines such as diisopropylethylamine, and alkali metal carbonates such as potassium carbonate. A reaction adjuvant may be added to the reaction to accelerate the reaction. Examples of the reaction adjuvant include inorganic salts such as sodium iodide and potassium iodide. The amount of the compound [d] to be used may be 0.1 to 10 molar equivalents, preferably 0.8 to 2 molar equivalents, relative to the compound [a]. The amount of the base to be used may be 1 to 10 molar equivalent(s), preferably 1 to 3 molar equivalent(s), relative to the compound [a]. The amount of the reaction adjuvant to be used may be 0.01 to 10 molar equivalents, preferably 0.1 to 1 molar equivalent(s), relative to the compound [a]. The reaction may be carried out at 0 to 150° C., preferably 20 to 100° C.

Synthesis Method A-3

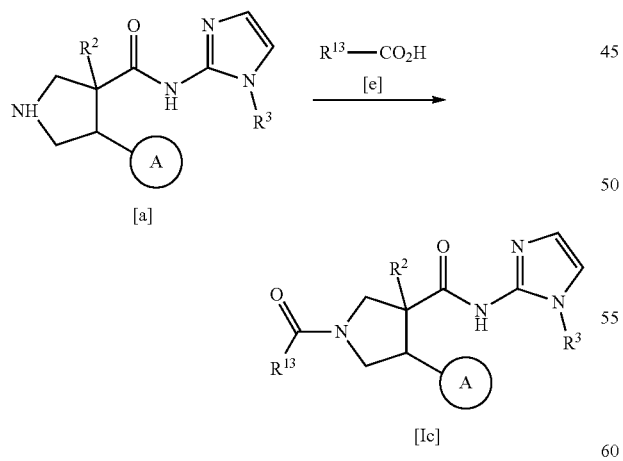

Among the target compound [I], the compound wherein $R^1$ represents an optionally substituted alkanoyl group represented by general formula [Ic] (wherein $R^{13}$ represents an optionally substituted alkyl group, and the other symbols are the same as defined above) may also be prepared, for example, as follows.

The compound [a] or a salt thereof is condensed with the compound represented by general formula [e] (wherein the symbol is the same as defined above) or a salt thereof, or an acid chloride thereof, and if desired, the product is converted into a pharmaceutically acceptable salt to prepare the target compound [I] or a pharmaceutically acceptable salt thereof.

The condensation reaction of the compound [a] or a salt thereof with the compound [e] or a salt thereof may be carried out according to a conventional method in an appropriate solvent, and for example, in the presence of a condensing agent. Examples of the salt of the compound [a] include inorganic acid salts such as hydrochloride and sulfate. Examples of the salt of the compound [e] include sodium salts and potassium salts. Any solvent may be used as long as it does not interfere with the reaction, and examples thereof include amides such as N,N-dimethylformamide, halogenated aliphatic hydrocarbons such as methylene chloride, ethers such as tetrahydrofuran, water, and mixed solvents thereof. Examples of the condensing agent include 1-ethyl-3-(3-dimethylaminopropyl)carbodiimide hydrochloride (EDAC), o-(7-azabenzotriazol-1-yl)-N,N,N', N'-tetramethyluronium hexafluorophosphate (HATU), and 4-(4,6-dimethoxy-1,3,5-triazin-2-yl)-4-methyl morpholinium chloride (DMT-MM). A base may be added to the reaction to accelerate the reaction. Examples of the base include amines such as triethylamine and diisopropylethylamine, and alkali metal carbonates such as potassium carbonate. Also, a reaction adjuvant may be added to the reaction to accelerate the reaction. Examples of the reaction adjuvant include 1-hydroxy-7-azabenzotriazole (HOAt), 1-hydroxybenzotriazole (HOBt), and 4-dimethylaminopyridine. The amount of the compound [e] to be used may be 0.1 to 10 molar equivalents, preferably 0.5 to 5 molar equivalents, relative to the compound [a]. The amount of the condensing agent to be used may be 0.5 to 10 molar equivalents, preferably 1 to 3 molar equivalent(s), relative to the compound [a]. The amount of the base to be used may be 0 to 10 molar equivalents, preferably 1 to 5 molar equivalent(s), relative to the compound [a]. The amount of the reaction adjuvant to be used may be 0.5 to 10 molar equivalents, preferably 1 to 3 molar equivalent(s), relative to the compound [a]. The reaction may be carried out at −10 to 100° C., preferably 10 to 80° C. Also, the condensation reaction of an acid chloride of the compound [a] with the compound [e] or a salt thereof may be carried out according to a conventional method, in an appropriate solvent, and in the presence of a base.

An acid chloride of the compound [e] may be prepared according to a conventional method, by treating the compound [e] with a conventional reagent such as thionyl chloride and oxalyl chloride. Preferable examples of the solvent and the base include those which are listed in the above condensation reaction of the compound [a] or a salt thereof with the compound [e] or a salt thereof.

Synthesis Method B

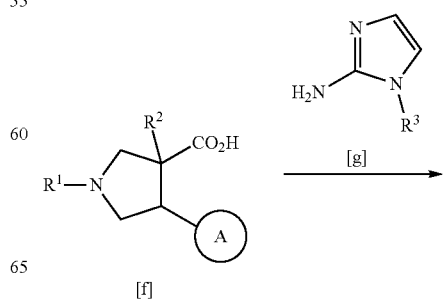

-continued

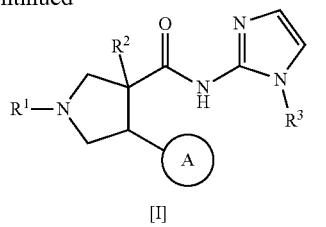

[I]

The target compound [I] of the present invention (wherein the symbols are the same as defined above) may also be prepared, for example, as follows.

The compound represented by general formula [f] (wherein the symbols are the same as defined above), a salt thereof, or an acid chloride thereof is condensed with the compound represented by general formula [g] (wherein the symbol is the same as defined above) or a salt thereof, and if desired, the product is converted into a pharmaceutically acceptable salt to prepare the target compound [I] or a pharmaceutically acceptable salt thereof.

The condensation reaction of the compound [f] or a salt thereof with the compound [g] or a salt thereof may be carried out according to a conventional method, in an appropriate solvent, and for example, in the presence of a condensing agent. Examples of the salt of the compound [f] include sodium salts and potassium salts. Examples of the salt of the compound [g] include inorganic acid salts such as hydrochloride and sulfate. Any solvent may be used as long as it does not interfere with the reaction, and examples thereof include amides such as N,N-dimethylformamide, halogenated aliphatic hydrocarbons such as methylene chloride, ethers such as tetrahydrofuran, water, and mixed solvents thereof. Examples of the condensing agent include 1-ethyl-3-(3-dimethylaminopropyl)carbodiimide hydrochloride (EDAC), o-(7-azabenzotriazol-1-yl)-N,N,N',N'-tetramethyluronium hexafluorophosphate (HATU), and 4-(4,6-dimethoxy-1,3,5-triazin-2-yl)-4-methyl morpholinium chloride (DMT-MM). A base may be added to the reaction to accelerate the reaction. Examples of the base include amines such as triethylamine and diisopropylethylamine, and alkali metal carbonates such as potassium carbonate. Also, a reaction adjuvant may be added to the reaction to accelerate the reaction. Examples of the reaction adjuvant include 1-hydroxy-7-azabenzotriazole (HOAt), 1-hydroxybenzotriazole (HOBt), and 4-dimethylaminopyridine. The amount of the compound [g] to be used may be 0.1 to 10 molar equivalents, preferably 0.5 to 5 molar equivalents, relative to the compound [f]. The amount of the condensing agent to be used may be 0.5 to 10 molar equivalents, preferably 1 to 3 molar equivalent(s), relative to the compound [f]. The amount of the base to be used may be 0 to 10 molar equivalents, preferably 1 to 5 molar equivalent(s), relative to the compound [f]. The amount of the reaction adjuvant to be used may be 0.5 to 10 molar equivalents, preferably 1 to 3 molar equivalent(s), relative to the compound [f]. The reaction may be carried out at −10 to 100° C., preferably 10 to 80° C. Also, the condensation reaction of an acid chloride of the compound [f] with the compound [g] or a salt thereof may be carried out according to a conventional method, in an appropriate solvent, and in the presence of a base.

An acid chloride of the compound [f] may be prepared according to a conventional method, by treating the compound [f] with a conventional reagent such as thionyl chloride and oxalyl chloride. Preferable examples of the solvent and the base include those listed in the above condensation reaction of the compound [f] or a salt thereof with the compound [g] or a salt thereof.

Intermediate Production Method a

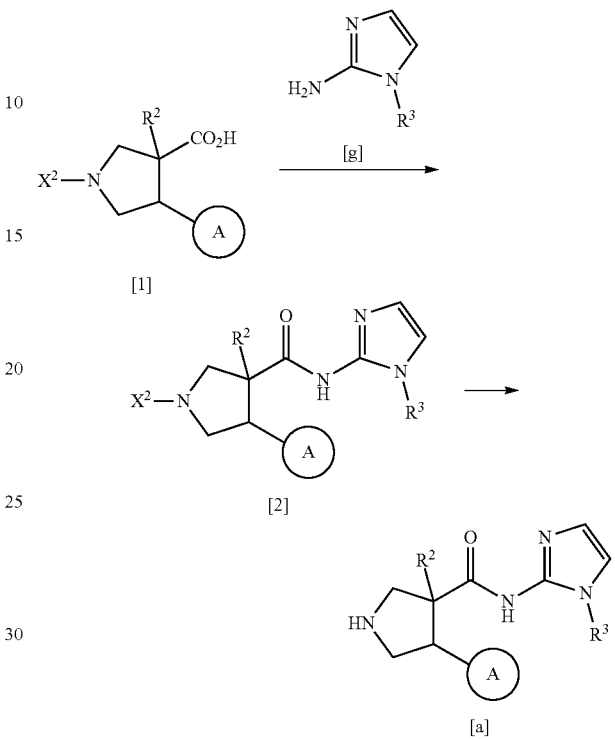

The compound [a] used in the above Synthesis Methods A-1 to A-3 may be prepared, for example, as follows.

The compound represented by general formula [1] (wherein $X^2$ represents a protecting group of the amino group, and the other symbols are the same as defined above) and the compound [g] are subjected to a condensation reaction to obtain the compound represented by general formula [2] (wherein the symbols are the same as defined above).

The protecting group of the amino group of the resulting compound [2] is removed to obtain the compound [a].

Examples of the protecting group of the amino group represented by $X^2$ include a benzyl group and a t-butoxycarbonyl group.

The condensation reaction of the compound [1] with the compound [g] may be carried out in a similar manner to the condensation reaction of the compound [f] with the compound [g] described in the above Synthesis Method B.

The removal reaction of the protecting group of the amino group of the compound [2] may be carried out according to a conventional method. For example, when $X^2$ represents a benzyl group, the reaction may be carried out in an appropriate solvent, and in the presence of hydrogen and a palladium catalyst. Any solvent may be used as long as it does not interfere with the reaction, and examples thereof include ethers such as tetrahydrofuran, alcohols such as methanol, esters such as ethyl acetate, and mixed solvents thereof. Examples of the palladium catalyst include an activated carbon-supported palladium catalyst. Also, when $X^2$ represents, for example, a t-butoxycarbonyl group, the reaction may be carried out in an appropriate solvent, and in the presence of an acid. Any solvent may be used as long as it does not interfere with the reaction, and examples thereof include halogenated aliphatic hydrocarbons such as methylene chloride, ethers such as 1,4-dioxane, and mixed solvents thereof. Examples of the acid include hydrochloric acid and trifluoroacetic acid.

Intermediate Production Method b-1

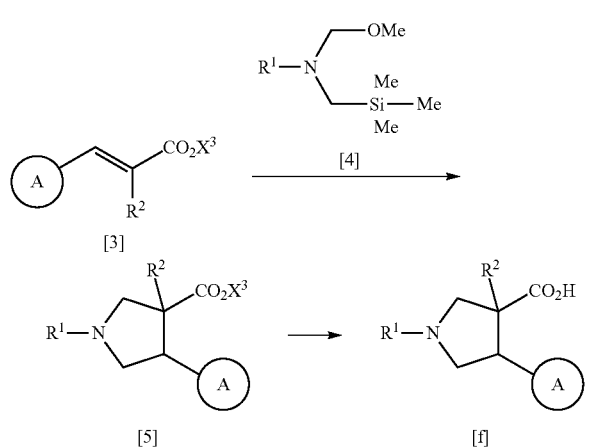

The compound [f] used in the above Synthesis Method B may be prepared, for example, as follows.

The compound represented by general formula [3] (wherein $X^3$ represents a protecting group of the carboxyl group, and the other symbols are the same as defined above) is reacted with the compound represented by general formula [4] (wherein the symbol is the same as defined above) to obtain the compound represented by general formula [5] (wherein the symbols are the same as defined above).

The protecting group of the carboxyl group of the resulting compound [5] is removed to obtain the compound [f].

Examples of the protecting group of the carboxyl group represented by $X^3$ include an alkyl group.

The reaction of the compound [3] with the compound [4] may be carried out in an appropriate solvent, and in the presence of an acid. Any solvent may be used as long as it does not interfere with the reaction, and examples thereof include halogenated aliphatic hydrocarbons such as methylene chloride, aromatic hydrocarbons such as toluene, nitriles such as acetonitrile, ethers such as tetrahydrofuran, and mixed solvents thereof. Examples of the acid include trifluoroacetic acid.

The removal reaction of the protecting group of the carboxyl group of the compound [5] into the compound [f] may be carried out depending on the type of the protecting group to be removed according to a conventional method, in an appropriate solvent, and by treating it with a base or an acid. For example, when the reaction is carried out in the presence of a base, any solvent may be used as long as it does not interfere with the reaction, and examples thereof include alcohols such as methanol, water, and mixed solvents thereof. Examples of the base include sodium hydroxide.

Also, when the reaction is carried out in the presence of an acid, any solvent may be used as long as it does not interfere with the reaction, and examples thereof include halogenated aliphatic hydrocarbons such as methylene chloride, ethers such as 1,4-dioxane, and mixed solvents thereof. Examples of the acid include trifluoroacetic acid and hydrochloric acid.

Intermediate Production Method b-2

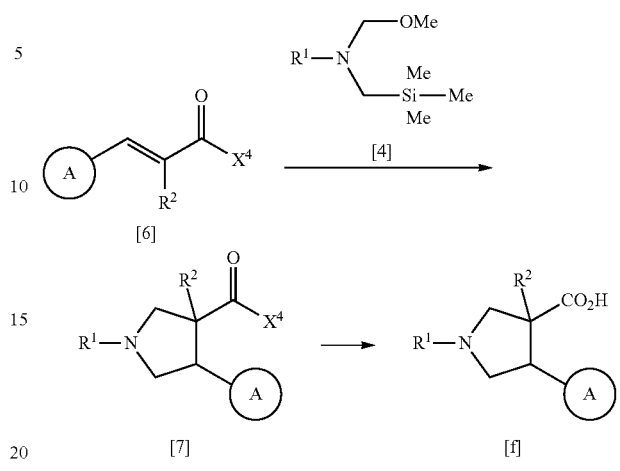

When an optically active compound is required as the compound [f] used in the above Synthesis Method B, it may be prepared, for example, as follows.

First, the compound represented by general formula [6] (wherein $X^4$ represents a chiral auxiliary group, and the other symbols are the same as defined above) is reacted with the compound [4] to obtain the compound represented by general formula [7] (wherein the symbols are the same as defined above).

The chiral auxiliary group of the compound [7] is removed to obtain the compound [f].

Examples of the chiral auxiliary group represented by $X^4$ include chiral 4-benzyl-2-oxazolidinone, chiral 4-phenyl-2-oxazolidinone, and chiral 10,2-camphorsultam.

The reaction of the compound [6] with the compound [4] may be carried out in a similar manner to the reaction of the compound [3] with the compound [4] in the above Intermediate Production Method b-1.

The removal reaction of the chiral auxiliary group of the compound [7] may be carried out according to a conventional method, in an appropriate solvent, for example, in the presence of water, and in the presence of a base. Any solvent may be used as long as it does not interfere with the reaction, and examples thereof include ethers such as tetrahydrofuran, alcohols such as methanol, water, and mixed solvents thereof. Examples of the base include sodium hydroxide and lithium hydroxide.

Intermediate Production Method b-3

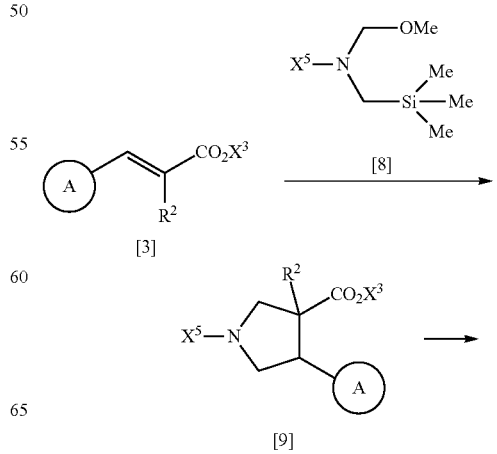

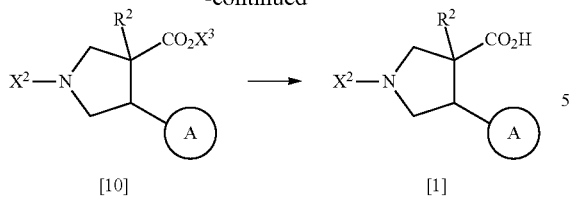

The compound [1] used in the above Intermediate Production Method a may be prepared, for example, as follows.

The compound [3] is reacted with the compound represented by general formula [8] (wherein $X^5$ represents the same or different protecting group of the amino group from $X^2$) to obtain the compound represented by general formula [9] (wherein the symbols are the same as defined above).

As needed, the protecting group of the amino group of the compound [9] is substituted with another protecting group to convert into the compound represented by general formula [(10] (wherein the symbols are the same as defined above).

The protecting group of the carboxyl group of the compound [10] is removed to obtain the compound [1].

The protecting group of the amino group represented by $X^5$ may be a conventional protecting group, and examples thereof include a benzyl group. When the protecting group of the amino group is substituted with another protecting group to prepare the compound [10] from the compound [9], $X^5$ is preferably a protecting group of the amino group which is not removed in an acidic condition, and examples thereof include a benzyl group.

The reaction of the compound [3] with the compound [8] may be carried out in a similar manner to the reaction of the compound [3] with the compound [4] in the above Intermediate Production Method b-1.

The substitution reaction of the protecting group of the amino group of the compound [9] into the compound [10] may be carried out according to a conventional method. For example, when $X^5$ represents a benzyl group, the reaction may be carried out in an appropriate solvent, and in the presence of hydrogen, a palladium catalyst, and a donor of a protecting group of the amino group. Any solvent may be used as long as it does not interfere with the reaction, and examples thereof include ethers such as tetrahydrofuran, alcohols such as ethanol, and mixed solvents thereof. Examples of the palladium catalyst include an activated carbon-supported palladium catalyst. Examples of the donor of a protecting group of the amino group, for example when $X^2$ represents a t-butoxycarbonyl group, include di-t-butyl dicarbonate.

The removal reaction of the protecting group of the carboxyl group of the compound [10] into the compound [1] may be carried out in a similar manner to the removal reaction of the protecting group of the carboxyl group of the compound [5] in the above Intermediate Production Method b-1.

Intermediate Production Method b-4

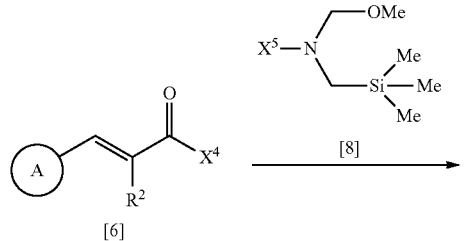

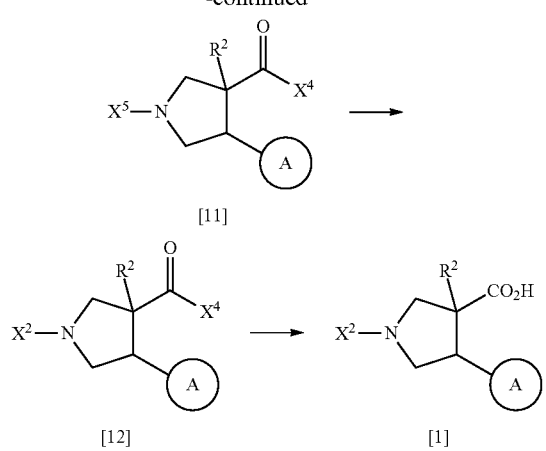

When an optically active compound is required as the compound [1)] used in the above Intermediate Production Method a, it may be prepared, for example, as follows.

The compound [6] is reacted with the compound [8] to obtain the compound represented by general formula [11] (wherein the symbols are the same as defined above).

The protecting group of the amino group of the compound [11] is substituted with another protecting group to convert into the compound represented by general formula [12] (wherein the symbols are the same as defined above).

The chiral auxiliary group of the compound [12] is removed to obtain the compound [1].

The reaction of the compound [6] with the compound [8] may be carried out in a similar manner to the reaction of the compound [3] with the compound [4] in the above Intermediate Production Method b-1.

The substitution reaction of the protecting group of the amino group of the compound [11] into the compound [12] may be carried out in a similar manner to the conversion reaction of the compound [9] into the compound [10] in the above Intermediate Production Method b-3.

The removal reaction of the chiral auxiliary group of the compound [12] into the compound [1] may be carried out in a similar manner to the removal reaction of the chiral auxiliary group of the compound [7] in the above Intermediate Production Method b-2.

Intermediate Production Method c-1

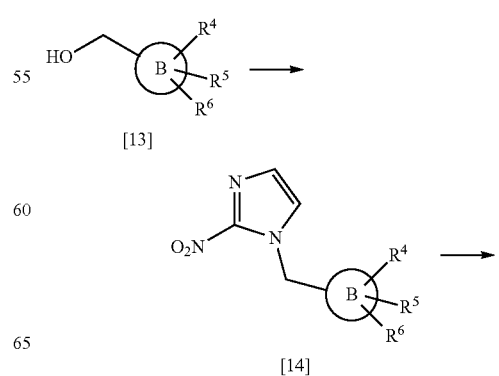

-continued

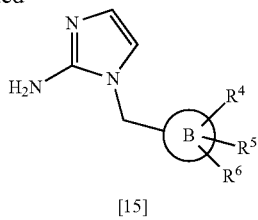

[15]

Among the compound [g] used in the above Synthesis Method B, the compound represented by general formula [15] (wherein the symbols are the same as defined above) may be prepared, for example, as follows.

The compound represented by general formula [13] (wherein the symbols are the same as defined above) may be converted to obtain the compound represented by general formula [14] (wherein the symbols are the same as defined above).

The resulting compound [14] is subjected to a reduction reaction to obtain the compound [15].

The conversion reaction of the compound [13] into the compound [14] may be carried out according to a conventional method, in an appropriate solvent, and in the presence of an azodicarboxylic acid derivative, a phosphine derivative, and nitroimidazole. Any solvent may be used as long as it does not interfere with the reaction, and examples thereof include ethers such as tetrahydrofuran, aromatic hydrocarbons such as toluene, halogenated aliphatic hydrocarbons such as methylene chloride, and mixed solvents thereof. Examples of the azodicarboxylic acid derivative include diethyl azodicarboxylate. Examples of the phosphine derivative include triphenylphosphine.

The reduction reaction of the compound [14] may be carried out according to a conventional method, in an appropriate solvent, and in the presence of a reducing agent. Any solvent may be used as long as it does not interfere with the reaction, and examples thereof include alcohols such as methanol, halogenated aliphatic hydrocarbons such as methylene chloride, ethers such as tetrahydrofuran, aromatic hydrocarbons such as toluene, and mixed solvents thereof. Examples of the reducing agent include hydrogen and palladium catalysts (for example, an activated carbon-supported palladium catalyst). An acid may be added to the reaction to accelerate the reduction reaction. Examples of the acid include hydrochloric acid and acetic acid.

Intermediate Production Method c-2

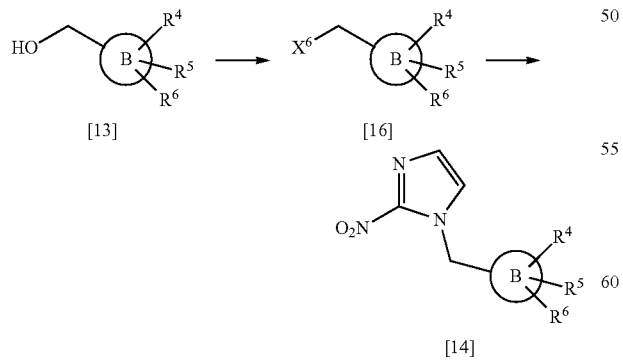

The compound [14] used in the above Intermediate Production Method c-1 may also be prepared, for example, as follows.

The hydroxy group of the compound [13] is converted into a leaving group to obtain the compound represented by general formula [16] (wherein $X^6$ represents a leaving group, and the other symbols are the same as defined above).

The resulting compound [16] may be converted to obtain the compound [14].

Examples of the leaving group represented by $X^6$ include halogen atoms (for example, a fluorine atom, a chlorine atom, a bromine atom, or an iodine atom), a methylsulfonyloxy group, and p-toluenesulfonyloxy group.

The conversion reaction of the compound [13] into the compound [16] may be carried out according to a conventional method, in an appropriate solvent, and in the presence of a halogenating agent. Any solvent may be used as long as it does not interfere with the reaction, and examples thereof include halogenated aliphatic hydrocarbons such as methylene chloride, ethers such as 1,4-dioxane, and mixed solvents thereof. Examples of the halogenating agent include thionyl chloride and oxalyl chloride. N,N-dimethylformamide and a base may be added to the reaction to accelerate the reaction. Examples of the base include amines such as triethylamine.

The reaction may also be carried out in an appropriate solvent, and in the presence of a sulfonylating agent and a base. Any solvent may be used as long as it does not interfere with the reaction, and examples thereof include halogenated aliphatic hydrocarbons such as methylene chloride, ethers such as 1,4-dioxane, and mixed solvents thereof. Examples of the sulfonylating agent include methanesulfonyl chloride and p-toluenesulfonyl chloride. Examples of the base include amines such as triethylamine.

The reaction of the compound [16] into the compound [14] may be carried out according to a conventional method, in an appropriate solvent, and in the presence of nitroimidazole and a base. Any solvent may be used as long as it does not interfere with the reaction, and examples thereof include amides such as N,N-dimethylformamide and dimethylsulfoxide, ethers such as tetrahydrofuran, aromatic hydrocarbons such as toluene, halogenated aliphatic hydrocarbons such as methylene chloride, and mixed solvents thereof. Examples of the base include alkali metal carbonates such as potassium carbonate and amines such as triethylamine.

Intermediate Production Method d-1

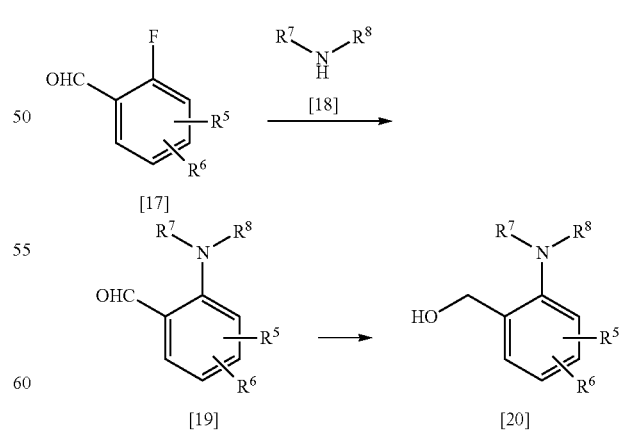

Among the compound [13] used in the above Intermediate Production Method c-1, the compound represented by general formula [20] (wherein $R^7$ and $R^8$ represent each independently an optionally substituted alkyl group, or are combined with each other at their terminals with the nitrogen atom to which they are attached to represent an optionally substituted nitrogen-containing aliphatic heterocyclic ring, and the other symbols are the same as defined above) may be prepared, for example, as follows.

The compound represented by general formula [17] (wherein the symbols are the same as defined above) is reacted with the compound represented by general formula [18] (wherein the symbols are the same as defined above) to obtain the compound represented by general formula [19] (wherein the symbols are the same as defined above).

The compound [19] is subjected to a reduction reaction to obtain the compound represented by general formula [20] (wherein the symbols are the same as defined above).

The reaction of the compound [17] with the compound [18] may be carried out according to a conventional method, in an appropriate solvent, and in the presence of a base. Any solvent may be used as long as it does not interfere with the reaction, and examples thereof include amides such as N,N-dimethylformamide and dimethylsulfoxide, nitriles such as acetonitrile, ethers such as 1,4-dioxane, and mixed solvents thereof. Examples of the base include alkali metal carbonates such as potassium carbonate and amines such as triethylamine.

The reduction reaction of the compound [19] may be carried out according to a conventional method, in an appropriate solvent, and for example, in the presence of a reducing agent. Any solvent may be used as long as it does not interfere with the reaction, and examples thereof include ethers such as tetrahydrofuran, aromatic hydrocarbons such as toluene, and mixed solvents thereof. Examples of the reducing agent include sodium borohydride.

Intermediate Production Method d-2

Preferable examples of the protecting group of the carboxyl group in the compound [21] include alkyl groups (for example, a methyl group or an ethyl group).

The reaction of the compound [21] with the compound [18] may be carried out according to a conventional method, in an appropriate solvent, and in the presence of a base. Any solvent may be used as long as it does not interfere with the reaction, and examples thereof include amides such as N,N-dimethylformamide and dimethylsulfoxide, nitriles such as acetonitrile, ethers such as 1,4-dioxane, and mixed solvents thereof. Examples of the base include alkali metal carbonates such as potassium carbonate and amines such as triethylamine.

The reduction reaction of the compound [22] may be carried out according to a conventional method, in an appropriate solvent, and for example, in the presence of a reducing agent. Any solvent may be used as long as it does not interfere with the reaction, and examples thereof include ethers such as tetrahydrofuran, aromatic hydrocarbons such as toluene, and mixed solvents thereof. Examples of the reducing agent include lithium aluminum hydride and sodium borohydride. When $X^7$ represents a hydrogen atom, the reaction may also be carried out in an appropriate solvent and in the presence of a base, by activating the compound with, for example, isobutyl chloroformate, and then reacting the resulting product with a reducing agent. Any solvent may be used as long as it does not interfere with the reaction, and examples thereof include ethers such as tetrahydrofuran, aromatic hydrocarbons such as toluene, and mixed solvents thereof. Examples of the base include amines such as triethylamine. Examples of the reducing agent include sodium borohydride.

Intermediate Production Method e

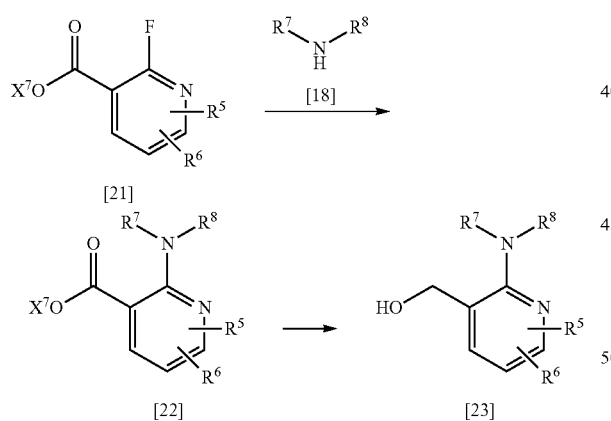

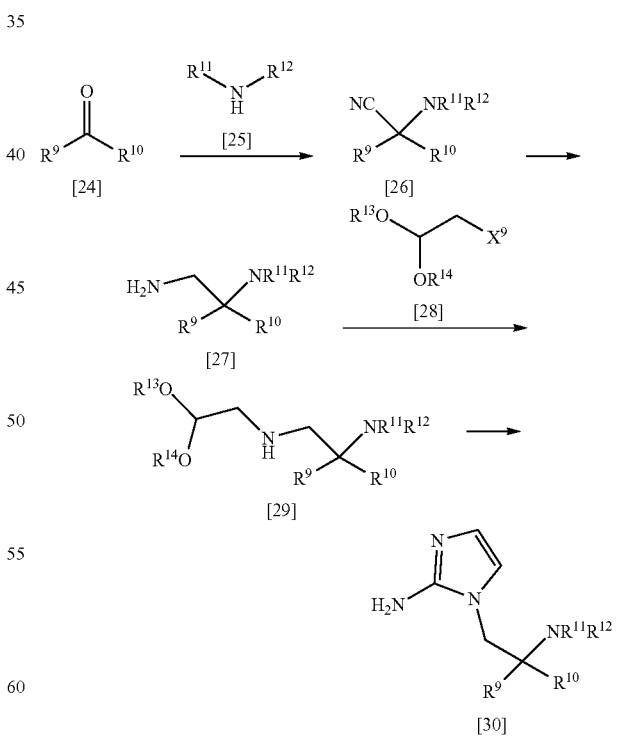

Among the compound [13] used in the above Intermediate Production Method c-1, the compound represented by general formula [23] (wherein the symbols are the same as defined above) may be prepared, for example, as follows.

The compound represented by general formula [21] (wherein $X^7$ represents a hydrogen atom or a protecting group of the carboxyl group, and the other symbols are the same as defined above) is reacted with the compound [18] to obtain the compound represented by general formula [22] (wherein the symbols are the same as defined above).

The compound [22] is subjected to a reduction reaction to obtain the compound represented by general formula [23] (wherein the symbols are the same as defined above).

Among the compound [g] used in the above Synthesis Method B, the compound represented by general formula [30] (wherein $R^9$ and $R^{10}$ represent each an optionally substituted alkyl group or are combined with each other at their terminals with the carbon atom to which they are attached to form an optionally substituted cycloalkyl ring, and $R^{11}$ and $R^{12}$ represent each independently an optionally substituted alkyl group or are combined with each other at their terminals with the nitrogen atom to which they are attached to form an optionally substituted nitrogen-containing aliphatic heterocyclic ring) may be prepared, for example, as follows.

The compound represented by general formula [24] (wherein the symbols are the same as defined above) is reacted with the compound represented by general formula [25] (wherein the symbols are the same as defined above) to obtain the compound represented by general formula [26] (wherein the symbols are the same as defined above).

The compound [26] is subjected to a reduction reaction to obtain the compound represented by general formula [27] (wherein the symbols are the same as defined above).

The compound [27] is reacted with the compound represented by general formula [28] (wherein $R^{13}$ and $R^{14}$ represent each an alkyl group, and $X^9$ represents a leaving group) to obtain the compound represented by general formula [29] (wherein the symbols are the same as defined above).

The compound [29] may be converted to obtain the compound [30].

Examples of the leaving group represented by $X^9$ include halogen atoms (for example, a fluorine atom, a chlorine atom, a bromine atom, or an iodine atom), a methylsulfonyloxy group, and p-toluenesulfonyloxy group.

The reaction of the compound [24] with the compound [25] may be carried out according to a conventional method, in an appropriate solvent, and in the presence of a cyano group donor and an acid. Any solvent may be used as long as it does not interfere with the reaction, and examples thereof include alcohols such as methanol, halogenated aliphatic hydrocarbons such as methylene chloride, and mixed solvents thereof. Examples of the cyano group donor include potassium cyanide and sodium cyanide. Examples of the acid include acetic acid and hydrochloric acid.

The reduction reaction of the compound [26] may be carried out according to a conventional method, in an appropriate solvent, and for example, in the presence of a reducing agent. Any solvent may be used as long as it does not interfere with the reaction, and examples thereof include ethers such as tetrahydrofuran, aromatic hydrocarbons such as toluene, and mixed solvents thereof. Examples of the reducing agent include lithium aluminum hydride.

The reaction of the compound [27] with the compound [28] may be carried out according to a conventional method, in an appropriate solvent, and in the presence of a base. Any solvent may be used as long as it does not interfere with the reaction, and examples thereof include amides such as N,N-dimethylformamide and dimethylsulfoxide, nitriles such as acetonitrile, ethers such as tetrahydrofuran, aromatic hydrocarbons such as toluene, halogenated aliphatic hydrocarbons such as methylene chloride, and mixed solvents thereof. Examples of the base include alkali metal carbonates such as potassium carbonate and amines such as triethylamine.

The reaction of the compound [29] into the compound [30] may be carried out according to a conventional method, in an appropriate solvent, and in the presence of cyanamide and an acid. Any solvent may be used as long as it does not interfere with the reaction, and examples thereof include water. Examples of the acid include acetic acid and hydrochloric acid.

Intermediate Production Method f

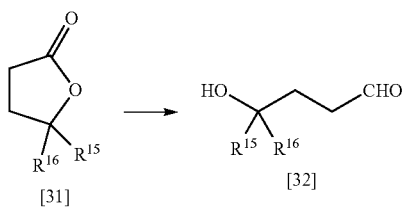

Among the compound [b] used in the above Synthesis Method A-1, the compound represented by general formula [32] (wherein $R^{15}$ and $R^{16}$ represent each an optionally substituted alkyl group) may be prepared, for example, as follows.

The compound represented by general formula [31] (wherein the symbols are the same as defined above) is subjected to a reduction reaction to obtain the compound [32].

The reduction reaction of the compound [31] may be carried out according to a conventional method, in an appropriate solvent, and in the presence of a reducing agent. Any solvent may be used as long as it does not interfere with the reaction, and examples thereof include ethers such as tetrahydrofuran, aliphatic hydrocarbons such as hexane, aromatic hydrocarbons such as toluene, and mixed solvents thereof. Examples of the reducing agent include diisobutylaluminum hydride.

Intermediate Production Method g

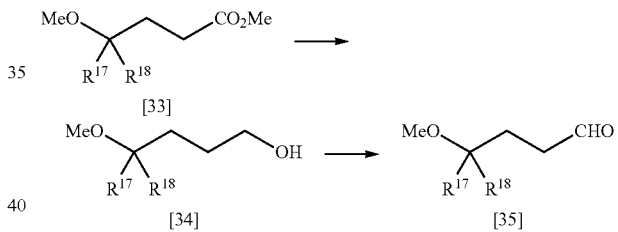

Among the compound [b] used in the above Synthesis Method A-1, the compound represented by general formula [35] (wherein $R^{17}$ and $R^{18}$ represent each an optionally substituted alkyl group) may be prepared, for example, as follows.

The compound [33] is subjected to a reduction reaction to obtain the compound represented by general formula [34] (wherein the symbols are the same as defined above).

The compound [34] is subjected to an oxidation reaction to obtain the compound [35].

The reduction reaction of the compound [33] may be carried out according to a conventional method, in an appropriate solvent, and in the presence of a reducing agent. Any solvent may be used as long as it does not interfere with the reaction, and examples thereof include ethers such as tetrahydrofuran, aliphatic hydrocarbons such as hexane, aromatic hydrocarbons such as toluene, and mixed solvents thereof. Examples of the reducing agent include sodium borohydride and lithium aluminum hydride.

The oxidation reaction of the compound [34] may be carried out according to a conventional method, in an appropriate solvent, and in the presence of an oxidizing agent. Any solvent may be used as long as it does not interfere with the reaction, and examples thereof include halogenated aliphatic hydrocarbons such as methylene chloride. Examples of the oxidizing agent include Dess-Martin periodinane and pyridinium chlorochromate. The reaction may also be carried out in an appropriate solvent, and in the presence of dimethyl sulfide, oxalyl chloride, and a base. Any solvent may be used as long as it does not interfere with the reaction, and examples thereof include halogenated aliphatic hydrocarbons such as methylene chloride. Examples of the base include amines such as pyridine and triethylamine.

Each starting compound in the above methods may be prepared in a similar manner to known methods and/or methods described in the following Examples.

Introduction of a protecting group into a functional group and removal of a protecting group of a functional group may be carried out with reference to a known method (for example, "PROTECTIVE GROUPS in ORGANIC SYNTHESIS" (by Theodora W. Greene and Peter G. M. Wuts)).

Also, the compounds of the present invention and Intermediate compounds prepared by the above methods may be further structurally converted into other target compounds or Intermediate compounds by the methods described in the following Examples and/or known methods, or combined methods thereof. Specific examples of the conversion include the following methods.

(1) Conversion of an Alkoxycarbonyl Group or the Like into a Carboxyl Group

An alkoxycarbonyl group may be converted into a carboxyl group by hydrolyzing it with an alkali metal hydroxide such as sodium hydroxide and potassium hydroxide; a benzyloxycarbonyl group may be converted into a carboxyl group by treating it with palladium carbon under hydrogen atmosphere to hydrocrack it; or a t-butoxycarbonyl group may be converted into a carboxyl group by treating it with an acid such as hydrochloric acid and trifluoroacetic acid.

(2) Conversion of a Carboxyl Group into a Carbamoyl Group

A carboxyl group or a salt thereof may be converted into a corresponding carbamoyl group by, for example, reacting it with an amine in the presence of a condensing agent, or by converting it into an acyl halide, and then reacting the resulting product with an amine.

(3) Conversion of a Carboxyl Group into an Alkoxycarbonyl Group

A carboxyl group may be converted into a corresponding alkoxycarbonyl group by reacting it with an alcohol in the presence of an acid, or by reacting it with an alcohol in the presence of a condensing agent. Alternatively, a carboxyl group may be converted into a corresponding alkoxycarbonyl group by reacting it with an alkylating agent in the presence of a base.

(4) Conversion of an Alkoxycarbonylalkynyl Group into a 3-Hydroxyisoxazolyl Group An alkoxycarbonylalkynyl group may be converted into a corresponding 3-hydroxyisoxazolyl group by reacting it with hydroxylamine hydrochloride in the presence of a base.

(5) Conversion of a Carboxyl Group into an Oxadiazolonyl Group

A carboxyl group may be converted into a corresponding oxadiazolonyl group by reacting it with a hydrazine derivative, deprotecting the resulting product as needed, and reacting the resulting product with 1,1'-carbonyldiimidazole.

(6) Conversion of a Cyano Group into a Tetrazolyl Group

A cyano group may be converted into a corresponding tetrazolyl group by reacting it with tributyltin azide.

(7) Conversion of a Carboxyl Group into an Alkylaminosulfonylaminocarbonyl Group A carboxyl group or a salt thereof may be converted into a corresponding alkylaminosulfonylaminocarbonyl group by reacting it with an alkylaminosulfonylamine in the presence of a condensing agent.

(8) Conversion of a Carboxyl Group into an Alkylsulfonylaminocarbonyl Group

A carboxyl group or a salt thereof may be converted into a corresponding alkylsulfonylaminocarbonyl group by reacting it with an alkylsulfonylamine in the presence of a condensing agent.

(9) Conversion of a t-butylamino Group or a Benzylamino Group into an Amino Group A t-butylamino group or a benzylamino group may be converted into a corresponding amino group by, for example, reacting it with 1-chloroethyl chloroformate in the presence of a base, and then reacting the resulting product with methanol.

(10) Conversion of a Carboxyl Group into a Hydroxymethyl Group

A carboxyl group may be converted into a hydroxymethyl group by activating it with isobutyl chloroformate or the like, and then reducing the resulting product with sodium borohydride or the like. Alternatively, a carboxyl group may be converted into a hydroxymethyl group by reducing it with lithium aluminum hydride or the like.

(11) Conversion of a Hydroxyalkyl Group into a Formyl Group

A hydroxyalkyl group may be converted into a corresponding formyl group by reacting it with an oxidizing agent.

(12) Conversion of a Formyl Group into an Alkenyl Group

A formyl group may be converted into a corresponding alkenyl group by, for example, reacting it with a Horner-Emmons reagent, a Wittig reagent, or the like in the presence of a base.

(13) Conversion of a Halogen Atom into an Amino Group

A halogen atom may be converted into a corresponding amino group by, for example, coupling a compound having a halogen atom with a desired amine, or reacting it with a desired amine in the presence of a base.

(14) Conversion of a Carbonyl Group into an Amino Group

A carbonyl group may be converted into an amino group by reacting it with a desired amine in the presence of a reducing agent.

(15) Conversion of an Amino Group into an Alkoxycarbonylamino Group

An amino group may be converted into a corresponding alkoxycarbonylamino group by reacting it with a desired alkoxycarbonyl halide.

(16) Conversion of an Amino Group into an Aminosulfonylamino Group

An amino group may be converted into a corresponding aminosulfonylamino group by reacting it with a desired aminosulfonyl donor.

(17) Conversion of an Amino Group into a Sulfonylamino Group

An amino group may be converted into a corresponding sulfonylamino group by reacting it with a desired sulfonyl halide.

(18) Conversion of a Formyl Group into a Hydroxymethyl Group

A formyl group may be converted into a hydroxymethyl group by reducing it with sodium borohydride or the like.

(19) Conversion of an Alkoxycarbonyl Group into a Hydroxymethyl Group

An alkoxycarbonyl group may be converted into a hydroxymethyl group by reducing it with diisobutylaluminum hydride or the like.

(20) Conversion of a Halogen Atom into an Aryl Group

A halogen atom may be converted into a corresponding aryl group by, for example, coupling a compound having a halogen atom with an arylboronic acid or the like.

(21) Conversion of a Halogen Atom into an Alkenyl Group

A halogen atom may be converted into a corresponding alkenyl group by, for example, coupling a compound having a halogen atom with an alkenylboronic acid derivative or the like.

(22) Conversion of an Alkenyl Group into an Alkyl Group

An alkenyl group may be converted into a corresponding alkyl group by reducing it with hydrogen, palladium carbon, or the like.

(23) Conversion of a Halogen Atom into a Cycloalkyl Group

A halogen atom may be converted into a corresponding cycloalkyl group by, for example, coupling a compound having a halogen atom with a cycloalkylboronic acid or the like, or coupling it with a cycloalkenylboronic acid ester or the like, and then reducing the resulting product with hydrogen, palladium carbon, or the like.

(24) Conversion of a Hydroxy Group into a Alkoxy Group

A hydroxy group may be converted into a corresponding alkoxy group by reacting it with a desired alkylating agent in the presence of a base. Alternatively, a hydroxy group may also be converted into a corresponding alkoxy group by reacting it with a desired alcohol in the presence of diethyl azodicarboxylate.

(25) Introduction of an Aryl Group into a Carbonyl Group

An aryl group may be introduced into a carbonyl group by, for example, reacting the carbonyl group with trifluoromethanesulfonic anhydride in the presence of a base, and then reacting the resulting product with bis(pinacolato)diboron, and coupling the resulting boronic acid ester derivative with a desired corresponding aryl halide.

(26) Conversion of a Formyl Group into a Dihalogenated Alkyl Group

A formyl group may be converted into a corresponding dihalogenated alkyl group by, for example, reacting it with a fluorinating agent such as bis(2-methoxyethyl)aminosulfur trifluoride.

(27) Conversion of a Sulfide Group into a Sulfonyl Group

A sulfide group may be converted into a corresponding sulfonyl group by, for example, reacting it with an oxidizing agent such as 3-chloroperbenzoic acid.

(28) Conversion of a Hydroxy Group into a Halogen Atom

A hydroxy group may be converted into a corresponding halogen atom by, for example, reacting it with a chlorinating agent such as thionyl chloride or the like.

(29) Conversion of a Halogen Atom into a Haloalkyl Group

A halogen atom may be converted into a corresponding haloalkyl group by reacting a compound having a halogen atom with a haloalkyl group donor. Examples of the haloalkyl group donor include methyl fluorosulfonyl difluoroacetate.

(30) Introduction of a Halogen Atom into an α-position of a Carbonyl Group

A corresponding halogen atom may be introduced into an α-position of a carbonyl group by reacting a carbonyl group having methylene at the α-position with, for example, bromine.

(31) Formylation of an Aryl Group

An aryl group may be converted into a corresponding formylated product by reacting it with, for example, a base such as s-butyllithium, and then reacting the resulting product with N,N-dimethylformamide.

The compound of the present invention or a starting compound thereof prepared as described above may be isolated or purified in the free form or in the form of a salt thereof. The salt may be prepared by subjecting the compound with a conventional salt formation. The isolation and purification may be carried out by applying a conventional chemical procedure such as extraction, concentration, crystallization, filtration, recrystallization, and various types of chromatography.

When the compound of the present invention or a pharmaceutically acceptable salt thereof exists as optical isomers on the basis of an asymmetric carbon, they may be separated into individual optical isomer by a conventional optical resolution method (for example, a fractional crystallization method or a resolution method using a chiral column). Also, an optical isomer may be synthesized by using an optically pure starting material. Further, an optical isomer may also be synthesized by stereoselectively carrying out each reaction using a chiral auxiliary group or an asymmetric catalyst.

EXAMPLES

Example 1

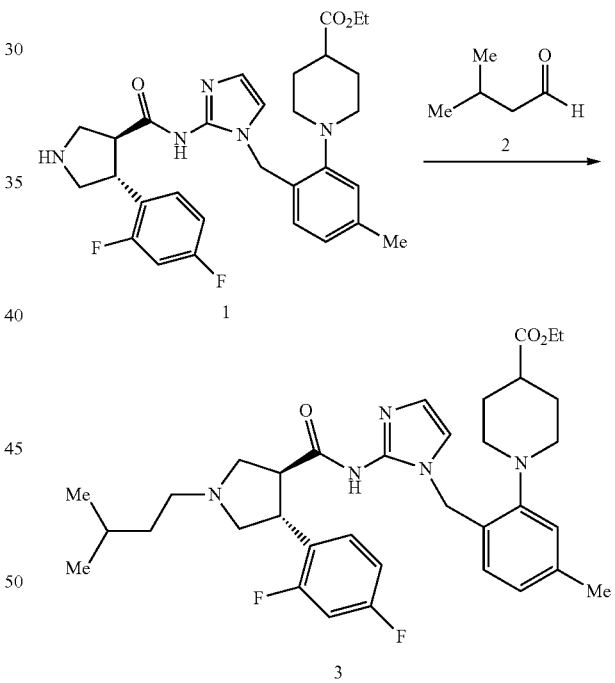

To a solution of the Compound 1 (132 mg) and the Compound 2 (39 μL) in dichloromethane (2 mL) was added acetic acid (28 μL) at room temperature, and the resulting mixture was stirred for 1 hour, and then sodium triacetoxyborohydride (76 mg) was added thereto, and the resulting mixture was stirred for 4 days. To the reaction mixture were added a saturated aqueous solution of sodium hydrogen carbonate and water, and the resulting mixture was stirred, and then extracted with chloroform. The resulting organic layers were dried, and then concentrated under reduced pressure. The resulting residues were purified by silica gel column chromatography (chloroform:methanol=98:2 to 90:10) to give ethyl 1-(2-{[2-({[(3S,4R)-4-(2,4-difluorophenyl)-1-(3-methylbutyl)pyrrolidin-3-yl]carbonyl}amino}-1H-imidazol-1-yl]methyl-5-methylphenyl)piperidine-4-carboxylate 3 (128 mg) as a colorless powder. MS (APCI): m/z 622 [M+H]$^+$ Example 2

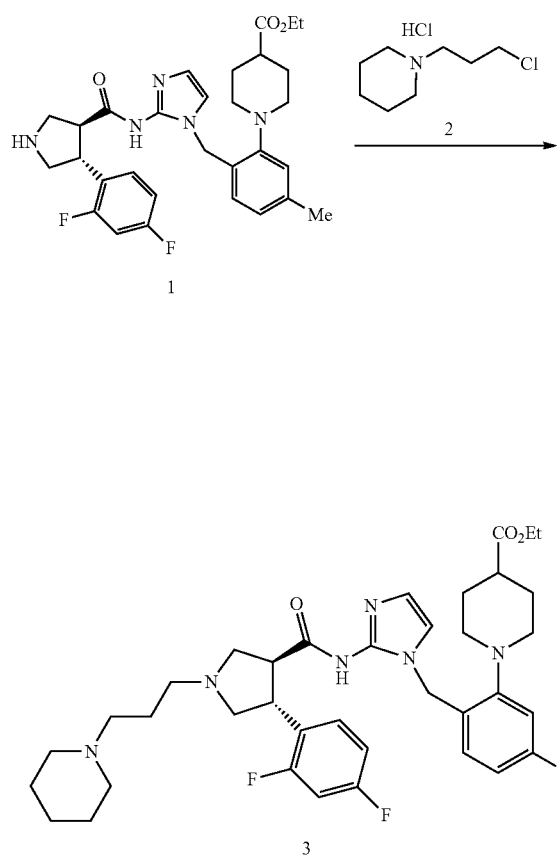

A mixture of the Compound 1 (110 mg), the Compound 2 (34 mg), diisopropylethylamine (105 μL), and acetonitrile (2 mL) was stirred at 80° C. for 15 hours. The reaction mixture was allowed to cool to room temperature, and then a saturated aqueous solution of sodium hydrogen carbonate, water, and chloroform were added thereto, and the resulting mixture was stirred, and then the resulting organic layers were separated, and concentrated under reduced pressure. The resulting residues were purified by silica gel column chromatography (chloroform:methanol=98:2 to 85:15) and NH silica gel column chromatography (chloroform:methanol=100:0 to 97:3) to give ethyl 1-[2-({2-[({(3S,4R)-4-(2,4-difluorophenyl)-1-[3-(piperidin-1-yl)propyl]pyrrolidin-3-yl}carbonyl)amino]-1H-imidazol-1-yl}methyl)-5-methylphenyl]piperidine-4-carboxylate 3 (83 mg) as a colorless powder. MS (APCI): m/z 677 [M+H]$^+$ Example 3

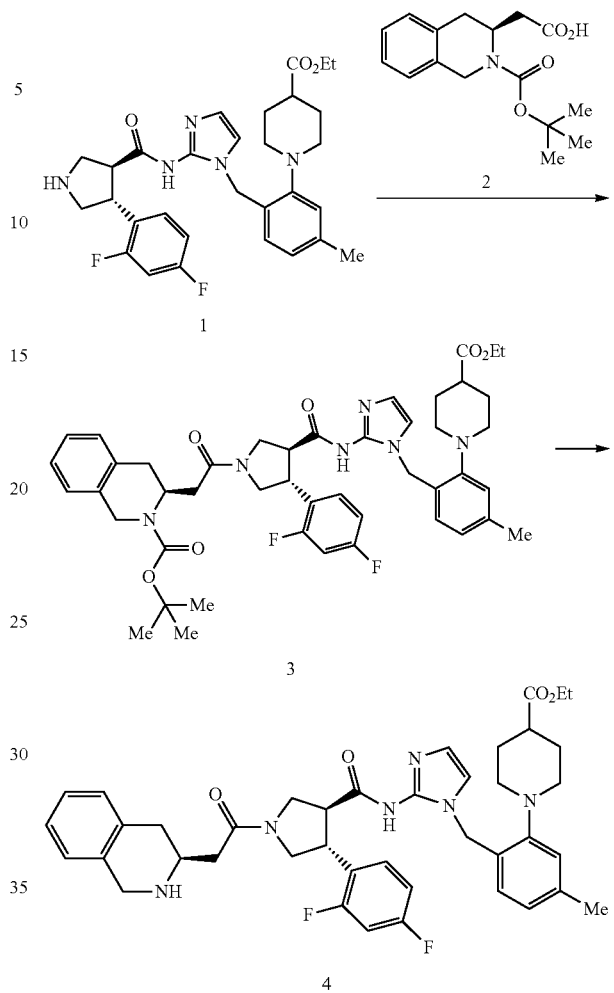

(1) A mixed solution of the Compound 1 (110 mg), the Compound 2 (70 mg), 1-ethyl-3-(3-dimethylaminopropyl)carbodiimide hydrochloride (46 mg), and 1-hydroxybenzotriazole hydrate (37 mg) in N,N-dimethylformamide (2 mL) was stirred at room temperature for 15 hours. To the reaction mixture were added a saturated aqueous solution of sodium hydrogen carbonate, water, and ethyl acetate, and the resulting mixture was stirred, and then extracted with ethyl acetate. The resulting organic layers were washed with water and saturated brine, dried, and concentrated under reduced pressure. The resulting residues were purified by silica gel column chromatography (chloroform:methanol=100:0 to 95:5) to give the Compound 3 (158 mg) as a colorless powder. MS (APCI): m/z 825 [M+H]$^+$ (2) To a solution of the Compound 3 (110 mg) in dichloromethane (2 mL) was added trifluoroacetic acid (285 μL), and the resulting mixture was stirred at room temperature for 2 days. To the reaction mixture were added a saturated aqueous solution of sodium hydrogen carbonate and water, and the resulting mixture was stirred, and then extracted with chloroform. The resulting organic layers were dried, and then concentrated under reduced pressure. The resulting residues were purified by silica gel column chromatography (chloroform:methanol=100:0 to 90:10) to give ethyl 1-[2-({2-[({(3S,4R)-4-(2,4-difluorophenyl)-1-[(3S)-1,2,3,4-tetrahydroisoquinolin-3-ylacetyl]pyrrolidin-3-yl}carbonyl)amino]-1H-imidazol-1-yl}methyl)-5-methylphenyl]piperidine-4-carboxylate 4 (145 mg) as a colorless powder. MS (APCI): m/z 725 [M+H]$^+$

Example 4
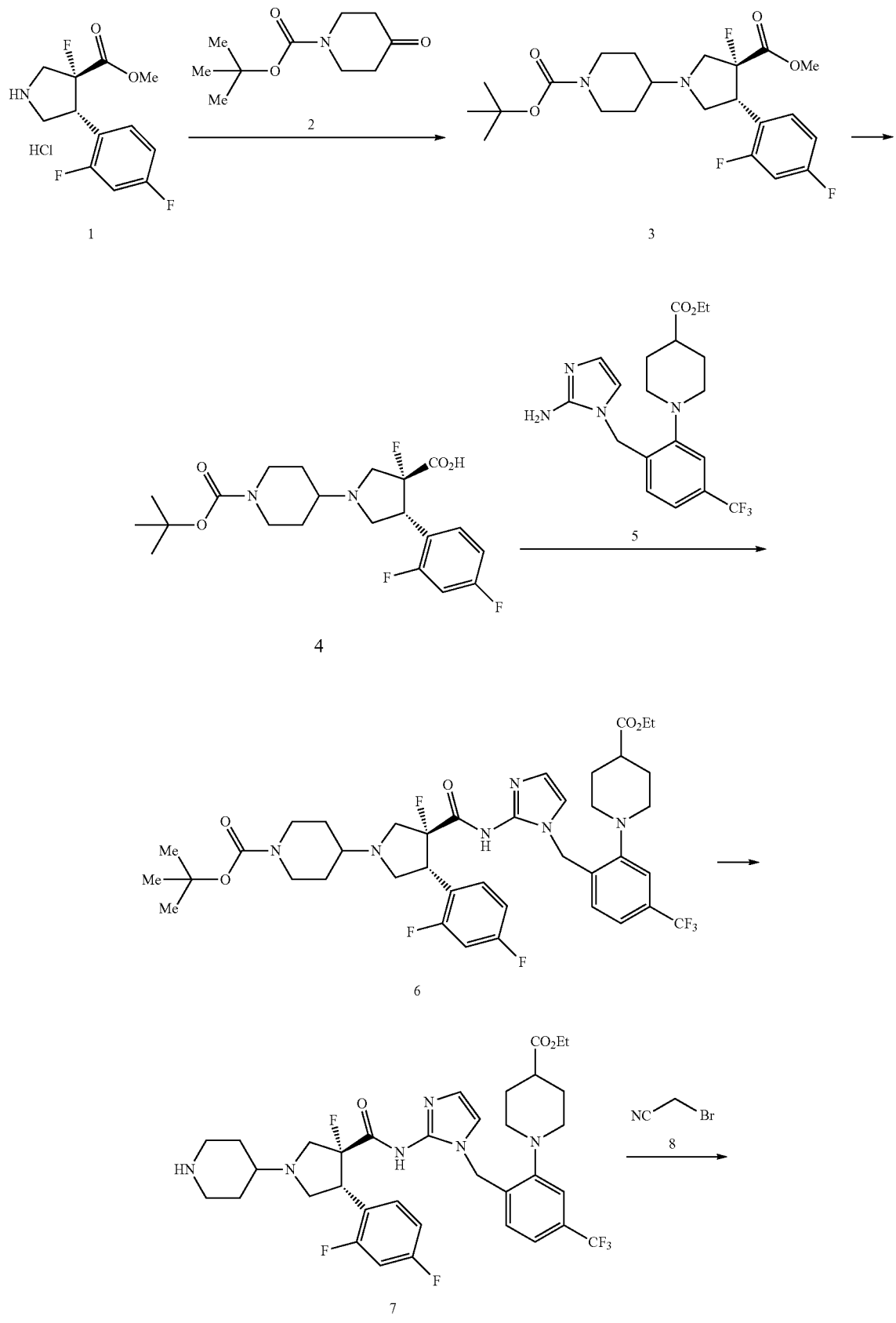

-continued

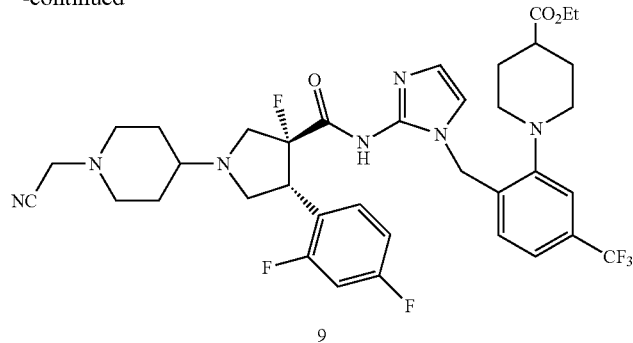

9

(1) To a suspension of the Compound 1 (1.18 g) in dichloromethane (15 mL) was added sodium acetate (492 mg), and the resulting mixture was stirred at room temperature for 30 minutes, and the Compound 2 (956 mg) was added thereto, and the resulting mixture was stirred for 30 minutes, and then sodium triacetoxyborohydride (76 mg) was added thereto, and the resulting mixture was stirred at the same temperature for 17 hours. To the reaction mixture were added a saturated aqueous solution of sodium hydrogen carbonate and water, and the resulting mixture was stirred, and then extracted with chloroform. The resulting organic layers were dried, and then concentrated under reduced pressure. The resulting residues were purified by silica gel column chromatography (hexane:ethyl acetate=90:10 to 60:40) to give the Compound 3 (1.83 g) as a colorless viscous material. MS (APCI): m/z 443 [M+H]$^+$ (2) To a solution of the Compound 3 (300 mg) in ethanol (2 mL) was added an aqueous solution of sodium hydroxide (2.0 mol/L, 680 µL), and the resulting mixture was stirred at room temperature for 17 hours. To the reaction mixture was added an aqueous solution of hydrochloric acid (2.0 mol/L, 680 µL), and the resulting mixture was stirred, and water and chloroform were added thereto, and the resulting mixture was stirred, and then the resulting organic layers were separated, and concentrated under reduced pressure to give the Compound 4 (300 mg) as a colorless powder. MS (APCI): m/z 429 [M+H]$^+$ (3) The Compound 4 (146 mg), the Compound 5 (111 mg), 1-ethyl-3-(3-dimethylaminopropyl)carbodiimide hydrochloride (81 mg), 1-hydroxy-7-azabenzotriazole (57 mg), and triethylamine (98 µL) were added to N,N-dimethylformamide (3 mL), and the resulting mixture was stirred at 50° C. for 20 hours. The reaction mixture was allowed to cool, and a saturated aqueous solution of sodium hydrogen carbonate, water, and ethyl acetate were added thereto, and the resulting mixture was stirred, and then extracted with ethyl acetate. The resulting organic layers were washed with water and saturated brine, dried, and concentrated under reduced pressure. The resulting residues were purified by silica gel column chromatography (chloroform:methanol=100:0 to 90:10) to give the Compound 6 (220.9 mg) as a pale yellow powder. MS (APCI): m/z 807 [M+H]$^+$ (4) To a solution of the Compound 6 (215 mg) in dichloromethane (2 mL) was added trifluoroacetic acid (1 mL), and the resulting mixture was stirred at room temperature for 1 hour. To the reaction mixture was added a saturated aqueous solution of sodium hydrogen carbonate, and the resulting mixture was stirred, then extracted with chloroform, dried, and concentrated under reduced pressure. To a solution of the resulting crude product in acetonitrile (2 mL) were added the Compound 8 (22 µL) and diisopropylethylamine (70 µL), and the resulting mixture was stirred at 80° C. for 65 hours. The reaction mixture was allowed to cool to room temperature, and water and chloroform were added thereto, and the resulting mixture was stirred, and then the resulting organic layers were separated, and concentrated under reduced pressure. The resulting residues were purified by silica gel column chromatography (chloroform:methanol=99:1 to 90:10) and NH silica gel column chromatography (chloroform:methanol=100:0 to 95:5) to give ethyl 1-[2-{[2-({[(3R,4R)-1-[1-(cyanomethyl)piperidin-4-yl]-4-(2,4-difluorophenyl)-3-fluoropyrrolidin-3-yl]carbonyl}amino)-1H-imidazol-1-yl]methyl}-5-(trifluoromethyl)phenyl]piperidine-4-carboxylate 9 (140.7 mg) as a pale yellow powder. MS (APCI): m/z 746 [M+H]$^+$ Example 5

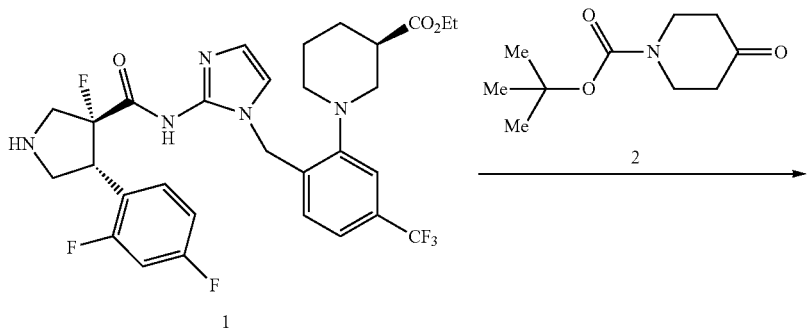

-continued

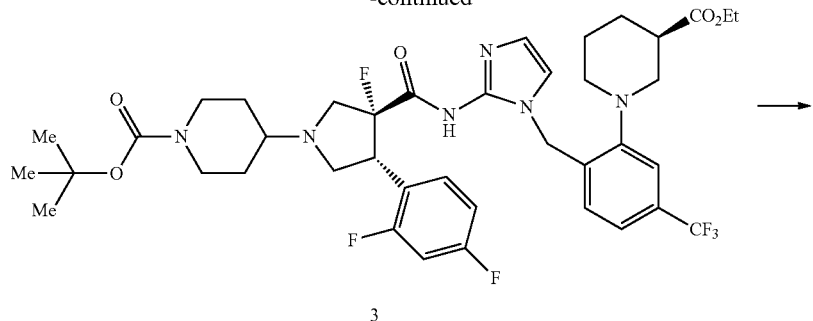

3

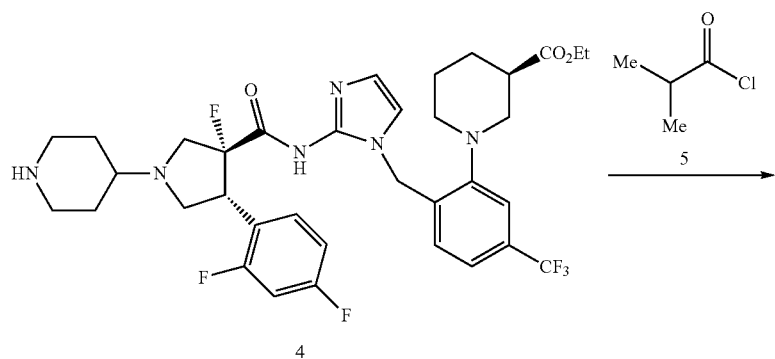

4

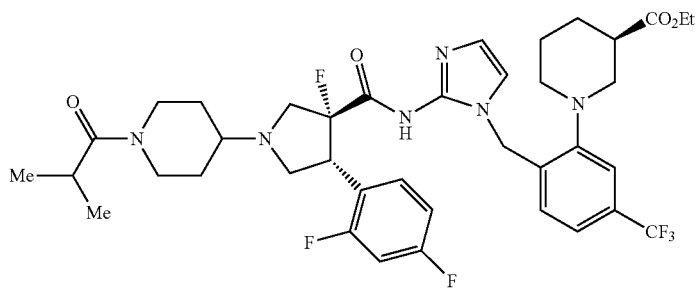

6

(1) To a solution of the Compound 1 (800 mg) and the Compound 2 (307 mg) in dichloromethane (5 mL) was added acetic acid (110 μL), and the resulting mixture was stirred at room temperature for 30 minutes, and then sodium triacetoxyborohydride (407 mg) was added thereto, and the resulting mixture was stirred at the same temperature for 15 hours. To the reaction mixture were added a saturated aqueous solution of sodium hydrogen carbonate and water, and the resulting mixture was stirred, and then extracted with chloroform. The resulting organic layers were dried, and then concentrated under reduced pressure. The resulting residues were purified by silica gel column chromatography (chloroform:methanol=99:1 to 95:5). To a solution of the resulting crude product in dichloromethane (3 mL) was added trifluoroacetic acid (2 mL), and the resulting mixture was stirred at room temperature for 1 hour. To the reaction mixture was added a saturated aqueous solution of sodium hydrogen carbonate, and the resulting mixture was stirred, then extracted with chloroform, dried, and concentrated under reduced pressure. The resulting residues were purified by NH silica gel column chromatography (chloroform:methanol=99:1 to 93:7) to give the Compound 4 (680 mg) as a pale yellow powder. MS (APCI): m/z 707 [M+H]$^+$ (2) To a solution of the Compound 4 (100 mg) and diisopropylethylamine (49 μL) in dichloromethane (2 mL) was added the Compound 5 (18 μL) under ice-cooling, and the resulting mixture was stirred at room temperature for 18 hours. To the reaction mixture were added water and chloroform, and the resulting mixture was stirred, and then the resulting organic layers were separated, dried, and concentrated under reduced pressure. The resulting residues were purified by silica gel column chromatography (chloroform:methanol=98:2 to 90:10) to give ethyl (3R)-1-[2-({2-[({(3R,4R)-4-(2,4-difluorophenyl)-3-fluoro-1-[1-(2-methylpropanoyl)piperidin-4-yl]pyrrolidin-3-yl}carbonyl)amino]-1H-imidazol-1-yl}methyl)-5-(trifluoromethyl)phenyl]piperidine-3-carboxylate 6 (99 mg) as a colorless powder. MS (APCI): m/z 777 [M+H]$^+$

Example 6

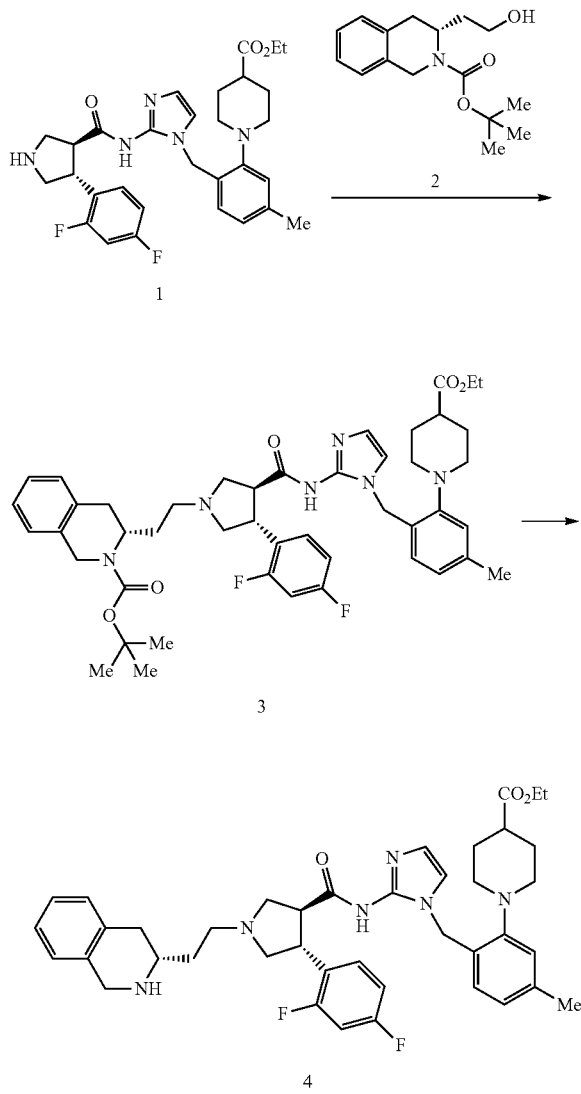

(1) To a solution of the Compound 2 (139 mg) and diisopropylethylamine (261 μL) in dichloromethane (1 mL) was added methanesulfonyl chloride (46 μL) under ice-cooling, and the resulting mixture was stirred at room temperature for 1 hour. To the reaction mixture was added water under ice-cooling, and the resulting mixture was stirred, then extracted with dichloromethane, dried, and then concentrated under reduced pressure. To a solution of the resulting crude product in acetonitrile (2 mL) were added the Compound 1 (139 mg) and diisopropylethylamine (261 μL), and the resulting mixture was stirred at 80° C. for 19 hours. The reaction mixture was allowed to cool to room temperature, and a saturated aqueous solution of sodium hydrogen carbonate, water, and chloroform were added thereto, and the resulting mixture was stirred, and then the resulting organic layers were separated, dried, and concentrated under reduced pressure. The resulting residues were purified by silica gel column chromatography (chloroform:methanol=100:0 to 94:6) and NH silica gel column chromatography (hexane:ethyl acetate=50:50 to 0:100) to give the Compound 3 (120 mg) as a colorless powder. MS (ESI): m/z 811 [M+H]$^+$ (2) To a solution of the Compound 3 (115 mg) in dichloromethane (2 mL) was added trifluoroacetic acid (218 μL), and the resulting mixture was stirred at room temperature for 15 hours. To the reaction mixture was added a saturated aqueous solution of sodium hydrogen carbonate, and the resulting mixture was stirred, and then extracted with chloroform. The resulting organic layers were dried, and then concentrated under reduced pressure. The resulting residues were purified by silica gel column chromatography (chloroform:methanol=99:1 to 93:7) to give ethyl 1-(2-{[2-({[(3S,4R)-4-(2,4-difluorophenyl)-1-{2-[(3R)-1,2,3,4-tetrahydroisoquinolin-3-yl]ethyl}pyrrolidin-3-yl]carbonyl}amino)-1H-imidazo-1-yl]methyl}-5-methylphenyl)piperidine-4-carboxylate 4 (95 mg) as a colorless powder. MS (APCI): m/z 711 [M+H]$^+$

Example 7

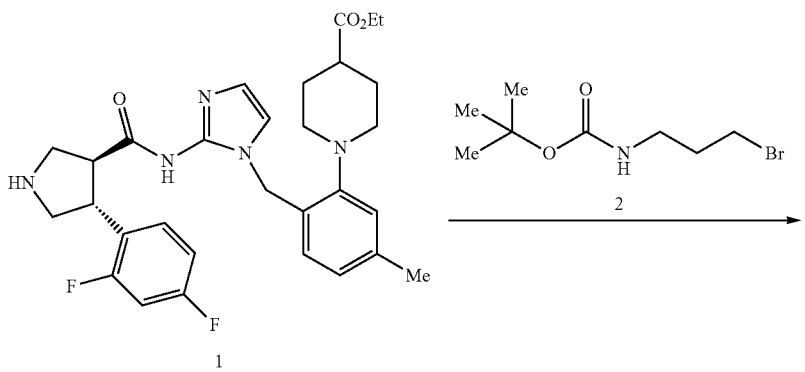

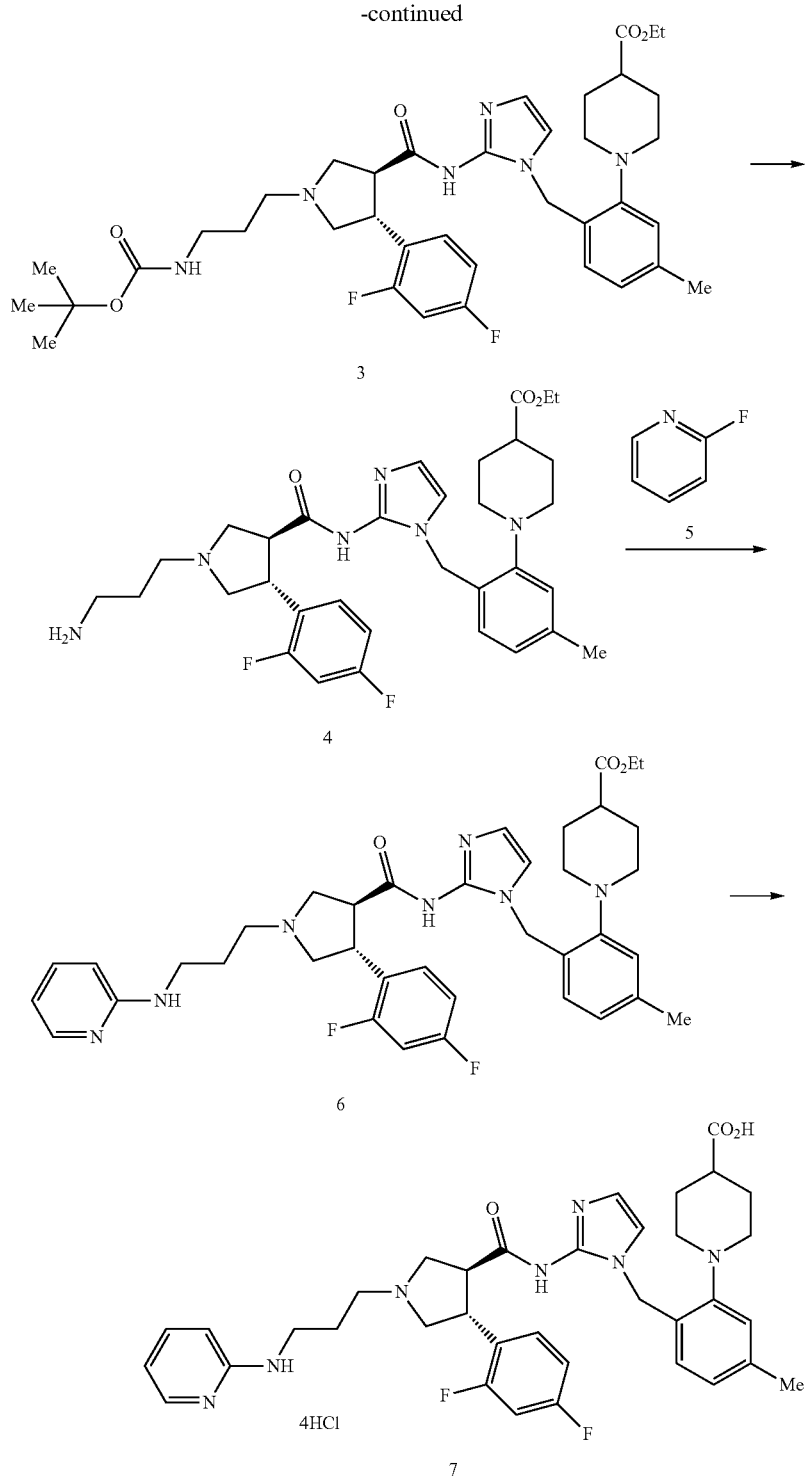

(1) A mixture of the Compound 1 (331 mg), the Compound 2 (143 mg), diisopropylethylamine (105 μL), and acetonitrile (2 mL) was stirred at 80° C. for 18 hours. The reaction mixture was allowed to cool to room temperature, and then a saturated aqueous solution of sodium hydrogen carbonate and water were added thereto, and the resulting mixture was stirred, and then extracted with chloroform. The resulting organic layers were dried, and then concentrated under reduced pressure. The resulting residues were purified by silica gel column chromatography (chloroform:methanol=100:0 to 90:10) to give the Compound 3 (358 mg) as a pale pink powder. MS (APCI): m/z 709 [M+H]$^+$ (2) To a solution of the Compound 3 (350 mg) in dichloromethane (2 mL) was added trifluoroacetic acid (380 μL), and the resulting mixture was stirred at room temperature for 69 hours. To the reaction mixture were added a saturated aqueous solution of sodium hydrogen carbonate and water, and the resulting mixture was stirred, and then extracted with chloroform. The resulting organic layers were dried, and then concentrated under reduced pressure. The resulting residues were purified by NH silica gel column chromatography (chloroform:methanol=100:0 to 90:10) to give the Compound 4 (259 mg) as a colorless powder. MS (APCI): m/z 609 [M+H]$^+$ (3) A mixture of the Compound 4 (80 mg), the Compound 5 (1 mL), and diisopropylethylamine (68 μL) was stirred at 120° C. for 20 hours. The reaction mixture was allowed to cool to room temperature, and then water and chloroform were added thereto, and the resulting mixture was stirred, and then the resulting organic layers were separated, dried, and concentrated under reduced pressure. The resulting residues were purified by silica gel column chromatography (chloroform:methanol=97:3 to 60:40). To a solution of the resulting compound in ethanol (2 mL) was added an aqueous solution of sodium hydroxide (2 mol/L, 86 μL), and the resulting mixture was stirred at room temperature for 14 hours. An aqueous solution of sodium hydroxide (2 mol/L, 86 μL) was further added thereto, and the resulting mixture was stirred at 40° C. for 3 hours. The reaction mixture was allowed to cool to room temperature, and an aqueous solution of hydrochloric acid (2 mol/L, 172 μL) was added thereto, and the resulting mixture was stirred, then extracted with chloroform, dried, and concentrated under reduced pressure. The resulting residues were purified by silica gel column chromatography (chloroform:methanol=98:2 to 70:30). The resulting compound was dissolved into a dichloromethane/diethyl ether solution, and a solution of hydrochloric acid in ethyl acetate (4 mol/L, 100 μL) was added thereto, and the resulting mixture was stirred. The resulting precipitates were collected by filtration, and dried under reduced pressure to give 1-[2-({2-[({(3S,4R)-4-(2,4-difluorophenyl)-1-[3-(pyridine-2-ylamino)propyl]pyrrolidin-3-yl}carbonyl)amino]-1H-imidazol-1-yl}methyl)-5-methylphenyl]piperidine-4-carboxylic acid tetrahydrochloride 7 (28.8 mg) as a colorless powder. MS (APCI): m/z 658 [M+H]$^+$ Example 8

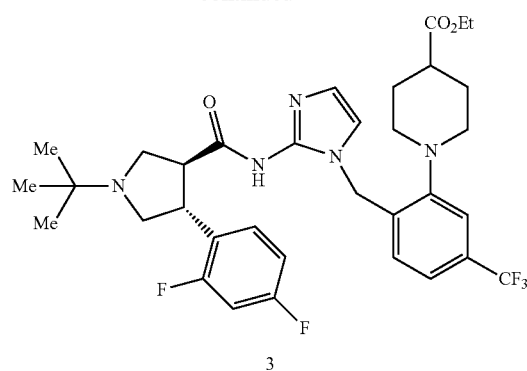

3

The Compound 1 (142 mg) synthesized according to the methods described in documents (*J. Org. Chem.* 2005, 70, 3592-3601 and WO2004/92126), the Compound 2 (198 mg), 1-ethyl-3-(3-dimethylaminopropyl)carbodiimide hydrochloride (115 mg), and 1-hydroxy-7-azabenzotriazole (82 mg) were added to N,N-dimethylformamide (3 mL), and the resulting mixture was stirred at 40° C. for 14 hours. The Compound 1 (70 mg), 1-ethyl-3-(3-dimethylaminopropyl)carbodiimide hydrochloride (60 mg), and 1-hydroxy-7-azabenzotriazole (40 mg) were further added thereto, and the resulting mixture was stirred at 50° C. for 3 hours. The reaction mixture was allowed to cool to room temperature, and a saturated aqueous solution of sodium hydrogen carbonate, water, and ethyl acetate were added thereto, and the resulting mixture was stirred, and then extracted with ethyl acetate. The resulting organic layers were washed with water and saturated brine, dried, and concentrated under reduced pressure. The resulting residues were purified by silica gel column chromatography (chloroform:methanol=98:2 to 75:25) and NH silica gel column chromatography (chloroform:methanol=100:0 to 98:2) to give ethyl 1-[2-{[2-({[(3S,4R)-1-tert-butyl-4-(2,4-difluorophenyl)pyrrolidin-3-yl]carbonyl}amino)-1H-imidazol-1-yl]methyl}-5-(trifluoromethyl)phenyl]piperidine-4-carboxylate 3 (280 mg) as a pale yellow powder. MS (APCI): m/z 662 [M+H]$^+$ Example 9

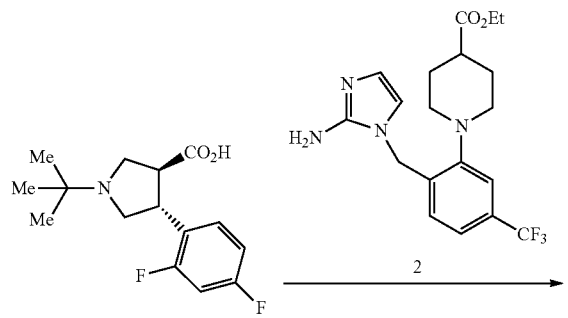

1

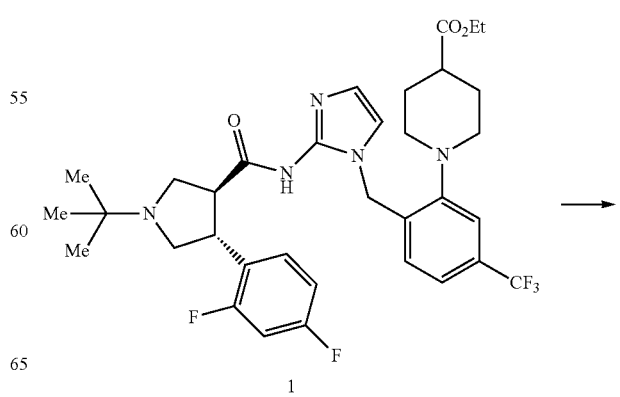

1

-continued

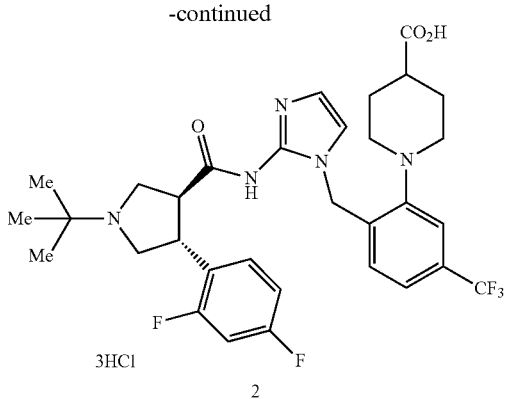

2

3HCl

To a solution of the Compound 1 (260 mg) in ethanol (6 mL) was added an aqueous solution of sodium hydroxide (2 mol/L, 420 μL), and the resulting mixture was stirred at room temperature for 15 hours. An aqueous solution of sodium hydroxide (2 mol/L, 210 μL) was further added thereto, and the resulting mixture was stirred at 35° C. for 4 hours. An aqueous solution of sodium hydroxide (2 mol/L, 100 μL) was further added thereto, and the resulting mixture was stirred at 35° C. for 3 hours. The reaction mixture was allowed to cool to room temperature, and an aqueous solution of hydrochloric acid (2 mol/L, 730 μL) was added thereto, and the resulting mixture was stirred, then extracted with ethyl acetate, dried, and concentrated under reduced pressure. The resulting mixture was powdered with ethyl acetate/diisopropyl ether, and collected by filtration, and dried under reduced pressure. The resulting compound was dissolved into an ethyl acetate/diethyl ether solution, and an excess amount of a solution of hydrochloric acid in ethyl acetate (4 mol/L) was added thereto, and the resulting mixture was stirred. The resulting precipitates were collected by filtration, and dried under reduced pressure to give 1-[2-{[2-({[(3S,4R)-1-tert-butyl-4-(2,4-difluorophenyl)pyrrolidin-3-yl]carbonyl}amino)-1H-imidazol-1-yl]methyl}-5-(trifluoromethyl)phenyl]piperidine-4-carboxylic acid trihydrochloride 2 (186 mg) as a colorless powder. MS (APCI): m/z 634 [M+H]$^+$ Examples 10 to 20

Each corresponding starting compound was treated in a similar manner to the above Example 1 and subsequently Example 9 to give each compound described in the following Table 1.

TABLE 1

| Example | Compound | Salt MS |
|---|---|---|
| 10 | ![structure] | 3 HCl (APCI): m/z 594 [M + H]$^+$ |
| 11 | ![structure] | 3 HCl (APCI): m/z 642 [M + H]$^+$ |

TABLE 1-continued

| Example | Compound | Salt MS |
|---|---|---|
| 12 | (structure) | 3 HCl (APCI): m/z 678 [M + H]⁺ |
| 13 | (structure) | 3 HCl (APCI): m/z 656 [M + H]⁺ |
| 14 | (structure) | (APCI): m/z 666 [M + H]⁺ |
| 15 | (structure) | (APCI): m/z 650 [M + H]⁺ |

TABLE 1-continued

| Example | Compound | Salt MS |
|---|---|---|
| 16 | | (APCI): m/z 664 [M + H]⁺ |
| 17 | | (APCI): m/z 652 [M + H]⁺ |
| 18 | | (APCI): m/z 638 [M + H]⁺ |
| 19 | | (APCI): m/z 710 [M + H]⁺ |

TABLE 1-continued

| Example | Compound | Salt MS |
|---|---|---|
| 20 | (structure) | 2 HCl (APCI): m/z 632 [M + H]⁺ |

Examples 21 to 28

Each corresponding starting compound was treated in a similar manner to the above Example 2 and subsequently Example 9 to give each compound described in the following Table 2.

TABLE 2

| Example | Compound | Salt MS |
|---|---|---|
| 21 | (structure) | 4 HCl (APCI): m/z 629 [M + H]⁺ |
| 22 | (structure) | 3 HCl (APCI): m/z 658 [M + H]⁺ |

TABLE 2-continued

| Example | Compound | Salt MS |
|---|---|---|
| 23 | | 4 HCl (APCI): m/z 649 [M + H]⁺ |
| 24 | | 3 HCl (APCI): m/z 709 [M + H]⁺ |
| 25 | | (APCI): m/z 663 [M + H]⁺ |
| 26 | | 3 HCl (APCI): m/z 771 [M + H]⁺ |

TABLE 2-continued

| Example | Compound | Salt MS |
|---|---|---|
| 27 | (structure) | 3 HCl (APCI): m/z 792 [M + H]⁺ |
| 28 | (structure, racemate, trans) | 3 HCl (APCI): m/z 759 [M + H]⁺ |

Example 29

A corresponding starting compound was treated in a similar manner to the above Example 3 and subsequently Example 9 to give the compound described in the following Table 3.

Example 30

A corresponding starting compound was treated in a similar manner to the above Example 4 and subsequently Example 9 to give the compound described in the following Table 4.

TABLE 3

| Example | Compound | Salt MS |
|---|---|---|
| 29 | (structure) | 3 HCl (APCI): m/z 697 [M + H]⁺ |

TABLE 4

| Example | Compound | MS |
|---|---|---|
| 30 | (structure) | (APCI): m/z 718 [M + H]⁺ |

Example 31

A corresponding starting compound was treated in a similar manner to the above Example 5 and subsequently Example 9 to give the compound described in the following Table 5.

TABLE 5

| Example | Compound | MS |
|---|---|---|
| 31 | (structure) | (APCI): m/z 749 [M + H]⁺ |

Examples 32 to 33

Each corresponding starting compound was treated in a similar manner to the above Example 6 and subsequently Example 9 to give each compound described in the following Table 6.

TABLE 6

| Example | Compound | Salt MS |
|---|---|---|
| 32 | (structure) | 4 HCl (APCI): m/z 683 [M + H]⁺ |

TABLE 6-continued

| Example | Compound | Salt | MS |
|---|---|---|---|
| 33 | 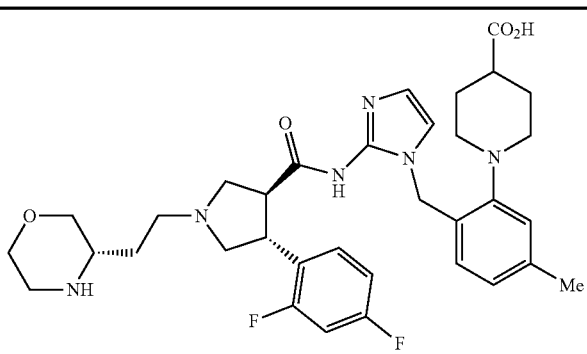 | 4 HCl | (APCI): m/z 637 [M + H]⁺ |

Example 34

A corresponding starting compound was treated in a similar manner to the above Example 7 and subsequently Example 9 to give the compound described in the following Table 7.

TABLE 7

| Example | Compound | Salt | MS |
|---|---|---|---|
| 34 | 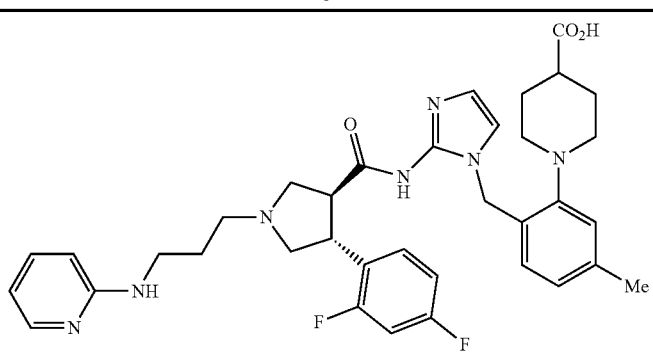 | 4 HCl | (APCI): m/z 658 [M + H]⁺ |

Examples 35 to 54

Each corresponding starting compound was treated in a similar manner to the above Example 8 and subsequently Example 9 to give each compound described in the following Table 8.

TABLE 8

| Example | Compound | Salt | MS |
|---|---|---|---|
| 35 | 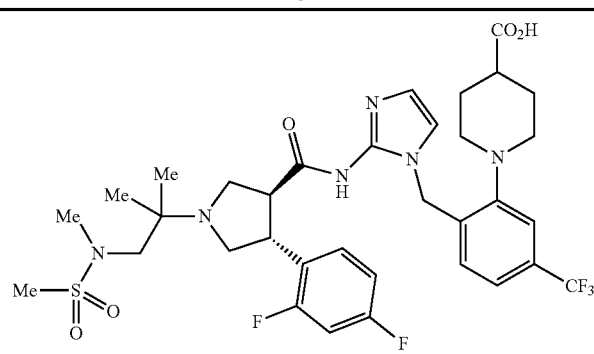 | 3 HCl | (APCI): m/z 741 [M + H]⁺ |

TABLE 8-continued

| Example | Compound | Salt MS |
|---|---|---|
| 36 | (structure) | (APCI): m/z 652 [M + H]⁺ |
| 37 | (structure) racemate | (APCI): m/z 664 [M + H]⁺ |
| 38 | (structure) | (APCI): m/z 757 [M + H]⁺ |
| 39 | (structure) | (APCI): m/z 616 [M + H]⁺ |

TABLE 8-continued

| Example | Compound | Salt MS |
|---|---|---|
| 40 | | (APCI): m/z 626 [M + H]⁺ |
| 41 | | (APCI): m/z 624 [M + H]⁺ |
| 42 | | 3 HCl (APCI): m/z 666 [M + H]⁺ |
| 43 | | 3 HCl (APCI): m/z 634 [M + H]⁺ |

TABLE 8-continued

| Example | Compound | Salt MS |
|---|---|---|
| 44 | (structure) | 3 HCl (APCI): m/z 634 [M + H]⁺ |
| 45 | (structure) | 3 HCl (APCI): m/z 612 [M + H]⁺ |
| 46 | (structure) | 3 HCl (APCI): m/z 626 [M + H]⁺ |
| 47 | (structure) | 2 HCl (APCI): m/z 651 [M + H]⁺ |

TABLE 8-continued

| Example | Compound | Salt MS |
|---|---|---|
| 48 | (structure) | 3 HCl (APCI): m/z 634 [M + H]⁺ |
| 49 | (structure) | 3 HCl (APCI): m/z 608 [M + H]⁺ |
| 50 | (structure) | 3 HCl (ESI): m/z 646 [M + H]⁺ |
| 51 | (structure) | 3 HCl (ESI): m/z 646 [M + H]⁺ |

TABLE 8-continued
| Example | Compound | Salt MS |
|---|---|---|
| 52 | 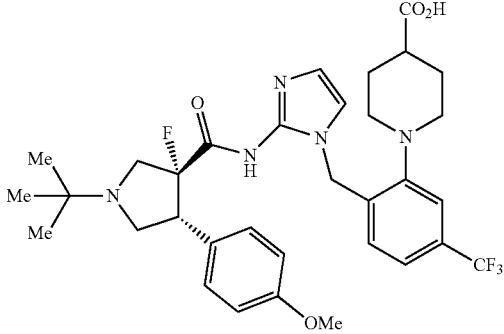 [SMILES: COc1ccc([C@@H]2CN(C(C)(C)C)C[C@@]2(F)C(=O)Nc2nccn2Cc2ccc(C(F)(F)F)cc2N2CCC(C(=O)O)CC2)cc1] | 3 HCl (ESI): m/z 646 [M + H]+ |
| 53 | 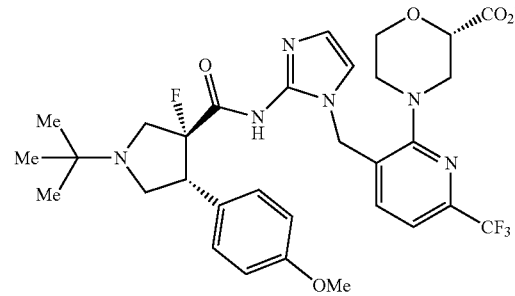 | 3 HCl (ESI): m/z 649 [M + H]+ |
| 54 | 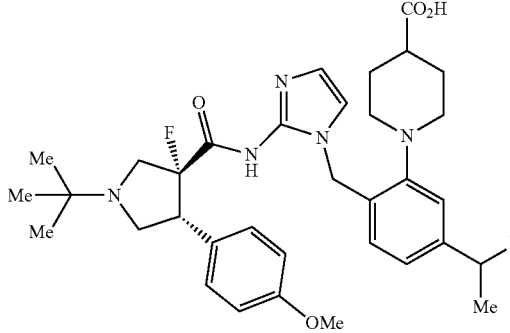 | 3 HCl (APCI): m/z 620 [M + H]+ |
Example 55
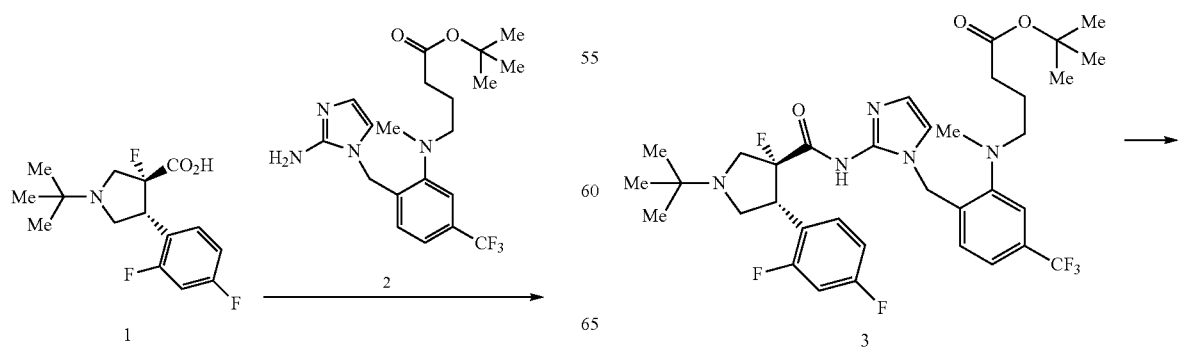

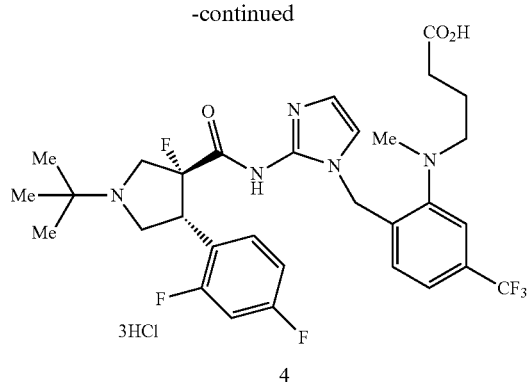

(1) The Compound 1 (150 mg), the Compound 2 (205 mg), 1-ethyl-3-(3-dimethylaminopropyl)carbodiimide hydrochloride (143 mg), and 1-hydroxy-7-azabenzotriazole (101 mg) were added to N,N-dimethylformamide (5 mL), and the resulting mixture was stirred at room temperature overnight. To the reaction mixture was added water, and the resulting mixture was stirred, and extracted with ethyl acetate. The resulting organic layers were washed with water and saturated brine, dried, and concentrated under reduced pressure. The resulting residues were purified by silica gel column chromatography (chloroform:methanol=100:0 to 90:10) to give the Compound 3 (230 mg) as a pale brown powder. MS (APCI): m/z 696 [M+H]$^+$ (2) To a solution of the Compound 3 (230 mg) in dichloromethane (1 mL) was added trifluoroacetic acid (1 mL), and the resulting mixture was stirred at room temperature for 1 hour. The reaction mixture was concentrated under reduced pressure, then dissolved into dichloromethane again, and a solution of hydrochloric acid in ethyl acetate was added thereto, and the resulting mixture was stirred, and then concentrated under reduced pressure. The resulting concentrated residues were dissolved into a small amount of dichloromethane, and diethyl ether was added dropwise thereto with stirring, and the resulting precipitates were collected by filtration, and dried under reduced pressure to give 4-{[2-{[2-({[(3R,4R)-1-tert-butyl-4-(2,4-difluorophenyl)-3-fluoropyrrolidin-3-yl]carbonyl}amino)-1H-imidazol-1-yl]methyl}-5-(trifluoromethyl)phenyl](methyl) amino}butanoic acid trihydrochloride 4 (198 mg) as a colorless powder. MS (APCI): m/z 640 [M+H]$^+$ Example 56

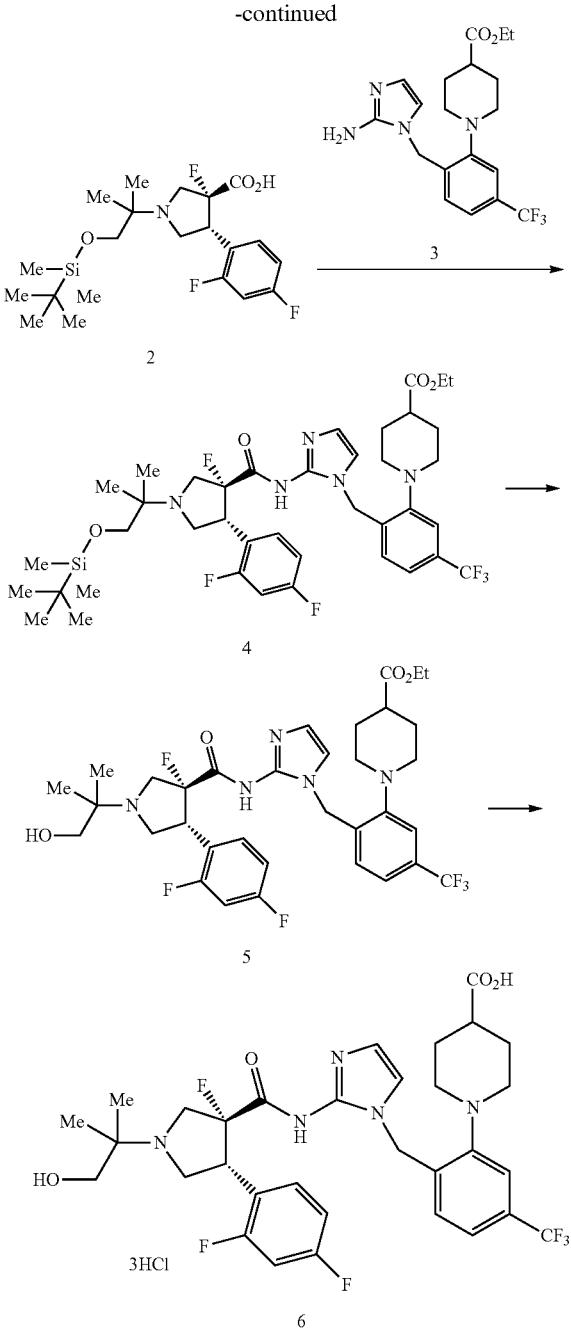

(1) To a solution of the Compound 1 (45 mg) in methanol (2 mL) was added an aqueous solution of sodium hydroxide (2 mol/L, 100 μL), and the resulting mixture was stirred at 40° C. for 3 hours. The reaction mixture was allowed to cool to room temperature, and then an aqueous solution of hydrochloric acid (2 mol/L, 100 μL) was added thereto, and the resulting mixture was stirred, and water and chloroform were added thereto, and the resulting mixture was stirred, and then the resulting organic layers were separated, and concentrated under reduced pressure. To a solution of the resulting crude product in N,N-dimethylformamide (2 mL) were added the Compound 3 (48 mg), 1-ethyl-3-(3-dimethylaminopropyl)carbodiimide hydrochloride (29 mg), 1-hydroxy-7-azabenzotriazole (20 mg), and triethylamine (42 μL), and the resulting mixture was stirred at 50° C. for 6 hours. The reaction mixture was allowed to cool to room temperature, and an aqueous solution of sodium hydrogen carbonate and ethyl acetate were added thereto, and the resulting mixture was stirred, and then extracted with ethyl acetate. The resulting organic layers were washed with water and saturated brine, dried, and concentrated under reduced pressure. The resulting residues were purified by silica gel column chromatography (chloroform:methanol=100:0 to 95:5) to give the Compound 4 (62 mg) as a pale yellow viscous material. MS (APCI): m/z 810 [M+H]$^+$ (2) To a solution of the Compound 4 (60 mg) in 1,4-dioxane (1 mL) was added a solution of hydrochloric acid in 1,4-dioxane (1 mL), and the resulting mixture was stirred at room temperature for 7 hours. The reaction mixture was concentrated under reduced pressure, and then a saturated aqueous solution of sodium hydrogen carbonate was added thereto, and the resulting mixture was stirred, and extracted with chloroform. The resulting organic layers were dried, and then concentrated under reduced pressure. To a solution of the resulting concentrated residues in ethanol (1 mL) was added an aqueous solution of sodium hydroxide (2 mol/L, 148 μL), and the resulting mixture was stirred at room temperature for 2 hours. An aqueous solution of sodium hydroxide (2 mol/L, 148 μL) was further added thereto, and the resulting mixture was stirred at room temperature for 1 hour. To the reaction mixture was added an aqueous solution of hydrochloric acid (2 mol/L, 296 μL), and the resulting mixture was stirred, and then water and chloroform were added thereto, and the resulting mixture was stirred, and the resulting organic layers were separated, then dried, and concentrated under reduced pressure. The resulting residues were purified by silica gel column chromatography (chloroform:methanol=97:3 to 60:40). The resulting compound was dissolved into dichloromethane, and a solution of hydrochloric acid in ethyl acetate (4 mol/L, 56 μL) was added thereto, and the resulting mixture was stirred, and then concentrated under reduced pressure. The resulting mixture was powdered with diethyl ether, collected by filtration, and then dried under reduced pressure to give 1-[2-{[2-({[(3R,4R)-4-(2,4-difluorophenyl)-3-fluoro-1-(1-hydroxy-2-methylpropan-2-yl)pyrrolidin-3-yl]carbonyl}amino)-1H-imidazol-1-yl]methyl}-5-(trifluoromethyl)phenyl]piperidine-4-carboxylic acid trihydrochloride 6 (35 mg) as a colorless powder. MS (APCI): m/z 668 [M+H]$^+$ Example 57

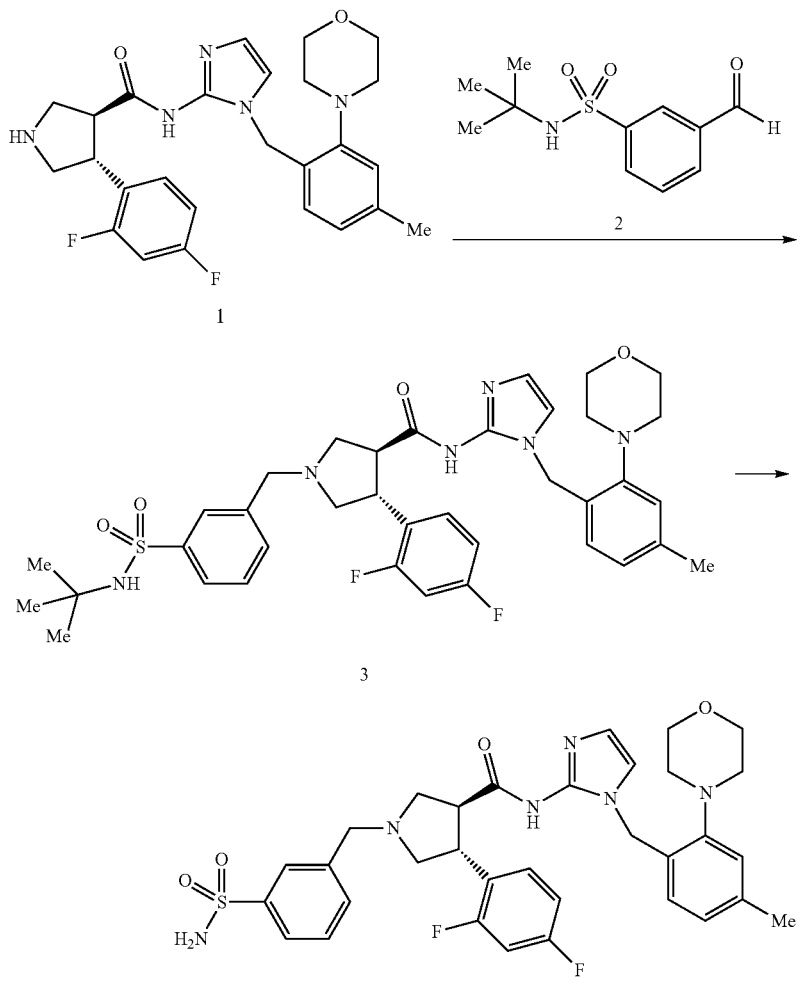

(1) The Compound 1 (150 mg) and the Compound 2 (75 mg) were treated in a similar manner to the above Example 1 to give the Compound 3 (199 mg) as a colorless powder. MS (APCI): m/z 707 [M+H]+

(2) The Compound 3 (185 mg) and trifluoroacetic acid (3 mL) were heated under reflux for 1 hour. The reaction mixture was allowed to cool to room temperature, and a saturated aqueous solution of sodium hydrogen carbonate was added thereto to alkalify the mixture, and then the resulting mixture was extracted with chloroform. The resulting organic layers were dried, and then concentrated under reduced pressure, and the resulting residues were purified by silica gel column chromatography (chloroform:methanol=100:0 to 90:10) to give (3S,4R)-4-(2,4-difluorophenyl)-N-{1-[4-methyl-2-(morpholin-4-yl)benzyl]-1H-imidazol-2-yl}-1-(3-sulfamoylbenzyl)pyrrolidine-3-carboxamide 4 (170 mg) as a colorless powder. MS (APCI): m/z 651 [M+H]+

Examples 58 to 62

Each corresponding starting compound was treated in a similar manner to the above Example 2 to give each compound described in the following Table 9. As needed, to a solution of the resulting compound in dichloromethane was added an excess amount of a solution of hydrochloric acid in ethyl acetate (4 mol/L), and then the reaction mixture was concentrated under reduced pressure, and the resulting residues were powdered with diisopropyl ether or the like, collected by filtration, and dried under reduced pressure to give each hydrochloride compound in the following Table 9.

TABLE 9

| Example | Compound | Salt MS |
|---|---|---|
| 58 | | (APCI): m/z 549 [M + H]+ |
| 59 | | 3 HCl (APCI): m/z 622 [M + H]+ |
| 60 | | 3 HCl (APCI): m/z 629 [M + H]+ |

TABLE 9-continued
| Example | Compound | Salt MS |
|---|---|---|
| 61 | 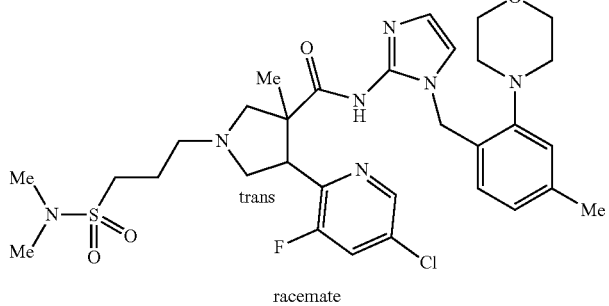 racemate | (APCI): m/z 662/664 [M + H]⁺ |
| 62 | 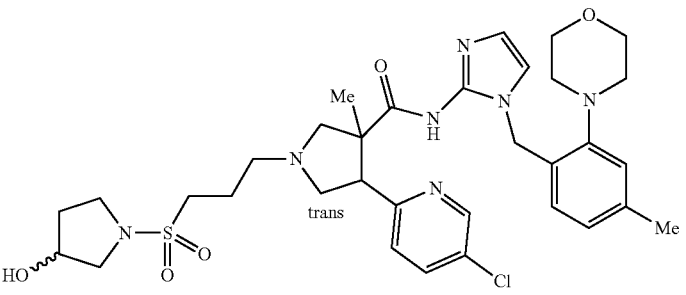 mixture of diastereomers | (APCI): m/z 686/688 [M + H]⁺ |
Example 63
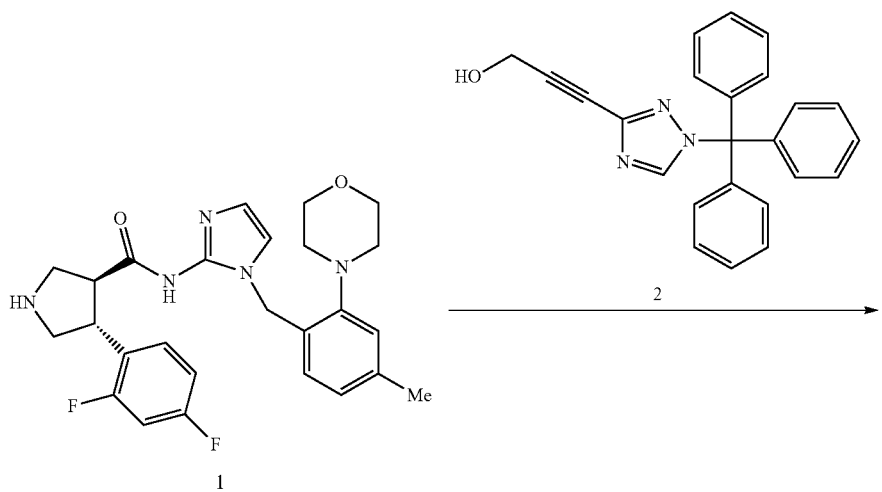

-continued

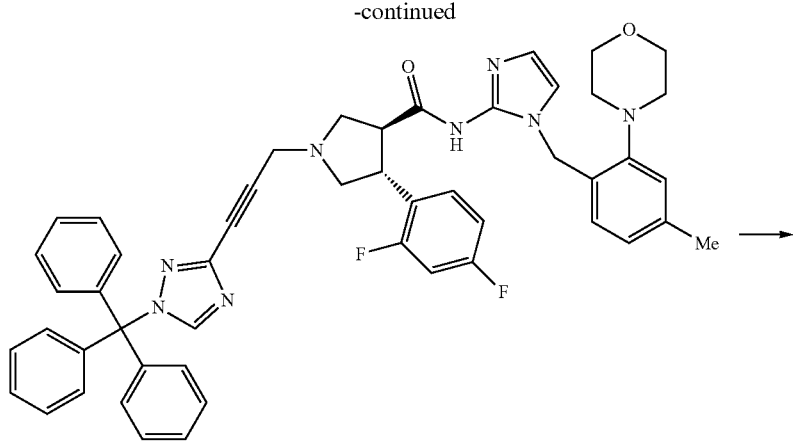

3

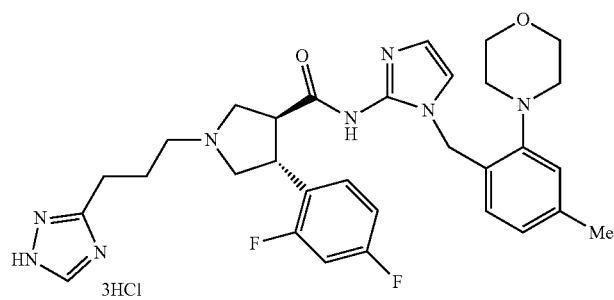

4

(1) The Compound 1 (439 mg) and the Compound 2 (500 mg) synthesized according to the methods described in documents (*Pesticide Science,* 1997, 50, 297-311 and U.S. Pat. No. 5,393,732A1) were treated in a similar manner to the above Example 6 to give the Compound 3 (372 mg) as a colorless powder. MS (APCI): m/z 829 [M+H]$^+$ (2) To a solution of the Compound 3 (230 mg) in methanol (6 mL) was added 10% palladium carbon (wetted with ca. 50% water, 600 mg), and the resulting mixture was stirred under hydrogen atmosphere (1 atm) for 5 hours. After nitrogen replacement, 10% palladium carbon (wetted with ca. 50% water, 500 mg) was further added thereto, and the resulting mixture was stirred under hydrogen atmosphere (1 atm) for 1.5 hours. Palladium carbon was removed by filtration, and the resulting filtrate was concentrated under reduced pressure. The resulting residues were purified by NH silica gel column chromatography (chloroform:methanol=99:1 to 85:15) and diol silica gel column chromatography (chloroform:methanol=99:1 to 90:10). The resulting compound was dissolved into chloroform/diethyl ether, and an excess amount of a solution of hydrochloric acid in ethyl acetate (4 mol/L) was added thereto, and the resulting mixture was stirred. The resulting mixture was powdered with diethyl ether, collected by filtration, and then dried under reduced pressure to give (3S,4R)-4-(2,4-difluorophenyl)-N-{1-[4-methyl-2-(morpholin-4-yl)benzyl]-1H-imidazol-2-yl}-1-[3-(1H-1,2,4-triazol-3-yl)propyl]pyrrolidine-3-carboxamide trihydrochloride 4 (78 mg) as a colorless powder. MS (APCI): m/z 591 [M+H]$^+$ Example 64

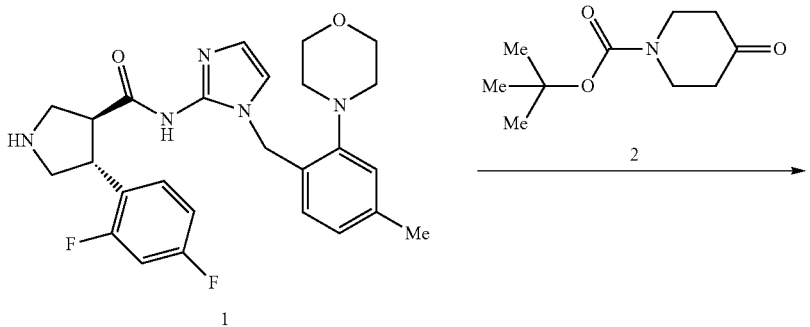

1

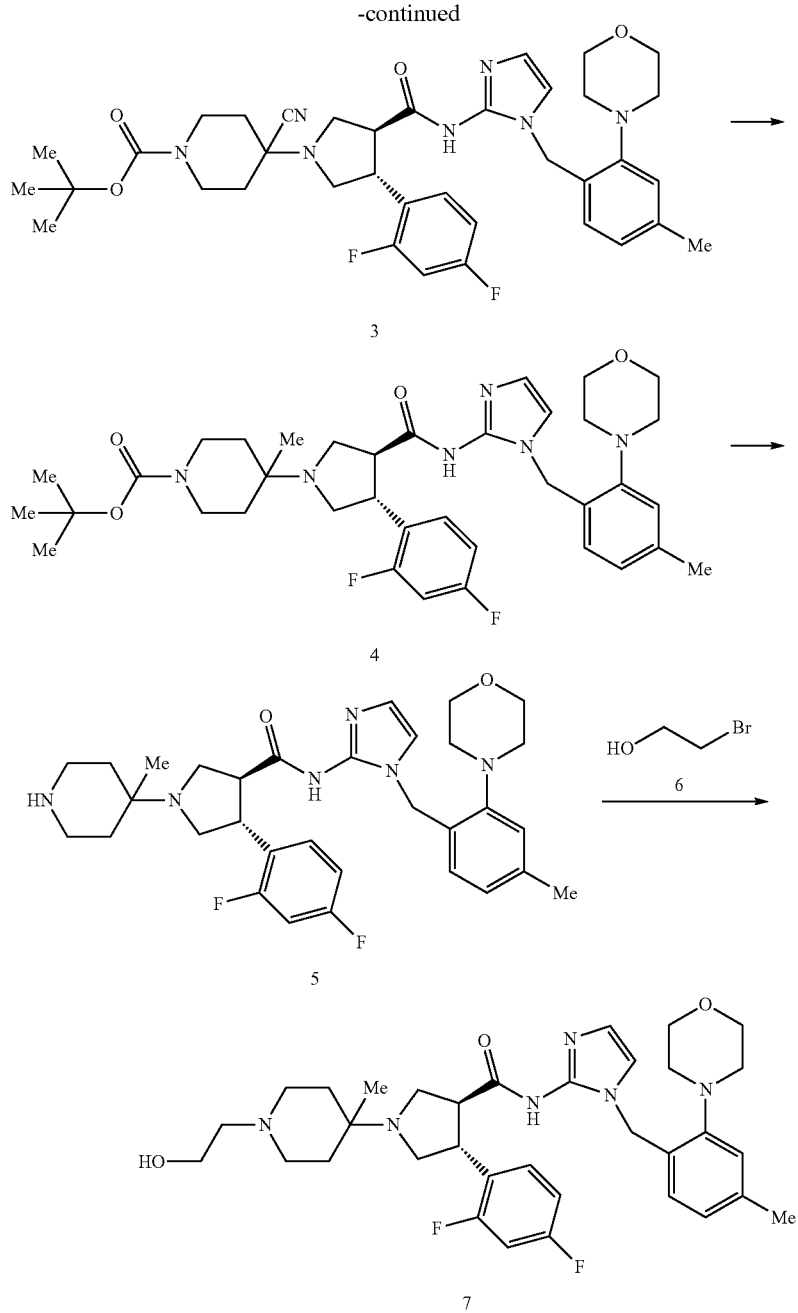

(1) To a solution of the Compound 1 (300 mg) in methanol (5 mL)/water (5 mL) was added an aqueous solution of hydrochloric acid (1 mol/L, 620 μL), and then the Compound 2 (124 mg) and a solution of sodium cyanide (35 mg) in water (1 mL) were added thereto, and the resulting mixture was stirred at 30° C. for 2 hours, and stirred at room temperature for 87 hours. The reaction mixture was concentrated under reduced pressure, and extracted with ethyl acetate. The resulting organic layers were washed with water and saturated brine, dried, and concentrated under reduced pressure. The resulting residues were purified by NH silica gel column chromatography (hexane:ethyl acetate=60:40 to 0:100) to give the Compound 3 (350 mg) as a colorless liquid. MS (APCI): m/z 690 [M+H]$^+$ (2) To a solution of the Compound 3 (227 mg) in tetrahydrofuran (10 mL) was added dropwise a solution of methylmagnesium bromide in toluene/tetrahydrofuran (1.4 mol/L, 2.27 mL), and the resulting mixture was stirred at room temperature for 1.5 hours. The mixture was combined with a reaction solution of another lot obtained by a similar process, and then an aqueous solution of ammonium chloride was added thereto, and the resulting mixture was stirred, and extracted with ethyl acetate. The resulting organic layers were washed with water and saturated brine, dried, and concentrated under reduced pressure. The resulting residues were purified by NH silica gel column chromatography (hexane:ethyl acetate=80:20 to 35:65) to give the Compound 4 (216 mg) as a colorless liquid. MS (APCI): m/z 679 [M+H]$^+$ (3) To a solution of the Compound 4 (216 mg) in dichloromethane (6 mL) was added trifluoroacetic acid (1 mL), and the resulting mixture was stirred at room temperature for 1 hour. The reaction mixture was concentrated under reduced pressure, and then an aqueous solution of potassium carbonate was added thereto to alkalify the mixture, and the resulting mixture was extracted with chloroform. The resulting organic layers were washed with saturated brine, dried, and concentrated under reduced pressure to give a brown powder (158 mg). To a solution of the resulting compound (50 mg) and the Compound 6 (7.4 μL) in acetonitrile (2 mL) was added diisopropylethylamine (30 μL), and the resulting mixture was stirred at 90° C. for 16 hours. The reaction mixture was concentrated under reduced pressure, and chloroform and water were added thereto, and the resulting mixture was stirred, and then the resulting organic layers were separated, and concentrated under reduced pressure. The resulting residues were purified by HPLC preparative isolation to give (3S,4R)-4-(2,4-difluorophenyl)-1-[1-(2-hydroxyethyl)-4-methylpiperidin-4-yl]-N-{1-[4-methyl-2-(morpholin-4-yl)benzyl]-1H-imidazol-2-yl}pyrrolidine-3-carboxamide 7 (27.9 mg) as a colorless solid. MS (APCI): m/z 623 [M+H]⁺

Example 65

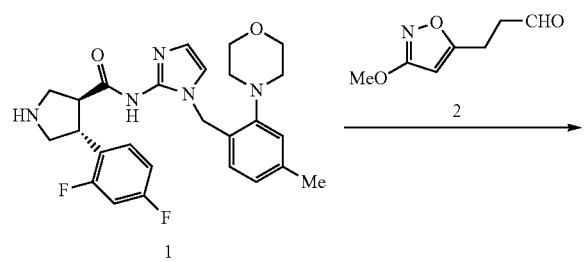

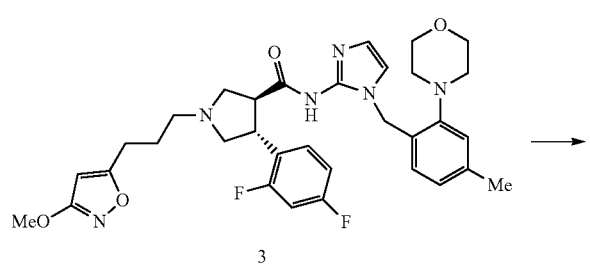

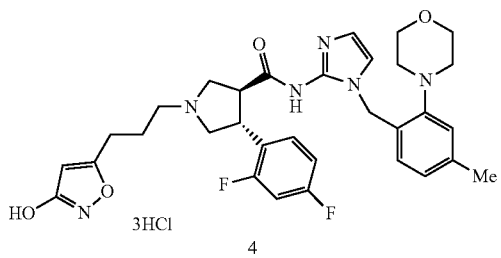

(1) The Compound 1 (248 mg) and the Compound 2 (80 mg) were treated in a similar manner to the above Example 1 to give the Compound 3 (97 mg) as a colorless powder. MS (APCI): m/z 621 [M+H]⁺

(2) A mixture of the Compound 3 (82 mg) and a solution of 25% hydrogen bromide/acetic acid in water (3 mL) was stirred at 110° C. for 1 hour. The reaction mixture was concentrated under reduced pressure, and then the resulting residues were subjected to azeotropic concentration with toluene. The resulting residues were diluted with chloroform and water, and then an aqueous solution of sodium hydrogen carbonate was added thereto until the pH of the mixture became 4, and the resulting mixture was extracted with chloroform. The resulting organic layers were dried, and then concentrated under reduced pressure. The resulting residues were purified by silica gel column chromatography (chloroform:methanol=99:1 to 85:15) and diol silica gel column chromatography (chloroform:methanol=100:0 to 97:3). The resulting compound was dissolved into dichloromethane, and then a solution of hydrochloric acid in 1,4-dioxane (4 mol/L, 60 μL) was added thereto, and the resulting mixture was stirred, and concentrated under reduced pressure. The resulting residues were powdered with diethyl ether, collected by filtration, and dried under reduced pressure to give (3S,4R)-4-(2,4-difluorophenyl)-1-[3-(3-hydroxyisoxazol-5-yl)propyl]-N-{1-[4-methyl-2-(morpholin-4-yl)benzyl]-1H-imidazol-2-yl}pyrrolidine-3-carboxamide trihydrochloride 4 (44.4 mg) as a colorless solid. MS (APCI): m/z 607 [M+H]⁺

Example 66

A corresponding starting compound was treated in a similar manner to the above Example 4, and the resulting compound was dissolved into a dichloromethane solution or the like, and then an excess amount of a solution of hydrochloric acid in ethyl acetate (4 mol/L) was added thereto. The reaction mixture was concentrated under reduced pressure, and the resulting precipitates were collected by filtration, and dried under reduced pressure to give the compound described in the following Table 10.

TABLE 10
| Example | Compound | Salt | MS |
|---|---|---|---|
| 66 | | 4 HCl | (APCI): m/z 661 [M + H]⁺ |
Example 67
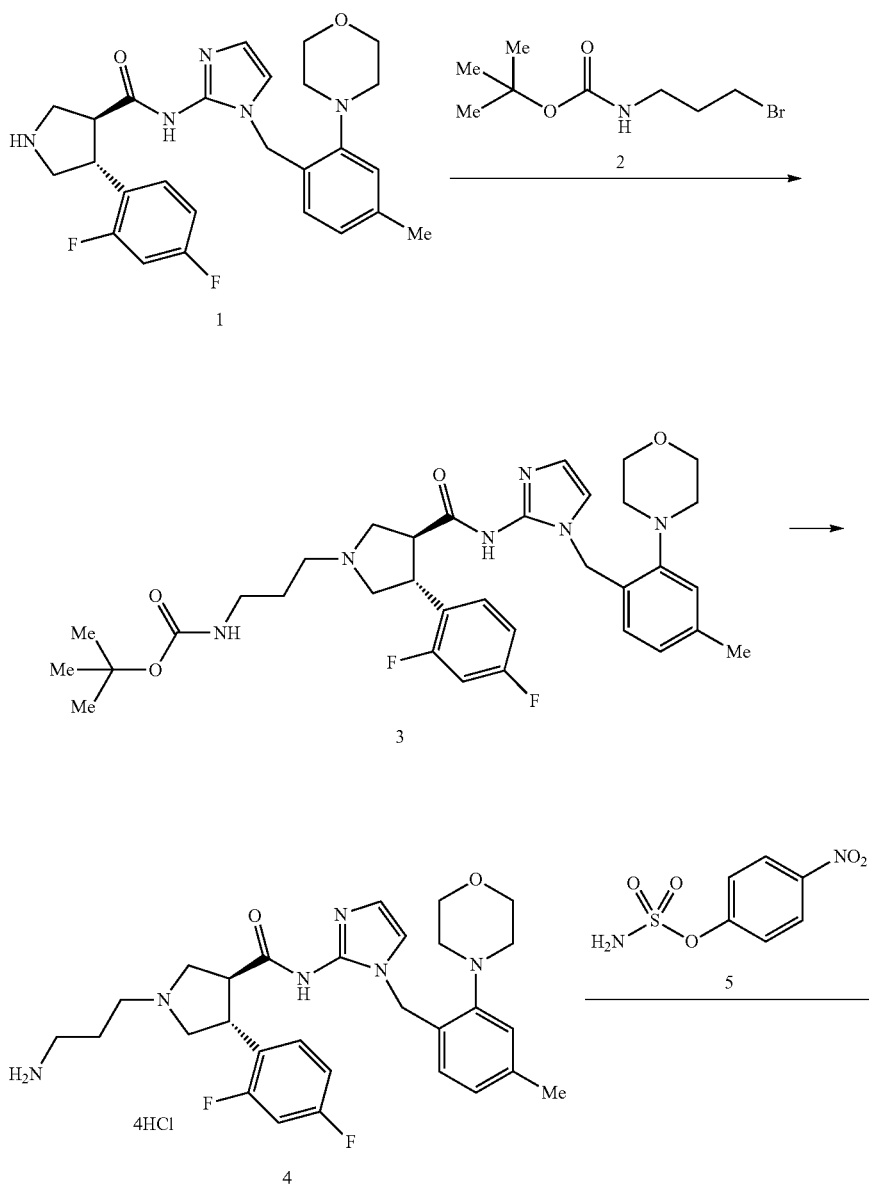

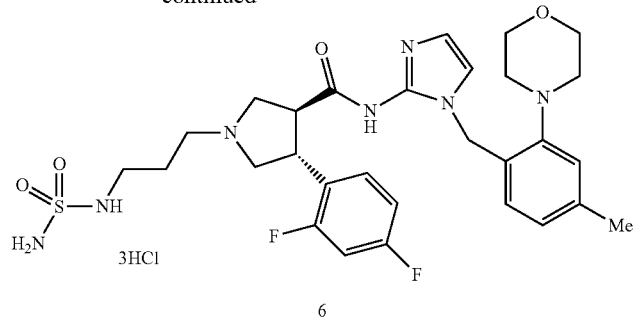

6

(1) To a solution of the Compound 1 (400 mg) and the Compound 2 (218 mg) in acetonitrile (6 mL) was added diisopropylethylamine (362 µL), and the resulting mixture was stirred at 50° C. for 4 hours, stirred at 70° C. for 15.5 hours, and stirred at 95° C. for 3.5 hours. The reaction mixture was concentrated under reduced pressure, and a saturated aqueous solution of sodium hydrogen carbonate was added thereto, and the resulting mixture was stirred, and then extracted with chloroform. The resulting organic layers were concentrated under reduced pressure, and the resulting residues were purified by silica gel column chromatography (chloroform:methanol=100:0 to 90:10). To a mixed solution of the resulting compound in dioxane (8 mL)/methanol (4 mL) was added a solution of hydrochloric acid in 1,4-dioxane (4 mol/L, 3.8 mL), and the resulting mixture was stirred at room temperature for 1.5 hours. The reaction mixture was concentrated under reduced pressure, and the resulting residues were dried under reduced pressure to give the Compound 4 (578 mg) as a pale yellow powder. MS (APCI): m/z 539 [M+H]⁺

(2) The Compound 4 (150 mg), the Compound 5 (57 mg), and triethylamine (153 µL) were added to chloroform (4 mL), and the resulting mixture was stirred at 45° C. for 1 hour. The Compound 5 (24 mg) was further added thereto, and the resulting mixture was stirred for 2 hours. The Compound 5 (24 mg) was further added thereto, and the resulting mixture was stirred for 16 hours. The reaction mixture was allowed to cool to room temperature, and then water was added thereto, and the resulting mixture was stirred, and extracted with chloroform. The resulting organic layers were dried, and then concentrated under reduced pressure. The resulting residues were purified by NH silica gel column chromatography (chloroform:methanol=99:1 to 90:10) and diol silica gel column chromatography (chloroform:methanol=99:1 to 90:10). To a solution of the resulting compound in chloroform was added an excess amount of a solution of hydrochloric acid in ethyl acetate (4 mol/L), and the resulting mixture was stirred, and then concentrated under reduced pressure. The resulting residues were powdered with diethyl ether, collected by filtration, and dried under reduced pressure to give (3S,4R)-4-(2,4-difluorophenyl)-N-{1-[4-methyl-2-(morpholin-4-yl)benzyl]-1H-imidazol-2-yl}-1-[3-(sulfamoylamino)propyl]pyrrolidine-3-carboxamide trihydrochloride 6 (60.8 mg) as a colorless powder. MS (APCI): m/z 618 [M+H]⁺

Example 68

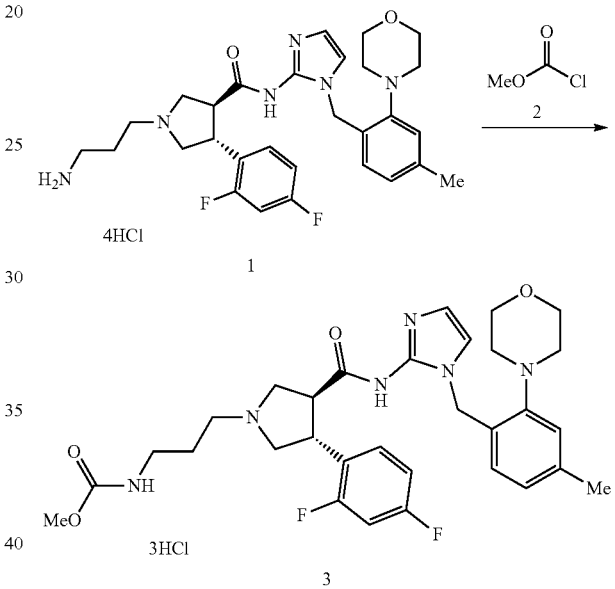

(1) To a suspension of the Compound 1 (70 mg) and the Compound 2 (9.5 µL) in dichloromethane (1 mL) was added triethylamine (85 µL), and the resulting mixture was stirred at room temperature for 2 hours. To the reaction mixture were added chloroform and water, and the resulting mixture was stirred, and then the resulting organic layers were separated, dried, and concentrated under reduced pressure. The resulting residues were purified by silica gel column chromatography (chloroform:methanol=100:0 to 85:15). To a solution of the resulting compound in dichloromethane (2 mL)/diethyl ether (1 mL) was added an excess amount of a solution of hydrochloric acid in ethyl acetate (4 mol/L, 100 µL), and the resulting mixture was stirred, and then concentrated under reduced pressure. The resulting residues were powdered with diethyl ether, collected by filtration, and dried under reduced pressure to give methyl {3-[(3R,4S)-3-(2,4-difluorophenyl)-4-({1-[4-methyl-2-(morpholin-4-yl)benzyl]-1H-imidazol-2-yl}carbamoyl)pyrrolidin-1-yl]propyl}carbamate trihydrochloride 3 (60.8 mg) as a colorless powder. MS (APCI): m/z 597 [M+H]⁺

Examples 69 to 80

Each corresponding starting compound was treated in a similar manner to the above Example 8, and the resulting compound was dissolved into a dichloromethane solution or the like, and then an excess amount of a solution of hydrochloric acid in ethyl acetate (4 mol/L) was added thereto. The reaction mixture was concentrated under reduced pressure, and the resulting residues were powdered with diisopropyl ether or the like, collected by filtration, and dried under reduced pressure to give each compound described in the following Table 11.

TABLE 11

| Example | Compound | Salt MS |
|---------|----------|---------|
| 69 | | 3 HCl (APCI): m/z 522 [M + H]⁺ |
| 70 | | 3 HCl (APCI): m/z 530 [M + H]⁺ |
| 71 | | 3 HCl (APCI): m/z 641 [M + H]⁺ |
| 72 | | 4 HCl (APCI): m/z 573 [M + H]⁺ |
| 73 | | (APCI): m/z 495 [M + H]⁺ |

TABLE 11-continued

| Example | Compound | Salt MS |
|---|---|---|
| 74 | | (APCI): m/z 561 [M + H]⁺ |
| 75 | | (APCI): m/z 538 [M + H]⁺ |
| 76 | | 3 HCl (APCI): m/z 565 [M + H]⁺ |
| 77 | | 3 HCl (APCI): m/z 658 [M + H]⁺ |

TABLE 11-continued

| Example | Compound | Salt MS |
|---------|----------|---------|
| 78 | | 3 HCl (APCI): m/z 590 [M + H]⁺ |
| 79 | | 3 HCl (APCI): m/z 687 [M + H]⁺ |
| 80 | | 3 HCl (APCI): m/z 594 [M + H]⁺ |

Example 81

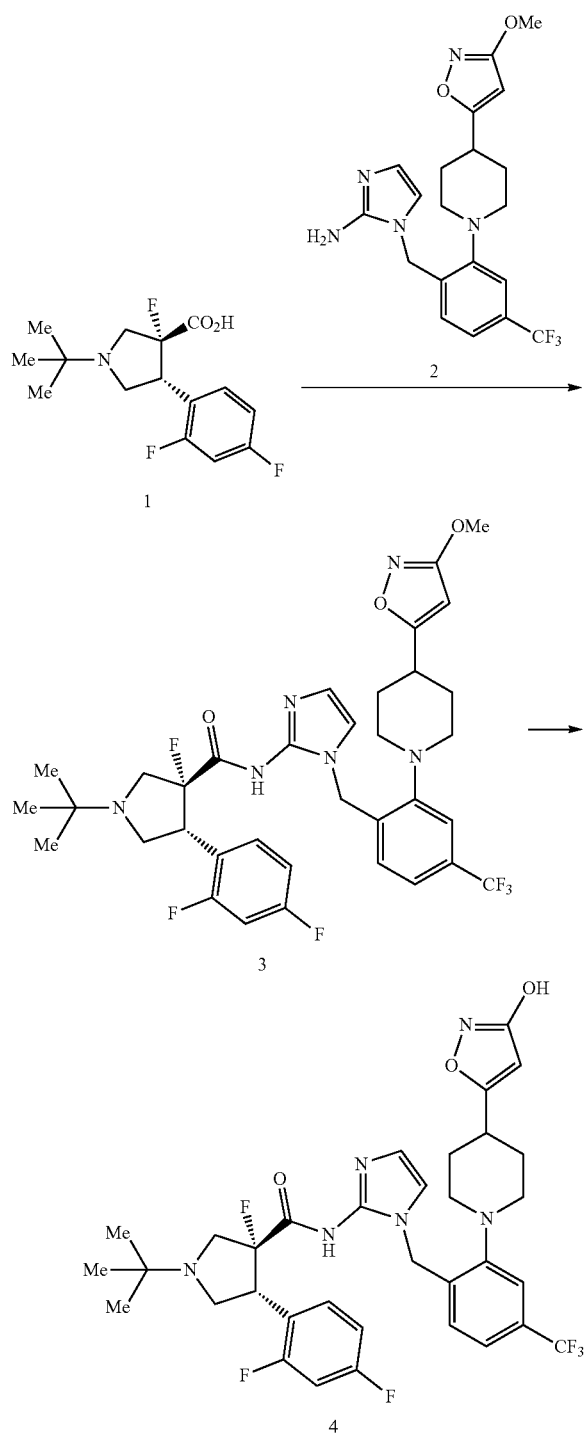

(1) The Compound 1 (114 mg), the Compound 2 (105 mg), 1-ethyl-3-(3-dimethylaminopropyl)carbodiimide hydrochloride (73 mg), 1-hydroxy-7-azabenzotriazole (52 mg), and triethylamine (88 μL) were added to N,N-dimethylformamide (2 mL), and the resulting mixture was stirred at 50° C. for 19 hours. The Compound 1 (45 mg), 1-ethyl-3-(3-dimethylaminopropyl)carbodiimide hydrochloride (73 mg), and 1-hydroxy-7-azabenzotriazole (52 mg) were further added thereto, and the resulting mixture was stirred at 50° C. for 3 hours. The reaction mixture was allowed to cool to room temperature, and then a saturated aqueous solution of sodium hydrogen carbonate and ethyl acetate were added thereto, and the resulting mixture was stirred, and extracted with ethyl acetate. The resulting organic layers were washed with water and saturated brine, dried, and concentrated under reduced pressure. The resulting residues were purified by silica gel column chromatography (chloroform:methanol=98:2 to 90:10) to give the Compound 3 (114.9 mg) as a pale yellow powder. MS (APCI): m/z 705 [M+H]$^+$ (2) A mixture of the Compound 3 (100 mg) and a solution of 25% hydrogen bromide/acetic acid in water (3 mL) was stirred at 110° C. for 1 hour. The reaction mixture was concentrated under reduced pressure, then diluted with water and chloroform, and a saturated aqueous solution of sodium hydrogen carbonate was added thereto until the pH of the mixture became 4 to 5, and then the resulting mixture was extracted with chloroform. The resulting organic layers were dried, and then concentrated under reduced pressure. The resulting residues were purified by silica gel column chromatography (chloroform:methanol=98:2 to 75:25) to give (3R,4R)-1-tert-butyl-4-(2,4-difluorophenyl)-3-fluoro-N-(1-{2-[4-(3-hydroxyisoxazol-5-yl)piperidin-1-yl]-4-(trifluoromethyl)benzyl}-1H-imidazol-2-yl)pyrrolidine-3-carboxamide 4 (78.3 mg) as a pale yellow powder. MS (APCI): m/z 691 [M+H]$^+$

Example 82

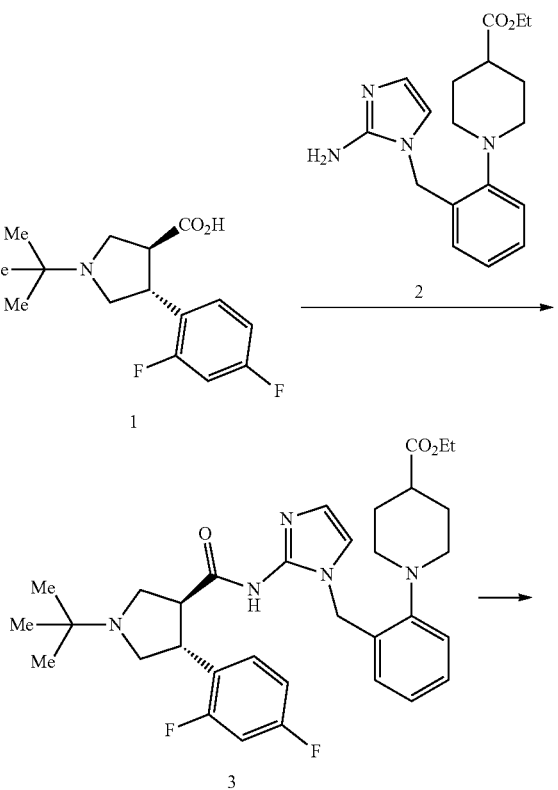

-continued

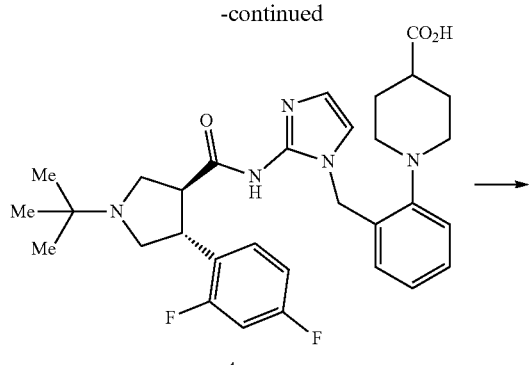

4

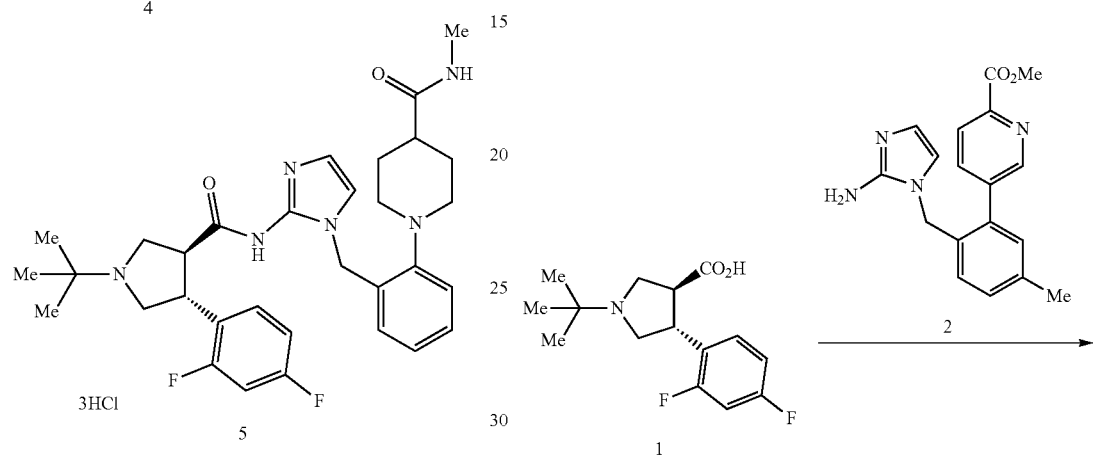

added an excess amount of a solution of hydrochloric acid in 1,4-dioxane (4 mol/L), and the resulting mixture was stirred, and then concentrated under reduced pressure. The resulting residues were powdered with diethyl ether, collected by filtration, and dried under reduced pressure to give 1-(2-{[2-({[(3S,4R)-1-tert-butyl-4-(2,4-difluorophenyl)pyrrolidin-3-yl]carbonyl}amino)-1H-imidazol-1-yl]methyl}phenyl)-N-methylpiperidine-4-carboxamide trihydrochloride 5 (99 mg) as a colorless powder. MS (APCI): m/z 579 [M+H]$^+$ Example 83

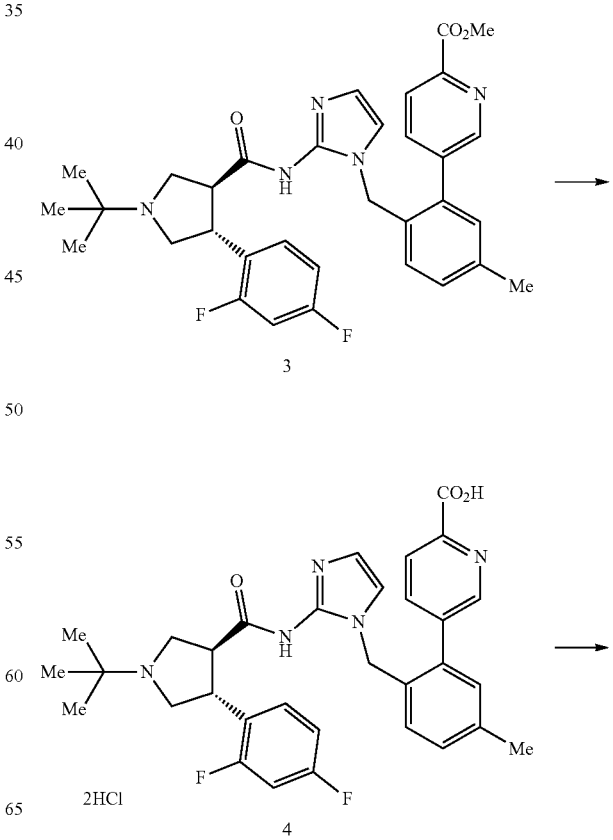

(1) The Compound 1 (1.176 g) and the Compound 2 (1.135 g) were treated in a similar manner to the above Example 8 to give the Compound 3 (1.736 g) as a pale yellow powder. MS (APCI): m/z 594 [M+H]$^+$ (2) To a solution of the Compound 3 (594 mg) in ethanol (4 mL) was added an aqueous solution of sodium hydroxide (2 mol/L, 1 mL), and the resulting mixture was stirred at room temperature for 16 hours, and then stirred at 50° C. for 46.5 hours. The reaction mixture was allowed to cool to room temperature, and then an aqueous solution of hydrochloric acid (2 mol/L, 1 mL) was added thereto, and the resulting mixture was stirred, and concentrated under reduced pressure. To the residues were added water and chloroform, and the resulting mixture was stirred, and then extracted with chloroform. The resulting organic layers were dried, and then concentrated under reduced pressure. The resulting residues were powdered with diisopropyl ether, collected by filtration, and dried under reduced pressure to give the Compound 4 (442 mg) as a pale brown powder. MS (APCI): m/z 566 [M+H]$^+$ (3) The Compound 4 (124 mg), methylamine hydrochloride (30 mg), 1-ethyl-3-(3-dimethylaminopropyl)carbodiimide hydrochloride (63 mg), 1-hydroxy-7-azabenzotriazole (45 mg), and triethylamine (92 μL) were added to N,N-dimethylformamide (2 mL), and the resulting mixture was stirred at room temperature for 17.5 hours. To the reaction mixture were added a saturated aqueous solution of sodium hydrogen carbonate and ethyl acetate, and the resulting mixture was stirred, and extracted with ethyl acetate. The resulting organic layers were washed with water and saturated brine, dried, and concentrated under reduced pressure. The resulting residues were purified by silica gel column chromatography (chloroform:methanol=99:1 to 10:90). To a solution of the resulting compound in dichloromethane (2 mL) was

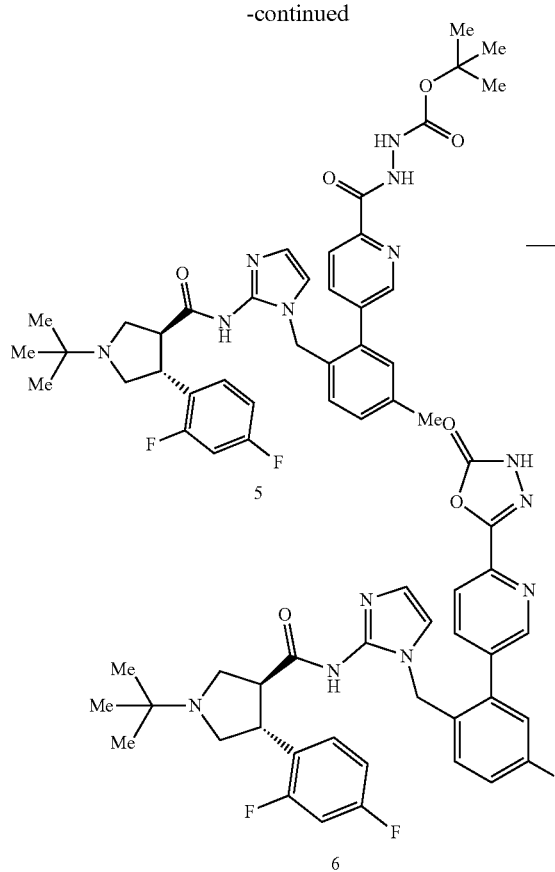

(1) The Compound 1 (276 mg), 1-ethyl-3-(3-dimethylaminopropyl)carbodiimide hydrochloride (177 mg), and 1-hydroxy-7-azabenzotriazole (126 mg) were added to chloroform (10 mL), and the resulting mixture was stirred at room temperature for 10 minutes, and then the Compound 2 (230 mg) was added thereto, and the resulting mixture was stirred at room temperature overnight. The reaction mixture was purified by silica gel column chromatography (chloroform:methanol=100:0 to 93:7) to give the Compound 3 (344 mg) as a pale yellow powder. MS (APCI): m/z 588 [M+H]⁺

(2) To a solution of the Compound 3 (320 mg) in ethanol (5 mL) was added an aqueous solution of sodium hydroxide (2 mol/L, 1.1 mL), and the resulting mixture was stirred at room temperature for 3 hours. To the reaction mixture was added an aqueous solution of hydrochloric acid (2 mol/L, 1.1 mL), and the resulting mixture was stirred, and then water was added thereto to dilute the mixture, and the resulting mixture was extracted with chloroform. The resulting organic layers were washed with saturated brine, dried, and concentrated under reduced pressure. The resulting residues were dissolved into dichloromethane, and an excess amount of a solution of hydrochloric acid in 1,4-dioxane (4 mol/L) was added thereto, and the resulting mixture was stirred at room temperature, and then concentrated under reduced pressure to give the Compound 4 (260 mg) as a colorless powder. MS (APCI): m/z 574 [M+H]⁺

(3) To a suspension of the Compound 4 (81 mg), t-butoxycarbonyl hydrazine (20 mg), 1-ethyl-3-(3-dimethylaminopropyl)carbodiimide hydrochloride (29 mg), and 1-hydroxy-7-azabenzotriazole (20 mg) in dichloromethane (2 mL) was added triethylamine (35 µL), and the resulting mixture was stirred at room temperature for 22 hours. The reaction mixture was purified by silica gel column chromatography (chloroform:methanol=93:7 to 83:17) to give the Compound 5 (72 mg) as a colorless powder. MS (APCI): m/z 688 [M+H]⁺

(4) To a solution of the Compound 5 (69 mg) in dichloromethane (1.5 mL) was added trifluoroacetic acid (1.5 mL), and the resulting mixture was stirred at room temperature for 3 hours. To the reaction mixture were added ethyl acetate and an aqueous solution of sodium hydrogen carbonate, and the resulting mixture was stirred, and then extracted with ethyl acetate. The resulting organic layers were washed with saturated brine, dried, and then concentrated under reduced pressure. To a solution of the resulting residues in tetrahydrofuran (2 mL) was added 1,1'-carbodiimidazole (49 mg), and the resulting mixture was stirred at room temperature for 1 hour. The reaction mixture was purified by silica gel column chromatography (chloroform:methanol=89:11 to 82:18) and HPLC preparative isolation to give (3S,4R)-1-tert-butyl-4-(2,4-difluorophenyl)-N-(1-{4-methyl-2-[6-(5-oxo-4,5-dihydro-1,3,4-oxadiazol-2-yl)pyridin-3-yl]benzyl}-1H-imidazol-2-yl)pyrrolidine-3-carboxamide 6 (15 mg) as a colorless powder. MS (APCI): m/z 614 [M+H]⁺

Example 84

A corresponding starting compound was treated in a similar manner to the above Example 83 to give the compound described in the following Table 12.

TABLE 12

| Example | Compound | Salt MS |
|---|---|---|
| 84 | ![structure] | 3 HCl (APCI): m/z 620 [M + H]⁺ |

Example 85

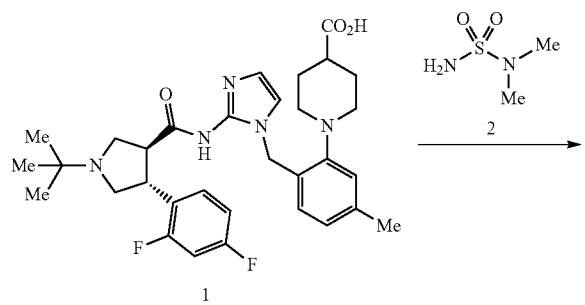

was stirred at room temperature for 18 hours. The reaction mixture was purified by silica gel column chromatography (chloroform:methanol=89:11 to 81:19). To a solution of the resulting compound in dichloromethane (2 mL) was added an excess amount of a solution of hydrochloric acid in 1,4-dioxane (4 mol/L), and the resulting mixture was stirred, and then concentrated under reduced pressure. The resulting residues were powdered with diisopropyl ether/diethyl ether, collected by filtration, and dried under reduced pressure to give 1-(2-{[2-({[(3S,4R)-1-tert-butyl-4-(2,4-difluorophenyl)pyrrolidin-3-yl]carbonyl}amino)-1H-imidazol-1-yl]methyl}-5-methylphenyl)-N-(dimethylsulfamoyl)piperidine-4-carboxamide trihydrochloride 3 (118 mg) as a colorless solid. MS (APCI): m/z 686 [M+H]+

Example 86

A corresponding starting compound was treated in a similar manner to the above Example 85 to give the compound described in the following Table 13.

TABLE 13

| Example | Compound | Salt MS |
|---|---|---|
| 86 | 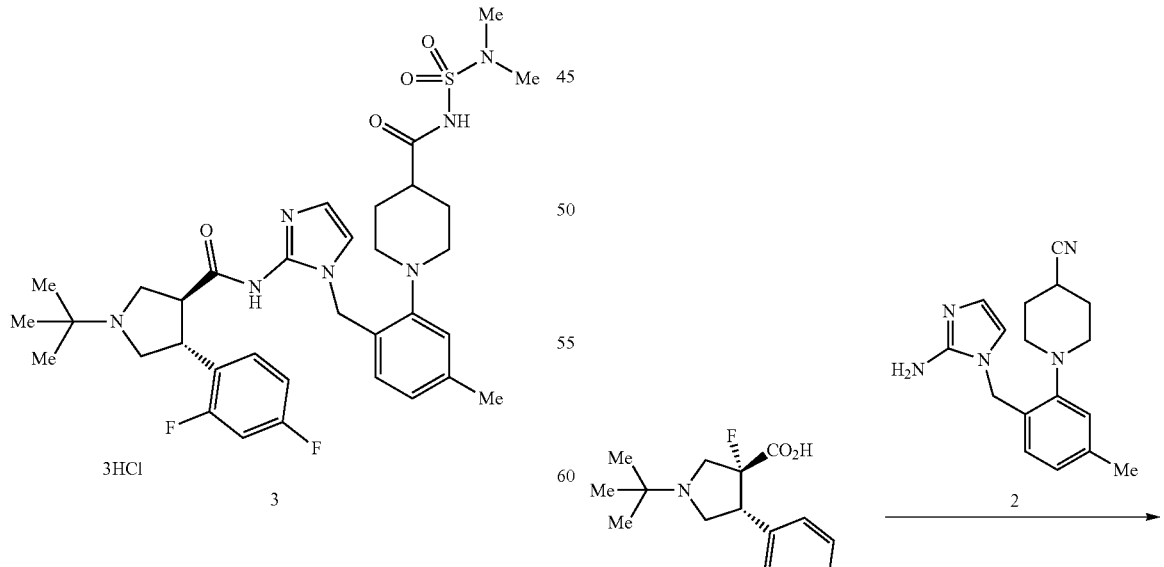 | 3 HCl (APCI): m/z 686 [M + H] + |

Example 87

(1) The Compound 1 (232 mg), the Compound 2 (49 mg), 1-ethyl-3-(3-dimethylaminopropyl)carbodiimide hydrochloride (115 mg), and 4-dimethylaminopyridine (49 mg) were added to chloroform (10 mL), and the resulting mixture -continued

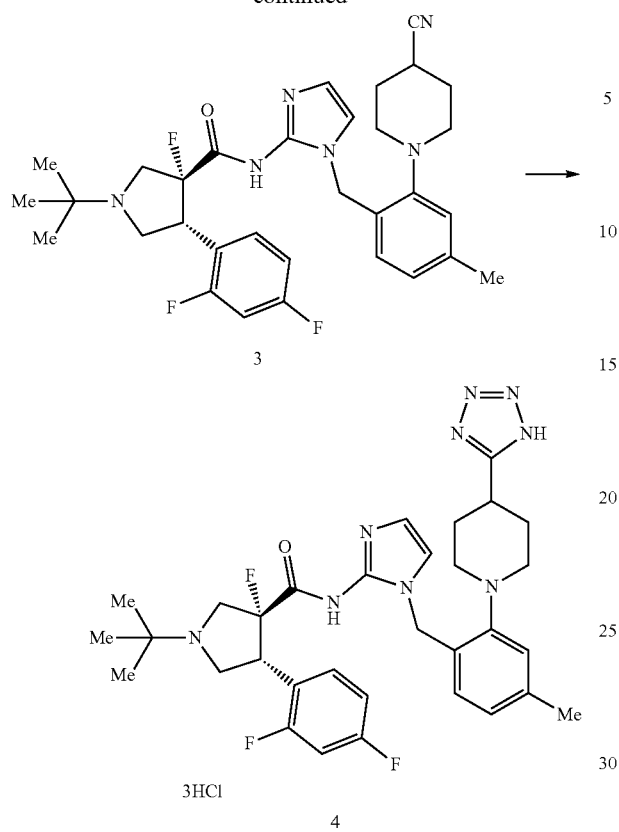

(1) The Compound 1 (150 mg), the Compound 2 (148 mg), 1-ethyl-3-(3-dimethylaminopropyl)carbodiimide hydrochloride (115 mg), 1-hydroxy-7-azabenzotriazole (82 mg), and triethylamine (84 μL) were added to N,N-dimethylformamide (3 mL), and the resulting mixture was stirred at 50° C. for 17 hours. The reaction mixture was allowed to cool to room temperature, and then a saturated aqueous solution of sodium hydrogen carbonate and ethyl acetate were added thereto, and the resulting mixture was stirred, and extracted with ethyl acetate. The resulting organic layers were washed with water and saturated brine, dried, and concentrated under reduced pressure. The resulting residues were purified by silica gel column chromatography (chloroform:methanol=99:1 to 90:10) to give the Compound 3 (253 mg) as a pale yellow powder. MS (APCI): m/z 579 [M+H]$^+$ (2) A mixture of the Compound 3 (148 mg), tributyltin azide (837 mg), and toluene (5 mL) was heated under reflux for 89 hours. The reaction mixture was concentrated under reduced pressure, and the resulting residues were purified by silica gel column chromatography (chloroform:methanol=100:0 to 80:20). To a solution of the resulting compound in dichloromethane (2 mL) was added a solution of hydrochloric acid in ethyl acetate (4 mol/L, 195 μL), and the resulting mixture was stirred, and then concentrated under reduced pressure. The resulting residues were powdered with diethyl ether, collected by filtration, and dried under reduced pressure to give (3R,4R)-1-tert-butyl-4-(2,4-difluorophenyl)-3-fluoro-N-(1-{4-methyl-2-[4-(1H-tetrazol-5-yl)piperidin-1-yl]benzyl}-1H-imidazol-2-yl)pyrrolidine-3-carboxamide trihydrochloride 4 (121 mg) as a pale yellow powder. MS (APCI): m/z 622 [M+H]$^+$ Example 88

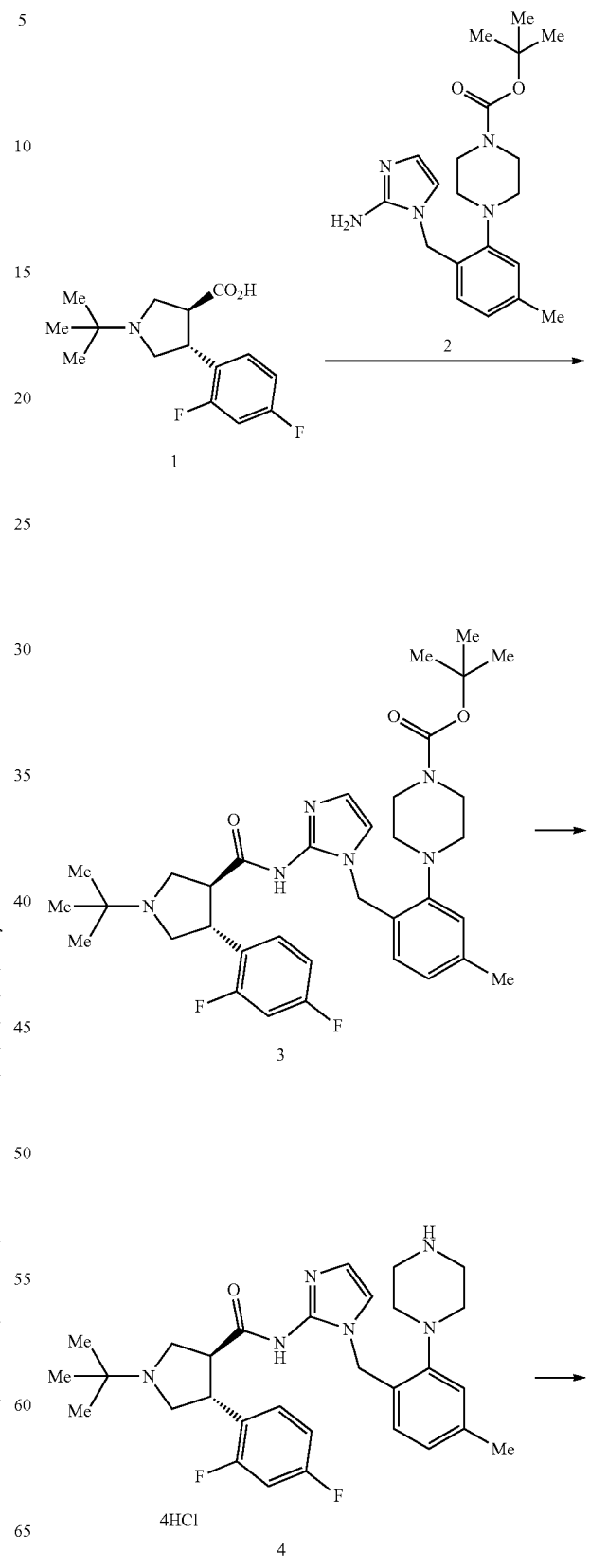

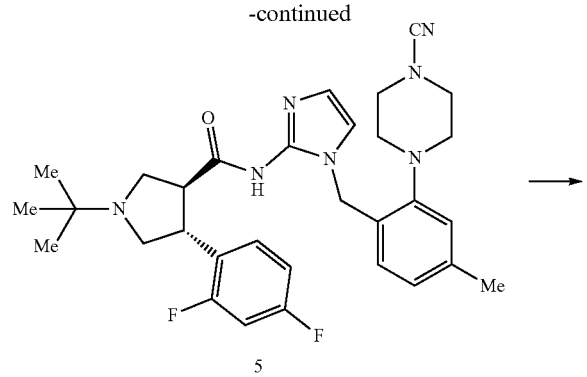

5

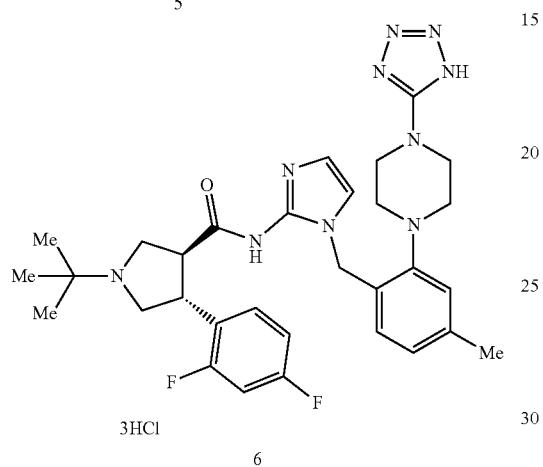

6 3HCl (1) The Compound 1 (255 mg), the Compound 2 (400 mg), 1-ethyl-3-(3-dimethylaminopropyl)carbodiimide hydrochloride (233 mg), and 1-hydroxy-7-azabenzotriazole (166 mg) were added to chloroform (10 mL), and the resulting mixture was stirred at room temperature overnight. The reaction mixture was diluted with chloroform, then washed with an aqueous solution of sodium hydrogen carbonate, dried, and concentrated under reduced pressure. The resulting residues were purified by silica gel column chromatography (chloroform:methanol=100:0 to 87:13) to give the Compound 3 (313 mg) as a pale brown powder. MS (APCI): m/z 637 [M+H]$^+$ (2) To a solution of the Compound 3 (313 mg) in chloroform (4 mL) were added a solution of hydrochloric acid in 1,4-dioxane (4 mol/L, 3 mL) and methanol (0.5 mL), and the resulting mixture was stirred at room temperature overnight. The reaction mixture was concentrated under reduced pressure to give the Compound 4 (376 mg) as a pale orange solid. MS (APCI): m/z 537 [M+H]$^+$ (3) To a suspension of sodium hydrogen carbonate (112 mg) in ethanol (5 mL) were added the Compound 4 (150 mg) and cyanogen bromide (28 mg), and the resulting mixture was stirred at room temperature for 3 days. The reaction mixture was diluted with chloroform, then washed with water, dried, and concentrated under reduced pressure. The resulting residues were purified by NH silica gel column chromatography (chloroform:methanol=100:0 to 98:2) to give the Compound 5 (55 mg) as a colorless powder. MS (APCI): m/z 562 [M+H]$^+$ (4) A mixture of the Compound 5 (43 mg), tributyltin azide (254 mg), and toluene (2 mL) was stirred at 110° C. for 3 hours. The reaction mixture was purified by silica gel column chromatography (chloroform:methanol=98:2 to 85:15). To a solution of the resulting compound in dichloromethane (2 mL) was added an excess amount of a solution of hydrochloric acid in ethyl acetate (4 mol/L), and the resulting mixture was stirred, and then concentrated under reduced pressure. The resulting residues were powdered with diethyl ether, collected by filtration, and dried under reduced pressure to give (3S,4R)-1-tert-butyl-4-(2,4-difluorophenyl)-N-(1-{4-methyl-2-[4-(1H-tetrazol-5-yl)piperazin-1-yl]benzyl}-1H-imidazol-2-yl)pyrrolidine-3-carboxamide trihydrochloride 6 (55 mg) as a colorless solid. MS (APCI): m/z 605 [M+H]$^+$ Example 89

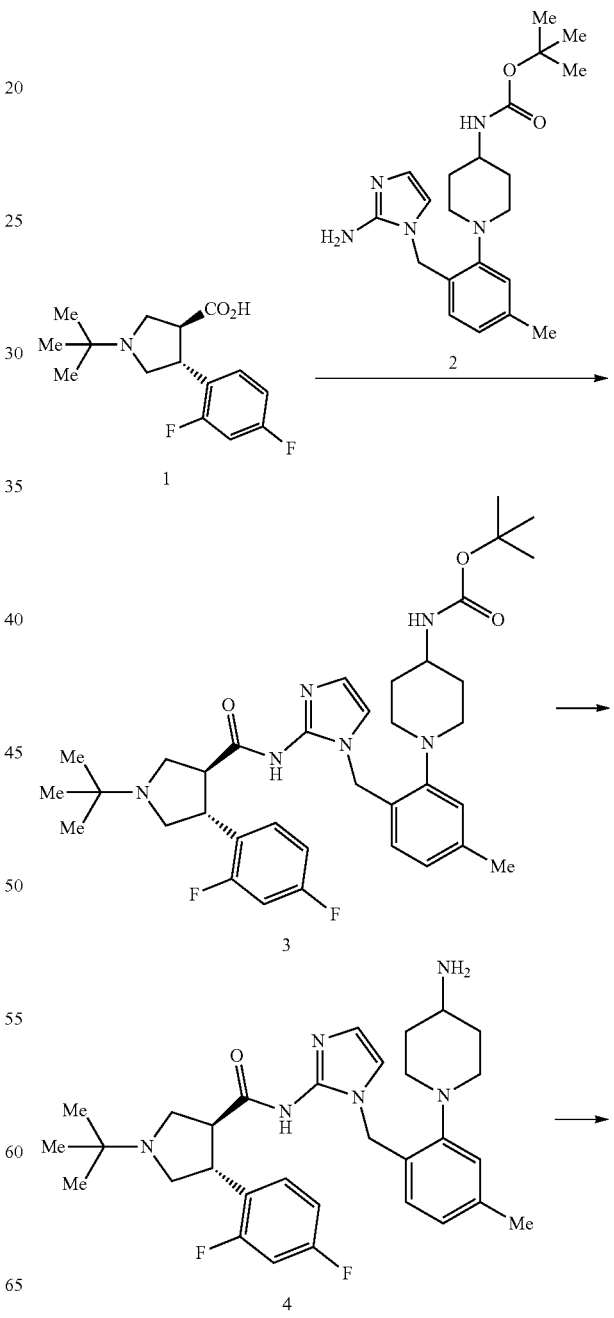

-continued

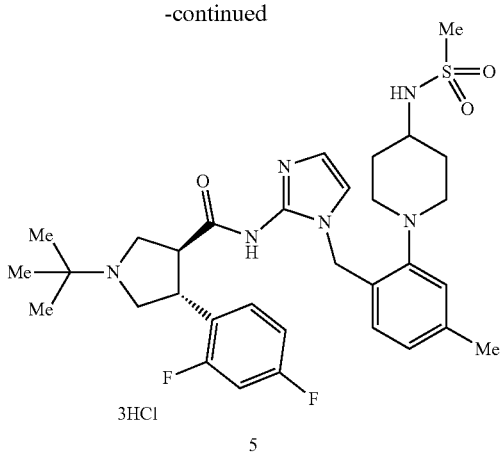

3HCl

5

(1) The Compound 1 (319 mg), the Compound 2 (386 mg), 1-ethyl-3-(3-dimethylaminopropyl)carbodiimide hydrochloride (249 mg), and 1-hydroxy-7-azabenzotriazole (177 mg) were added to chloroform (5 mL), and the resulting mixture was stirred at room temperature for 17 hours. To the reaction mixture were added chloroform and an aqueous solution of sodium hydrogen carbonate, and the resulting mixture was stirred, and then extracted with chloroform. The resulting organic layers were dried, and then concentrated under reduced pressure. The resulting residues were purified by silica gel column chromatography (chloroform:methanol=100:0 to 90:10) to give the Compound 3 (490 mg) as a pale yellow powder. MS (APCI): m/z 651 [M+H]$^+$ (2) To a solution of the Compound 3 (465 mg) in dichloromethane (7.5 mL) was added trifluoroacetic acid (1.5 mL), and the resulting mixture was stirred at room temperature for 2 hours. The reaction mixture was concentrated under reduced pressure, and then the resulting residues were diluted with chloroform, and an aqueous solution of sodium hydroxide (1 mol/L) was added thereto until the pH of the mixture became 10, and then the resulting mixture was extracted with chloroform. The resulting organic layers were dried, and then concentrated under reduced pressure to give the Compound 4 (367 mg) as a pale yellow powder. MS (APCI): m/z 551 [M+H]$^+$ (3) To a solution of the Compound 4 (110 mg) in dichloromethane (2 mL)/acetonitrile (2 mL) were added methanesulfonyl chloride (19 μL) and triethylamine (36 μL), and the resulting mixture was stirred at room temperature for 2.5 hours. To the reaction mixture were added ethyl acetate and an aqueous solution of sodium hydrogen carbonate, and the resulting mixture was stirred, and then extracted with ethyl acetate. The resulting organic layers were dried, and then concentrated under reduced pressure. The resulting residues were purified by NH silica gel column chromatography (chloroform:methanol=100:0 to 95:5). To a solution of the resulting compound in dichloromethane (2 mL)/diisopropyl ether (1 mL) was added a solution of hydrochloric acid in 1,4-dioxane (4 mol/L, 200 μL), and the resulting mixture was stirred, and then concentrated under reduced pressure. The resulting residues were powdered with diisopropyl ether, collected by filtration, and dried under reduced pressure to give (3S,4R)-1-tert-butyl-4-(2,4-difluorophenyl)-N-[1-(4-methyl-2-{4-[(methylsulfonyl)amino]piperidin-1-yl}benzyl)-1H-imidazol-2-yl]pyrrolidine-3-carboxamide trihydrochloride 5 (128 mg) as a pale yellow powder. MS (APCI): m/z 629 [M+H]$^+$ Example 90

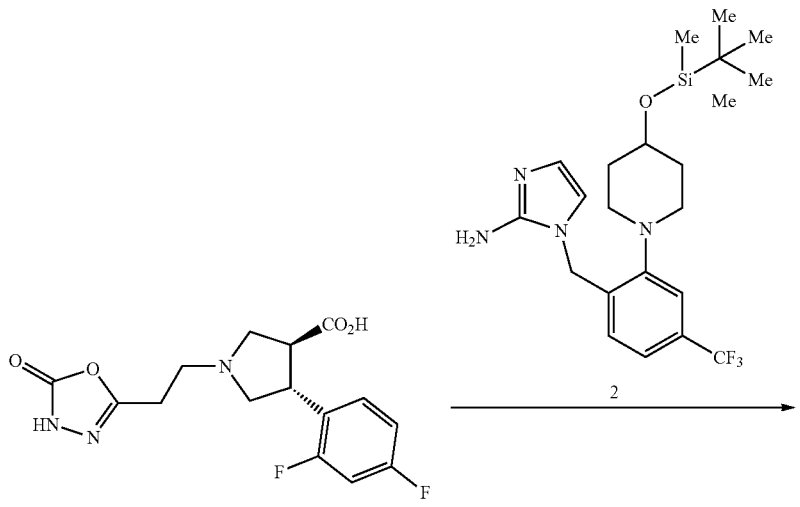

-continued

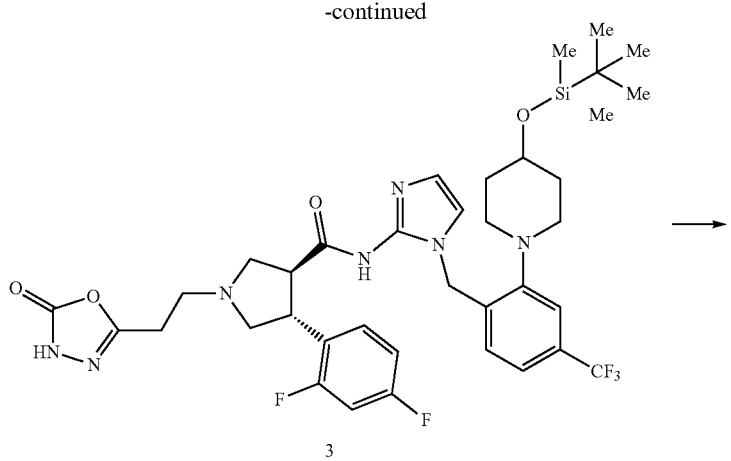

3

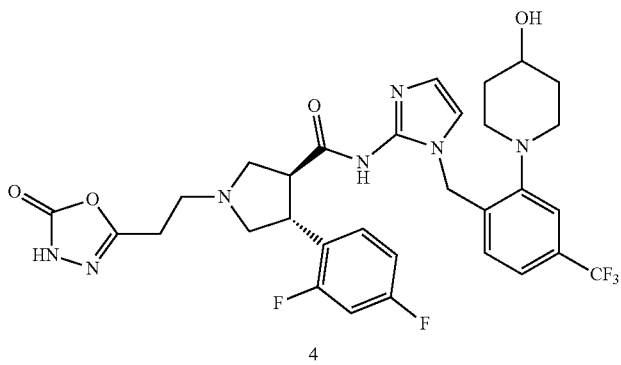

4

(1) The Compound 1 (227 mg), the Compound 2 (189 mg), 1-ethyl-3-(3-dimethylaminopropyl)carbodiimide hydrochloride (208 mg), and 1-hydroxy-7-azabenzotriazole (125 mg) were added to chloroform (4 mL)/N,N-dimethylformamide (0.1 mL), and the resulting mixture was stirred at room temperature for 16 hours. To the reaction mixture were added chloroform and water, and the resulting mixture was stirred, and then extracted with chloroform. The resulting organic layers were dried, and then concentrated under reduced pressure. The resulting residues were purified by silica gel column chromatography (chloroform:methanol=100:0 to 93:7) and preparative thin-layer chromatography (manufactured by Merck) (chloroform:methanol=9:1) to give the Compound 3 (150 mg) as a pink powder. MS (APCI): m/z 776 [M+H]$^+$ (2) To a solution of the Compound 3 (145 mg) in methanol (2 mL) was added an aqueous solution of hydrochloric acid (6 mol/L, 37 µL), and the resulting mixture was stirred at room temperature for 20 minutes. Two drops of concentrated hydrochloric acid was added thereto, and the resulting mixture was stirred at room temperature for 30 minutes. To the reaction mixture was added an aqueous solution of sodium hydrogen carbonate until the pH of the mixture became 8, and then the resulting mixture was extracted with ethyl acetate. The resulting organic layers were dried, and then concentrated under reduced pressure, and the resulting residues were purified by silica gel column chromatography (chloroform:methanol=99:1 to 80:20) to give (3S,4R)-4-(2, 4-difluorophenyl)-N-{1-[2-(4-hydroxypiperidin-1-yl)-4-(trifluoromethyl)benzyl]-1H-imidazol-2-yl}-1-[2-(5-oxo-4, 5-dihydro-1,3,4-oxadiazol-2-yl)ethyl]pyrrolidine-3-carboxamide 4 (106 mg) as a pink solid. MS (APCI): m/z 662 [M+H]$^+$ Example 91

A corresponding starting compound was treated in a similar manner to the above Example 90 to give the compound described in the following Table 14.

TABLE 14

| Example | Compound | Salt | MS |
|---------|----------|------|-----|
| 91 | | | (APCI): m/z 676 [M + H]⁺ |

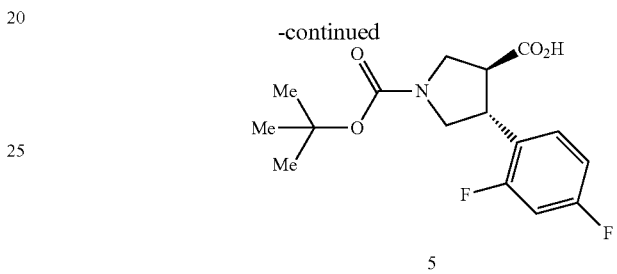

REFERENCE EXAMPLES

Reference Example 1

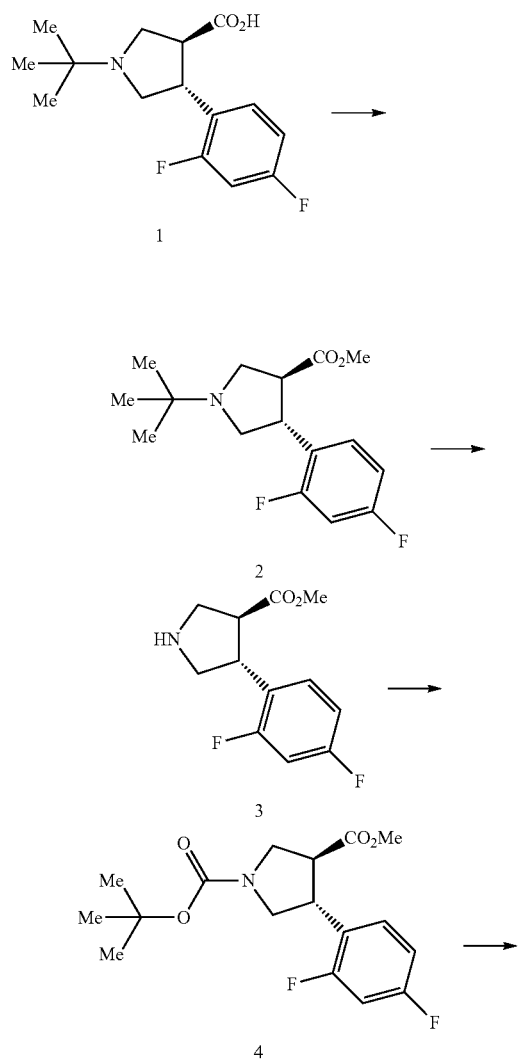

(1) To a solution of the Compound 1 (136.6 g) synthesized according to the methods described in documents (*J. Org. Chem.* 2005, 70, 3592-3601 and WO2004/92126) in methanol (1.5 L) was added thionyl chloride (98.8 mL) under ice-cooling, and the resulting mixture was stirred at the same temperature for 4.5 hours. The reaction mixture was concentrated under reduced pressure, and then ethyl acetate and an aqueous solution of sodium hydrogen carbonate were added thereto, and the resulting mixture was stirred. The resulting insoluble matters were removed by filtration, and then the resulting organic layers were separated. The resulting aqueous layers were extracted with ethyl acetate, and the resulting organic layers were combined, washed with saturated brine, dried, and concentrated under reduced pressure to give the Compound 2 (141.3 g) as a pale yellow liquid. MS (APCI): m/z 298 [M+H]⁺

(2) To a solution of the Compound 2 (141.3 g) in 1,2-dichloroethane (920 mL) was added 1-chloroethyl chloroformate (76.9 mL), and the resulting mixture was stirred at 70° C. for 10 minutes, and then diisopropylethylamine (124.1 mL) was added thereto, and the resulting mixture was stirred at the same temperature for 2 hours. The reaction mixture was ice-cooled, and methanol (920 mL) was added thereto, and the resulting mixture was stirred at 70° C. for 1.5 hours. The reaction mixture was concentrated under reduced pressure, and then chloroform and a saturated aqueous solution of sodium hydrogen carbonate were added thereto, and the resulting mixture was stirred, and extracted with chloroform. The resulting organic layers were washed with saturated brine, dried, and concentrated under reduced pressure. The resulting residues were purified by silica gel column chromatography (hexane:ethyl acetate=2:1 to 0:1, followed by chloroform:methanol=9:1 to 8:2) to give the Compound 3 (98 g) as a brown liquid. MS (APCI): m/z 242 [M+H]⁺

(3) To a solution of the Compound 3 (28 g) in tetrahydrofuran (70 mL)/ethyl acetate (70 mL) were added sodium hydrogen carbonate (19.5 g) and water (115 mL), and then dicarbonate di-t-butyl (2.84 g) was added thereto under ice-cooling, and the resulting mixture was stirred at room temperature for 30 minutes. The reaction mixture was concentrated under reduced pressure until the volume became approximately half, and then ethyl acetate and water were added thereto, and the resulting mixture was stirred, and extracted with ethyl acetate. The resulting organic layers were washed with saturated brine, dried, and concentrated under reduced pressure. The resulting residues were purified by silica gel column chromatography (hexane:ethyl acetate=4:1 to 2:1) to give the Compound 4 (39 g) as a pale yellow powder. MS (APCI): m/z 242 [M-Boc+H]$^+$ (4) To a solution of the Compound 4 (39 g) in methanol (400 mL) was added an aqueous solution of sodium hydroxide (2 mol/L, 70 mL), and the resulting mixture was stirred at room temperature for 16 hours. The reaction mixture was concentrated under reduced pressure, and then an aqueous solution of citric acid (citric acid (35 g)+water (150 mL)) and ethyl acetate were added thereto, and the resulting mixture was stirred, and extracted with ethyl acetate. The resulting organic layers were washed with saturated brine, then dried, and concentrated under reduced pressure. The resulting residues were powdered with hexane, collected by filtration, and dried under reduced pressure to give the Compound 5 (33.1 g) as a colorless powder. MS (APCI): m/z 228 [M-Boc+H]$^+$ Reference Example 2

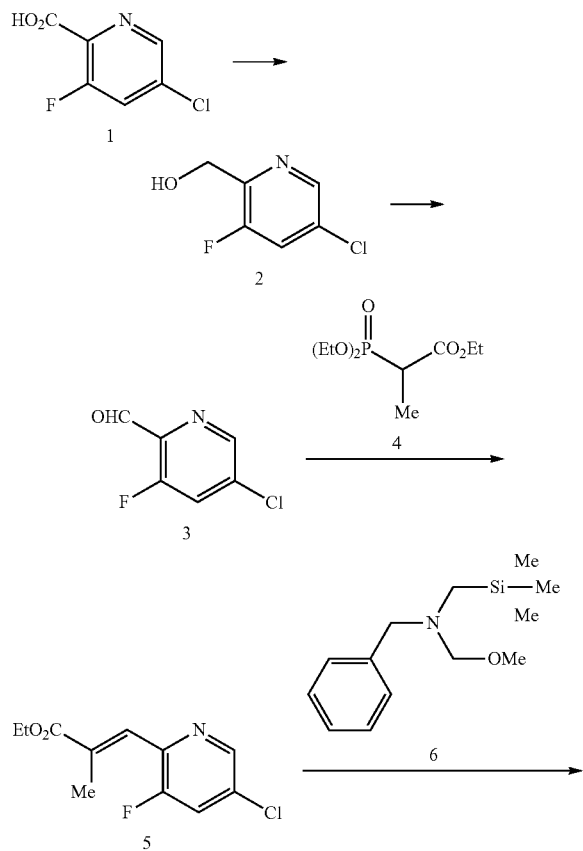

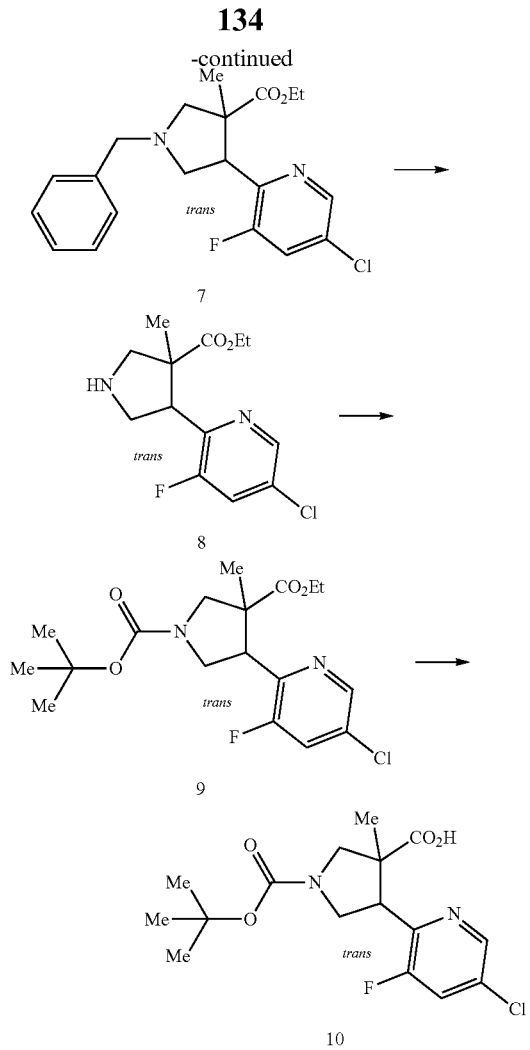

(1) To a suspension of the Compound 1 (5.21 g) in 1,2-dimethoxyethane (30 mL) were added isobutyl chloroformate (4.24 mL) and N-methylmorpholine (3.6 mL) under ice-cooling, and the resulting mixture was stirred at the same temperature for 1 hour. The resulting insoluble matters were removed by filtration, and to the resulting filtrate was added an aqueous solution of sodium borohydride (sodium borohydride (1.69 g)+water (15 mL)) under ice-cooling, and the resulting mixture was stirred at room temperature for 2 hours. To the reaction mixture were added water and chloroform, and the resulting mixture was stirred, and then extracted with chloroform. The resulting organic layers were dried, and then concentrated under reduced pressure. The resulting residues were purified by NH silica gel column chromatography (hexane:ethyl acetate=95:5 to 65:35) to give the Compound 2 (1.88 g) as a colorless solid. MS (APCI): m/z 162/164 [M+H]$^+$ (2) A suspension of the Compound 2 (1.77 g) and manganese dioxide (2.87 g) in dichloromethane (20 mL) was stirred at room temperature for 24.5 hours. Manganese dioxide (1.0 g) was further added thereto, and the resulting mixture was stirred at room temperature for 19 hours. The resulting insoluble matters were removed by filtration, and then the resulting filtrate was concentrated under reduced pressure. The resulting residues were purified by silica gel column chromatography (hexane:ethyl acetate=95:5 to 85:15) to give the Compound 3 (975 mg) as a colorless powder. MS (APCI): m/z 160/162 [M+H]$^+$ (3) To a suspension of sodium hydride (60% in oil, 328 mg) in toluene (10 mL) was added a solution of the Compound 4 (1.95 g) in toluene (10 mL) under ice-cooling, and the resulting mixture was stirred at the same temperature for 1.5 hours, and then a solution of the Compound 3 (1.09 g) in toluene (20 mL) was added thereto, and the resulting mixture was heated under reflux for 2 hours. The reaction mixture was allowed to cool to room temperature, and then water and ethyl acetate were added thereto, and the resulting mixture was stirred, and extracted with ethyl acetate. The resulting organic layers were dried, and then concentrated under reduced pressure. The resulting residues were purified by silica gel column chromatography (hexane:ethyl acetate=95:5 to 90:10) to give the Compound 5 (1.08 g) as a colorless solid. MS (APCI): m/z 244/246 [M+H]$^+$ (4) To a solution of the Compound 5 (1.08 g) and the Compound 6 (3.16 g) in dichloromethane (5 mL) was added trifluoroacetic acid (70 μL) under ice-cooling, and the resulting mixture was stirred at room temperature for 1.5 hours. To the reaction mixture were added an aqueous solution of sodium hydrogen carbonate and chloroform, and the resulting mixture was stirred, and then the resulting organic layers were separated, dried, and concentrated under reduced pressure. The resulting residues were purified by silica gel column chromatography (hexane:ethyl acetate=90:10 to 80:20) to give the Compound 7 (1.64 g) as a colorless viscous material of a racemate (trans compound). MS (APCI): m/z 377/379 [M+H]$^+$ (5) To a solution of the Compound 7 (1.33 g) in 1,2-dichloroethane (15 mL) were added 1-chloroethyl chloroformate (765 μL) and diisopropylethylamine (925 μL), and the resulting mixture was stirred at 70° C. for 1 hour. The reaction mixture was ice-cooled, and methanol (15 mL) was added thereto, and the resulting mixture was stirred at 70° C. for 1 hour. The reaction mixture was concentrated under reduced pressure, and then chloroform and a saturated aqueous solution of sodium hydrogen carbonate were added thereto, and the resulting mixture was stirred, and extracted with chloroform. The resulting organic layers were dried, and then concentrated under reduced pressure. The resulting residues were purified by silica gel column chromatography (chloroform:methanol=99:1 to 92:8) to give the Compound 8 (938.6 mg) as a pale yellow viscous material of a racemate (trans compound). MS (APCI): m/z 287/289 [M+H]$^+$ (6) To a solution of the Compound 8 (965.5 mg) in dichloromethane (20 mL) were added diisopropylethylamine (1.17 mL) and dicarbonate di-t-butyl (881.7 mg), and the resulting mixture was stirred at room temperature for 1 hour. The reaction mixture was concentrated under reduced pressure, and then the resulting residues were purified by silica gel column chromatography (hexane:ethyl acetate=95:5 to 85:15) to give the Compound 9 (1.30 g) as a colorless viscous material of a racemate (trans compound). MS (APCI): m/z 387/389 [M+H]$^+$ (7) To a solution of the Compound 9 (1.29 g) in ethanol (15 mL) was added an aqueous solution of sodium hydroxide (2 mol/L, 8.3 mL), and the resulting mixture was stirred at 50° C. for 4 hours. The reaction mixture was allowed to cool to room temperature, and then an aqueous solution of hydrochloric acid (2 mol/L, 7 mL) was added thereto, and then chloroform and water were added thereto, and the resulting mixture was stirred. An aqueous solution of hydrochloric acid (2 mol/L) was added thereto until the pH of the mixture became 5, and the resulting organic layers were separated, then dried, and concentrated under reduced pressure to give the Compound 10 (1.23 g) as a colorless viscous material of a racemate (trans compound). MS (APCI): m/z 359/361 [M+H]$^+$ Reference Example 3

A corresponding starting compound was treated in a similar manner to the above Reference Example 2 to give the compound described in the following Table 15.

TABLE 15

| Reference Example | Compound | MS |
|---|---|---|
| 3 | ![structure] | (APCI): m/z 341/343 [M + H]$^+$ | racemate

Reference Example 4

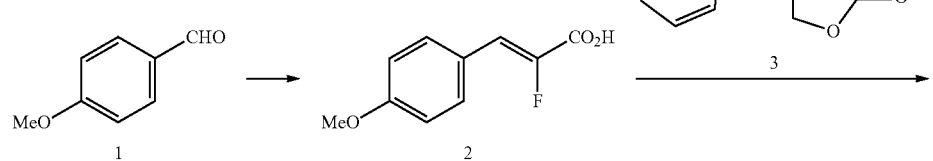

-continued

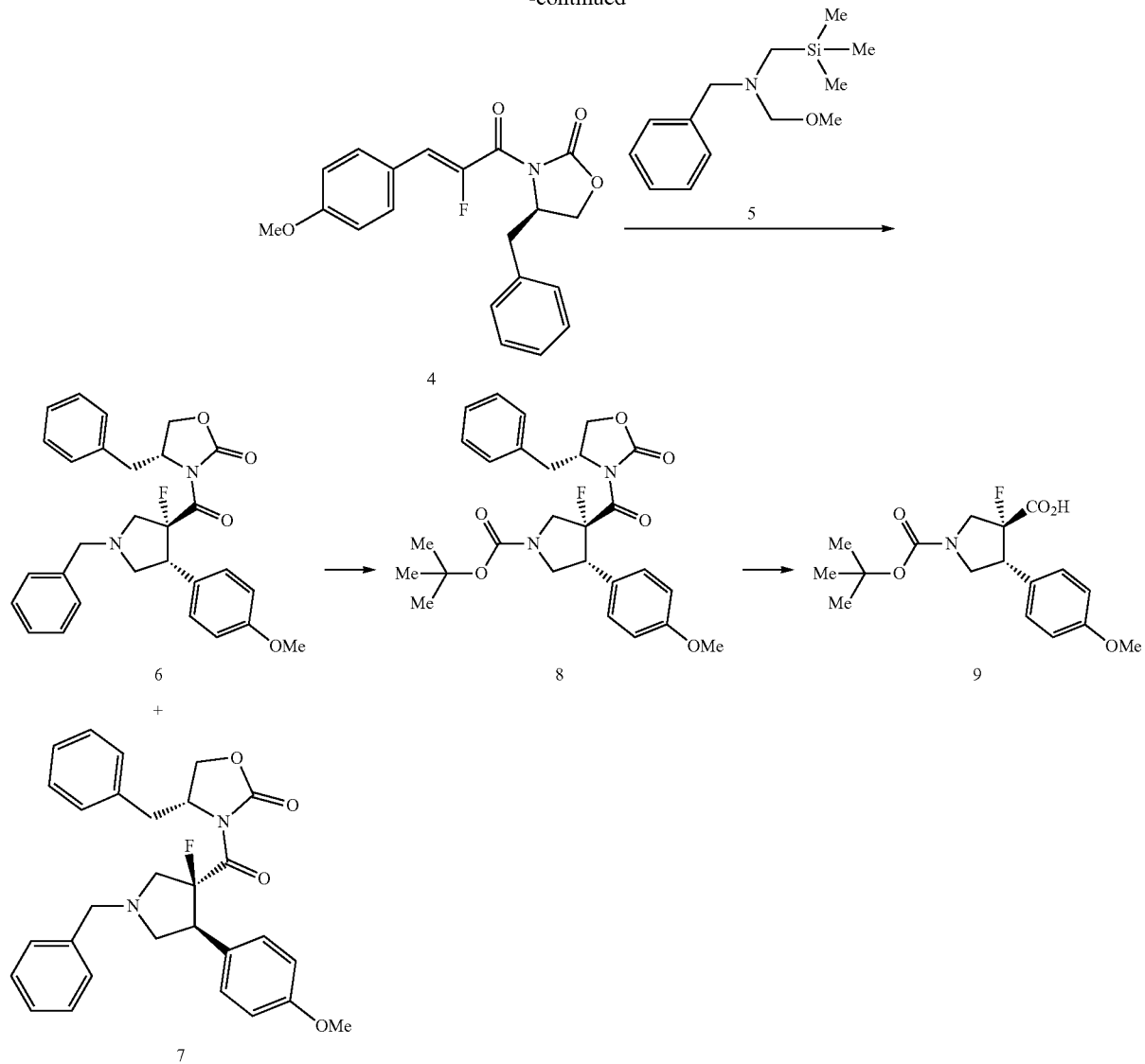

(1) Under a nitrogen atmosphere, to a solution of triethyl 2-fluoro-2-phosphonoacetate (55.6 g) in tetrahydrofuran (100 mL) were added a magnesium bromide-diethyl ether complex (71.3 g) and triethylamine (35.3 mL) under ice-cooling, and the resulting mixture was stirred at room temperature for 1.5 hours. To the reaction mixture was added dropwise a solution of the Compound 1 (25 g) in tetrahydrofuran (375 mL) under ice-cooling, and then the resulting mixture was stirred at room temperature for 15 hours. The reaction mixture was concentrated under reduced pressure until the volume became approximately half, and water (400 mL) and ethyl acetate (500 mL) were added thereto, and the resulting mixture was stirred. The resulting insoluble matters were removed by filtration, and the resulting organic layers were separated. The resulting organic layers were washed with saturated brine, dried, and concentrated under reduced pressure. To a solution of the resulting residues in tetrahydrofuran (210 mL)/ethanol (210 mL) was added an aqueous solution of sodium hydroxide (2 mol/L, 188 mL) at room temperature. To the reaction mixture were further added ethanol (300 mL) and tetrahydrofuran (100 mL), and the resulting mixture was stirred for 1 hour, and then an aqueous solution of hydrochloric acid (1 mol/L, 390 mL) was added thereto, and then tetrahydrofuran was evaporated under reduced pressure. To the resulting suspension was added water (300 mL), and the resulting mixture was stirred at room temperature for 1 hour, and then the resulting precipitates were collected by filtration. The resulting precipitates were washed with water and then diisopropyl ether, and air-dried at 60° C. for 12 hours to give the Compound 2 (26.63 g) as a colorless powder. MS (APCI): m/z 197 [M+H]$^+$ (2) To a suspension of the Compound 2 (26.6 g) in dichloromethane (270 mL) were added thionyl chloride (29.7 mL) and N,N-dimethylformamide (1.04 mL), and the resulting mixture was heated under reflux for 4 hours. The resulting reaction solution was concentrated under reduced pressure, and then the resulting residues were subjected to azeotropic concentration twice with toluene. To a solution of the resulting residues in dichloromethane (532 mL) were added the Compound 3 (26.3 g) and lithium chloride (12.5 g), and triethylamine (65.9 mL) was added dropwise thereto with ice-cooling under a nitrogen atmosphere, and then the resulting mixture was stirred at room temperature for 15 hours. The resulting reaction suspension was poured into an aqueous solution of citric acid (citric acid (102 g)+water (950 mL)) under ice-cooling, and the resulting mixture was extracted with chloroform (300 mL). The resulting organic layers were washed with saturated brine, dried, and concentrated under reduced pressure. The resulting residues were powdered with diisopropyl ether, collected by filtration, and then dried to give the Compound 4 (44.7 g) as a colorless powder. MS (APCI): m/z 356 [M+H]$^+$ (3) To a suspension of the Compound 4 (10 g) and the Compound 5 (13.3 g) in dichloromethane (100 mL) was added trifluoroacetic acid (215 μL) at room temperature, and the resulting mixture was heated under reflux under a nitrogen atmosphere for 1 hour. To the resulting reaction solution were further added the Compound 5 (3.34 g) and trifluoroacetic acid (54 μL) at room temperature, and the resulting mixture was heated under reflux for additional 30 minutes. The resulting reaction solution was poured into an aqueous solution of citric acid (citric acid (35 g)+water (350 mL)) under ice-cooling, and the resulting mixture was extracted with dichloromethane. The resulting organic layers were washed with a saturated aqueous solution of sodium hydrogen carbonate and saturated brine, then dried, and concentrated under reduced pressure. The resulting residues were purified by silica gel column chromatography (hexane:ethyl acetate=80:20 to 40:60), and crystallized with diisopropyl ether to give each of the Compound 6 (6.06 g) and the Compound 7 (3.3 g) as a colorless powder. Each MS (APCI): m/z 489 [M+H]$^+$ TLC (hexane:ethyl acetate=80: 20): Rf value of the Compound 6≈0.45, and Rf value of the Compound 7≈0.2 (TLC plate: 1.05715.0001 TLC Silica gel 60 F$_{254}$ manufactured by Merck KGaA). The Compound 6 was dissolved into a small amount of a mixed solution of dichloromethane and ethyl acetate, and diethyl ether was added thereto to recrystallize the compound. The resulting crystal was subject to X-ray crystallography to confirm that the Compound 6 and the Compound 7 have the above configurations respectively.

(4) To a solution of the Compound 6 (6.05 g) and dicarbonate di-t-butyl (2.84 g) in ethanol (85 mL)/tetrahydrofuran (150 mL) was added 10% palladium carbon (wetted with ca. 50% water, 1.8 g) with stirring, and the resulting mixture was stirred under hydrogen atmosphere (1 atm) for 24 hours. The resulting precipitates were dissolved into chloroform (100 mL) and methanol (20 mL), and palladium carbon was removed by filtration. The resulting filtrate was concentrated, and the resulting residues were powdered with hexane, collected by filtration, and dried under reduced pressure to give the Compound 8 (6.28 g) as a colorless powder. MS (APCI): m/z 399 [M-Boc+H]$^+$ (5) To a suspension of the Compound 8 (6.28 g) in tetrahydrofuran (45 mL) was added an aqueous solution of lithium hydroxide (lithium hydroxide (monohydrate) (635 mg)+ water (20 mL)) under ice-cooling, and the resulting mixture was stirred at room temperature for 1 hour, and then tetrahydrofuran was evaporated. To the resulting residues was added water (20 mL), and then the resulting mixture was washed four times with a mixed solution (30 mL) of ethyl acetate and diethyl ether (1:1). The resulting aqueous layers were acidified with an aqueous solution of hydrochloric acid (1 mol/L, 15.5 mL), and then the resulting mixture was extracted twice with chloroform. The resulting organic layers were combined, washed with saturated brine, and dried, and the solvent was evaporated to give the Compound 9 (4.11 g) as a colorless powder. MS (APCI): m/z 338 [M−H]$^−$ Reference Example 5

A corresponding starting compound was treated in a similar manner to the above Reference Example 4 to give the compound described in the following Table 16.

TABLE 16

| Reference Example | Compound | MS |
|---|---|---|
| 5 | 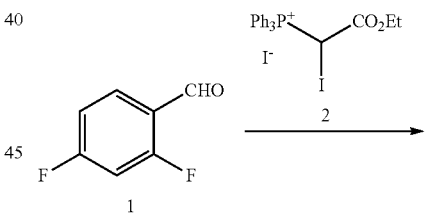 | (APCI): m/z 246 [M − Boc + H]$^+$ |

Reference Example 6

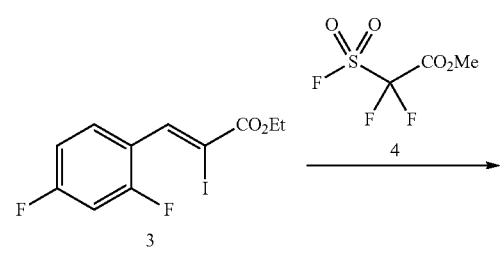

-continued

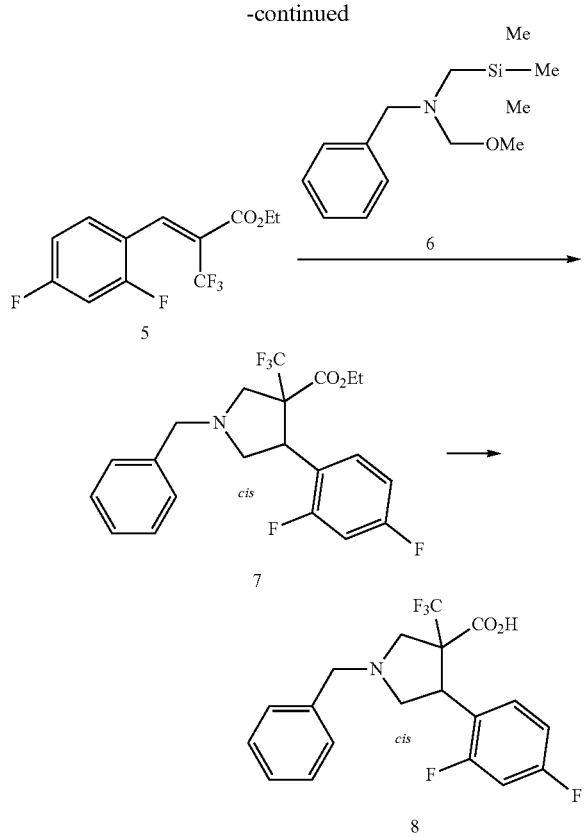

(1) To a mixture of the Compound 1 (1.42 g), the Compound 2 (6.02 g) synthesized according to the method described in a document (*Synthesis*, 1987, 5, 498-499), and methanol (100 mL) was added potassium carbonate (691 mg) at 40° C., and the resulting mixture was stirred at the same temperature for 7.5 hours, and then stirred at room temperature overnight. The reaction mixture was concentrated under reduced pressure, and a small amount of ethyl acetate was added thereto, and then hexane was added thereto, and the resulting mixture was stirred. The resulting insoluble matters were removed by filtration, washed with hexane, and then the resulting filtrate was concentrated under reduced pressure. The resulting residues were purified by silica gel column chromatography (hexane:ethyl acetate=100:0 to 90:10) to give the Compound 3 (2.734 g) as a pale yellow viscous material. MS (APCI): m/z 356 [M+NH$_4$]$^+$ (2) Under a nitrogen atmosphere, a mixture of the Compound 3 (2.734 g), copper iodide (385 mg), hexamethylphosphoric triamide (4.08 mL), and N,N-dimethylformamide (60 mL) was heated to 65° C., and a solution of the Compound 4 (3.11 g) in N,N-dimethylformamide (40 mL) was added dropwise thereto over 3 hours, and the resulting mixture was stirred at the same temperature for 19 hours. The reaction mixture was allowed to cool to room temperature, and then a saturated aqueous solution of ammonium chloride was added thereto, and the resulting mixture was stirred, and extracted with diethyl ether. The resulting organic layers were washed with saturated brine, then dried, and concentrated under reduced pressure. The resulting residues were purified by silica gel column chromatography (hexane:ethyl acetate=98:2 to 95:5) to give the Compound 5 (1.77 g) as a colorless viscous material. MS (APCI): m/z 298 [M+NH$_4$]$^+$ (3) To a solution of the Compound 5 (1.19 g) and the Compound 6 (4.033 g) in dichloromethane (20 mL) was added trifluoroacetic acid (65 μL) under ice-cooling, and the resulting mixture was stirred at 45° C. for 2 hours. The reaction mixture was allowed to cool to room temperature, and then a saturated aqueous solution of sodium hydrogen carbonate was added thereto, and the resulting mixture was stirred, and extracted with chloroform. The resulting organic layers were dried, and then concentrated under reduced pressure. The resulting residues were purified by silica gel column chromatography (hexane:ethyl acetate=93:7 to 85:15) to give the Compound 7 as a colorless viscous material (1.58 g) of a racemate (cis compound). MS (APCI): m/z 414 [M+H]$^+$ (4) To a solution of the Compound 7 (1.58 g) in ethanol (30 mL) was added an aqueous solution of sodium hydroxide (2 mol/L, 9.55 mL), and the resulting mixture was stirred at 85° C. for 23 hours. The reaction mixture was allowed to cool to room temperature, and then an aqueous solution of hydrochloric acid (2 mol/L) was added thereto to neutralize the mixture, and the resulting mixture was concentrated under reduced pressure. The resulting residues were subjected to azeotropic concentration with ethanol and chloroform, and then dried under reduced pressure to give the Compound 8 (racemate, cis compound) as a colorless viscous material (2.75 g) comprising sodium chloride. MS (APCI): m/z 386 [M+H]$^+$ Reference Example 7

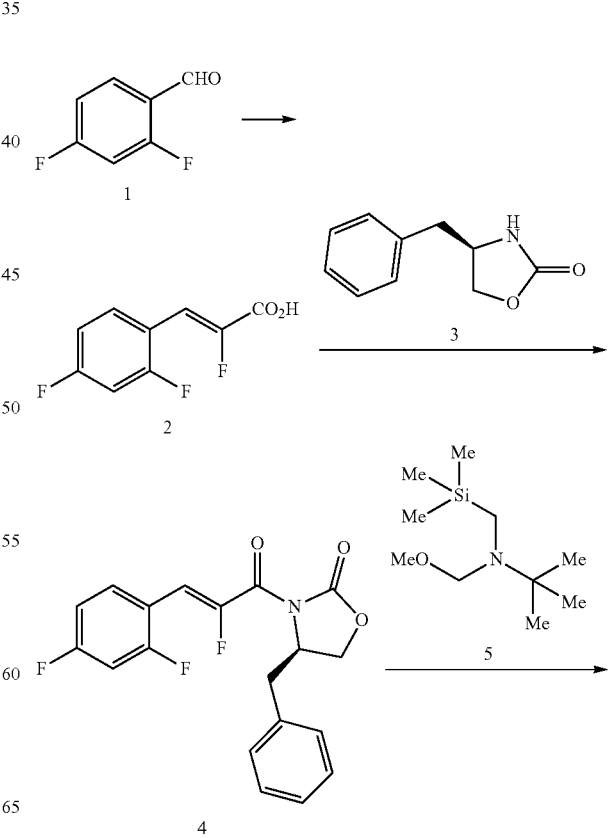

-continued

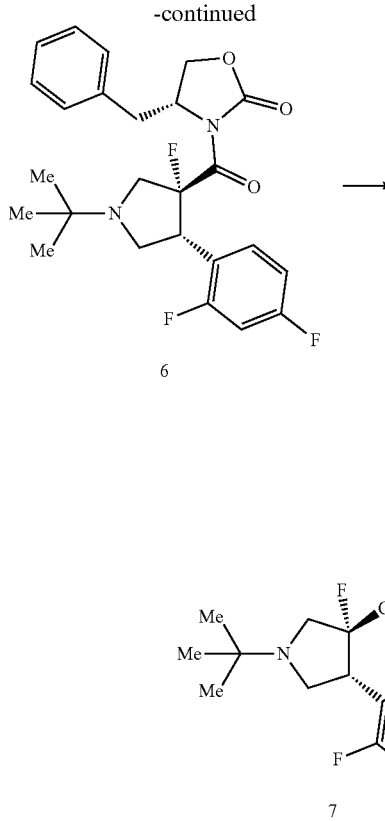

(1) The Compound 1 (30 g) was treated in a similar manner to the above Reference Example 4 to give the Compound 4 (31.42 g) as a colorless powder. MS (APCI): m/z 362 [M+H]$^+$ (2) The Compound 4 (2.8 g) and the Compound 5 (6.31 g) synthesized according to the method described in WO2004/089307 were treated in a similar manner to the above Reference Example 4 to give the Compound 6 (1.49 g) as a pale yellow powder (TLC (hexane:ethyl acetate=80:20): Rf value of the Compound 6≈0.45 (TLC plate: 1.05715.0001 TLC Silica gel 60 F$_{254}$ manufactured by Merck KGaA)). MS (APCI): m/z 461 [M+H]$^+$ (3) To a solution of the Compound 6 (1.39 g) in tetrahydrofuran (30 mL) was added an aqueous solution of lithium hydroxide (lithium hydroxide hydrate (151 mg)+water (15 mL)) under ice-cooling, and the resulting mixture was stirred at the same temperature for 1 hour. To a solution of the reaction mixture was added an aqueous solution of hydrochloric acid (1 mol/L, 3.64 mL), and the resulting mixture was stirred, and then concentrated under reduced pressure. The resulting residues were subjected to azeotropic concentration with toluene. The resulting residues were purified by silica gel column chromatography (chloroform:methanol=3:1 to 2:1) to give the Compound 7 (612 mg) as a colorless powder. MS (APCI): m/z 302 [M+H]$^+$ Reference Examples 8 to 10

Each corresponding starting compound was treated in a similar manner to the above Reference Example 7 to give each compound described in the following Table 17.

TABLE 17

| Reference Example | Compound | MS |
|---|---|---|
| 8 | Me—C(Me)(Me)—N-pyrrolidine-F,CO$_2$H-(4-fluorophenyl) | (APCI): m/z 284 [M + H]$^+$ |
| 9 | Me—C(Me)(Me)—N-pyrrolidine-F,CO$_2$H-(4-methoxyphenyl) | (APCI): m/z 296 [M + H]$^+$ |
| 10 | Me—C(Me)(Me)—N-pyrrolidine-F,CO$_2$H-(5-fluoropyridin-2-yl) | (APCI): m/z 285 [M + H]$^+$ |

Reference Example 11

The intermediate compound of Reference Example 10 was synthesized according to the following method.

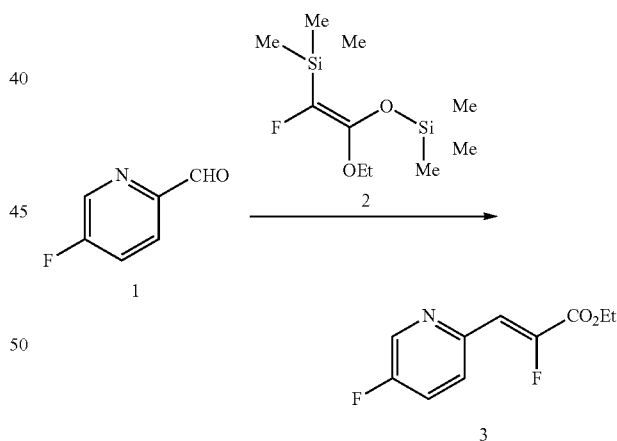

To a solution of the Compound 1 (1.0 g) and a solution of tetrabutylammonium acetate in tetrahydrofuran (0.1 mol/L, 3.997 mL) in dichloromethane (20 mL) was added the Compound 2 (2.402 g), and the resulting mixture was stirred at room temperature for 1 hour. To the reaction mixture was added a saturated aqueous solution of ammonium chloride, and the resulting mixture was stirred, and extracted with chloroform. The resulting organic layers were dried, and then concentrated under reduced pressure. The resulting residues were purified by NH silica gel column chromatography (hexane:ethyl acetate=99:1 to 90:10), powdered with hexane, collected by filtration, and dried under reduced pressure to give the Compound 3 (667 mg) as a colorless powder. MS (ESI): m/z 214 [M+H]$^+$ Reference Example 12

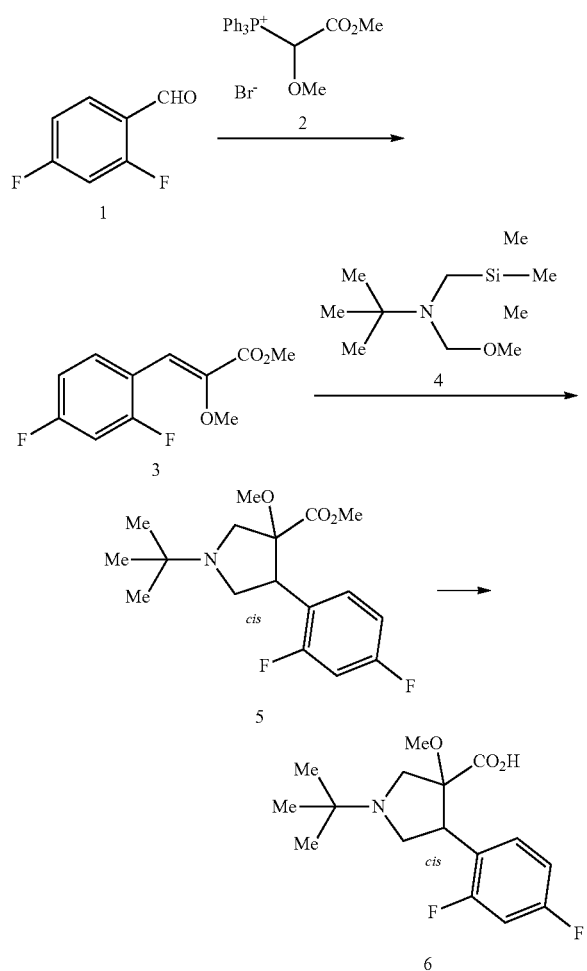

(1) To a mixture of the Compound 2 (9.40 g) synthesized according to the method described in a document (*Tetrahedron*, 1997, 53, 17097-17114) and dichloromethane (80 mL) was added 1,1,3,3,-tetramethylguanidine (4.86 g) under ice-cooling, and then the Compound 1 (3.0 g) was added thereto at room temperature, and the resulting mixture was stirred at the same temperature for 5 days. The reaction mixture was concentrated under reduced pressure, and then ethyl acetate and a saturated aqueous solution of ammonium chloride were added thereto, and the resulting mixture was stirred, and extracted with ethyl acetate. The resulting organic layers were dried, and then concentrated under reduced pressure. The resulting residues were purified by silica gel column chromatography (hexane:ethyl acetate=98:2 to 85:15) to give the Compound 3 (2.76 g) as a colorless powder. MS (APCI): m/z 229 [M+H]$^+$ (2) To a solution of the Compound 3 (0.76 g) and the Compound 4 (2.71 g) in dichloromethane (10 mL) was added trifluoroacetic acid (51 μL) under ice-cooling, and the resulting mixture was stirred at 45° C. for 1 hour. To the reaction mixture was added an aqueous solution of sodium hydrogen carbonate, and the resulting mixture was stirred, and then extracted with chloroform. The resulting organic layers were dried, and then concentrated under reduced pressure. The resulting residues were purified by silica gel column chromatography (hexane:ethyl acetate=85:15 to 70:30, followed by chloroform:methanol=97:3 to 90:10) to give the Compound 5 (1.25 g) as a colorless viscous material of a racemate (cis compound). MS (APCI): m/z 328 [M+H]$^+$ (3) To a solution of the Compound 5 (1.25 g) in ethanol (20 mL) was added an aqueous solution of sodium hydroxide (2 mol/L, 9.55 mL), and the resulting mixture was stirred at 80° C. for 4 hours. The reaction mixture was allowed to cool to room temperature, and then an aqueous solution of hydrochloric acid (2 mol/L) was added thereto to neutralize the mixture, and the resulting mixture was concentrated under reduced pressure. The resulting residues were subjected to azeotropic concentration with ethanol and chloroform, and then dried under reduced pressure to give the Compound 6 (racemate, cis compound) as a colorless powder (2.40 g) comprising sodium chloride. MS (APCI): m/z 314 [M+H]$^+$ Reference Example 13

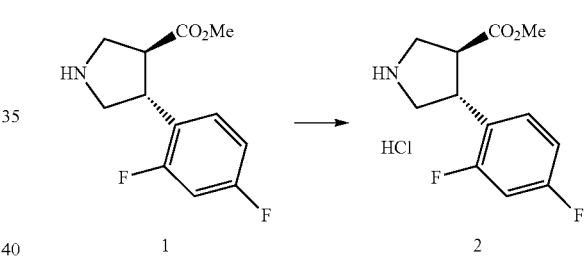

To a solution of the Compound 1 (1.90 g) in chloroform (13 mL) was added a solution of hydrochloric acid in 1,4-dioxane (4 mol/L, 2.0 mL) under ice-cooling, and the resulting mixture was stirred at room temperature for 10 minutes. The reaction mixture was concentrated under reduced pressure, and the resulting residues were powdered with diethyl ether, collected by filtration, and dried under reduced pressure to give the Compound 2 (1.74 g) as a colorless powder. MS (APCI): m/z 242 [M+H]$^+$ Reference Example 14

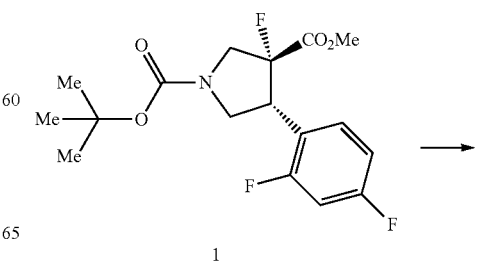

-continued

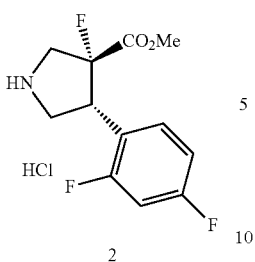

To a solution of the Compound 1 (3.45 g) in methanol (4 mL) was added thionyl chloride (2.92 mL), and the resulting mixture was stirred at room temperature for 64 hours. The reaction mixture was concentrated under reduced pressure, and then the resulting residues were powdered with diethyl ether, collected by filtration, and dried under reduced pressure to give the Compound 2 (2.76 g) as a colorless powder. MS (APCI): m/z 260 [M+H]$^+$ Reference Example 15

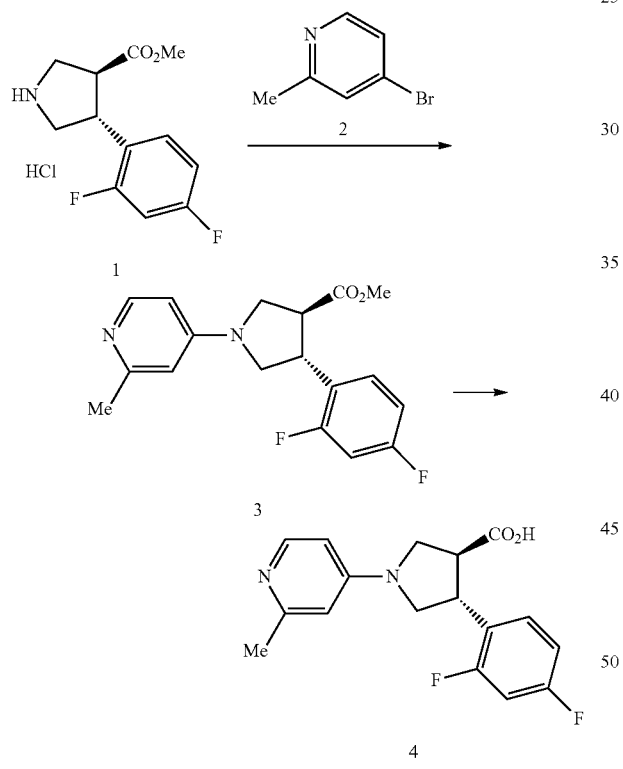

(1) A suspension of the Compound 1 (194 mg), the Compound 2 (134 μL), palladium acetate (31 mg), 1,1'-bis(diphenylphosphino)ferrocene (115 mg), and cesium carbonate (596 mg) in toluene (4 mL) was heated under reflux under a nitrogen atmosphere for 19 hours. The reaction mixture was allowed to cool to room temperature, and then an aqueous solution of sodium hydrogen carbonate and chloroform were added thereto, and the resulting mixture was stirred, and extracted with chloroform. The resulting organic layers were separated, dried, and then concentrated under reduced pressure. The resulting residues were purified by NH silica gel column chromatography (hexane:ethyl acetate=90:10 to 60:40) to give the Compound 3 (210 mg) as a pale yellow viscous material. MS (APCI): m/z 333 [M+H]$^+$ (2) To a solution of the Compound 3 (200 mg) in ethanol (3 mL) was added an aqueous solution of sodium hydroxide (2 mol/L, 900 μL), and the resulting mixture was stirred at room temperature for 18 hours. To the reaction mixture was added an aqueous solution of hydrochloric acid (2 mol/L, 900 μL), and the resulting mixture was stirred, and then concentrated under reduced pressure. The resulting residues were purified by silica gel column chromatography (chloroform:methanol=97:3 to 50:50) to give the Compound 4 (178.3 mg) as a colorless powder. MS (APCI): m/z 319 [M+H]$^+$ Reference Example 16

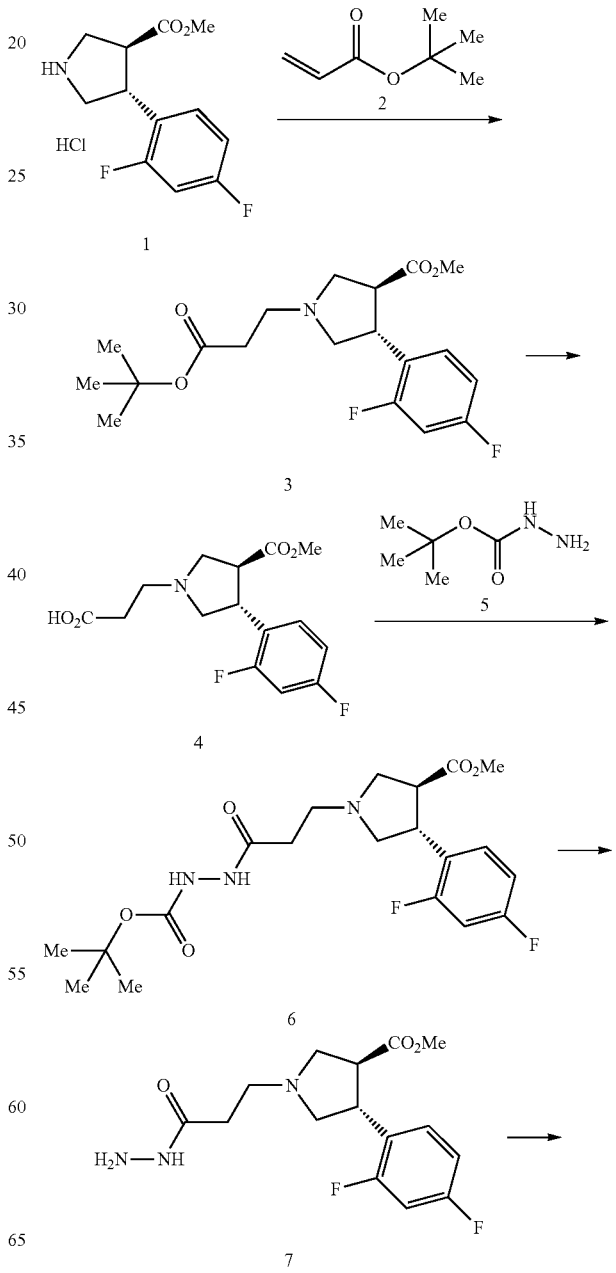

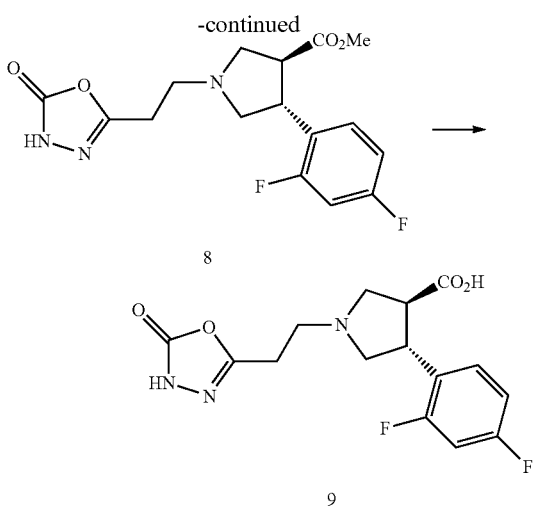

(1) A solution of the Compound 1 (4.0 g), the Compound 2 (2.2 g), and diisopropylethylamine (3.0 mL) in acetonitrile (10 mL) was heated under reflux for 2 hours. The reaction mixture was concentrated under reduced pressure, and then chloroform and an aqueous solution of sodium hydrogen carbonate were added thereto, and the resulting mixture was stirred, and extracted with chloroform. The resulting organic layers were dried, and then concentrated under reduced pressure. The resulting residues were purified by silica gel column chromatography (hexane:ethyl acetate=90:10 to 60:40) to give the Compound 3 (4.19 g) as a yellow viscous material. MS (APCI): m/z 370 [M+H]⁺

(2) A mixture of the Compound 3 (4.19 g), trifluoroacetic acid (10 mL), and water (1 mL) was stirred at room temperature for 2 hours. The reaction mixture was concentrated under reduced pressure, and to a solution of the resulting residues in chloroform (10 mL) was added triethylamine (5.70 mL) under ice-cooling, and the resulting mixture was stirred, and then the Compound 5 (1.79 g), 1-ethyl-3-(3-dimethylaminopropyl)carbodiimide hydrochloride (2.60 g), and 1-hydroxy-7-azabenzotriazole (1.85 g) were added thereto, and the resulting mixture was stirred at room temperature for 17 hours. To the reaction mixture was added an aqueous solution of sodium hydrogen carbonate, and the resulting mixture was stirred, and then extracted with chloroform. The resulting organic layers were washed with saturated brine, dried, and concentrated under reduced pressure. The resulting residues were purified by silica gel column chromatography (chloroform:methanol=100:0 to 95:5) to give the Compound 6 (3.91 g) as a colorless viscous material. MS (APCI): m/z 428 [M+H]⁺

(3) To a solution of the Compound 6 (3.91 g) in dichloromethane (15 mL) was added trifluoroacetic acid (5 mL), and the resulting mixture was stirred at room temperature for 24 hours. To the reaction mixture was added a saturated aqueous solution of sodium hydrogen carbonate until the pH of the mixture became 7, and then the resulting mixture was extracted with chloroform. The resulting organic layers were dried, and then concentrated under reduced pressure. The resulting residues were purified by silica gel column chromatography (chloroform:methanol=100:0 to 92:8). To a solution of the resulting compound in tetrahydrofuran (10 mL) was added 1,1'-carbonyldiimidazole (967 mg) under ice-cooling, and the resulting mixture was stirred at room temperature for 1.5 hours. To the reaction mixture were added ethyl acetate, water, and saturated brine, and the resulting mixture was stirred, and then extracted with ethyl acetate. The resulting organic layers were dried, and then concentrated under reduced pressure. The resulting residues were purified by silica gel column chromatography (hexane:ethyl acetate=65:35 to 20:80) to give the Compound 8 (0.99 g) as a colorless viscous material. MS (APCI): m/z 354 [M+H]⁺ (4) To a solution of the Compound 8 (0.99 g) in ethanol (10 mL) was added an aqueous solution of sodium hydroxide (2 mol/L, 5.58 mL), and the resulting mixture was stirred at room temperature for 1 hour. To the reaction mixture was added an aqueous solution of hydrochloric acid (2 mol/L) until the pH of the mixture became 7, and the resulting mixture was concentrated under reduced pressure. The resulting residues were dissolved into ethanol, and the resulting insoluble matters were removed by filtration, and then the resulting filtrate was concentrated under reduced pressure to give the Compound 9 (1018 mg) as a colorless powder comprising sodium chloride. MS (APCI): m/z 340 [M+H]⁺

Reference Example 17

A corresponding starting compound was treated in a similar manner to the above Reference Example 16 to give the compound described in the following Table 18.

TABLE 18

| Reference Example | Compound | MS |
|---|---|---|
| 17 | (structure shown) | (APCI): m/z 354 [M + H]⁺ |

Reference Example 18

The intermediate compound of Reference Example 17 was synthesized according to the following method.

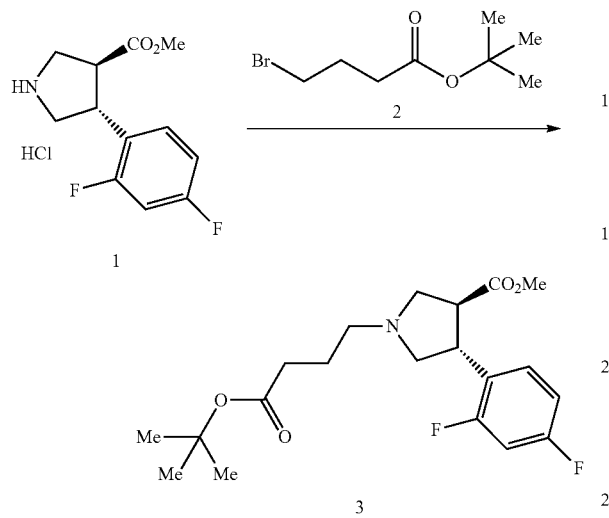

A solution of the Compound 1 (3.67 g), the Compound 2 (3.54 g), and diisopropylethylamine (7.07 mL) in acetonitrile (15 mL) was stirred at 80° C. for 2 hours. The reaction mixture was concentrated under reduced pressure, and then chloroform and an aqueous solution of sodium hydrogen carbonate were added thereto, and the resulting mixture was stirred, and extracted with chloroform. The resulting organic layers were dried, and then concentrated under reduced pressure. The resulting residues were purified by silica gel column chromatography (hexane:ethyl acetate=90:10 to 65:35) to give the Compound 3 (3.53 g) as a yellow viscous material. MS (APCI): m/z 384 [M+H]$^+$

Reference Example 19

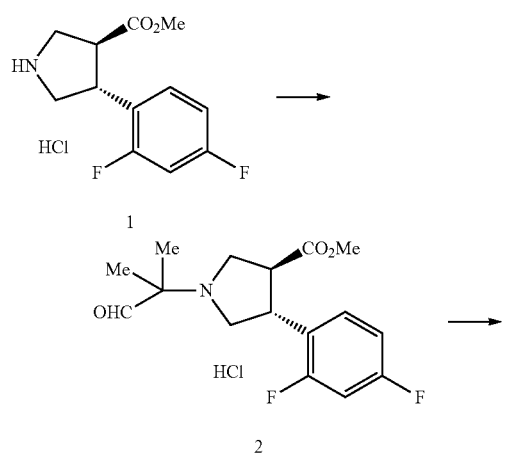

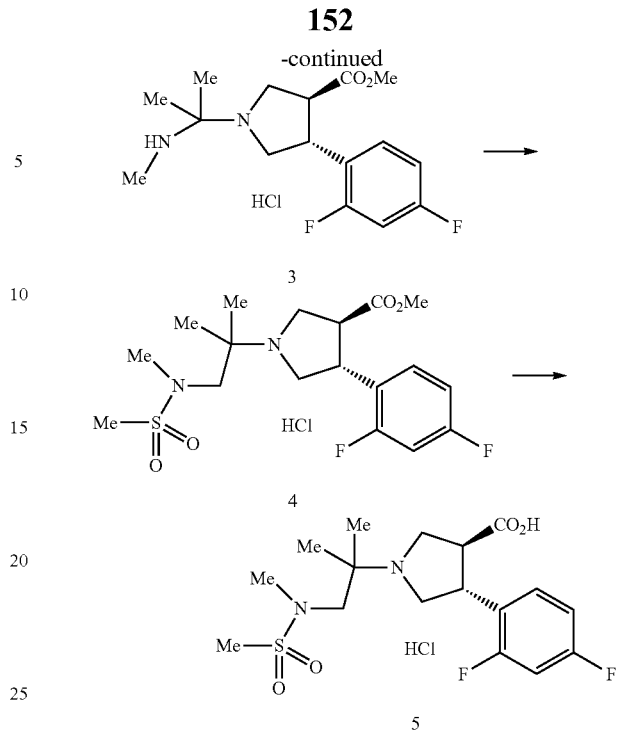

(1) To a solution of isobutyraldehyde (2.7 mL) in diethyl ether (30 mL) was added bromine (1.5 mL) under ice-cooling, and the resulting mixture was stirred at room temperature for 3 hours. To the reaction mixture was added iced water, and the resulting mixture was stirred, and then extracted with diethyl ether. The resulting organic layers were dried, and then concentrated under reduced pressure. To a solution of the resulting residues in 1,2-dimethoxyethane (40 mL) were added the Compound 1 (4.17 g), diisopropylethylamine (2.6 mL), and potassium carbonate (6.2 g), and the resulting mixture was heated under reflux for 16 hours. The reaction mixture was allowed to cool to room temperature, and then water was added thereto, and the resulting mixture was stirred, and extracted with ethyl acetate. The resulting organic layers were dried, and then concentrated under reduced pressure. The resulting residues were purified by silica gel column chromatography (hexane: ethyl acetate=90:10 to 35:65) to give the Compound 2 (4.13 g) as a pale yellow viscous material. MS (APCI): m/z 312 [M+H]$^+$ (2) To a solution of the Compound 2 (200 mg) in dichloromethane (3 mL) were added a solution of methylamine in tetrahydrofuran (2.0 mol/L, 385 µL) and acetic acid (55 µL), and the resulting mixture was stirred at room temperature for 30 minutes, and then sodium triacetoxyborohydride (203 mg) was added thereto, and the resulting mixture was stirred at room temperature for 3 days. To the reaction mixture was added a saturated aqueous solution of sodium hydrogen carbonate, and the resulting mixture was stirred, and then extracted with chloroform. The resulting organic layers were dried, and then concentrated under reduced pressure. The resulting residues were purified by NH silica gel column chromatography (hexane:ethyl acetate=90:10 to 30:70) to give the Compound 3 (175 mg) as a colorless viscous material. MS (APCI): m/z 327 [M+H]$^+$ (3) To a solution of the Compound 3 (168 mg) and diisopropylethylamine (134 µL) in dichloromethane (2 mL) was added methanesulfonyl chloride (47 µL) under ice-cooling, and the resulting mixture was stirred at room temperature for 2 hours. To the reaction mixture was added water, and the resulting mixture was stirred, and then extracted with dichloromethane. The resulting organic layers were dried, and then concentrated under reduced pressure. The resulting residues were purified by silica gel column chromatography (hexane:ethyl acetate=80:20 to 40:60). To a solution of the resulting compound in ethanol (2 mL) was added an aqueous solution of sodium hydroxide (2 mol/L, 510 μL), and the resulting mixture was stirred at room temperature for 17 hours. To the reaction mixture was added an aqueous solution of hydrochloric acid (2 mol/L, 510 μL), and the resulting mixture was stirred, and then concentrated under reduced pressure. The resulting residues were purified by silica gel column chromatography (chloroform:methanol=98:2 to 40:60) to give the Compound 5 (213 mg) as a colorless powder. MS (APCI): m/z 391 [M+H]$^+$ Reference Example 20 silica gel column chromatography (hexane:ethyl acetate=90:10 to 60:40) to give the Compound 3 (1.83 g) as a colorless viscous material. MS (APCI): m/z 443 [M+H]$^+$ (2) To a solution of the Compound 3 (300 mg) in ethanol (2 mL) was added an aqueous solution of sodium hydroxide (2 mol/L, 680 μL), and the resulting mixture was stirred at room temperature for 17 hours. To the reaction mixture was added an aqueous solution of hydrochloric acid (2 mol/L, 680 μL), and the resulting mixture was stirred, and then water and chloroform were added thereto, and the resulting mixture was stirred, and extracted with chloroform. The resulting organic layers were dried, and then concentrated under reduced pressure to give the Compound 4 (300 mg) as a colorless powder. MS (APCI): m/z 429 [M+H]$^+$ Reference Example 21

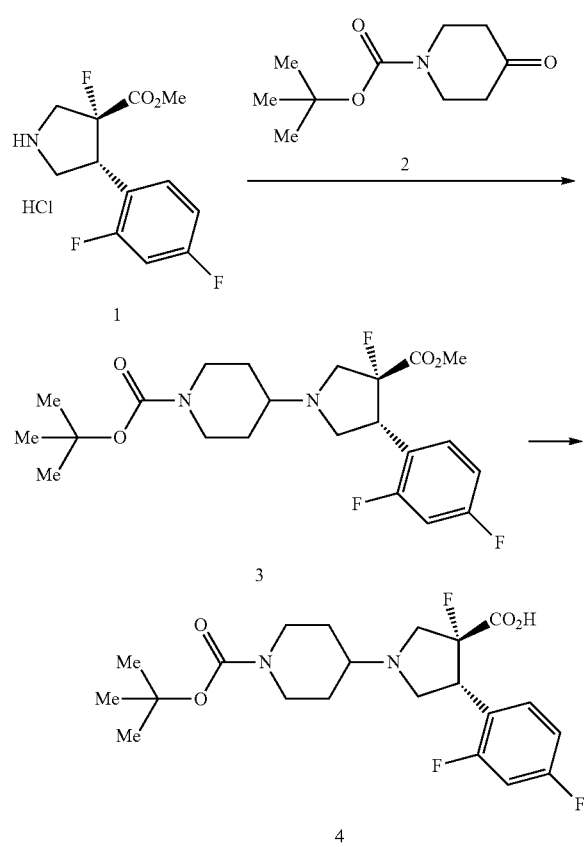

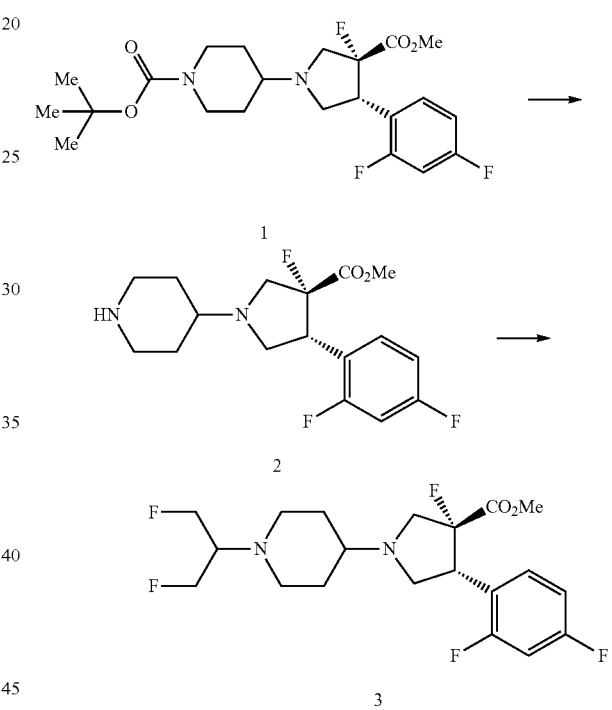

(1) To a suspension of the Compound 1 (1.18 g) in dichloromethane (15 mL) was added sodium acetate (492 mg), and the resulting mixture was stirred at room temperature for 30 minutes, and then the Compound 2 (956 mg) was added thereto, and the resulting mixture was stirred at room temperature for 30 minutes. To the reaction mixture was added sodium triacetoxyborohydride (1.27 g), and the resulting mixture was stirred at room temperature for 17 hours. To the reaction mixture was added a saturated aqueous solution of sodium hydrogen carbonate, and the resulting mixture was stirred, and then extracted with chloroform. The resulting organic layers were dried, and then concentrated under reduced pressure. The resulting residues were purified by (1) To a solution of the Compound 1 (900 mg) in dichloromethane (4 mL) was added trifluoroacetic acid (2 mL), and the resulting mixture was stirred at room temperature for 17 hours. To the reaction mixture was added a saturated aqueous solution of sodium hydrogen carbonate, and the resulting mixture was stirred, and then extracted with chloroform. The resulting organic layers were dried, and then concentrated under reduced pressure to give the Compound 2 (700 mg) as a colorless viscous material. MS (APCI): m/z 343 [M+H]$^+$ (2) To a solution of the Compound 2 (263 mg) and 1,3-difluoroacetone (145 mg) in dichloromethane (2 mL) was added acetic acid (88 μL), and the resulting mixture was stirred at room temperature for 30 minutes, and then sodium triacetoxyborohydride (326 mg) was added thereto, and the resulting mixture was stirred at room temperature for 20 hours. To the reaction mixture was added a saturated aqueous solution of sodium hydrogen carbonate, and the resulting mixture was stirred, and then extracted with chloroform. The resulting organic layers were dried, and then concentrated under reduced pressure. The resulting residues were purified by silica gel column chromatography (chloroform:methanol=100:0 to 90:10) to give the Compound 3 (77 mg) as a colorless powder. MS (APCI): m/z 421 [M+H]$^+$ Reference Example 22

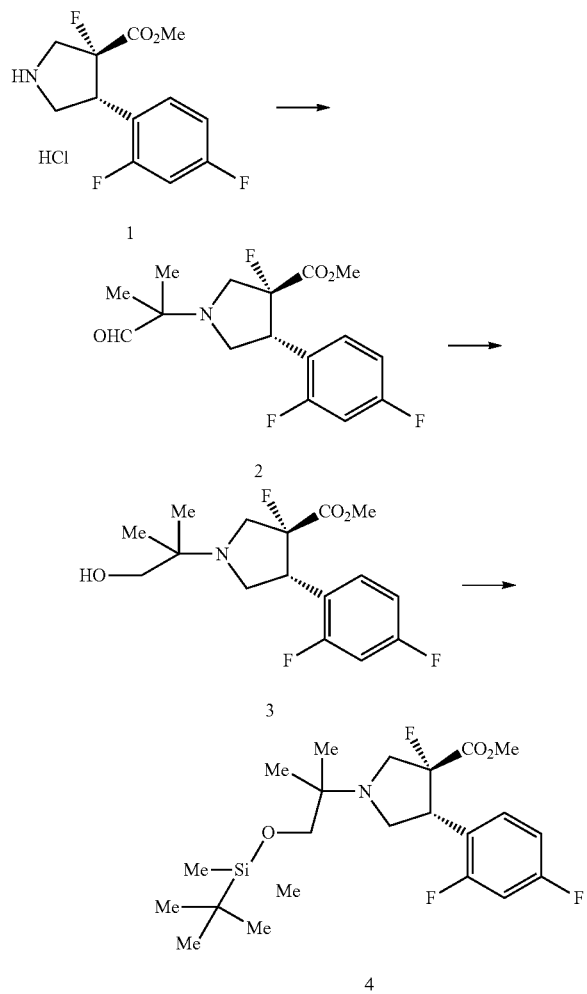

(1) The Compound 1 (596 mg) was treated in a similar manner to the above Reference Example 19 to give the Compound 2 (242 mg) as a colorless viscous material. MS (ESI): m/z 330 [M+H]$^+$
(2) To a solution of the Compound 2 (235 mg) in methanol (3 mL)/tetrahydrofuran (3 mL) was added sodium borohydride (32 mg) under ice-cooling, and the resulting mixture was stirred at the same temperature for 20 minutes. To the reaction mixture was added water, and the resulting mixture was stirred, and extracted with ethyl acetate. The resulting organic layers were dried, and then concentrated under reduced pressure. The resulting residues were purified by silica gel column chromatography (hexane:ethyl acetate=80:20 to 40:60) to give the Compound 3 (140 mg) as a pale yellow viscous material. MS (ESI): m/z 332 [M+H]$^+$
(3) To a solution of the Compound 3 (135 mg) and imidazole (33 mg) in N,N-dimethylformamide (2 mL) was added a solution of t-butyldimethylsilyl chloride (74 mg) in N,N-dimethylformamide (1 mL) under ice-cooling, and the resulting mixture was stirred at room temperature for 2 hours. To the reaction mixture were added water and ethyl acetate, and the resulting mixture was stirred, and then extracted with ethyl acetate. The resulting organic layers were washed with water and saturated brine, dried, and concentrated under reduced pressure. The resulting residues were purified by silica gel column chromatography (hexane:ethyl acetate=95:5 to 80:20) to give the Compound 4 (50 mg) as a pale yellow viscous material. MS (ESI): m/z 446 [M+H]$^+$ Reference Example 23

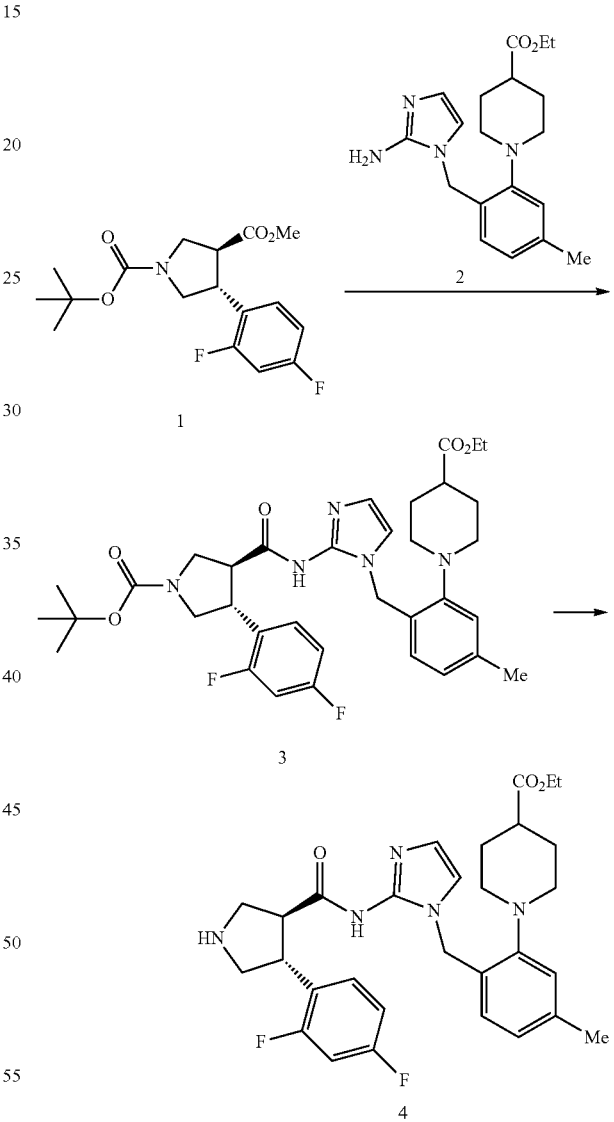

(1) The Compound 1 (5.7 g), the Compound 2 (5.0 g), 1-ethyl-3-(3-dimethylaminopropyl)carbodiimide hydrochloride (3.4 g), and 1-hydroxy-7-azabenzotriazole (2.4 g) were added to N,N-dimethylformamide (20 mL), and the resulting mixture was stirred at 50° C. for 16 hours. The reaction mixture was allowed to cool to room temperature, and then an aqueous solution of sodium hydrogen carbonate and ethyl acetate were added thereto, and the resulting mixture was stirred, and extracted with ethyl acetate. The resulting organic layers were washed with water and saturated brine, dried, and concentrated under reduced pressure. The resulting residues were purified by silica gel column chromatography (chloroform:methanol=100:0 to 92:8) to give the Compound 3 (8.5 g) as a colorless powder. MS (APCI): m/z 652 [M+H]⁺

(2) To a solution of the Compound 3 (4.0 g) in dichloromethane (30 mL) was added trifluoroacetic acid (4.73 mL) under ice-cooling, and the resulting mixture was stirred at room temperature for 15 hours. Trifluoroacetic acid (4.73 mL) was added thereto, and the resulting mixture was stirred at room temperature for 3 hours. To the reaction mixture was added an aqueous solution of sodium hydrogen carbonate, and the resulting mixture was stirred, and then extracted with chloroform. The resulting organic layers were dried, and then concentrated under reduced pressure. The resulting residues were purified by silica gel column chromatography (chloroform:methanol=97:3 to 75:25) and NH silica gel column chromatography (chloroform:methanol=100:0 to 92:8) to give the Compound 4 (2.88 g) as a pink powder. MS (APCI): m/z 552 [M+H]⁺

Reference Examples 24 to 31

Each corresponding starting compound was treated in a similar manner to the above Reference Example 23 to give each compound described in the following Table 19.

TABLE 19

| Reference Example | Compound | MS |
|---|---|---|
| 24 | 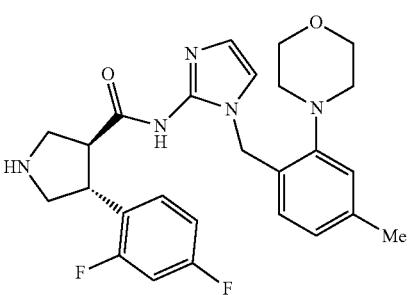 [SMILES: Cc1ccc(Cn2ccnc2NC(=O)[C@@H]2CNC[C@H]2c2ccc(F)cc2F)c(N2CCOCC2)c1] | (APCI): m/z 482 [M + H]⁺ |
| 25 | 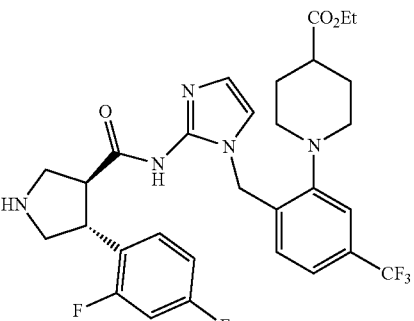 | (APCI): m/z 606 [M + H]⁺ |
| 26 | 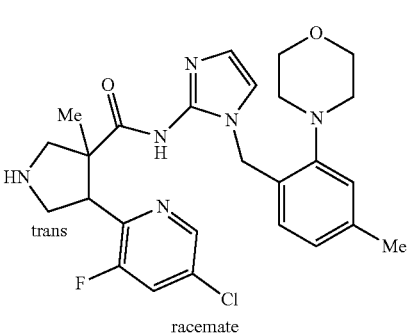 [SMILES: Cc1ccc(Cn2ccnc2NC(=O)C2(C)CNCC2c2ncc(Cl)cc2F)c(N2CCOCC2)c1] | (APCI): m/z 513/515 [M + H]⁺ |

TABLE 19-continued
| Reference Example | Compound | MS |
|---|---|---|
| 27 | 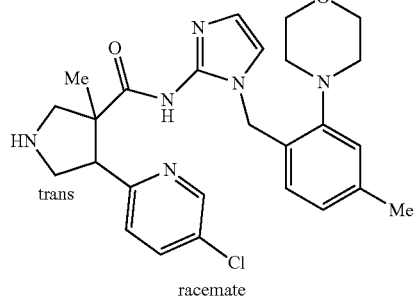 trans racemate | (APCI): m/z 495/497 [M + H]+ |
| 28 | 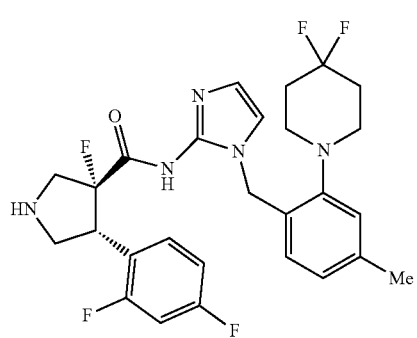 [SMILES: Cc1ccc(Cn2ccnc2NC(=O)[C@]2(F)CNC[C@H]2c2ccc(F)cc2F)c(N2CCC(F)(F)CC2)c1] | (APCI): m/z 534 [M + H]+ |
| 29 | 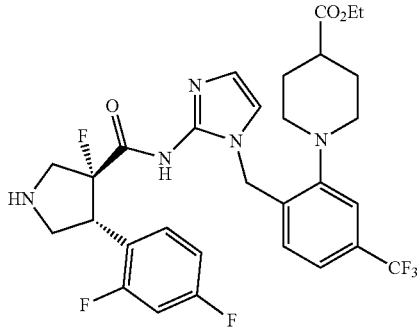 [SMILES: CCOC(=O)C1CCN(c2cc(C(F)(F)F)ccc2Cn2ccnc2NC(=O)[C@]2(F)CNC[C@H]2c2ccc(F)cc2F)CC1] | (APCI): m/z 624 [M + H]+ |
| 30 | 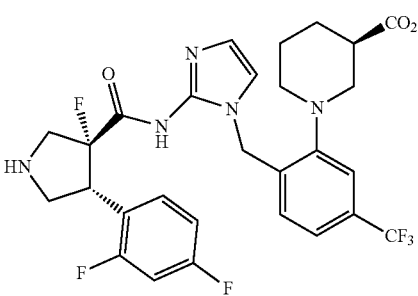 | (APCI): m/z 624 [M + H]+ |
| 31 | 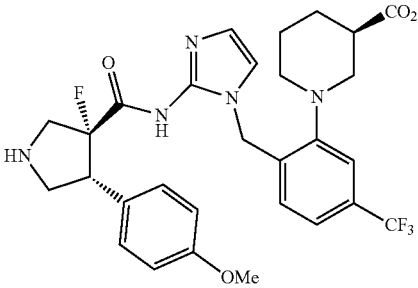 | (APCI): m/z 618 [M + H]+ |

Reference Example 32

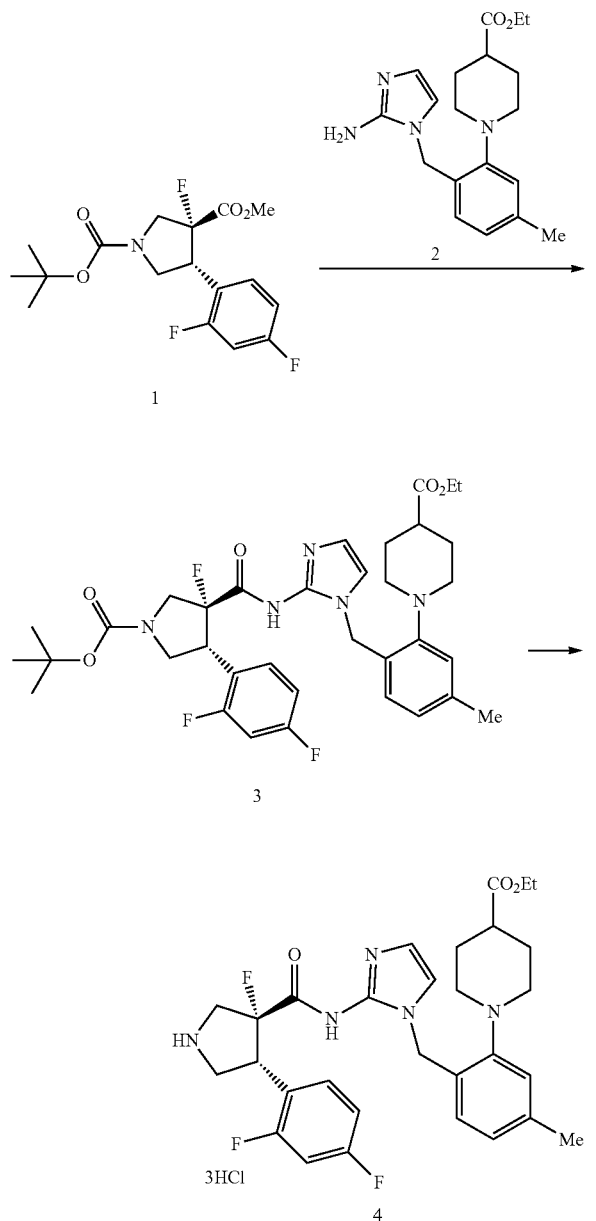

(1) The Compound 1 (604 mg) and the Compound 2 (719 mg) were treated in a similar manner to the above Reference Example 23 to give the Compound 3 (679 mg) as a colorless viscous material. MS (ESI): m/z 670 [M+H]$^+$ (2) To a solution of the Compound 3 (678 mg) in 1,4-dioxane (18 mL)/ethanol (9 mL) was added a solution of hydrochloric acid in 1,4-dioxane (4 mol/L, 2.53 mL), and the resulting mixture was stirred at 45° C. for 2 hours. A solution of hydrochloric acid in 1,4-dioxane (4 mol/L, 1.26 mL) was added thereto, and the resulting mixture was stirred at 45° C. for 20 hours. The reaction mixture was concentrated under reduced pressure to give the Compound 4 (647 mg) as a pale yellow powder. MS (APCI): m/z 570 [M+H]$^+$

Reference Example 33

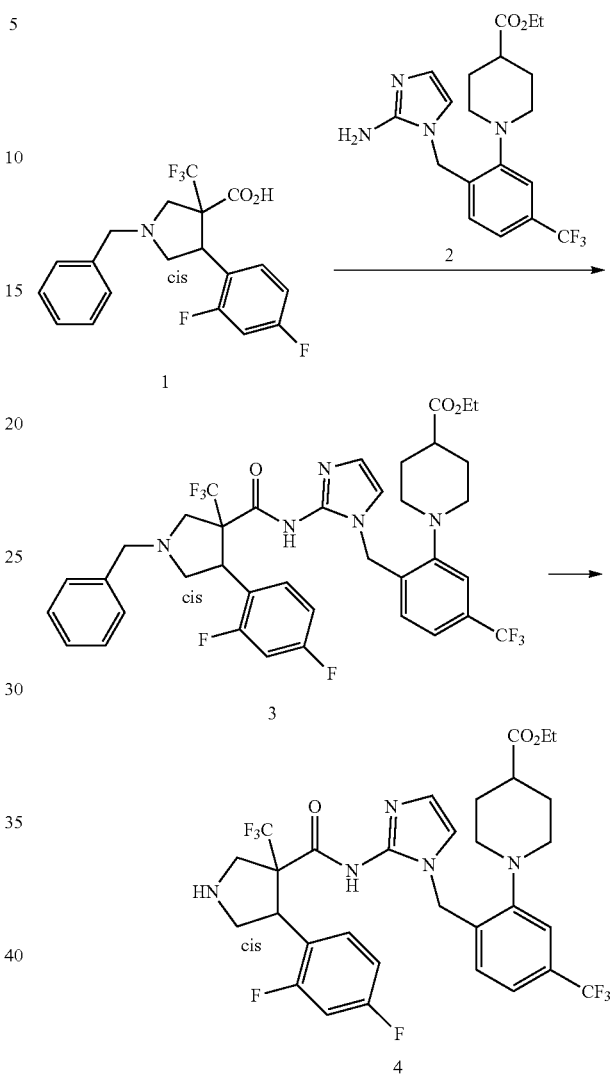

(1) The Compound 1 (2.75 g), the Compound 2 (1.52 g), 1-ethyl-3-(3-dimethylaminopropyl)carbodiimide hydrochloride (1.1 g), 1-hydroxy-7-azabenzotriazole (0.78 g), and triethylamine (1.07 mL) were added to N,N-dimethylformamide (16 mL), and the resulting mixture was heated at 110° C. under microwave radiation for 1 hour. To the reaction mixture was added an aqueous solution of sodium hydrogen carbonate, and the resulting mixture was stirred, and then extracted with ethyl acetate. The resulting organic layers were washed with water and saturated brine, dried, and concentrated under reduced pressure. The resulting residues were purified by silica gel column chromatography (chloroform:methanol=100:0 to 95:5) to give the Compound 2 (2.56 g) as a pale yellow powder. MS (APCI): m/z 764 [M+H]$^+$ (2) To a solution of the Compound 2 (2.56 g) in ethanol (50 mL) was added 10% palladium carbon (wetted with ca. 50% water, 2.0 g), and the resulting mixture was stirred under hydrogen atmosphere (1 atm) for 1.5 hours. After nitrogen replacement, 10% palladium carbon (wetted with ca. 50% water, 2.0 g) and ethanol (30 mL) were further added thereto, and the resulting mixture was stirred under hydrogen atmosphere (1 atm) for 11 hours. Palladium carbon was removed by filtration, and the resulting filtrate was concentrated under reduced pressure. The resulting residues were purified by silica gel column chromatography (chloroform:methanol=98:2 to 85:15) to give the Compound 3 (1.68 g) as a colorless powder. MS (APCI): m/z 674 [M+H]$^+$ Reference Example 34

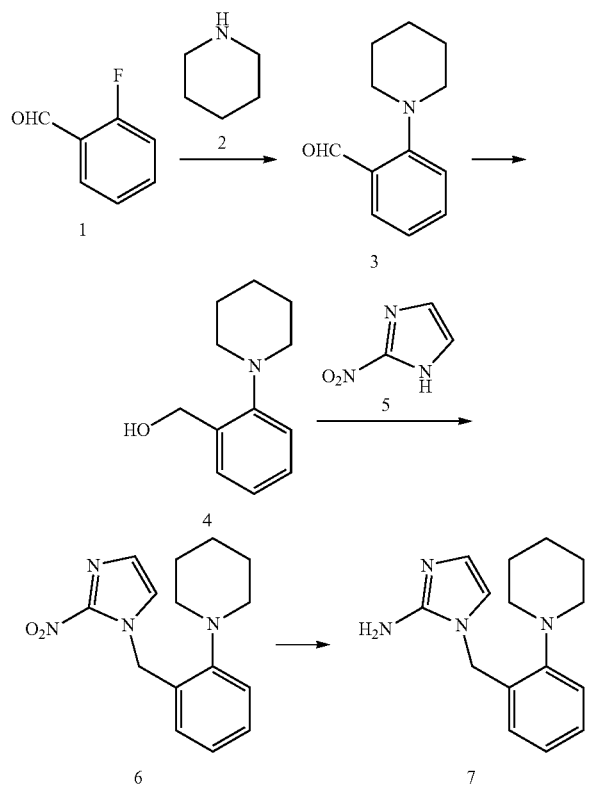

(1) A suspension of the Compound 1 (1.05 mL), the Compound 2 (1.09 mL), and potassium carbonate (2.76 g) in N,N-dimethylformamide (10 mL) was stirred at 110° C. for 5 hours, and stirred at 150° C. for 18 hours. The reaction mixture was allowed to cool to room temperature, and then water and ethyl acetate were added thereto, and the resulting mixture was stirred, and extracted with ethyl acetate. The resulting organic layers were washed with water and saturated brine, dried, and concentrated under reduced pressure. The resulting residues were purified by silica gel column chromatography (hexane:ethyl acetate=99:1 to 88:12) to give the Compound 3 (1.72 g) as a yellow liquid. MS (APCI): m/z 190 [M+H]$^+$ (2) To a solution of the Compound 3 (568 mg) in ethanol (6 mL) was added sodium borohydride (114 mg) under ice-cooling, and the resulting mixture was stirred at the same temperature for 1 hour. To the reaction mixture was added acetic acid, and the resulting mixture was stirred, and then concentrated under reduced pressure. To the resulting residues were added ethyl acetate and a saturated aqueous solution of sodium hydrogen carbonate, and the resulting mixture was stirred, and then extracted with ethyl acetate. The resulting organic layers were washed with saturated brine, dried, and concentrated under reduced pressure to give the Compound 4 (572 mg) as a pale yellow liquid. MS (APCI): m/z 192 [M+H]$^+$ (3) To a suspension of the Compound 4 (569 mg), the Compound 5 (339 mg), and triphenylphosphine (944 mg) in tetrahydrofuran (12 mL) was added diethyl azodicarboxylate (40 wt % solution in toluene, 1.65 mL) under ice-cooling, and the resulting mixture was stirred at room temperature for 14.5 hours. The reaction mixture was concentrated under reduced pressure, and then the resulting residues were purified by silica gel column chromatography (hexane:ethyl acetate=95:5 to 70:30) to give the Compound 6 (661 mg) as a yellow viscous material. MS (APCI): m/z 287 [M+H]$^+$ (4) To a solution of the Compound 6 (655 mg) in ethanol (11 mL) was added 10% palladium carbon (wetted with ca. 50% water, 63 mg), and the resulting mixture was stirred at room temperature under hydrogen atmosphere (1 atm) for 17 hours. Palladium carbon was removed by filtration, and then the resulting filtrate was concentrated under reduced pressure. The resulting residues were powdered with diisopropyl ether, collected by filtration, and dried under reduced pressure to give the Compound 7 (441 mg) as a yellow powder. MS (APCI): m/z 257 [M+H]$^+$ Reference Examples 35 to 39

Each corresponding starting compound was treated in a similar manner to the above Reference Example 34 to give each compound described in the following Table 20.

TABLE 20

| Reference Example | Compound | MS |
|---|---|---|
| 35 | 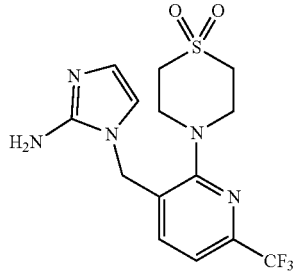 | (APCI): m/z 376 [M + H]$^+$ |
| 36 | 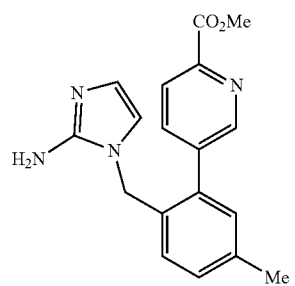 [SMILES: COC(=O)c1ccc(-c2cc(C)ccc2Cn2ccnc2N)cn1] | (APCI): m/z 323 [M + H]$^+$ |

TABLE 20-continued

| Reference Example | Compound | MS |
|---|---|---|
| 37 | (structure) | (APCI): m/z 372 [M + H]⁺ |
| 38 | (structure) | (APCI): m/z 386 [M + H]⁺ |
| 39 | (structure) | (APCI): m/z 413 [M + H]⁺ |

Reference Example 40

The intermediate compound of Reference Example 35 was synthesized according to the following method.

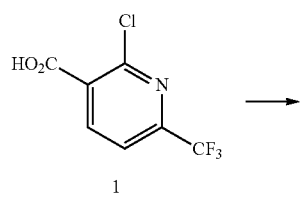

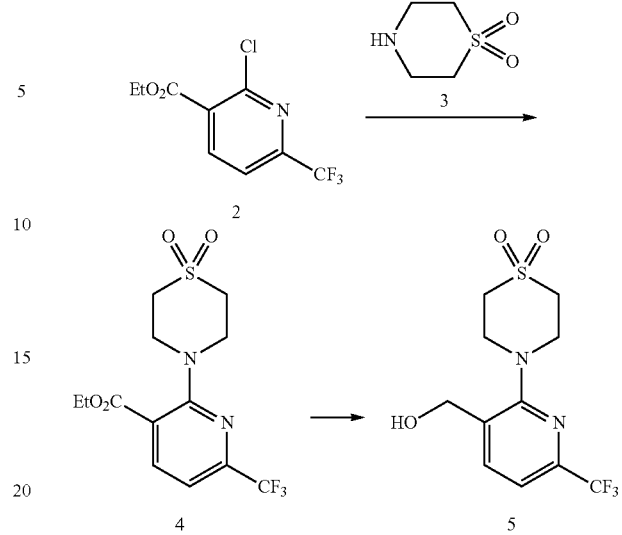

(1) The Compound 1 (1.0 g), N,N'-dicyclohexylcarbodiimide (1.37 g), 4-dimethylaminopyridine (162 mg), ethanol (5 mL) and dichloromethane (10 mL) were stirred at room temperature for 15 hours. To the reaction mixture were added an aqueous solution of sodium hydrogen carbonate and chloroform, and the resulting mixture was stirred, and extracted with chloroform. The resulting organic layers were dried, and then concentrated under reduced pressure. The resulting residues were purified by silica gel column chromatography (hexane:ethyl acetate=100:0 to 80:20) to give the Compound 2 (773 mg) as a colorless solid. MS (APCI): m/z 254/256 [M+H]⁺

(2) A solution of the Compound 2 (770 mg), the Compound 3 (822 mg), and diisopropylethylamine (1.06 mL) in tetrahydrofuran (10 mL)/acetonitrile (4 mL) was stirred at room temperature for 15 hours. To the reaction mixture was added the Compound 3 (411 mg), and the resulting mixture was stirred at 90° C. for 24 hours. The reaction mixture was allowed to cool to room temperature, and then water and ethyl acetate were added thereto, and the resulting mixture was stirred, and extracted with ethyl acetate. The resulting organic layers were dried, and then concentrated under reduced pressure. The resulting residues were purified by silica gel column chromatography (hexane:ethyl acetate=90:10 to 55:45) to give the Compound 4 (815.6 mg) as a colorless powder. MS (APCI): m/z 353 [M+H]⁺

(3) To a solution of the Compound 4 (810 mg) in tetrahydrofuran (25 mL) was added dropwise a solution of diisobutylaluminum hydride in toluene (1 mol/L, 9.2 mL) under a nitrogen atmosphere at −78° C., and the resulting mixture was stirred at the same temperature for 10 minutes, and then stirred at room temperature for 1 hour. The mixture was cooled to −78° C. again, and then methanol was added thereto until a gas bubble was not formed, and then the resulting mixture was warmed to room temperature, and an aqueous solution of hydrochloric acid (1 mol/L, 10 mL) was added thereto, and the resulting mixture was stirred. An aqueous solution of sodium hydroxide (2 mol/L) and a saturated aqueous solution of sodium hydrogen carbonate were added thereto to alkalify the mixture, and then the resulting mixture was extracted with ethyl acetate. The resulting organic layers were dried, and then concentrated under reduced pressure to give the Compound 5 (697 mg) as a colorless powder. MS (APCI): m/z 311 [M+H]$^+$ Reference Example 41

The intermediate compound of Reference Example 36 was synthesized according to the following method.

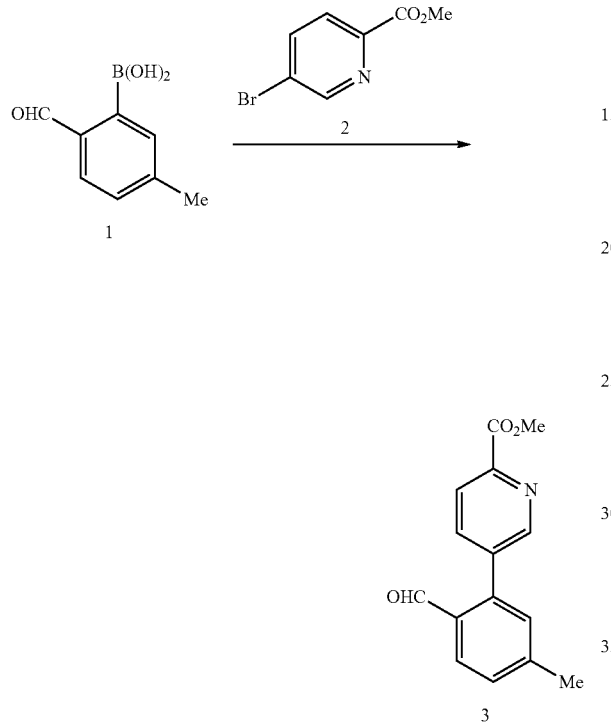

A mixture of the Compound 1 (830 mg), the Compound 2 (1.0 g), tetrakis(triphenylphosphine)palladium (802 mg), an aqueous solution of sodium carbonate (2 mol/L, 4.63 mL), toluene (15 mL), ethanol (5 mL), and water (2 mL) was heated under reflux for 3 hours. The reaction mixture was allowed to cool to room temperature, and then ethyl acetate was added thereto, and the resulting mixture was stirred, and then the resulting organic layers were separated, washed with water, dried, and concentrated under reduced pressure. The resulting residues were purified by silica gel column chromatography (hexane:ethyl acetate=90:10 to 55:45) to give the Compound 3 (706 mg) as a colorless powder. MS (APCI): m/z 256 [M+H]$^+$ Reference Example 42

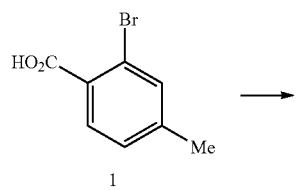

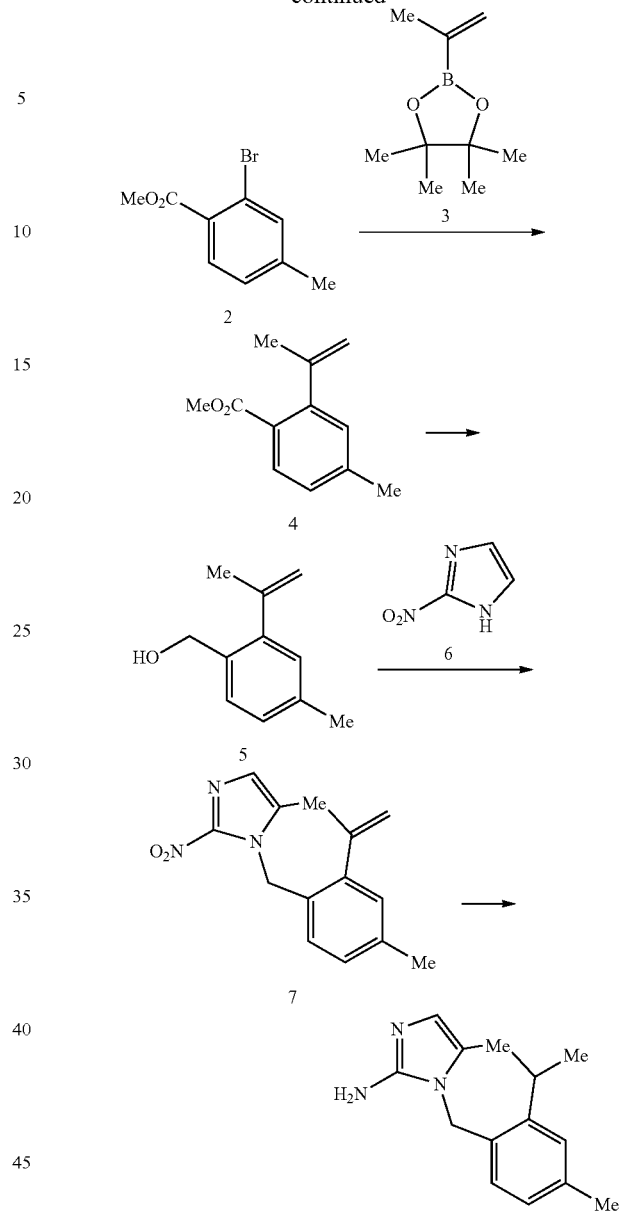

(1) To a solution of the Compound 1 (15 g) in methanol (200 mL) was added dropwise thionyl chloride (10.2 mL) under ice-cooling, and the resulting mixture was stirred at the same temperature for 1 hour. Thionyl chloride (10.2 mL) was added thereto, and the resulting mixture was stirred at 40° C. for 15 minutes, stirred at 45° C. for 45 minutes, and then stirred at room temperature for 16 hours. The reaction mixture was concentrated under reduced pressure, and then a saturated aqueous solution of sodium hydrogen carbonate and chloroform were added thereto, and the resulting mixture was stirred, and then extracted with chloroform. The resulting organic layers were dried, and then concentrated under reduced pressure to give the Compound 2 (17.84 g) as a pale yellow viscous material. MS (APCI): m/z 229/231 [M+H]$^+$ (2) A suspension of the Compound 2 (4.0 g), the Compound 3 (3.52 g), [1,1'-bis(diphenylphosphino) ferrocene]palladium(II) dichloromethane adduct (1.43 g), and potassium carbonate (7.24 g) in N,N-dimethylformamide (80 mL) was stirred at 80° C. under a nitrogen atmosphere for 6 hours. To the reaction mixture was added diethyl ether (200 mL), and the resulting mixture was stirred, and then the resulting insoluble matters were removed by filtration. To the resulting filtrate were added water and ethyl acetate, and the resulting mixture was stirred, and then extracted with ethyl acetate. The resulting organic layers were washed with water and saturated brine, then dried, and concentrated under reduced pressure. The resulting residues were purified by silica gel column chromatography (hexane:ethyl acetate=95:5 to 80:20) to give the Compound 4 (2.78 g) as a pale yellow viscous material. MS (APCI): m/z 191 [M+H]$^+$ (3) To a solution of the Compound 4 (2.78 g) in dichloromethane (60 mL) was added dropwise a solution of diisobutylaluminum hydride in hexane (1 mol/L, 43.8 mL) under ice-cooling, and the resulting mixture was stirred at the same temperature for 10 minutes. To the reaction mixture was added methanol (15 mL), and then water was added thereto, and the resulting mixture was stirred. The reaction mixture was diluted with dichloromethane, and the resulting insoluble matters were removed by filtration, and then the resulting filtrate was concentrated under reduced pressure. The resulting residues were purified by silica gel column chromatography (hexane:ethyl acetate=95:5 to 65:35) to give the Compound 5 (2.18 g) as a pale yellow viscous material. MS (APCI): m/z 145 [M–H$_2$O+H]$^+$ (4) To a suspension of the Compound 5 (2.18 g), the Compound 6 (1.82 g), and triphenylphosphine (7.76 g) in tetrahydrofuran (50 mL) was added a solution of diethyl azodicarboxylate in toluene (2.2 mol/L, 11.0 mL) under ice-cooling, and the resulting mixture was stirred at room temperature for 30 minutes. The reaction mixture was concentrated under reduced pressure, and then diethyl ether was added thereto, and the resulting insoluble matters were removed by filtration, and the resulting filtrate was concentrated under reduced pressure. The resulting residues were purified by silica gel column chromatography (hexane:ethyl acetate=80:20 to 40:60) to give the Compound 7 (2.99 g) as a pale yellow powder. MS (APCI): m/z 258 [M+H]$^+$ (5) To a solution of the Compound 7 (2.99 g) in methanol (50 mL) was added 10% palladium carbon (wetted with ca. 50% water, 3.0 g), and the resulting mixture was stirred at room temperature under hydrogen atmosphere (1 atm) for 4.5 hours. Palladium carbon was removed by filtration, and then the resulting filtrate was concentrated under reduced pressure to give the Compound 8 (2.23 g) as an orange viscous material. MS (APCI): m/z 230 [M+H]$^+$ Reference Example 43

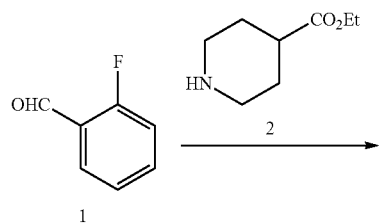

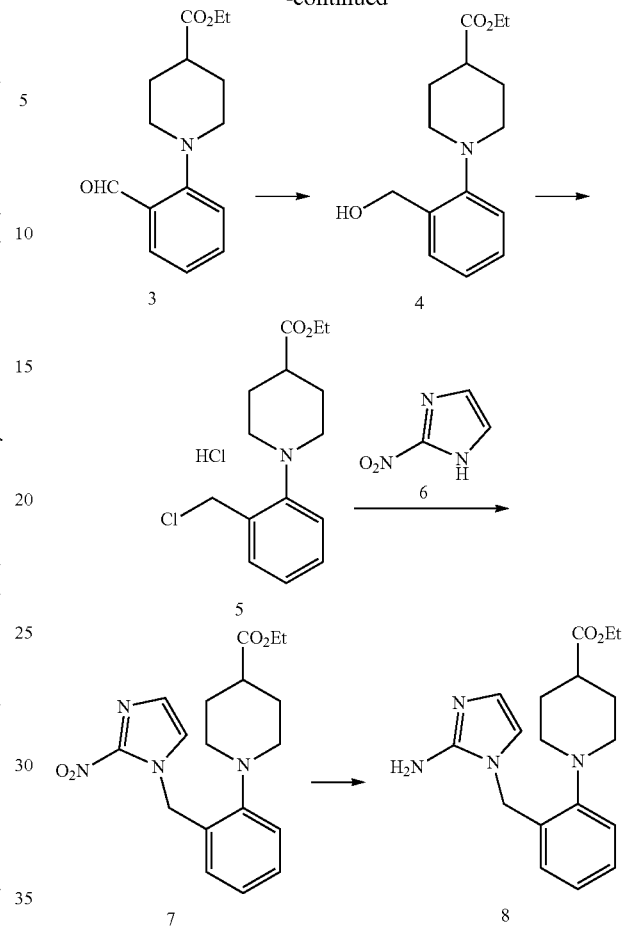

(1) A suspension of the Compound 1 (2.65 mL), the Compound 2 (4.25 mL), and potassium carbonate (6.91 g) in N,N-dimethylformamide (25 mL) was stirred at 140° C. for 14.5 hours. The reaction mixture was allowed to cool to room temperature, and then water and ethyl acetate were added thereto, and the resulting mixture was stirred, and extracted with ethyl acetate. The resulting organic layers were washed with water and saturated brine, dried, and concentrated under reduced pressure. The resulting residues were purified by silica gel column chromatography (hexane: ethyl acetate=98:2 to 70:30) to give the Compound 3 (5.37 g) as a yellow liquid. MS (APCI): m/z 262 [M+H]$^+$ (2) To a solution of the Compound 3 (5.37 g) in ethanol (62 mL) was added sodium borohydride (582 mg) under ice-cooling, and the resulting mixture was stirred at the same temperature for 1 hour. To the reaction mixture was added acetic acid, and the resulting mixture was stirred, and then concentrated under reduced pressure. To the residues were added ethyl acetate and a saturated aqueous solution of sodium hydrogen carbonate, and the resulting mixture was stirred, and then extracted with ethyl acetate. The resulting organic layers were washed with saturated brine, dried, and concentrated under reduced pressure to give the Compound 4 (5.42 g) as a pale yellow liquid. MS (APCI): m/z 264 [M+H]$^+$ (3) To a solution of the Compound 4 (1.317 g) in chloroform (15 mL) was added thionyl chloride (730 μL) under ice-cooling, and the resulting mixture was stirred at room temperature for 15 hours. The reaction mixture was concentrated under reduced pressure, and to a solution of the resulting compound in N,N-dimethylformamide (10 mL) were added the Compound 6 (622 mg) and potassium carbonate (1.382 g) under ice-cooling, and the resulting mixture was stirred at room temperature for 17 hours, and stirred at 80° C. for 2 hours. The reaction mixture was allowed to cool to room temperature, and water and ethyl acetate were added thereto, and the resulting mixture was stirred, and then extracted with ethyl acetate. The resulting organic layers were washed with water and saturated brine, dried, and concentrated under reduced pressure. The resulting residues were purified by silica gel column chromatography (hexane:ethyl acetate=90:10 to 65:35) to give the Compound 7 (1.55 g) as a yellow viscous material. MS (APCI): m/z 359 [M+H]+

(4) To a solution of the Compound 7 (1.544 g) in ethanol (22 mL) was added 10% palladium carbon (wetted with ca. 50% water, 155 mg), and the resulting mixture was stirred at room temperature under hydrogen atmosphere (1 atm) for 15 hours. Palladium carbon was removed by filtration, and then the resulting filtrate was concentrated under reduced pressure. The resulting residues were purified by silica gel column chromatography (hexane:ethyl acetate=98:2 to 70:30), then powdered with diisopropyl ether, collected by filtration, and dried under reduced pressure to give the Compound 8 (2.23 g) as a pale yellow solid. MS (APCI): m/z 329 [M+H]+

Reference Examples 44 to 64

Each corresponding starting compound was treated in a similar manner to the above Reference Example 43 to give each compound described in the following Table 21.

TABLE 21

| Reference Example | Compound | MS |
|---|---|---|
| 44 | (structure) | (APCI): m/z 397 [M + H]+ |
| 45 | (structure) | (APCI): m/z 343 [M + H]+ |
| 46 | (structure) | (APCI): m/z 273 [M + H]+ |
| 47 | (structure) | (APCI): m/z 296 [M + H]+ |
| 48 | (structure) | (APCI): m/z 455 [M + H]+ |
| 49 | (structure) | (APCI): m/z 300 [M + H]+ |
| 50 | (structure) | (APCI): m/z 307 [M + H]+ |

TABLE 21-continued

| Reference Example | Compound | MS |
|---|---|---|
| 51 | (structure: 2-aminoimidazole-CH2-phenyl(CF3)-piperazine-SO2Me) | (APCI): m/z 404 [M + H]+ |
| 52 | (structure: 2-aminoimidazole-CH2-phenyl(Me)-piperidine with 4-F, 4-CO2Et) | (APCI): m/z 361 [M + H]+ |
| 53 | (structure: 2-aminoimidazole-CH2-phenyl(iPr)-piperidine-4-CO2Et) | (APCI): m/z 371 [M + H]+ |
| 54 | (structure: 2-aminoimidazole-CH2-phenyl(cyclopropyl)-piperidine-4-CO2Et) | (APCI): m/z 369 [M + H]+ |
| 55 | (structure: 2-aminoimidazole-CH2-phenyl(CF3)-piperidine-3-methoxyisoxazole) | (APCI): m/z 422 [M + H]+ |
| 56 | (structure: 2-aminoimidazole-CH2-phenyl(CF3)-piperidine-3-CO2Et, stereo) | (APCI): m/z 397 [M + H]+ |
| 57 | (structure: 2-aminoimidazole-CH2-phenyl(Me,CF3)-piperidine-4-CO2Et) | (APCI): m/z 411 [M + H]+ |
| 58 | (structure: 2-aminoimidazole-CH2-phenyl(Me)-piperidine-4-CO2Et) | (APCI): m/z 357 [M + H]+ |
| 59 | (structure: 2-aminoimidazole-CH2-phenyl(iPr)-piperidine-3-CO2Et, stereo) | (APCI): m/z 371 [M + H]+ |

TABLE 21-continued

| Reference Example | Compound | MS |
|---|---|---|
| 60 | ![Compound 60: 2-aminoimidazole-CH2-phenyl(CF3)-cyclohexyl-CO2Et, cis/trans mixture] | (APCI): m/z 396 [M + H]+ |
| 61 | ![Compound 61: 2-aminoimidazole-CH2-phenyl(CHF2)-piperidine-CO2Et] | (APCI): m/z 379 [M + H]+ |
| 62 | ![Compound 62: 2-aminoimidazole-CH2-pyridine(CF3)-morpholine] | (APCI): m/z 328 [M + H]+ |
| 63 | ![Compound 63: 2-aminoimidazole-CH2-phenyl(CF3)-piperidine-CO2Et] | (APCI): m/z 397 [M + H]+ |
| 64 | ![Compound 64: 2-aminoimidazole-CH2-pyridine(CF3)-morpholine-CO2Me] | (APCI): m/z 386 [M + H]+ |

Reference Example 65

The intermediate compound of Reference Example 46 was synthesized according to the following method.

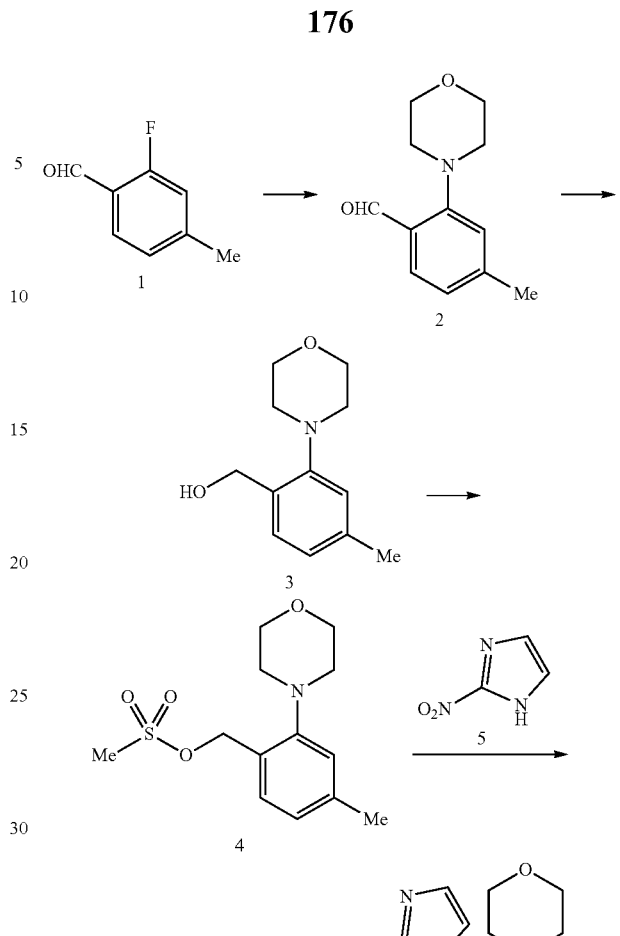

(1) A suspension of the Compound 1 (4.0 g), morpholine (3.04 mL), and potassium carbonate (6.0 g) in N,N-dimethylformamide (25 mL) was stirred at 130° C. for 3 hours. The reaction mixture was allowed to cool to room temperature, and then water and ethyl acetate were added thereto, and the resulting mixture was stirred, and extracted with ethyl acetate. The resulting organic layers were washed with water and saturated brine, dried, and concentrated under reduced pressure. The resulting residues were purified by silica gel column chromatography (hexane:ethyl acetate=90:10 to 67:33) to give the Compound 2 (3.4 g) as a yellow viscous material. MS (APCI): m/z 206 [M+H]+

(2) To a solution of the Compound 2 (3.4 g) in methanol (25 mL) was added sodium borohydride (615 mg) under ice-cooling, and the resulting mixture was stirred at room temperature for 1 hour. The reaction mixture was concentrated under reduced pressure, and ethyl acetate and water were added thereto, and the resulting mixture was stirred, and then extracted with ethyl acetate. The resulting organic layers were dried, and then concentrated under reduced pressure. The resulting residues were purified by silica gel column chromatography (hexane:ethyl acetate=80:20 to 20:80) to give the Compound 3 (3.44 g) as a pale yellow viscous material. MS (APCI): m/z 208 [M+H]+

(3) To a solution of the Compound 3 (3.44 g) and triethylamine (4.63 mL) in dichloromethane (100 mL) was added methanesulfonyl chloride (1.54 mL) under ice-cooling, and the resulting mixture was stirred at room temperature for 1 hour. The reaction mixture was concentrated under reduced pressure, and to a solution of the resulting compound in N,N-dimethylformamide (80 mL) were added the Compound 5 (2.82 g) and potassium carbonate (4.59 g), and the resulting mixture was stirred at 80° C. for 1.5 hours, and stirred at 100° C. for 2 hours. The reaction mixture was allowed to cool to room temperature, and ethyl acetate and water were added thereto, and the resulting mixture was stirred, and then extracted with ethyl acetate. The resulting organic layers were washed with water and saturated brine, dried, and concentrated under reduced pressure. The resulting residues were purified by silica gel column chromatography (hexane:ethyl acetate=80:20 to 20:80) to give the Compound 6 (3.44 g) as a yellow powder. MS (APCI): m/z 303 [M+H]$^+$ Reference Example 66

The intermediate compound of Reference Example 48 was synthesized according to the following method.

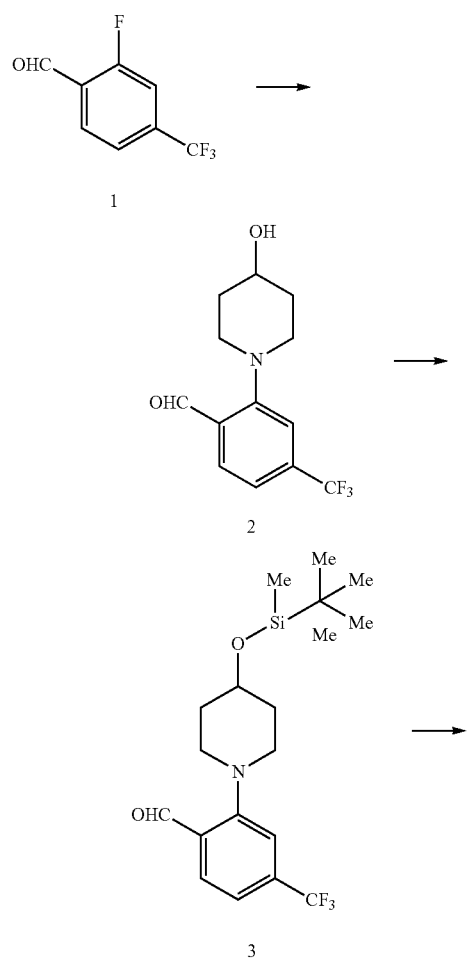

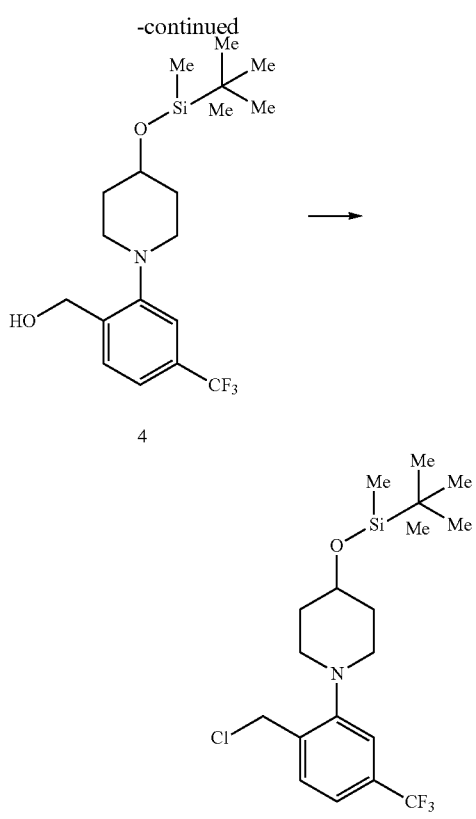

(1) A suspension of the Compound 1 (3.84 g), 4-hydroxypiperidine (2.53 g), and potassium carbonate (4.13 g) in N,N-dimethylformamide (15 mL) was stirred at 130° C. for 15 hours. The reaction mixture was allowed to cool to room temperature, and ethyl acetate was added thereto, and then the resulting mixture was washed with an aqueous solution of sodium hydrogen carbonate and saturated brine, dried, and concentrated under reduced pressure. The resulting residues were purified by silica gel column chromatography (hexane:ethyl acetate=71:29 to 15:85) to give the Compound 2 (3.57 g) as a yellow powder. MS (APCI): m/z 274 [M+H]$^+$ (2) To a solution of the Compound 2 (3.57 g), triethylamine (3.65 mL), and 4-dimethylaminopyridine (160 mg) in N,N-dimethylformamide (30 mL) was added t-butyldimethylsilyl chloride (2.57 g), and the resulting mixture was stirred at room temperature for 17 hours. To the reaction mixture were added an aqueous solution of sodium hydrogen carbonate and ethyl acetate, and the resulting mixture was stirred, and then extracted with ethyl acetate. The resulting organic layers were washed with water and saturated brine, dried, and concentrated under reduced pressure. The resulting residues were purified by silica gel column chromatography (hexane:ethyl acetate=99:1 to 93:7) to give the Compound 3 (5.07 g) as a yellow viscous material. MS (APCI): m/z 388 [M+H]$^+$ (3) To a solution of the Compound 3 (5.07 g) in ethanol (20 mL) was added sodium borohydride (198 mg) under ice-cooling, and the resulting mixture was stirred at room temperature for 30 minutes. The reaction mixture was concentrated under reduced pressure, and ethyl acetate and water were added thereto, and the resulting mixture was stirred, and then extracted with ethyl acetate. The resulting organic layers were dried, and then concentrated under reduced pressure. The resulting residues were purified by silica gel column chromatography (hexane:ethyl acetate=95:5 to 75:25) to give the Compound 4 (4.88 g) as a pale yellow viscous material. MS (APCI): m/z 390 [M+H]⁺

(4) To a solution of the Compound 4 (4.88 g) in chloroform (20 mL) were added pyridine (1.31 mL) and p-toluenesulfonyl chloride (2.86 g) under ice-cooling, and the resulting mixture was stirred at room temperature for 15 hours. To the reaction mixture was added an aqueous solution of sodium hydrogen carbonate, and the resulting mixture was stirred, and then extracted with diethyl ether. The resulting organic layers were dried, and then concentrated under reduced pressure. The resulting residues were purified by silica gel column chromatography (hexane:ethyl acetate=99:1 to 95:5) to give the Compound 5 (1.52 g) as a colorless viscous material. MS (APCI): m/z 408/410 [M+H]⁺

Reference Example 67

The intermediate compound of Reference Example 52 was synthesized according to the following method.

(1) To a solution of the Compound 1 (1.5 g) in 1,4-dioxane (5 mL) was added a solution of hydrochloric acid in 1,4-dioxane (4 mol/L, 5 mL), and the resulting mixture was stirred at room temperature for 17 hours. The reaction mixture was concentrated under reduced pressure to give the Compound 2 (1.12 g) as a colorless powder. MS (APCI): m/z 176 [M+H]⁺

(2) A suspension of the Compound 2 (300 mg), the Compound 3 (338 mg), phosphine ligand 4 (123 mg), palladium acetate (31 mg), and cesium carbonate (1.39 g) in 1,4-dioxane (9 mL) was stirred at 100° C. under a nitrogen atmosphere for 3 hours. The reaction mixture was allowed to cool to room temperature, and then the resulting insoluble matters were removed by filtration, and the resulting filtrate was concentrated under reduced pressure. The resulting residues were purified by silica gel column chromatography (hexane:ethyl acetate=95:5 to 80:20) to give the Compound 5 (167 mg) as a yellow powder. MS (APCI): m/z 294 [M+H]⁺

Reference Example 68

The intermediate compound of Reference Example 53 was synthesized according to the following method.

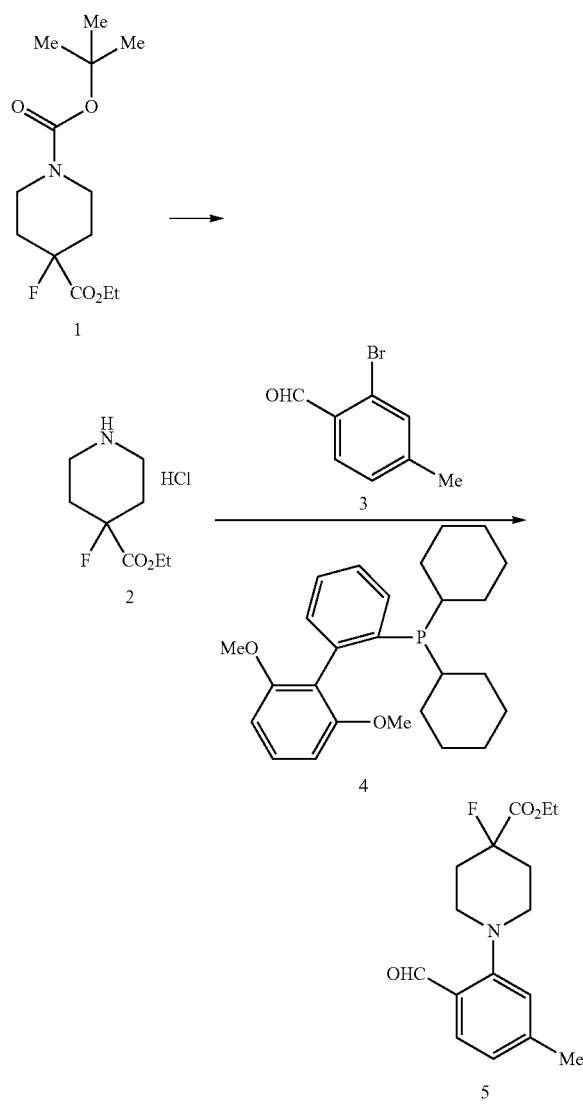

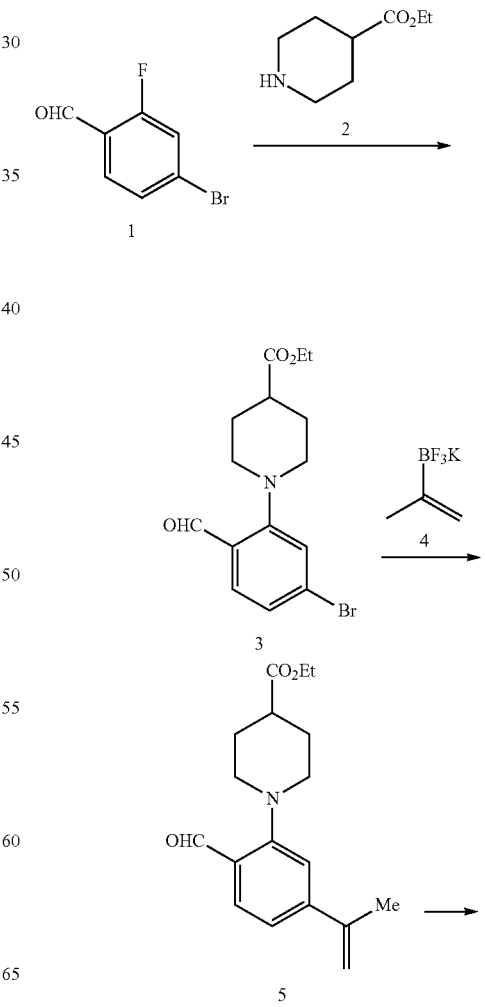

-continued

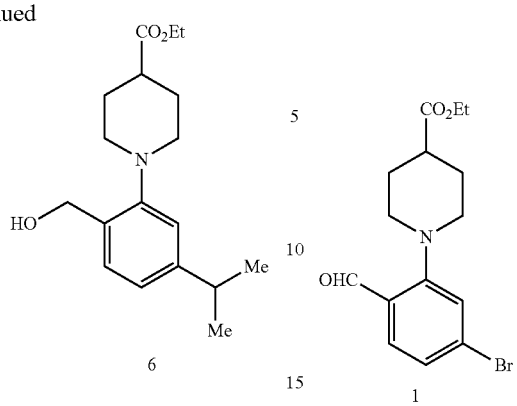

6

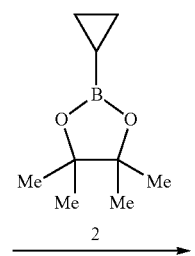

2

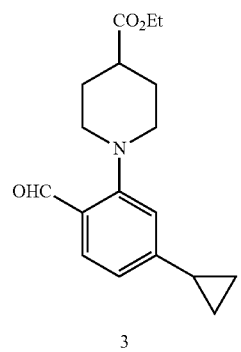

3

(1) A suspension of the Compound 1 (5.0 g), the Compound 2 (4.56 mL), and potassium carbonate (5.11 g) in N-methylpyrrolidone (25 mL) was stirred at 130° C. for 2 hours. The reaction mixture was ice-cooled, and water and ethyl acetate were added thereto, and the resulting mixture was stirred, and then extracted with ethyl acetate. The resulting organic layers were washed with brine, dried, and concentrated under reduced pressure. The resulting residues were purified by silica gel column chromatography (hexane:ethyl acetate=90:10 to 80:20) to give the Compound 3 (7.39 g) as a yellow viscous material. MS (APCI): m/z 340/342 [M+H]$^+$ (2) The Compound 3 (1.0 g), the Compound 4 (652 mg), triethylamine (479 µL), and [1,1'-bis(diphenylphosphino)ferrocene]palladium(II) dichloromethane adduct (120 mg) were added to n-propanol (20 mL), and the resulting mixture was stirred at 90° C. under a nitrogen atmosphere for 3 hours. The reaction mixture was concentrated under reduced pressure, and then ethyl acetate and water were added thereto, and the resulting mixture was stirred, and extracted with ethyl acetate. The resulting organic layers were dried, and then concentrated under reduced pressure. The resulting residues were purified by silica gel column chromatography (hexane:ethyl acetate=90:10 to 80:20) to give the Compound 5 (806 mg) as a yellow viscous material. MS (APCI): m/z 302 [M+H]$^+$ (3) To a solution of the Compound 5 (800 mg) in methanol (18 mL) was added 10% palladium carbon (wetted with ca. 50% water, 80 mg), and the resulting mixture was stirred at room temperature under hydrogen atmosphere (1 atm) for 2 hours. Palladium carbon was removed by filtration, and then the resulting filtrate was concentrated under reduced pressure. The resulting residues were purified by silica gel column chromatography (hexane:ethyl acetate=80:20 to 67:33) to give the Compound 6 (792 mg) as a colorless viscous material. MS (APCI): m/z 306 [M+H]$^+$ Reference Example 69

The intermediate compound of Reference Example 54 was synthesized according to the following method.

(1) The Compound 1 (1.0 g), the Compound 2 (536 µL), [1,1'-bis(diphenylphosphino) ferrocene]palladium(II) dichloromethane adduct (240 mg), cesium carbonate (2.39 g), and water (5 mL) were added to 1,4-dioxane (20 mL), and the resulting mixture was stirred at 110° C. under a nitrogen atmosphere for 2.5 hours. The reaction mixture was allowed to cool to room temperature, and ethyl acetate, water, and activated carbon were added thereto, and the resulting mixture was stirred, and then the resulting insoluble matters were removed by filtration. The resulting organic layers were separated, and the resulting aqueous layers were extracted with ethyl acetate, and then the resulting organic layers were combined, washed with saturated brine, dried, and concentrated under reduced pressure. The resulting residues were purified by silica gel column chromatography (hexane:ethyl acetate=90:10 to 80:20) to give the Compound 3 (774 mg) as a yellow viscous material. MS (APCI): m/z 302 [M+H]$^+$ Reference Example 70

The intermediate compound of Reference Example 55 was synthesized according to the following method.

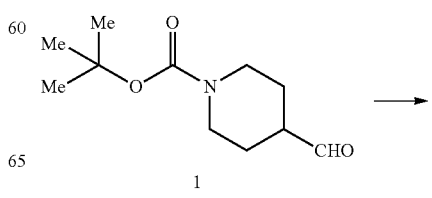

1

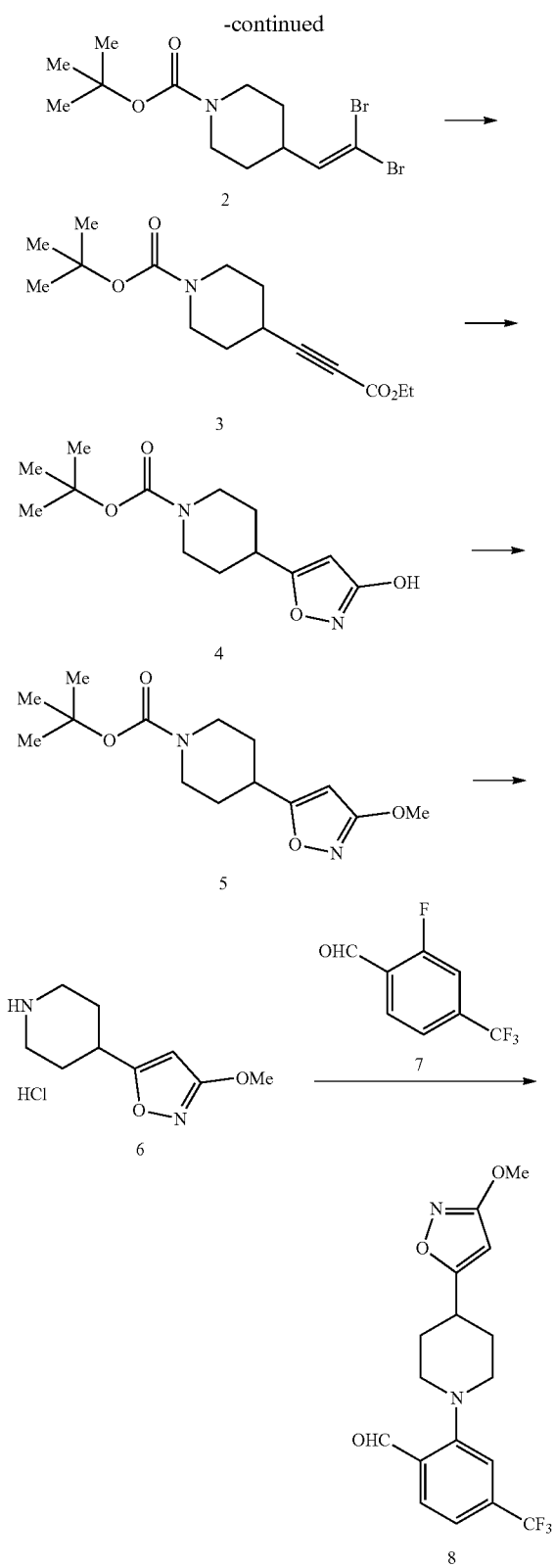

the reaction mixture was added diethyl ether (200 mL), and the resulting mixture was stirred, and then the resulting precipitates were removed by filtration, and the resulting filtrate was concentrated under reduced pressure. The resulting residues were purified by silica gel column chromatography (hexane:ethyl acetate=100:0 to 90:10) to give the Compound 2 (3.59 g) as a colorless powder. MS (APCI): m/z 368/370 [M+H]$^+$ (2) To a solution of the Compound 2 (3.59 g) in tetrahydrofuran (80 mL) was added dropwise a solution of n-butyllithium in hexane (2.6 mol/L, 8.23 mL) at −78° C. under a nitrogen atmosphere, and the resulting mixture was stirred at the same temperature for 10 minutes, and stirred under ice-cooling for 1 hour. To the reaction mixture was added dropwise ethyl chloroformate (3.3 mL) at −78° C., and the resulting mixture was stirred at room temperature for 1 hour. The reaction mixture was concentrated under reduced pressure until the volume became approximately half, and water was added thereto, and the resulting mixture was stirred, and then extracted with ethyl acetate. The resulting organic layers were dried, and then concentrated under reduced pressure. The resulting residues were purified by silica gel column chromatography (hexane:ethyl acetate=95:5 to 80:20) to give the Compound 3 (2.15 g) as a colorless viscous material. MS (APCI): m/z 282 [M+H]$^+$ (3) To a solution of hydroxylamine hydrochloride (634 mg) in methanol (40 mL) was added an aqueous solution of sodium hydroxide (2 mol/L, 9.88 mL) under ice-cooling, and then a solution of the Compound 3 (2.14 g) in methanol (20 mL) was added dropwise thereto, and the resulting mixture was stirred at room temperature for 17 hours. The reaction mixture was concentrated under reduced pressure, and then citric acid was added thereto under ice-cooling until the pH of the mixture became 3 to 4. Water and chloroform were added thereto, and the resulting mixture was stirred, and then extracted with chloroform. The resulting organic layers were dried, and then concentrated under reduced pressure. The resulting residues were purified by silica gel column chromatography (hexane:ethyl acetate=70:30 to 30:70 and chloroform:methanol=99/1 to 95/5) to give the Compound 4 (1.63 g) as a colorless powder. MS (APCI): m/z 269 [M+H]$^+$ (4) To a suspension of the Compound 4 (730 mg) and potassium carbonate (752 mg) in N,N-dimethylformamide (8 mL) was added methyl iodide (186 μL), and the resulting mixture was stirred at 40° C. for 1 hour. The reaction mixture was allowed to cool to room temperature, and water and ethyl acetate were added thereto, and the resulting mixture was stirred, and then extracted with ethyl acetate. The resulting organic layers were washed with water and saturated brine, dried, and concentrated under reduced pressure. The resulting residues were purified by silica gel column chromatography (hexane:ethyl acetate=93:7 to 72:28) to give the Compound 5 (295 mg) as a colorless viscous material. MS (APCI): m/z 283 [M+H]$^+$ (5) To a solution of the Compound 5 (290 mg) in 1,4-dioxane (1 mL) was added a solution of hydrochloric acid in 1,4-dioxane (4 mol/L, 1 mL), and the resulting mixture was stirred at room temperature for 24 hours. The reaction mixture was concentrated under reduced pressure, and to the resulting concentrated residues were added N-methylpyrrolidone (4 mL), diisopropylethylamine (179 μL), potassium carbonate (357 mg), and the Compound 7 (238 mg), and the resulting mixture was stirred at 130° C. for 17 hours. The reaction mixture was allowed to cool to room temperature, and water and ethyl acetate were added thereto, and the resulting mixture was stirred, and then extracted with ethyl (1) To a solution of carbon tetrabromide (12.5 g) and triphenylphosphine (19.7 g) in dichloromethane (200 mL) was added a solution of the Compound 1 (4.0 g) in dichloromethane (20 mL) under ice-cooling, and the resulting mixture was stirred at the same temperature for 1 hour. To acetate. The resulting organic layers were washed with water and saturated brine, dried, and concentrated under reduced pressure. The resulting residues were purified by silica gel column chromatography (hexane:ethyl acetate=95:5 to 75:25) to give the Compound 8 (239 mg) as a yellow powder. MS (APCI): m/z 355 [M+H]$^+$ Reference Example 71

The intermediate compound of Reference Example 57 was synthesized according to the following method.

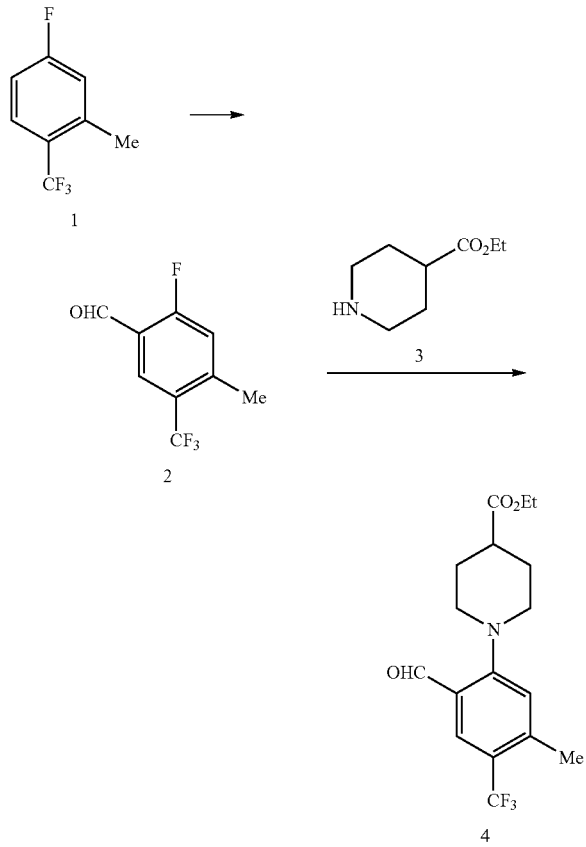

To tetrahydrofuran (7 mL) was added a solution of s-butyllithium in cyclohexane/hexane (1.03 mol/L, 13.6 mL) at −78° C. under a nitrogen atmosphere, and then a solution of the Compound 1 (2.0 g) in tetrahydrofuran (7 mL) was added dropwise thereto, and the resulting mixture was stirred at the same temperature for 1 hour. N,N-dimethylformamide (1.5 mL) was added dropwise thereto at the same temperature, and then an aqueous solution of hydrochloric acid (1 mol/L, 30 mL) was added thereto, and the resulting mixture was stirred at room temperature for 30 minutes. The mixture was extracted with hexane, and then the resulting organic layers were washed with water and saturated brine, dried, and concentrated under reduced pressure. The resulting residues were purified by silica gel column chromatography (hexane:ethyl acetate=98:2 to 85:15). To a solution of the resulting compound in N-methylpyrrolidone (15 mL) were added the Compound 3 (1.34 g) and potassium carbonate (1.47 g), and the resulting mixture was stirred at 130° C. for 3 hours. The reaction mixture was allowed to cool to room temperature, and water and ethyl acetate were added thereto, and the resulting mixture was stirred, and then extracted with ethyl acetate. The resulting organic layers were washed with water and saturated brine, dried, and concentrated under reduced pressure. The resulting residues were purified by silica gel column chromatography (hexane: ethyl acetate=95:5 to 80:20) to give the Compound 4 (1.79 g) as a yellow viscous material. MS (APCI): m/z 344 [M+H]$^+$ Reference Example 72

The intermediate compound of Reference Example 58 was synthesized according to the following method.

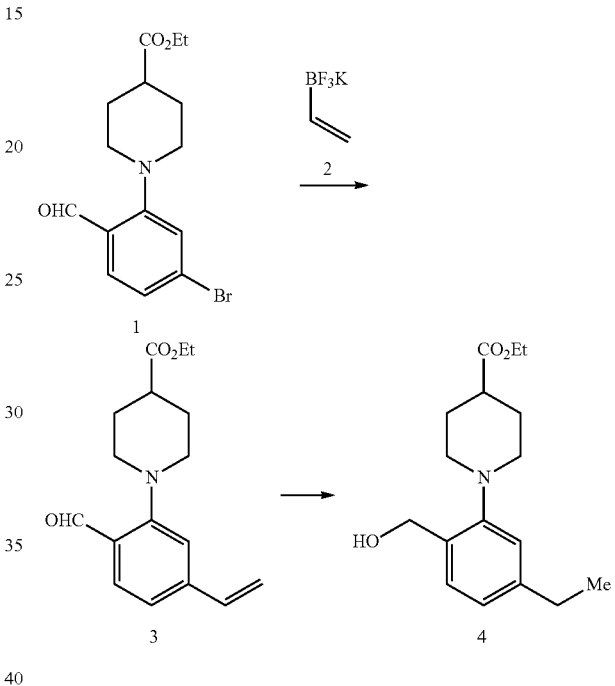

(1) The Compound 1 (2.0 g), the Compound 2 (1.18 g), triethylamine (959 µL), and [1,1′-bis(diphenylphosphino)ferrocene]palladium(II) dichloromethane adduct (240 mg) were added to n-propanol (30 mL), and the resulting mixture was stirred at 90° C. under a nitrogen atmosphere for 3 hours. The reaction mixture was concentrated under reduced pressure, and then ethyl acetate and water were added thereto, and the resulting mixture was stirred, and extracted with ethyl acetate. The resulting organic layers were washed with saturated brine, dried, and concentrated under reduced pressure. The resulting residues were purified by silica gel column chromatography (hexane:ethyl acetate=98:2 to 80:20) to give the Compound 3 (1.54 g) as a yellow viscous material. MS (APCI): m/z 288 [M+H]$^+$ (2) To a solution of the Compound 3 (1.54 g) in methanol (24 mL)/ethyl acetate (20 mL)/tetrahydrofuran (10 mL) was added 10% palladium carbon (wetted with ca. 50% water, 154 mg), and the resulting mixture was stirred at room temperature under hydrogen atmosphere (1 atm) for 2 hours. After nitrogen replacement, 10% palladium carbon (wetted with ca. 50% water, 280 mg) was added thereto, and the resulting mixture was stirred at room temperature under hydrogen atmosphere (1 atm) for 15 minutes. Palladium carbon was removed by filtration, and then the resulting filtrate was concentrated under reduced pressure to give the Compound 4 (1.55 g) as a pale brown viscous material. MS (APCI): m/z 292 [M+H]$^+$

Reference Example 73

The intermediate compound of Reference Example 59 was synthesized according to the following method.

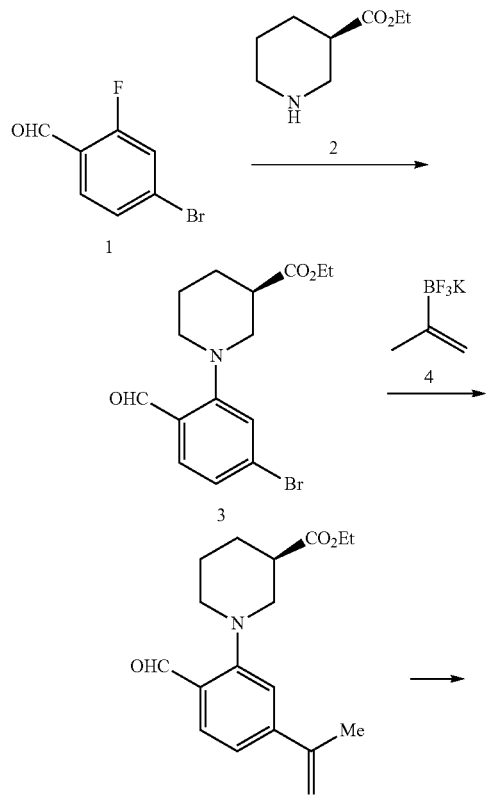

(1) A suspension of the Compound 1 (5.0 g), the Compound 2 (4.56 mL), and potassium carbonate (5.11 g) in N-methylpyrrolidone (25 mL) was stirred at 130° C. for 1.5 hours. The reaction mixture was allowed to cool to room temperature, and water and ethyl acetate were added thereto, and the resulting mixture was stirred, and then extracted with ethyl acetate. The resulting organic layers were washed with brine, dried, and concentrated under reduced pressure. The resulting residues were purified by silica gel column chromatography (hexane:ethyl acetate=99:1 to 70:30) to give the Compound 3 (7.51 g) as a yellow viscous material. MS (APCI): m/z 340/342 [M+H]$^+$ (2) The Compound 3 (2.0 g), the Compound 4 (1.31 g), triethylamine (985 µL), and [1,1'-bis(diphenylphosphino)ferrocene]palladium(II) dichloromethane adduct (240 mg) were added to n-propanol (40 mL), and the resulting mixture was stirred at 90° C. under a nitrogen atmosphere for 3 hours. The reaction mixture was allowed to cool to room temperature, and then ethyl acetate and water were added thereto, and the resulting mixture was stirred, and extracted with ethyl acetate. The resulting organic layers were washed with saturated brine, dried, and concentrated under reduced pressure. The resulting residues were purified by silica gel column chromatography (hexane:ethyl acetate=95:5 to 80:20) to give the Compound 5 (1.29 g) as a yellow viscous material. MS (APCI): m/z 302 [M+H]$^+$ (3) To a solution of the Compound 5 (1.27 g) in methanol (30 mL) was added 10% palladium carbon (wetted with ca. 50% water, 120 mg), and the resulting mixture was stirred at room temperature under hydrogen atmosphere (1 atm) for 2 hours. Palladium carbon was removed by filtration, and then the resulting filtrate was concentrated under reduced pressure. The resulting residues were purified by silica gel column chromatography (hexane:ethyl acetate=80:20 to 65:35) to give the Compound 6 (1.23 g) as a colorless liquid. MS (APCI): m/z 306 [M+H]$^+$

Reference Example 74

The intermediate compound of Reference Example 60 was synthesized according to the following method.

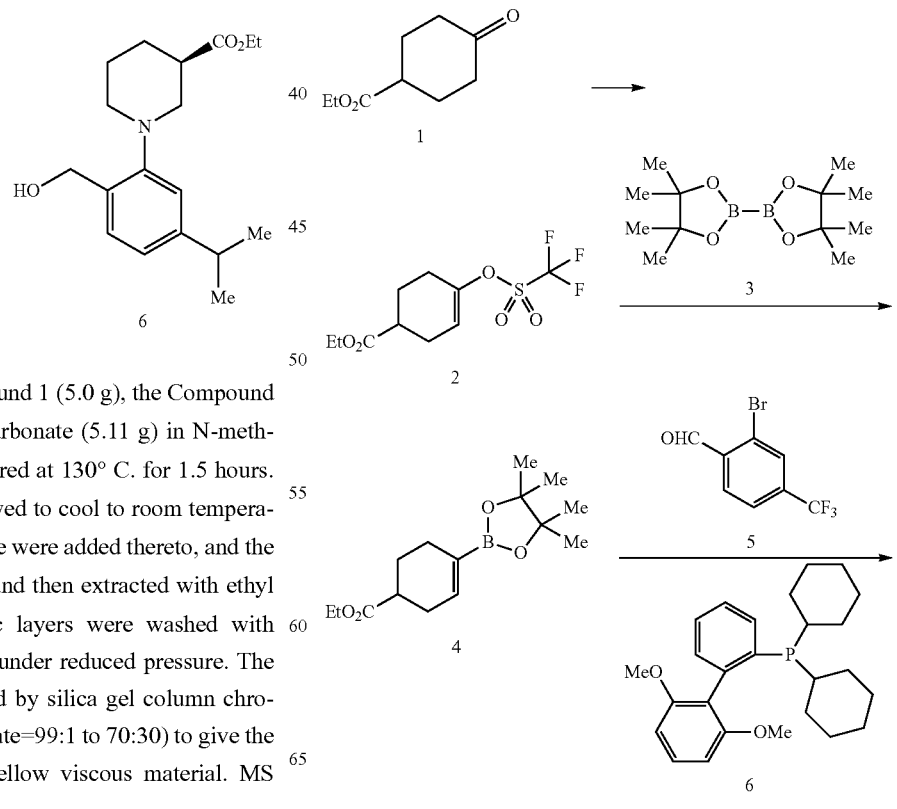

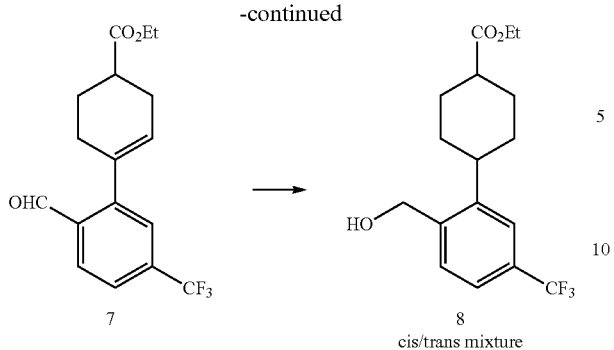

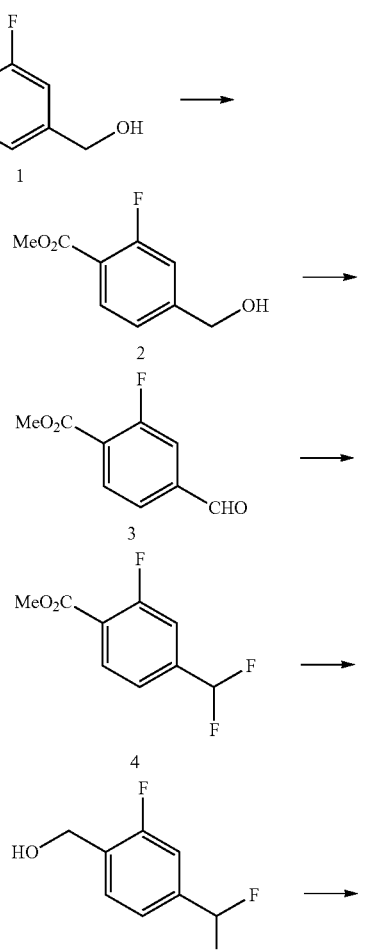

(1) To a solution of the Compound 1 (10 g) and 2,6-lutidine (10.3 mL) in dichloromethane (100 mL) was added dropwise trifluoromethanesulfonic anhydride (19.8 mL), and the resulting reaction mixture was stirred at room temperature for 1 hour, and then concentrated under reduced pressure. The resulting residues were purified by silica gel column chromatography (hexane:ethyl acetate=99:1 to 90:10) to give the Compound 2 (11.97 g) as a pale yellow liquid. MS (APCI): m/z 320 [M+NH$_4$]$^+$ (2) A suspension of the Compound 2 (2.0 g), the Compound 3 (1.85 g), dichloro[1,1'-bis(diphenylphosphino)ferrocene] palladium(II) dichloromethane adduct (270 mg), 1,1'-bis(diphenylphosphino)ferrocene (183 mg), and potassium acetate (1.95 g) in 1,4-dioxane (33 mL) was stirred at 60° C. under a nitrogen atmosphere for 18 hours. The reaction mixture was allowed to cool to room temperature, and then ethyl acetate, water, and saturated brine were added thereto, and the resulting mixture was stirred, and extracted with ethyl acetate. The resulting organic layers were washed with saturated brine, dried, and concentrated under reduced pressure. The resulting residues were purified by silica gel column chromatography (hexane:ethyl acetate=99:10 to 90:10) to give the Compound 4 (1.44 g) as a colorless liquid. MS (APCI): m/z 296 [M+NH$_4$)]$^+$ (3) A suspension of the Compound 4 (100 mg), the Compound 5 (96 mg), phosphine ligand 6 (12 mg), palladium acetate (3 mg), and potassium phosphate (121 mg) in tetrahydrofuran (2 mL) was stirred at 50° C. under a nitrogen atmosphere for 16 hours. The reaction mixture was allowed to cool to room temperature, and then the resulting insoluble matters were removed by filtration, and the resulting filtrate was concentrated under reduced pressure. The resulting residues were purified by silica gel column chromatography (hexane:ethyl acetate=99:1 to 92:8) to give the Compound 7 (60.6 mg) as a colorless liquid. MS (APCI): m/z 344 [M+NH$_4$]$^+$ (4) To a solution of the Compound 7 (60 mg) in methanol (3 mL) was added 10% palladium carbon (wetted with ca. 50% water, 12 mg), and the resulting mixture was stirred at room temperature under hydrogen atmosphere (1 atm) for 2 hours. Palladium carbon was removed by filtration, and then the resulting filtrate was concentrated under reduced pressure. The resulting residues were purified by silica gel column chromatography (hexane:ethyl acetate=80:20 to 60:40) to give the Compound 8 (cis compound:trans compound=3.4:1) as a colorless liquid (43.3 mg). MS (APCI): m/z 348 [M+NH$_4$]$^+$ Reference Example 75

The intermediate compound of Reference Example 61 was synthesized according to the following method.

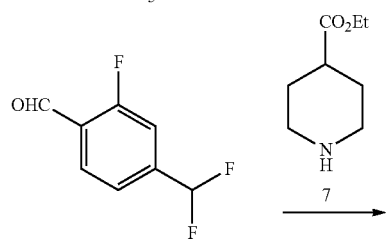

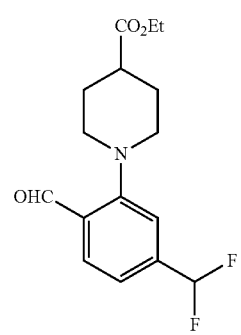

(1) To a solution of the Compound 1 (5.5 g) in methanol (120 mL) was added concentrated hydrochloric acid (12 mL), and the resulting mixture was heated under reflux for 7 hours.

The reaction mixture was allowed to cool to room temperature, and then concentrated under reduced pressure. The resulting concentrated residues were added dropwise to an ice-cooled saturated aqueous solution of sodium hydrogen carbonate, and the resulting mixture was stirred, and then extracted with chloroform. The resulting organic layers were dried, and then concentrated under reduced pressure. The resulting residues were purified by silica gel column chromatography (hexane:ethyl acetate=80:20 to 50:50) to give the Compound 2 (5.28 g) as a colorless powder. MS (APCI): m/z 185 [M+H]$^+$ (2) To a solution of the Compound 2 (2.53 g) in dimethylsulfoxide (40 mL) was added 2-iodoxybenzoic acid (4.59 g), and the resulting mixture was stirred at 50° C. for 30 minutes. The reaction mixture was allowed to cool to room temperature, and then water and ethyl acetate were added thereto, and the resulting mixture was stirred. The resulting insoluble matters were removed by filtration, and the resulting filtrate was extracted with ethyl acetate. The resulting organic layers were washed with water and saturated brine, dried, and concentrated under reduced pressure. The resulting residues were purified by silica gel column chromatography (hexane:ethyl acetate=95:5 to 75:25). To a solution of the resulting compound in dichloromethane (20 mL) was added dropwise bis(2-methoxyethyl)aminosulfur trifluoride (2.64 mL) under ice-cooling, and the resulting mixture was stirred at room temperature for 3 hours. The reaction mixture was concentrated under reduced pressure, and the resulting residues were purified by silica gel column chromatography (hexane:ethyl acetate=95:5 to 80:20) to give the Compound 4 (2.18 g) as a colorless powder. MS (APCI): m/z 205 [M+H]$^+$ (3) To a solution of the Compound 4 (2.17 g) in tetrahydrofuran (20 mL) was added a solution of lithium borohydride in tetrahydrofuran (2 mol/L, 15.9 mL), and the resulting mixture was stirred at 50° C. for 3 hours. The reaction mixture was concentrated under reduced pressure, and diluted with water, and then an aqueous solution of hydrochloric acid (1 mol/L) was added thereto until a gas bubble was not formed, and the resulting mixture was extracted with ethyl acetate. The resulting organic layers were washed with saturated brine, dried, and concentrated under reduced pressure. The resulting residues were purified by silica gel column chromatography (hexane:ethyl acetate=90:10 to 60:40). To a solution of the resulting compound in dimethylsulfoxide (30 mL) was added 2-iodoxybenzoic acid (3.47 g), and the resulting mixture was stirred at 50° C. for 30 minutes. The reaction mixture was allowed to cool to room temperature, and then water and ethyl acetate were added thereto, and the resulting mixture was stirred. The resulting insoluble matters were removed by filtration, and the resulting filtrate was extracted with ethyl acetate. The resulting organic layers were washed with water and saturated brine, dried, and concentrated under reduced pressure. The resulting residues were purified by silica gel column chromatography (hexane:ethyl acetate=95:5 to 80:20). To a solution of the resulting compound (600 mg) in N-methylpyrrolidone (6 mL) were added the Compound 7 (651 mg) and potassium carbonate (716 mg), and the resulting mixture was stirred at 130° C. for 2 hours. The reaction mixture was allowed to cool to room temperature, and water and ethyl acetate were added thereto, and the resulting mixture was stirred, and then extracted with ethyl acetate. The resulting organic layers were washed with water and saturated brine, dried, and concentrated under reduced pressure. The resulting residues were purified by silica gel column chromatography (hexane:ethyl acetate=95:5 to 80:20) to give the Compound 8 (710 mg) as a colorless liquid. MS (APCI): m/z 312 [M+H]$^+$ Reference Example 76

The intermediate compound of Reference Example 62 was synthesized according to the following method.

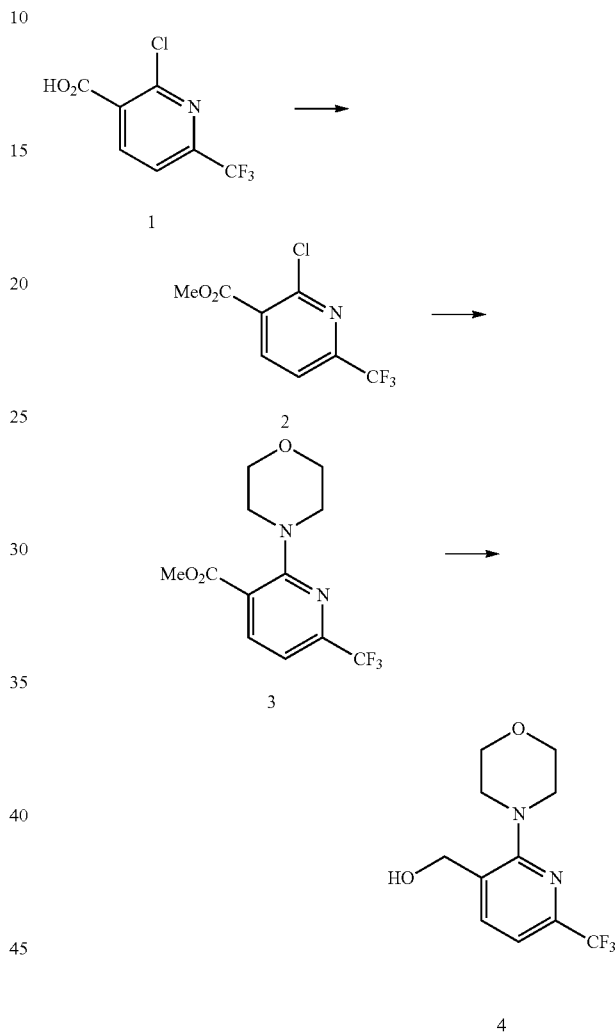

(1) To a suspension of the Compound 1 (5.21 g) and potassium carbonate (3.51 g) in N,N-dimethylformamide (50 mL) was added methyl iodide (1.6 mL), and the resulting mixture was stirred at room temperature for 21.5 hours. To the reaction mixture were added ethyl acetate and water, and the resulting mixture was stirred, and then extracted with ethyl acetate. The resulting organic layers were washed with saturated brine, dried, and concentrated under reduced pressure. The resulting residues were purified by silica gel column chromatography (hexane:ethyl acetate=95:5 to 65:35) to give the Compound 2 (5.29 g) as a pale yellow liquid. MS (APCI): m/z 240/242 [M+H]$^+$ (2) A solution of the Compound 2 (5.28 g), morpholine (3.8 mL), and diisopropylethylamine (7.7 mL) in acetonitrile (50 mL) was stirred at 80° C. for 5.5 hours. The reaction mixture was allowed to cool to room temperature, and then ethyl acetate and water were added thereto, and the resulting mixture was stirred, and extracted with ethyl acetate. The resulting organic layers were washed with saturated brine, dried, and concentrated under reduced pressure. The resulting residues were purified by silica gel column chromatography (hexane:ethyl acetate=90:10 to 60:40) to give the Compound 3 (6.02 g) as a colorless solid. MS (APCI): m/z 291 [M+H]$^+$ (3) To a solution of the Compound 3 (6.01 g) in tetrahydrofuran (200 mL) was added dropwise a solution of diisobutylaluminum hydride in toluene (1 mol/L, 50 mL) at −78° C. under a nitrogen atmosphere, and the resulting mixture was stirred at the same temperature for 30 minutes, and then stirred at room temperature for 22 hours. The mixture was cooled to −78° C. again, and methanol (10 mL) was added thereto, and then water was added thereto, and the resulting mixture was stirred at room temperature. The mixture was diluted with diethyl ether, and the resulting insoluble matters were removed by filtration. To the resulting filtrate were added chloroform and an aqueous solution of sodium hydrogen carbonate, and the resulting mixture was stirred, and extracted with chloroform. The resulting organic layers were dried, and then concentrated under reduced pressure. The resulting residues were purified by silica gel column chromatography (hexane:ethyl acetate=85:15 to 35:65) to give the Compound 4 (5.18 g) as a colorless viscous material. MS (APCI): m/z 263 [M+H]$^+$ Reference Example 77

The intermediate compound of Reference Example 64 was synthesized according to the following method.

pyrrolidone (14 mL) was stirred at 100° C. for 4 hours. The reaction mixture was allowed to cool to room temperature, and then diluted with ethyl acetate and water, and then an aqueous solution of hydrochloric acid (2 mol/L) was added thereto until the pH of the mixture became 3, and the resulting mixture was extracted with ethyl acetate. The resulting organic layers were washed with water and saturated brine, dried, and concentrated under reduced pressure. To a solution of the resulting crude product in chloroform (36 mL) were added triethylamine (1.11 mL) and isobutyl chloroformate (1.03 mL) under ice-cooling, and the resulting mixture was stirred at room temperature for 1.5 hours. To the reaction mixture was added water, and the resulting mixture was stirred, and then extracted with chloroform. The resulting organic layers were washed with saturated brine, dried, and concentrated under reduced pressure. To a solution of the resulting concentrated residues in methanol (36 mL) was added sodium borohydride (191 mg) under ice-cooling, and the resulting mixture was stirred at the same temperature for 30 minutes. To the reaction mixture was added water under ice-cooling, and the resulting mixture was stirred, and then extracted with ethyl acetate. The resulting organic layers were washed with an aqueous solution of sodium hydrogen carbonate and saturated brine, dried, and concentrated under reduced pressure. The resulting residues were purified by silica gel column chromatography (hexane:ethyl acetate=80:20 to 0:100) to give the Compound 4 (870 mg) as a pale yellow liquid. MS (ESI): m/z 321 [M+H]$^+$ Reference Example 78

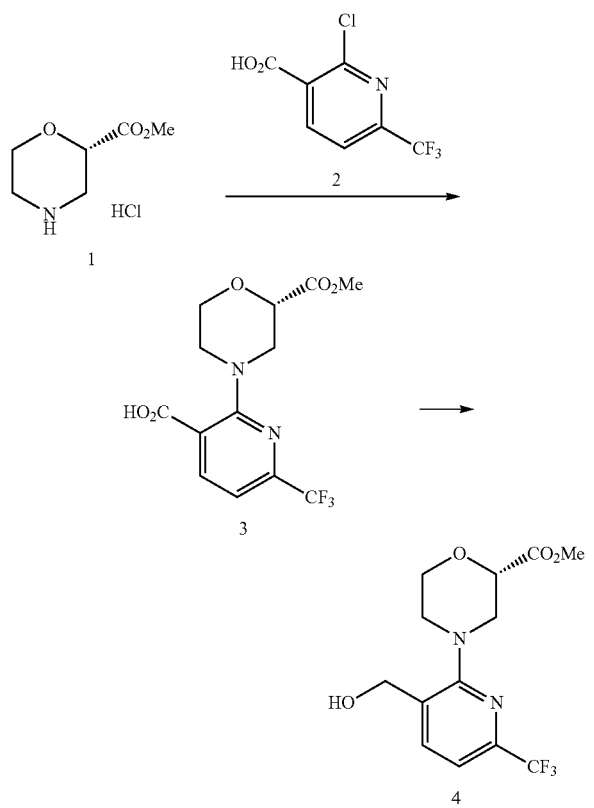

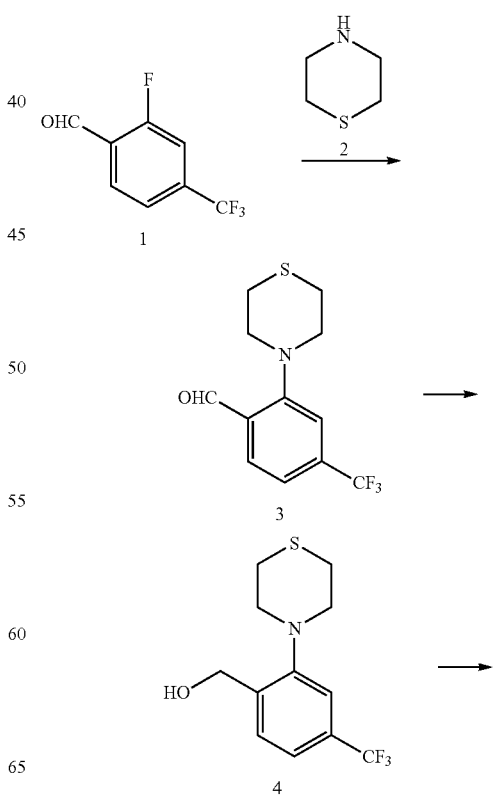

A suspension of the Compound 1 (1.7 g), the Compound 2 (1.62 g), and potassium carbonate (3.0 g) in N-methyl-

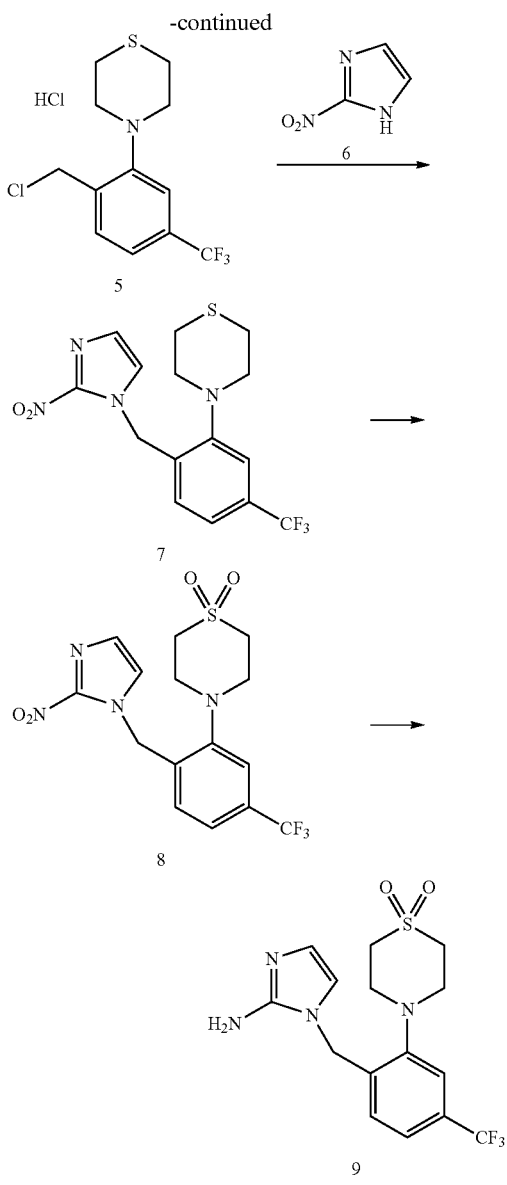

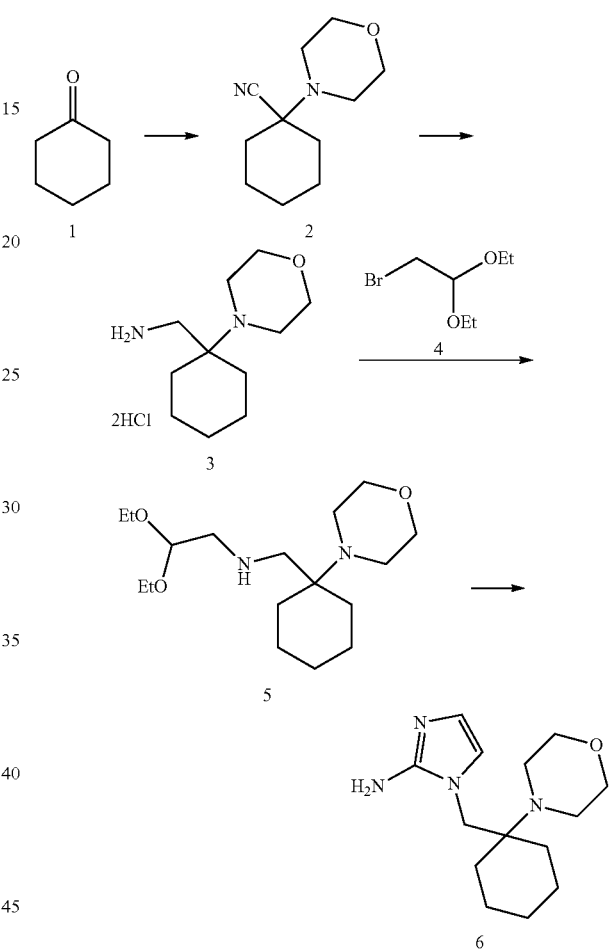

(1) The Compound 1 (3.0 g) and the Compound 2 (1.92 mL) were treated in a similar manner to the above Example 43 to give the Compound 7 (2.72 g) as a pale yellow powder. MS (APCI): m/z 373 [M+H]+

(2) To a solution of the Compound 7 (2.70 g) in dichloromethane (30 mL) was added 3-chloroperbenzoic acid (4.4 g) under ice-cooling, and the resulting mixture was stirred at room temperature for 30 minutes. The resulting insoluble matters were removed by filtration, and to the resulting filtrate were added chloroform and an aqueous solution of sodium hydrogen carbonate, and the resulting mixture was stirred, and then extracted with chloroform. The resulting organic layers were dried, and then concentrated under reduced pressure. The resulting residues were purified by silica gel column chromatography (hexane:ethyl acetate=50:50 to 10:90) to give the Compound 8 (1.45 g) as a colorless powder. MS (APCI): m/z 405 [M+H]+

(3) To a solution of the Compound 8 (1.44 g) in methanol (50 mL) was added 10% palladium carbon (wetted with ca. 50% water, 140 mg), and the resulting mixture was stirred at room temperature under hydrogen atmosphere (1 atm) for 4 hours. Palladium carbon was removed by filtration, and then the resulting filtrate was concentrated under reduced pressure. The resulting residues were purified by NH silica gel column chromatography (chloroform:methanol=100:0 to 96:4) to give the Compound 9 (920 mg) as a pale yellow powder. MS (APCI): m/z 375 [M+H]+

Reference Example 79

(1) To a solution of the Compound 1 (2.07 mL) in methanol (50 mL) were added morpholine (1.78 mL), acetic acid (1.26 mL), and potassium cyanide (1.33 g), and the resulting mixture was stirred at 55° C. for 68 hours. The reaction mixture was allowed to cool to room temperature, and an aqueous solution of sodium hydrogen carbonate was added thereto, and the resulting mixture was stirred, and then extracted with ethyl acetate. The resulting organic layers were dried, and then concentrated under reduced pressure to give the Compound 2 (3.05 g) as a yellow viscous material. MS (APCI): m/z 195 [M+H]+

(2) To a suspension of lithium aluminum hydride (2.07 g) in tetrahydrofuran (80 mL) was added a solution of the Compound 2 (3.04 g) in tetrahydrofuran (20 mL) under ice-cooling, and the resulting mixture was stirred at room temperature under a nitrogen atmosphere for 3 hours. The reaction mixture was ice-cooled, and sodium sulfate (5.32 g) and water (4.16 mL) were added thereto, and the resulting mixture was stirred at room temperature, and then the resulting insoluble matters were removed by filtration. The resulting filtrate was concentrated under reduced pressure, and then to a solution of the resulting residues in diethyl ether (50 mL) was added a solution of hydrochloric acid in ethyl acetate (4 mol/L, 10 mL), and the resulting mixture was stirred. The resulting precipitates were collected by filtration, and dried under reduced pressure to give the Compound 3 (3.32 g) as a colorless powder. MS (APCI): m/z 199 [M+H]$^+$ (3) A solution of the Compound 3 (1.41 g), the Compound 4 (782 μL), and diisopropylethylamine (3.17 mL) in acetonitrile (32 mL) was heated under reflux for 15 hours. The reaction mixture was allowed to cool to room temperature, and an aqueous solution of sodium hydrogen carbonate and ethyl acetate were added thereto, and the resulting mixture was stirred, and then extracted with ethyl acetate. The resulting residues were purified by silica gel column chromatography (chloroform:methanol=100:0 to 80:20) to give the Compound 5 (905 mg) as an orange viscous material. MS (APCI): m/z 315 [M+H]$^+$ (4) To a solution of cyanamide (361 mg) in acetic acid (3 mL)/water (3 mL) was added the Compound 5 (900 mg), and the resulting mixture was stirred at 100° C. for 17 hours. The reaction mixture was concentrated under reduced pressure, and then to the resulting residues was added concentrated hydrochloric acid (3 mL), and the resulting mixture was stirred at 100° C. for 1 hour. The reaction mixture was ice-cooled, and an aqueous solution of sodium hydroxide (2 mol/L) was added thereto to alkalify the mixture, and then the resulting mixture was extracted with ethyl acetate and chloroform. The resulting organic layers were combined, dried, and then concentrated under reduced pressure. The resulting residues were purified by NH silica gel column chromatography (chloroform:methanol=100:0 to 97:3) to give the Compound 6 (192 mg) as a pale yellow powder. MS (APCI): m/z 265 [M+H]$^+$ Reference Example 80

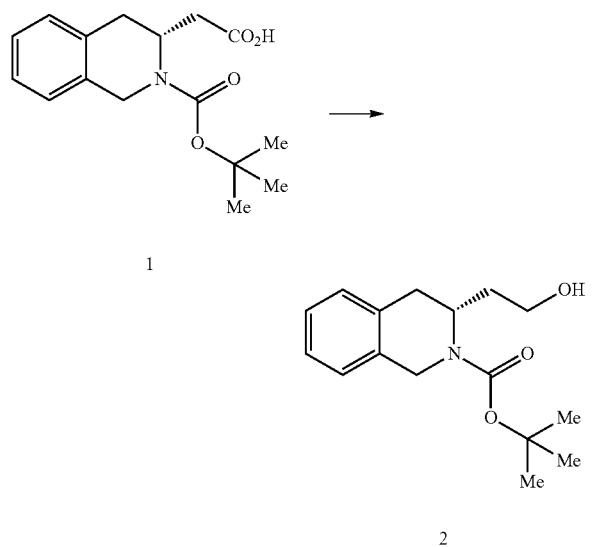

To a solution of the Compound 1 (1.46 g) in 1,2-dimethoxyethane (10 mL) were added N-methylmorpholine (604 μL) and isobutyl chloroformate (714 μL) under ice-cooling, and the resulting mixture was stirred at the same temperature for 40 minutes. The precipitated insoluble matters were removed by filtration, and to the resulting filtrate was added a solution of sodium borohydride (284 mg) in water (5 mL) under ice-cooling, and the resulting mixture was stirred at the same temperature for 2 hours. To the reaction mixture were added water and ethyl acetate, and the resulting mixture was stirred, and then the resulting organic layers were separated, dried, and then concentrated under reduced pressure. The resulting residues were purified by NH silica gel column chromatography (hexane:ethyl acetate=90:10 to 60:40) and silica gel column chromatography (hexane:ethyl acetate=85:15 to 60:40) to give the Compound 2 (1.15 g) as a colorless solid. MS (APCI): m/z 278 [M+H]$^+$ Reference Example 81

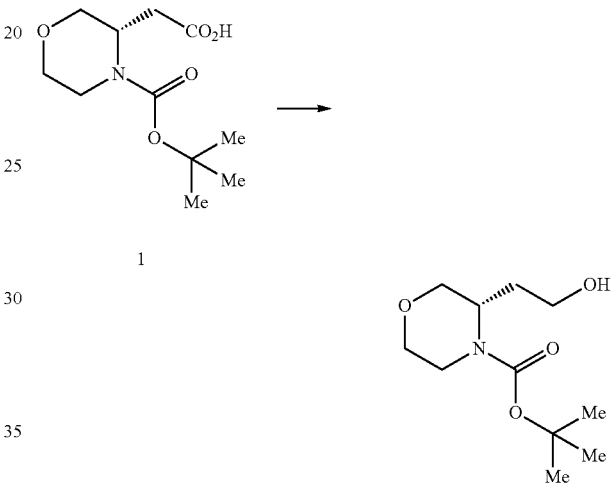

The Compound 1 (1.0 g) was treated in a similar manner to Reference Example 80 to give the Compound 2 (1.04 g) as a colorless liquid. MS (APCI): m/z 232 [M+H]$^+$ Reference Example 82

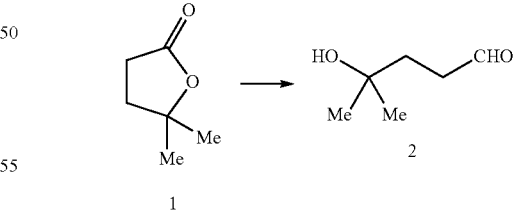

To a solution of the Compound 1 (500 mg) in diethyl ether (12 mL) was added dropwise a solution of diisobutylaluminum hydride in hexane (1.0 mol/L, 6.6 mL) at −78° C. over 20 minutes, and the resulting mixture was stirred at the same temperature for 40 minutes. The reaction mixture was warmed to room temperature, and methanol (4 mL) was added thereto, and then water was added thereto, and the resulting mixture was stirred. The resulting insoluble matters were removed by Celite filtration, and then the resulting organic layers were separated. The resulting aqueous layers were extracted with diethyl ether, and the resulting organic layers were combined, dried, and then concentrated under reduced pressure to give the Compound 2 (149.5 mg) as a pale yellow liquid. 1H-NMR (CDCl₃) δ 1.20 (s, 3H), 1.41 (s, 3H), 1.72-1.77 (m, 1H), 1.94-2.14 (m, 3H), 2.75 (br, 1H), 5.29 (br, 1H)

Reference Example 83

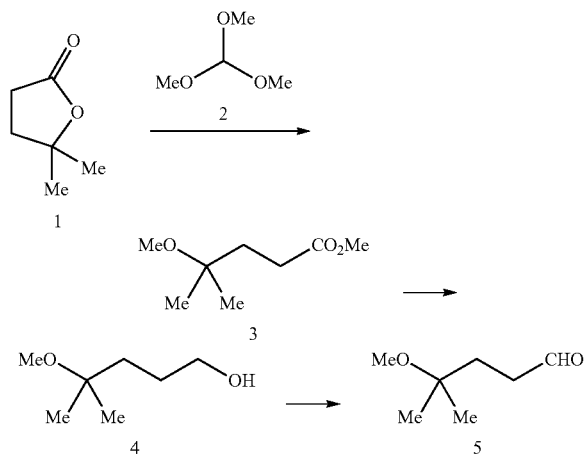

(1) To a solution of the Compound 1 (5.13 g) and the Compound 2 (1.3 mL) in methanol (45 mL) was added dropwise concentrated sulfuric acid (350 µL), and the resulting mixture was stirred at 50° C. for 2 hours. To the reaction mixture was added a saturated aqueous solution of sodium hydrogen carbonate at room temperature to alkalify the mixture, and chloroform was added thereto, and the resulting mixture was stirred. The resulting organic layers were separated, then washed with saturated brine, dried, and concentrated under reduced pressure. The resulting residues were purified by silica gel column chromatography (hexane:ethyl acetate=97:3 to 85:15) to give the Compound 3 (6.2 g) as a pale yellow liquid. 1H-NMR (CDCl₃) δ 1.15 (s, 6H), 1.80-1.84 (m, 2H), 2.34-2.38 (m, 2H), 3.17 (s, 3H), 3.67 (s, 3H)
(2) To a solution of the Compound 3 (6.2 g) in methanol (60 mL) was added sodium borohydride (4.4 g) under ice-cooling, and then the resulting mixture was stirred at room temperature for 5 hours. To the reaction mixture was added water, and the resulting mixture was stirred, and then methanol was evaporated under reduced pressure at room temperature. To the resulting aqueous solution was added chloroform, and the resulting mixture was stirred, and then the resulting organic layers were separated. The resulting organic layers were washed with saturated brine, dried, and evaporated under reduced pressure at room temperature. The resulting residues were purified by silica gel column chromatography (chloroform:methanol=100:0 to 94:6) to give the Compound 4 (3.65 g) as a colorless liquid. 1H-NMR (CDCl₃) δ 1.18 (s, 6H), 1.55-1.68 (m, 4H), 2.28 (t, J=5.4 Hz, 1H), 3.20 (s, 3H), 3.64 (td, J=5.7, 5.7 Hz, 2H)
(3) To a solution of dimethylsulfoxide (4.81 mL) in dichloromethane (40 mL) was added dropwise a solution of oxalyl chloride (2.91 mL) in dichloromethane (60 mL) at −78° C., and the mixture was stirred for 2 minutes, and then a solution of the Compound 4 (3.64 g) and pyridine (4.97 mL) in dichloromethane (30 mL) was added dropwise thereto at the same temperature, and the resulting mixture was stirred for 15 minutes. To the reaction mixture was added dropwise a solution of triethylamine (21.5 mL) in dichloromethane (15 mL) at the same temperature, and then the resulting mixture was stirred under ice-cooling for 1 hour. To the reaction mixture was added an aqueous solution of hydrochloric acid (1 mol/L, 240 mL), and the resulting mixture was stirred, and extracted with dichloromethane. The resulting organic layers were washed with saturated brine, dried, and evaporated under reduced pressure at room temperature. The resulting residues were purified by silica gel column chromatography (hexane:ethyl acetate=95:5 to 75:25) to give the Compound 5 (3.29 g) as a pale yellow liquid. ¹H-NMR (CDCl₃) δ 1.16 (s, 6H), 1.82 (t, J=7.5 Hz, 2H), 2.49 (td, J=7.5, 1.5 Hz, 2H), 3.15 (s, 3H), 9.78 (t, J=1.8 Hz, 1H)

Reference Example 84

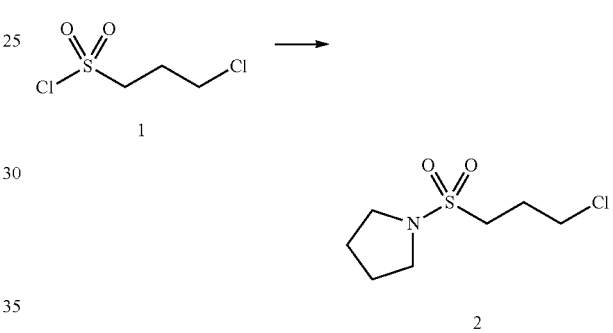

To a solution of the Compound 1 (3.53 g) in tetrahydrofuran (50 mL) was added a solution of pyrrolidine (2.13 g) and triethylamine (1.9 mL) in tetrahydrofuran (20 mL) under a nitrogen atmosphere, and the resulting mixture was stirred at room temperature for 1 hour. The resulting insoluble matters were removed by filtration, and the resulting filtrate was concentrated under reduced pressure. The resulting residues were purified by silica gel column chromatography (hexane:ethyl acetate=80:20 to 60:40) to give the Compound 2 (4.0 g) as a colorless powder. MS (APCI): m/z 212/214 [M+H]⁺

Reference Example 85

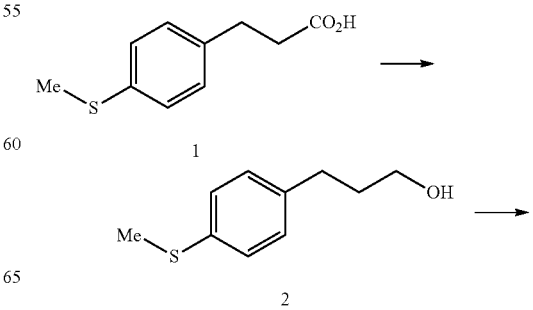

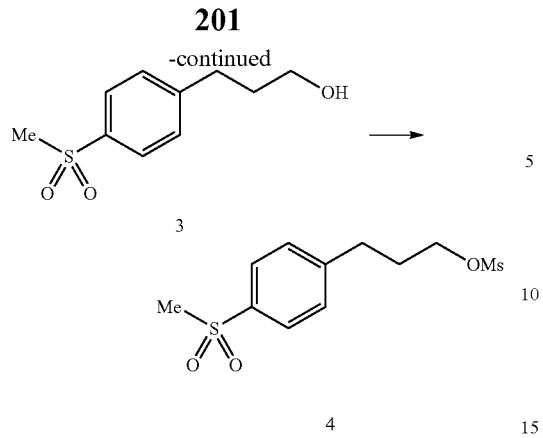

(1) To a solution of the Compound 1 (1.54 g) in tetrahydrofuran (15 mL) was added a borane-dimethyl sulfide complex (10 mol/L, 1.18 mL) under ice-cooling, and the resulting mixture was stirred at the same temperature for 1 hour. A borane-dimethyl sulfide complex (10 mol/L, 0.5 mL) was added thereto, and the resulting mixture was stirred at room temperature for 15 hours. To the reaction mixture was added saturated brine, and the resulting mixture was stirred, and then extracted with ethyl acetate. The resulting organic layers were washed with a saturated aqueous solution of sodium hydrogen carbonate and saturated brine, dried, and concentrated under reduced pressure. The resulting residues were purified by silica gel column chromatography (chloroform:methanol=100:0 to 95:5) to give the Compound 2 (1.41 g) as a colorless viscous material. MS (APCI): m/z 183 [M+H]$^+$ (2) To a solution of the Compound 2 (1.41 g) in dichloromethane (30 mL) was added 3-chloroperbenzoic acid (5.34 g) under ice-cooling, and the resulting mixture was stirred at room temperature for 19.5 hours. 3-Chloroperbenzoic acid (2.67 g) was added thereto, and the resulting mixture was stirred at room temperature for 20 minutes. To the reaction mixture was added a saturated aqueous solution of sodium hydrogen carbonate, and the resulting mixture was stirred, and then extracted with chloroform. The resulting organic layers were washed with saturated brine, dried, and concentrated under reduced pressure. The resulting residues were purified by silica gel column chromatography (chloroform:methanol=100:0 to 95:5) to give the Compound 3 (1.32 g) as a colorless powder. MS (APCI): m/z 215 [M+H]$^+$ (3) To a solution of the Compound 3 (400 mg) and diisopropylethylamine (975 μL) in dichloromethane (10 mL) was added methanesulfonyl chloride (235 mg) under ice-cooling, and the resulting mixture was stirred at room temperature for 1 hour. To the reaction mixture was added a saturated aqueous solution of sodium hydrogen carbonate, and the resulting mixture was stirred, and then extracted with dichloromethane. The resulting organic layers were dried, and then concentrated under reduced pressure. The resulting residues were purified by silica gel column chromatography (hexane:ethyl acetate=20:80 to 0:100) to give the Compound 4 (496 mg) as a colorless powder. MS (APCI): m/z 310 [M+NH$_4$]$^+$ Reference Example 86

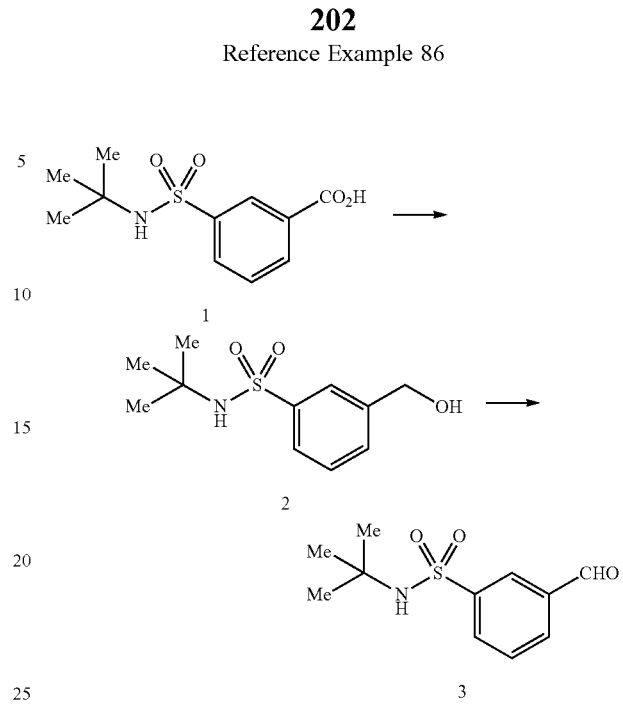

(1) To a solution of the Compound 1 (1.43 g) in tetrahydrofuran (20 mL) was added dropwise a borane-tetrahydrofuran complex (1.09 mol/L, 15.3 mL) under ice-cooling under a nitrogen atmosphere, and the resulting mixture was stirred at room temperature for 1 hour. The reaction mixture was ice-cooled, and water was added thereto, and the resulting mixture was stirred, then diluted with saturated brine, and extracted with ethyl acetate. The resulting organic layers were washed with saturated brine, dried, and concentrated under reduced pressure. The resulting residues were purified by silica gel column chromatography (hexane:ethyl acetate=75:25 to 35:65) to give the Compound 2 (1.21 g) as a colorless viscous material. MS (APCI): m/z 261 [M+NH$_4$]$^+$ (2) To a solution of the Compound 2 (1.2 g) in acetone (10 mL)/dichloromethane (15 mL) was added pyridinium chlorochromate (1.59 g), and the resulting mixture was stirred at room temperature overnight. To the reaction mixture was added hexane (12 mL), and the resulting mixture was stirred, and then the resulting insoluble matters were removed by filtration, and the resulting filtrate was concentrated under reduced pressure. The resulting residues were purified by silica gel column chromatography (hexane:ethyl acetate=50:50 to 40:60) to give the Compound 3 (1.11 g) as a colorless viscous material. MS (APCI): m/z 242 [M+H]$^+$ Reference Example 87

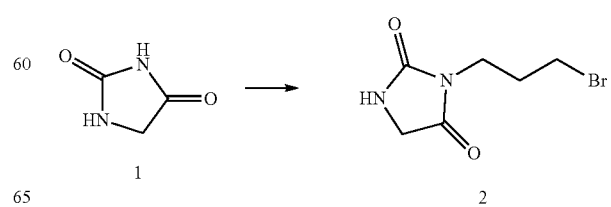

To a solution of the Compound 1 (100 mg) in N,N-dimethylformamide (1.5 mL) was added sodium hydride (60% in oil, 44 mg) under ice-cooling, and the resulting mixture was stirred at room temperature for 30 minutes, and then 1,3-dibromopropane (205 μL) was added thereto, and the resulting mixture was stirred at room temperature for 1 hour. To the reaction mixture were added water and ethyl acetate, and the resulting mixture was stirred, and then the resulting organic layers were separated, dried, and then concentrated under reduced pressure. The resulting residues were purified by silica gel column chromatography (chloroform:methanol=99:1 to 93:7) to give the Compound 2 (18.1 mg) as a colorless powder. MS (APCI): m/z 221/223 [M+H]$^+$ Reference Example 88

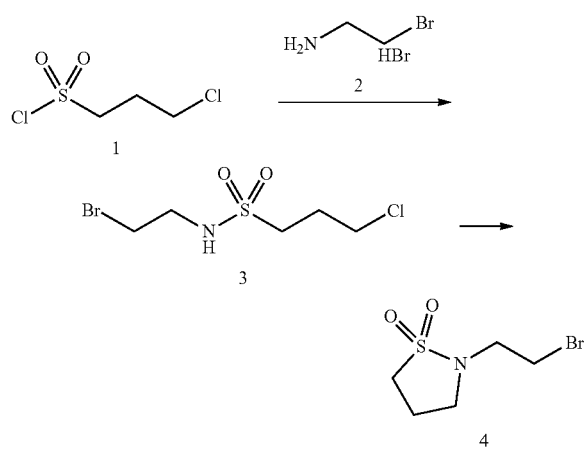

To a solution of the Compound 2 (200 mg) and triethylamine (410 μL) in dichloromethane (2 mL) was added the Compound 1 (120 μL) under ice-cooling, and the resulting mixture was stirred at room temperature for 1.5 hours. To the reaction mixture was added an aqueous solution of hydrochloric acid (1 mol/L), and the resulting mixture was stirred, and then the resulting organic layers were separated, dried, and concentrated under reduced pressure. To a solution of the resulting compound in N,N-dimethylformamide (2 mL) was added sodium hydride (60% in oil, 45.2 mg) under ice-cooling, and the resulting mixture was stirred at 80° C. for 16.5 hours. The reaction mixture was allowed to cool to room temperature, and chloroform and water were added thereto, and the resulting mixture was stirred, and then the resulting organic layers were separated, dried, and concentrated under reduced pressure. The resulting residues were purified by silica gel column chromatography (hexane:ethyl acetate=70:30 to 50:50) to give the Compound 3 (78.4 mg) as a colorless liquid. MS (APCI): m/z 228/230 [M+H]$^+$ Reference Example 89

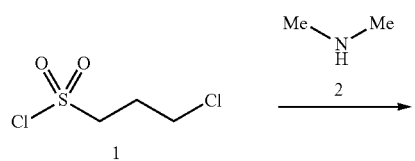

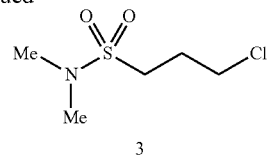

The Compound 1 (1.77 g) and the Compound 2 (2 mol/L solution in tetrahydrofuran, 15 mL) were treated in a similar manner to Reference Example 88 to give the Compound 3 (1.86 g) as a colorless liquid. MS (APCI): m/z 186 [M+H]$^+$ Reference Example 90

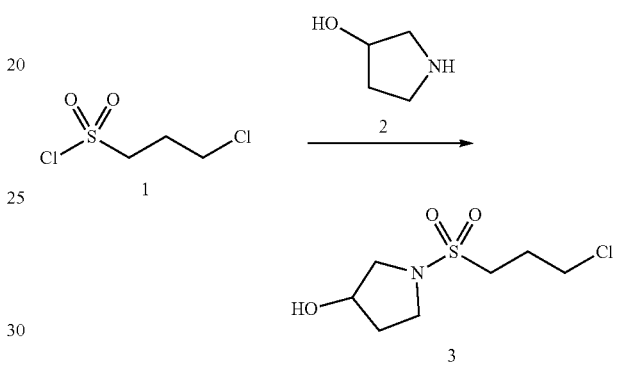

The Compound 1 (1.0 g) and the Compound 2 (1.35 mL) were treated in a similar manner to Reference Example 89 to give the Compound 3 (1.12 g) as a colorless viscous material of a racemate. MS (APCI): m/z 228/230 [M+H]$^+$ Reference Example 91

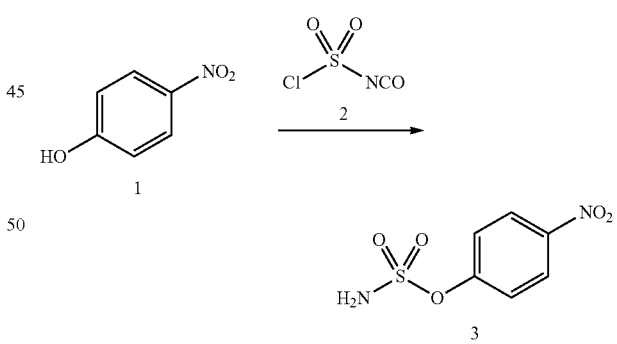

A mixture of the Compound 1 (13.9 g), the Compound 2 (14.8 g), and toluene (100 mL) was heated under reflux for 16 hours. The reaction mixture was ice-cooled, and water was added thereto, and the resulting mixture was stirred, and then the resulting precipitates were collected by filtration, washed with water and toluene, and then air-dried. To a solution of the resulting compound in acetonitrile (100 mL) was added water (30 mL), and the resulting mixture was stirred at room temperature overnight. The reaction mixture was concentrated under reduced pressure to evaporate acetonitrile, and the resulting concentrated residues were ice-cooled, and water (100 mL) was added thereto, and the resulting mixture was stirred at the same temperature for 2 hours. The resulting precipitates were collected by filtration, and dried under reduced pressure to give the Compound 3 (5.68 g) as a colorless powder. MS (APCI): m/z 217 [M−H]$^-$ Reference Example 92

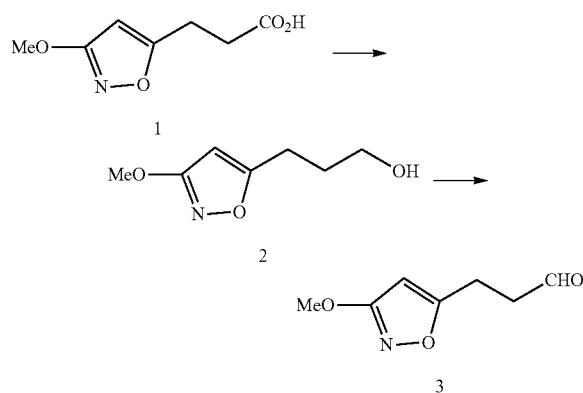

(1) To a solution of the Compound 1 (342 mg) and N-methylmorpholine (242 μL) in 1,2-dimethoxyethane (4 mL) was added isobutyl chloroformate (1.03 mL) under ice-cooling, and the resulting mixture was stirred at the same temperature for 30 minutes. The resulting insoluble matters were collected by filtration, and to the resulting filtrate was added an aqueous solution of sodium borohydride (sodium borohydride (113 mg)+water (2 mL)) under ice-cooling, and the resulting mixture was stirred at the same temperature for 2 hours. To the reaction mixture was added water, and the resulting mixture was stirred, and then extracted with ethyl acetate. The resulting organic layers were dried, and then concentrated under reduced pressure. The resulting residues were purified by silica gel column chromatography (chloroform:methanol=98:2 to 90:10) to give the Compound 2 (228 mg) as a colorless viscous material. MS (APCI): m/z 158 [M+H]$^+$ (2) A suspension of the Compound 2 (220 mg) and 2-iodoxybenzoic acid (470 mg) in dimethylsulfoxide (2.5 mL) was stirred at 50° C. for 4.5 hours. The reaction mixture was allowed to cool to room temperature, and water and chloroform were added thereto, and the resulting mixture was stirred, and then extracted with chloroform. The resulting organic layers were washed with water, dried, and concentrated under reduced pressure. The resulting residues were purified by silica gel column chromatography (hexane:ethyl acetate=85:15 to 61:39) to give the Compound 3 (85 mg) as a colorless viscous material. MS (APCI): m/z 156 [M+H]$^+$

EXPERIMENTAL EXAMPLES

Experimental Example 1: MCR Agonist Measurement (cAMP Measurement)

(1) Method for Culturing Cells

Human MC1R agonistic activity measurement was carried out by using human melanoma cell line HBL. Culture of HBL: F-10 Nutrient Mixture comprising 10% FCS and Penicillin-streptomycin was used in the culture.

(2) cAMP Assay and Data Calculation

Each compound solution having each concentration was mixed with a cAMP assay buffer (HBSS (Hank's Balanced Salt Solution) comprising 10 mM HEPES and 0.1% BSA), and dispensed into a 96 well plate. HBL was suspended into a cAMP assay buffer comprising 0.5 mM IBMX so that the concentration became $5 \times 10^4$/mL, and the resulting suspension was dispensed into the above 96 well plate, then mixed, and left to stand at 37° C. for 30 minutes, and then the intracellular cAMP concentration was measured by a fluorescence method using Envision (ex. 320 nm, em. 590 nm and 665 nm). Each ratio value (665 nm measurement value/590 nm measurement value×10,000) was calculated from the resulting data, and the quantitative value of each cAMP concentration was calculated by using Prism 5.02, and induction % value (% of each sample when the average concentration value of cAMP of vehicle was set to be 0% and the average concentration value of cAMP of αMSH at 10$^{-6}$ M was set to be 100%) was calculated, and EC$_{50}$ value and Intrinsic Activity (IA) % value were calculated. The results are shown in the following Table 22.

TABLE 22

| Example | Compound | Human MC1R (cAMP EC$_{50}$) nM | Human MC1R IA % |
|---|---|---|---|
| 13 | [structure] | 22 | 89 |

TABLE 22-continued

| Example | Compound | Human MC1R (cAMP EC$_{50}$) nM | Human MC1R IA % |
|---|---|---|---|
| 16 | | 6.7 | 88 |
| 19 | | 3.5 | 83 |
| 26 | | 7.6 | 97 |
| 28 | | 25 | 91 |

TABLE 22-continued

| Example | Compound | Human MC1R (cAMP EC$_{50}$) nM | Human MC1R IA % |
|---|---|---|---|
| 36 | | 7.9 | 89 |
| 43 | | 6.0 | 108 |
| 49 | | 2.0 | 96 |
| 52 | | 1.6 | 118 |

TABLE 22-continued
| Example | Compound | Human MC1R (cAMP EC$_{50}$) nM | Human MC1R IA % |
|---|---|---|---|
| 54 | 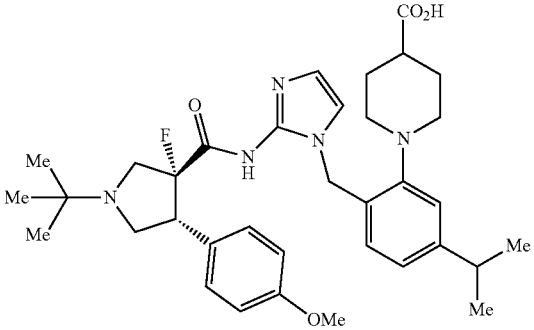 [SMILES: COc1ccc([C@@H]2CN(C(C)(C)C)C[C@@]2(F)C(=O)Nc2nccn2Cc2ccc(C(C)C)cc2N2CCC(C(=O)O)CC2)cc1] | 2.8 | 109 |
| 64 | 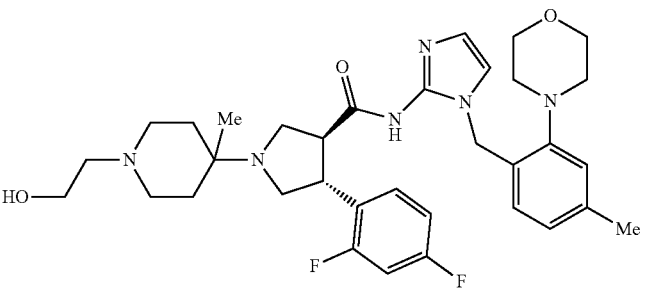 [SMILES: Cc1ccc(Cn2ccnc2NC(=O)[C@@H]2CN(C3(C)CCN(CCO)CC3)C[C@H]2c2ccc(F)cc2F)c(N2CCOCC2)c1] | 2.3 | 79 |
| 70 | 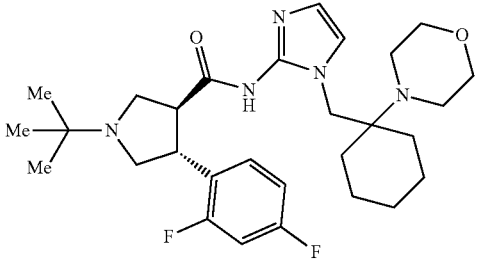 [SMILES: CC(C)(C)N1C[C@@H](C(=O)Nc2nccn2CC2(N3CCOCC3)CCCCC2)[C@H](c2ccc(F)cc2F)C1] | 83 | 58 |
| 72 | 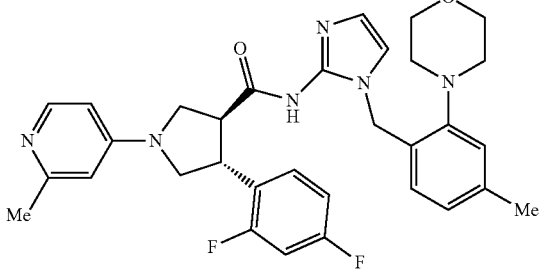 | 20 | 66 |
| 80 | 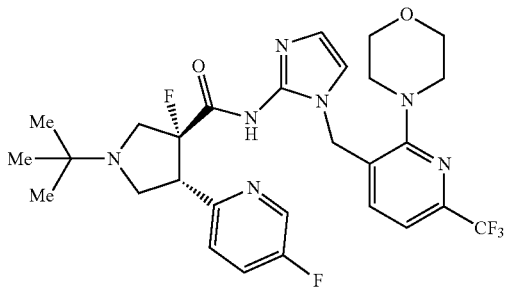 [SMILES: CC(C)(C)N1C[C@@H](c2ccc(F)cn2)[C@](F)(C(=O)Nc2nccn2Cc2ccc(C(F)(F)F)nc2N2CCOCC2)C1] | 68 | 76 |

| Example | Compound | Human MC1R (cAMP EC$_{50}$) nM | Human MC1R IA % |
|---|---|---|---|
| 85 | 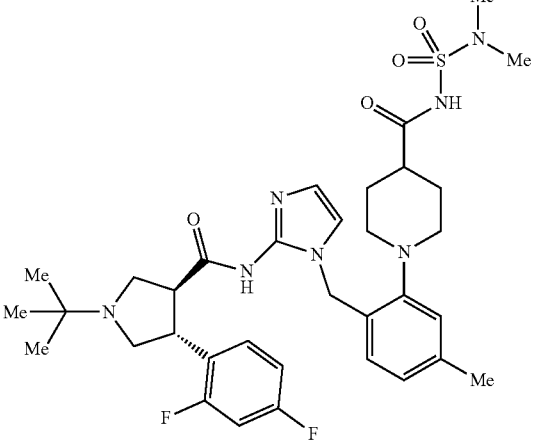 | 16 | 98 |

INDUSTRIAL APPLICABILITY

The target compound [I] of the present invention or a pharmaceutically acceptable salt thereof has an excellent MCR agonistic activity, especially an MC1R agonistic activity, and may be used as an agent for preventing or treating various diseases and/or symptoms of which a pathological condition is expected to be improved by the activation of MC1R such as rheumatoid arthritis, gouty arthritis, osteoarthritis, inflammatory bowel disease, systemic sclerosis, psoriasis, fibrosis, protoporphyria, systemic lupus erythematosus, melanoma, skin cancer, vitiligo, alopecia, poliosis, pain, ischemia/reperfusion injury, cerebral inflammatory disease, hepatitis, sepsis/septic shock, nephritis, transplantation, HIV disease exacerbation, vasculitis, uveitis, retinitis pigmentosa, age-related macular degeneration, microbial infection, celiac disease, nephrotic syndrome, and melanoma invasion, or an agent for improving the prognosis of these diseases.

The invention claimed is:
1. A compound represented by formula [I]:

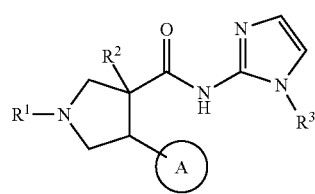

or a pharmaceutically acceptable salt thereof,
wherein:
Ring A represents:
(1) 6- to 10-membered monocyclic or bicyclic aryl, optionally substituted with 1, 2 or 3 substituents independently selected from the group consisting of halogen and alkoxy; or
(2) 5- to 10-membered monocyclic or bicyclic heteroaryl comprising 1, 2, 3 or 4 heteroatoms independently selected from the group consisting of nitrogen, oxygen, and sulfur, optionally substituted with 1, 2 or 3 substituents independently selected from the group consisting of halogen and alkoxy;

R$^1$ represents:
(1) hydrogen;
(2) alkyl, optionally substituted with 1, 2 or 3 substituents independently selected from the group consisting of (a) halogen, (b) cyano, (c) hydroxy, (d) alkanoyl, (e) alkoxy, optionally substituted by 1 or 2 independently selected 6- to 10-membered monocyclic or bicyclic aryl, (f) amino, optionally substituted by 1 or 2 substituents independently selected from the group consisting of alkyl, alkoxycarbonyl, alkylsulfonyl, aminosulfonyl, and 5- to 10-membered monocyclic or bicyclic heteroaryl comprising 1, 2, 3 or 4 heteroatoms independently selected from the group consisting of nitrogen, oxygen, and sulfur, (g) carbamoyl, optionally substituted by 1 or 2 independently selected alkyl, (h) alkylsulfonyl, optionally substituted by 1 or 2 substituents independently selected from the group consisting of 4- to 8-membered monocyclic aliphatic heterocyclyl comprising 1, 2 or 3 heteroatoms independently selected from the group consisting of nitrogen, oxygen, and sulfur, optionally substituted with hydroxy, and amino, optionally substituted with 1 or 2 independently selected alkyl, (i) 4- to 8-membered monocyclic aliphatic heterocyclyl comprising 1, 2 or 3 heteroatoms independently selected from the group consisting of nitrogen, oxygen, and sulfur, optionally substituted by 1 or 2 oxo, (j) 6- to 10-membered monocyclic or bicyclic aryl, optionally substituted by 1 or 2 substituents independently selected from the group consisting of alkylsulfonyl and aminosulfonyl, (k) partially hydrogenated 5- to 10-membered monocyclic or bicyclic heteroaryl comprising 1, 2, 3 or 4 heteroatoms independently selected from the group consisting of nitrogen, oxygen, and sulfur, optionally substituted by 1 or 2 substituents independently selected from the group consisting of oxo and hydroxy, and (l) 5- to 10-membered monocyclic or bicyclic heteroaryl comprising 1, 2, 3 or 4 heteroatoms independently selected from the group consisting of nitrogen, oxygen, and sulfur, optionally substituted by 1 or 2 hydroxy;

3) alkanoyl, optionally substituted with 1, 2 or 3 substituents independently selected from the group consisting of (a) halogen, (b) cyano, (c) hydroxy, (d) alkyl, optionally substituted by 1 or 2 substituents independently selected from the group consisting of halogen, cyano, and hydroxy, (e) alkanoyl, (f) alkoxy, optionally substituted by 1 or 2 independently selected 6- to 10-membered monocyclic or bicyclic aryl, (g) amino, optionally substituted by 1 or 2 substituents independently selected from the group consisting of alkyl, alkoxycarbonyl, alkylsulfonyl, amino sulfonyl, and 5- to 10-membered monocyclic or bicyclic heteroaryl comprising 1, 2, 3 or 4 heteroatoms independently selected from the group consisting of nitrogen, oxygen, and sulfur, (h) carbamoyl, optionally substituted by 1 or 2 independently selected alkyl, (i) alkylsulfonyl, optionally substituted by 1 or 2 substituents independently selected from the group consisting of 4- to 8-membered monocyclic aliphatic heterocyclyl comprising 1, 2 or 3 heteroatoms independently selected from the group consisting of nitrogen, oxygen, and sulfur, optionally substituted with hydroxy, and amino, optionally substituted with 1 or 2 independently selected alkyl, (j) 4- to 8-membered monocyclic aliphatic heterocyclyl comprising 1, 2 or 3 heteroatoms independently selected from the group consisting of nitrogen, oxygen, and sulfur, optionally substituted by 1 or 2 oxo, (k) 6- to 10-membered monocyclic or bicyclic aryl, optionally substituted by 1 or 2 substituents independently selected from the group consisting of alkylsulfonyl and aminosulfonyl, (l) partially hydrogenated 5- to 10-membered monocyclic or bicyclic heteroaryl comprising 1, 2, 3 or 4 heteroatoms independently selected from the group consisting of nitrogen, oxygen, and sulfur, optionally substituted by 1 or 2 substituents independently selected from the group consisting of oxo and hydroxy, and (m) 5- to 10-membered monocyclic or bicyclic heteroaryl comprising 1, 2, 3 or 4 heteroatoms independently selected from the group consisting of nitrogen, oxygen, and sulfur, optionally substituted by 1 or 2 hydroxy;

(4) cycloalkyl, optionally substituted with 1, 2 or 3 substituents independently selected from the group consisting of (a) halogen, (b) cyano, (c) hydroxy, (d) alkyl, optionally substituted by 1 or 2 substituents independently selected from the group consisting of halogen, cyano, and hydroxy, (e) alkanoyl, (f) alkoxy, optionally substituted by 1 or 2 independently selected 6- to 10-membered monocyclic or bicyclic aryl, (g) amino, optionally substituted by 1 or 2 substituents independently selected from the group consisting of alkyl, alkoxycarbonyl, alkylsulfonyl, amino sulfonyl, and 5- to 10-membered monocyclic or bicyclic heteroaryl comprising 1, 2, 3 or 4 heteroatoms independently selected from the group consisting of nitrogen, oxygen, and sulfur, (h) carbamoyl, optionally substituted by 1 or 2 independently selected alkyl, (i) alkylsulfonyl, optionally substituted by 1 or 2 substituents independently selected from the group consisting of 4- to 8-membered monocyclic aliphatic heterocyclyl comprising 1, 2 or 3 heteroatoms independently selected from the group consisting of nitrogen, oxygen, and sulfur, optionally substituted with hydroxy, and amino, optionally substituted with 1 or 2 independently selected alkyl, (j) 4- to 8-membered monocyclic aliphatic heterocyclyl comprising 1, 2 or 3 heteroatoms independently selected from the group consisting of nitrogen, oxygen, and sulfur, optionally substituted by 1 or 2 oxo, (k) 6- to 10-membered monocyclic or bicyclic aryl, optionally substituted by 1 or 2 substituents independently selected from the group consisting of alkylsulfonyl and aminosulfonyl, (l) partially hydrogenated 5- to 10-membered monocyclic or bicyclic heteroaryl comprising 1, 2, 3 or 4 heteroatoms independently selected from the group consisting of nitrogen, oxygen, and sulfur, optionally substituted by 1 or 2 substituents independently selected from the group consisting of oxo and hydroxy, and (m) 5- to 10-membered monocyclic or bicyclic heteroaryl comprising 1, 2, 3 or 4 heteroatoms independently selected from the group consisting of nitrogen, oxygen, and sulfur, optionally substituted by 1 or 2 hydroxy;

(5) 4- to 8-membered monocyclic aliphatic heterocyclyl comprising 1, 2 or 3 heteroatoms independently selected from the group consisting of nitrogen, oxygen, and sulfur, optionally substituted with 1, 2 or 3 substituents independently selected from the group consisting of (a) halogen, (b) cyano, (c) hydroxy, (d) alkyl, optionally substituted by 1 or 2 substituents independently selected from the group consisting of halogen, cyano, and hydroxy, (e) alkanoyl, (f) alkoxy, optionally substituted by 1 or 2 independently selected 6- to 10-membered monocyclic or bicyclic aryl, (g) amino, optionally substituted by 1 or 2 substituents independently selected from the group consisting of alkyl, alkoxycarbonyl, alkylsulfonyl, aminosulfonyl, and 5- to 10-membered monocyclic or bicyclic heteroaryl comprising 1, 2, 3 or 4 heteroatoms independently selected from the group consisting of nitrogen, oxygen, and sulfur, (h) carbamoyl, optionally substituted by 1 or 2 independently selected alkyl, (i) alkylsulfonyl, optionally substituted by 1 or 2 substituents independently selected from the group consisting of 4- to 8-membered monocyclic aliphatic heterocyclyl comprising 1, 2 or 3 heteroatoms independently selected from the group consisting of nitrogen, oxygen, and sulfur, optionally substituted with hydroxy, and amino, optionally substituted with 1 or 2 independently selected alkyl, (j) 4- to 8-membered monocyclic aliphatic heterocyclyl comprising 1, 2 or 3 heteroatoms independently selected from the group consisting of nitrogen, oxygen, and sulfur, optionally substituted by 1 or 2 oxo, (k) 6- to 10-membered monocyclic or bicyclic aryl, optionally substituted by 1 or 2 substituents independently selected from the group consisting of alkylsulfonyl and aminosulfonyl, (l) partially hydrogenated 5- to 10-membered monocyclic or bicyclic heteroaryl comprising 1, 2, 3 or 4 heteroatoms independently selected from the group consisting of nitrogen, oxygen, and sulfur, optionally substituted by 1 or 2 substituents independently selected from the group consisting of oxo and hydroxy, and (m) 5- to 10-membered monocyclic or bicyclic heteroaryl comprising 1, 2, 3 or 4 heteroatoms independently selected from the group consisting of nitrogen, oxygen, and sulfur, optionally substituted by 1 or 2 hydroxy;

(6) 6- to 10-membered monocyclic or bicyclic aryl, optionally substituted with 1, 2 or 3 substituents independently selected from the group consisting of (a) halogen, (b) cyano, (c) hydroxy, (d) alkyl, optionally substituted by 1 or 2 substituents independently selected from the group consisting of halogen, cyano, and hydroxy, (e) alkanoyl, (f) alkoxy, optionally substituted by 1 or 2 independently selected 6- to 10-membered monocyclic or bicyclic aryl, (g) amino, optionally substituted by 1 or 2 substituents independently selected from the group consisting of alkyl, alkoxycarbonyl, alkylsulfonyl, aminosulfonyl, and 5- to 10-membered monocyclic or bicyclic heteroaryl comprising 1, 2, 3 or 4 heteroatoms independently selected from the group consisting of nitrogen, oxygen, and sulfur, (h) carbamoyl, optionally substituted by 1 or 2 independently selected alkyl, (i) alkylsulfonyl, optionally substituted by 1 or 2 substituents independently selected from the group consisting of 4-to 8-membered monocyclic aliphatic heterocyclyl comprising 1, 2 or 3 heteroatoms independently selected from the group consisting of nitrogen, oxygen, and sulfur, optionally substituted with hydroxy, and amino, optionally substituted with 1 or 2 independently selected alkyl, (j) 4- to 8-membered monocyclic aliphatic heterocyclyl comprising 1, 2 or 3 heteroatoms independently selected from the group consisting of nitrogen, oxygen, and sulfur, optionally substituted by 1 or 2 oxo, (k) 6- to 10-membered monocyclic or bicyclic aryl, optionally substituted by 1 or 2 substituents independently selected from the group consisting of alkylsulfonyl and aminosulfonyl, (l) partially hydrogenated 5- to 10-membered monocyclic or bicyclic heteroaryl comprising 1, 2, 3 or 4 heteroatoms independently selected from the group consisting of nitrogen, oxygen, and sulfur, optionally substituted by 1 or 2 substituents independently selected from the group consisting of oxo and hydroxy, and (m) 5- to 10-membered monocyclic or bicyclic heteroaryl comprising 1, 2, 3 or 4 heteroatoms independently selected from the group consisting of nitrogen, oxygen, and sulfur, optionally substituted by 1 or 2 hydroxy; or (7) 5- to 10-membered monocyclic or bicyclic heteroaryl comprising 1, 2, 3 or 4 heteroatoms independently selected from the group consisting of nitrogen, oxygen, and sulfur, optionally substituted with 1, 2 or 3 substituents independently selected from the group consisting of (a) halogen, (b) cyano, (c) hydroxy, (d) alkyl, optionally substituted by 1 or 2 substituents independently selected from the group consisting of halogen, cyano, and hydroxy, (e) alkanoyl, (f) alkoxy, optionally substituted by 1 or 2 independently selected 6- to 10-membered monocyclic or bicyclic aryl, (g) amino, optionally substituted by 1 or 2 substituents independently selected from the group consisting of alkyl, alkoxycarbonyl, alkylsulfonyl, aminosulfonyl, and 5- to 10-membered monocyclic or bicyclic heteroaryl comprising 1, 2, 3 or 4 heteroatoms independently selected from the group consisting of nitrogen, oxygen, and sulfur, (h) carbamoyl, optionally substituted by 1 or 2 independently selected alkyl, (i) alkylsulfonyl, optionally substituted by 1 or 2 substituents independently selected from the group consisting of 4- to 8-membered monocyclic aliphatic heterocyclyl comprising 1, 2 or 3 heteroatoms independently selected from the group consisting of nitrogen, oxygen, and sulfur, optionally substituted with hydroxy, and amino, optionally substituted with 1 or 2 independently selected alkyl, (j) 4- to 8-membered monocyclic aliphatic heterocyclyl comprising 1, 2 or 3 heteroatoms independently selected from the group consisting of nitrogen, oxygen, and sulfur, optionally substituted by 1 or 2 oxo, (k) 6- to 10-membered monocyclic or bicyclic aryl, optionally substituted by 1 or 2 substituents independently selected from the group consisting of alkylsulfonyl and aminosulfonyl, (l) partially hydrogenated 5-to 10-membered monocyclic or bicyclic heteroaryl comprising 1, 2, 3 or 4 heteroatoms independently selected from the group consisting of nitrogen, oxygen, and sulfur, optionally substituted by 1 or 2 substituents independently selected from the group consisting of oxo and hydroxy, and (m) 5- to 10-membered monocyclic or bicyclic heteroaryl comprising 1, 2, 3 or 4 heteroatoms independently selected from the group consisting of nitrogen, oxygen, and sulfur, optionally substituted by 1 or 2 hydroxy;

$R^2$ represents:
(1) hydrogen;
(2) halogen;
(3) alkyl;
(4) haloalkyl; or
(5) alkoxy; and $R^3$ represents formula [II]:

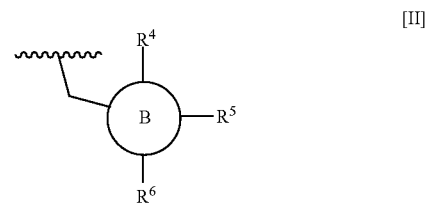

wherein:
Ring B represents:
(1) cycloalkyl;
(2) 6- to 10-membered monocyclic or bicyclic aryl; or
(3) 5- to 10-membered monocyclic or bicyclic heteroaryl comprising 1, 2, 3 or 4 heteroatoms independently selected from the group consisting of nitrogen, oxygen, and sulfur; and $R^4$, $R^5$ and $R^6$ independently represent:
(1) hydrogen;
(2) halogen;
(3) alkyl, optionally substituted with 1 or 2 substituents independently selected from the group consisting of oxo, halogen, cyano, hydroxy, carboxy, alkoxycarbonyl, optionally substituted carbamoyl, alkylsulfonyl, alkylsulfonylamino, alkylsulfonylaminocarbonyl, optionally substituted aminosulfonylaminocarbonyl, and optionally substituted 5- to 10-membered monocyclic or bicyclic heteroaryl comprising 1, 2, 3 or 4 heteroatoms independently selected from the group consisting of nitrogen, oxygen, and sulfur, wherein the carbamoyl and the aminosulfonylaminocarbonyl are optionally and independently substituted with 1 or 2 independently selected alkyl, and further wherein the heteroaryl is optionally substituted by 1 or 2 hydroxy;
(4) amino, optionally substituted with 1 or 2 independently selected alkyl, wherein the alkyl is optionally substituted by 1 or 2 carboxy;
(5) cycloalkyl, optionally substituted with 1 or 2 substituents independently selected from the group consisting of oxo, halogen, cyano, hydroxy, alkyl, carboxy, alkoxycarbonyl, optionally substituted carbamoyl, alkylsulfonyl, alkylsulfonylamino, alkylsulfonylaminocarbonyl, optionally substituted aminosulfonylaminocarbonyl, and optionally substituted 5- to 10-membered monocyclic or bicyclic heteroaryl comprising 1, 2, 3 or 4 heteroatoms independently selected from the group consisting of nitrogen, oxygen, and sulfur, wherein the carbamoyl and the aminosulfonylaminocarbonyl are optionally and independently substituted with 1 or 2 independently selected alkyl, and further wherein the heteroaryl is optionally substituted by 1 or 2 hydroxy;

(6) 4- to 8-membered monocyclic aliphatic heterocyclyl comprising 1, 2 or 3 heteroatoms independently selected from the group consisting of nitrogen, oxygen, and sulfur, optionally substituted with 1 or 2 substituents independently selected from the group consisting of oxo, halogen, cyano, hydroxy, alkyl, carboxy, alkoxycarbonyl, optionally substituted carbamoyl, alkylsulfonyl, alkylsulfonylamino, alkylsulfonylaminocarbonyl, optionally substituted aminosulfonylaminocarbonyl, and optionally substituted 5- to 10-membered monocyclic or bicyclic heteroaryl comprising 1, 2, 3 or 4 heteroatoms independently selected from the group consisting of nitrogen, oxygen, and sulfur, wherein the carbamoyl and the aminosulfonylaminocarbonyl are optionally and independently substituted with 1 or 2 independently selected alkyl, and further wherein the heteroaryl is optionally substituted by 1 or 2 hydroxy; or (7) 5- to 10-membered monocyclic or bicyclic heteroaryl comprising 1, 2, 3 or 4 heteroatoms independently selected from the group consisting of nitrogen, oxygen, and sulfur, optionally substituted with 1 or 2 substituents independently selected from the group consisting of halogen, cyano, hydroxy, alkyl, carboxy, alkoxycarbonyl, optionally substituted carbamoyl, alkylsulfonyl, alkylsulfonylamino, alkylsulfonylaminocarbonyl, optionally substituted aminosulfonylaminocarbonyl, and optionally substituted 5- to 10-membered monocyclic or bicyclic heteroaryl comprising 1, 2, 3 or 4 heteroatoms independently selected from the group consisting of nitrogen, oxygen, and sulfur, wherein the carbamoyl and the aminosulfonylaminocarbonyl are optionally and independently substituted with 1 or 2 independently selected alkyl, and further wherein the heteroaryl is optionally substituted by 1 or 2 hydroxy.

2. The compound according to claim 1, or a pharmaceutically acceptable salt thereof, wherein:

$R^4$ represents:
(1) optionally substituted alkyl;
(2) amino, optionally substituted with 1 or 2 independently selected optionally substituted alkyl;
(3) optionally substituted cycloalkyl;
(4) optionally substituted 4- to 8-membered monocyclic aliphatic heterocyclyl comprising 1, 2 or 3 heteroatoms independently selected from the group consisting of nitrogen, oxygen, and sulfur; or
(5) optionally substituted 5- to 10-membered monocyclic or bicyclic heteroaryl comprising 1, 2, 3 or 4 heteroatoms independently selected from the group consisting of nitrogen, oxygen, and sulfur; and $R^5$ and $R^6$ independently represent:
(1) hydrogen;
(2) halogen;
(3) alkyl, optionally substituted with 1 or 2 independently selected halogens; or
(4) cycloalkyl.

3. The compound according to claim 1, or a pharmaceutically acceptable salt thereof, wherein:

$R^1$ represents:
(1) hydrogen;
(2) alkyl, optionally substituted with 1 or 2 substituents independently selected from the group consisting of (a) halogen, (b) cyano, (c) hydroxy, (d) alkanoyl, (e) alkoxy, optionally substituted by a 6- to 10-membered monocyclic or bicyclic aryl, (f) amino, optionally substituted by 1 or 2 substituents independently selected from the group consisting of alkyl, alkoxycarbonyl, alkylsulfonyl, aminosulfonyl, and 5- to 10-membered monocyclic or bicyclic heteroaryl comprising 1, 2, 3 or 4 heteroatoms independently selected from the group consisting of nitrogen, oxygen, and sulfur, (g) carbamoyl, optionally substituted by 1 or 2 independently selected alkyl, (h) alkylsulfonyl, optionally substituted by a substituent selected from the group consisting of 4- to 8-membered monocyclic aliphatic heterocyclyl comprising 1, 2 or 3 heteroatoms independently selected from the group consisting of nitrogen, oxygen, and sulfur, optionally substituted with a hydroxy, and amino, optionally substituted with 1 or 2 independently selected alkyl, (i) 4- to 8-membered monocyclic aliphatic heterocyclyl comprising 1, 2 or 3 heteroatoms independently selected from the group consisting of nitrogen, oxygen, and sulfur, optionally substituted by 1 or 2 oxo, (j) 6- to 10-membered monocyclic or bicyclic aryl, optionally substituted by a substituent selected from the group consisting of alkylsulfonyl and aminosulfonyl, (k) partially hydrogenated 5- to 10-membered monocyclic or bicyclic heteroaryl comprising 1, 2, 3 or 4 heteroatoms independently selected from the group consisting of nitrogen, oxygen, and sulfur, optionally substituted by 1 or 2 substituents independently selected from the group consisting of oxo and hydroxy, and (l) 5- to 10-membered monocyclic or bicyclic heteroaryl comprising 1, 2, 3 or 4 heteroatoms independently selected from the group consisting of nitrogen, oxygen, and sulfur, optionally substituted by a hydroxy;

(3) alkanoyl, optionally substituted with 1, 2 or 3 substituents independently selected from the group consisting of (a) halogen, (b) cyano, (c) hydroxy, (d) alkyl, optionally substituted by 1 or 2 substituents independently selected from the group consisting of halogen, cyano, and hydroxy, (e) alkanoyl, (f) alkoxy, optionally substituted by a 6- to 10-membered monocyclic or bicyclic aryl, (g) amino, optionally substituted by 1 or 2 substituents independently selected from the group consisting of alkyl, alkoxycarbonyl, alkylsulfonyl, aminosulfonyl, and 5- to 10-membered monocyclic or bicyclic heteroaryl comprising 1, 2, 3 or 4 heteroatoms independently selected from the group consisting of nitrogen, oxygen, and sulfur, (h) carbamoyl, optionally substituted by 1 or 2 independently selected alkyl, (i) alkylsulfonyl, optionally substituted by a substituent selected from the group consisting of 4- to 8-membered monocyclic aliphatic heterocyclyl comprising 1, 2 or 3 heteroatoms independently selected from the group consisting of nitrogen, oxygen, and sulfur, optionally substituted with hydroxy, and amino, optionally substituted with 1 or 2 independently selected alkyl, (j) 4- to 8-membered monocyclic aliphatic heterocyclyl comprising 1, 2 or 3 heteroatoms independently selected from the group consisting of nitrogen, oxygen, and sulfur, optionally substituted by 1 or 2 oxo, (k) 6- to 10-membered monocyclic or bicyclic aryl, optionally substituted by a substituent selected from the group consisting of alkylsulfonyl and aminosulfonyl, (1) partially hydrogenated 5- to 10-membered monocyclic or bicyclic heteroaryl comprising 1, 2, 3 or 4 heteroatoms independently selected from the group consisting of nitrogen, oxygen, and sulfur, optionally substituted by 1 or 2 substituents independently selected from the group consisting of oxo and hydroxy, and (m) 5- to 10-membered monocyclic or bicyclic heteroaryl comprising 1, 2, 3 or 4 heteroatoms independently selected from the group consisting of nitrogen, oxygen, and sulfur, optionally substituted by a hydroxy;

(4) cycloalkyl, optionally substituted with 1, 2 or 3 substituents independently selected from the group consisting of (a) halogen, (b) cyano, (c) hydroxy, (d) alkyl, optionally substituted by 1 or 2 substituents independently selected from the group consisting of halogen, cyano, and hydroxy, (e) alkanoyl, (f) alkoxy, optionally substituted by a 6- to 10-membered monocyclic or bicyclic aryl, (g) amino, optionally substituted by 1 or 2 substituents independently selected from the group consisting of alkyl, alkoxycarbonyl, alkylsulfonyl, aminosulfonyl, and 5- to 10-membered monocyclic or bicyclic heteroaryl comprising 1, 2, 3 or 4 heteroatoms independently selected from the group consisting of nitrogen, oxygen, and sulfur, (h) carbamoyl, optionally substituted by 1 or 2 independently selected alkyl, (i) alkylsulfonyl, optionally substituted by a substituent selected from the group consisting of 4- to 8-membered monocyclic aliphatic heterocyclyl comprising 1, 2 or 3 heteroatoms independently selected from the group consisting of nitrogen, oxygen, and sulfur, optionally substituted with hydroxy, and amino, optionally substituted with 1 or 2 independently selected alkyl, (j) 4- to 8-membered monocyclic aliphatic heterocyclyl comprising 1, 2 or 3 heteroatoms independently selected from the group consisting of nitrogen, oxygen, and sulfur, optionally substituted by 1 or 2 oxo, (k) 6- to 10-membered monocyclic or bicyclic aryl, optionally substituted by a substituent selected from the group consisting of alkylsulfonyl and aminosulfonyl, (1) partially hydrogenated 5- to 10-membered monocyclic or bicyclic heteroaryl comprising 1, 2, 3 or 4 heteroatoms independently selected from the group consisting of nitrogen, oxygen, and sulfur, optionally substituted by 1 or 2 substituents independently selected from the group consisting of oxo and hydroxy, and (m) 5- to 10-membered monocyclic or bicyclic heteroaryl comprising 1, 2, 3 or 4 heteroatoms independently selected from the group consisting of nitrogen, oxygen, and sulfur, optionally substituted by a hydroxy;

(5) 4- to 8-membered monocyclic aliphatic heterocyclyl comprising 1, 2 or 3 heteroatoms independently selected from the group consisting of nitrogen, oxygen, and sulfur, optionally substituted with 1, 2 or 3 substituents independently selected from the group consisting of (a) halogen, (b) cyano, (c) hydroxy, (d) alkyl, optionally substituted by 1 or 2 substituents independently selected from the group consisting of halogen, cyano, and hydroxy, (e) alkanoyl, (f) alkoxy, optionally substituted by a 6- to 10-membered monocyclic or bicyclic aryl, (g) amino, optionally substituted by 1 or 2 substituents independently selected from the group consisting of alkyl, alkoxycarbonyl, alkylsulfonyl, aminosulfonyl, and 5- to 10-membered monocyclic or bicyclic heteroaryl comprising 1, 2, 3 or 4 heteroatoms independently selected from the group consisting of nitrogen, oxygen, and sulfur, (h) carbamoyl, optionally substituted by 1 or 2 independently selected alkyl, (i) alkylsulfonyl, optionally substituted by a substituent selected from the group consisting of 4- to 8-membered monocyclic aliphatic heterocyclyl comprising 1, 2 or 3 heteroatoms independently selected from the group consisting of nitrogen, oxygen, and sulfur, optionally substituted with hydroxy, and amino, optionally substituted with 1 or 2 independently selected alkyl, (j) 4- to 8-membered monocyclic aliphatic heterocyclyl comprising 1, 2 or 3 heteroatoms independently selected from the group consisting of nitrogen, oxygen, and sulfur, optionally substituted by 1 or 2 oxo, (k) 6- to 10-membered monocyclic or bicyclic aryl, optionally substituted by a substituent selected from the group consisting of alkylsulfonyl and aminosulfonyl, (1) partially hydrogenated 5- to 10-membered monocyclic or bicyclic heteroaryl comprising 1, 2, 3 or 4 heteroatoms independently selected from the group consisting of nitrogen, oxygen, and sulfur, optionally substituted by 1 or 2 substituents independently selected from the group consisting of oxo and hydroxy, and (m) 5- to 10-membered monocyclic or bicyclic heteroaryl comprising 1, 2, 3 or 4 heteroatoms independently selected from the group consisting of nitrogen, oxygen, and sulfur, optionally substituted by a hydroxy;

(6) 6- to 10-membered monocyclic or bicyclic aryl, optionally substituted with 1, 2 or 3 substituents independently selected from the group consisting of (a) halogen, (b) cyano, (c) hydroxy, (d) alkyl, optionally substituted by 1 or 2 substituents independently selected from the group consisting of halogen, cyano, and hydroxy, (e) alkanoyl, (f) alkoxy, optionally substituted by a 6- to 10-membered monocyclic or bicyclic aryl, (g) amino, optionally substituted by 1 or 2 substituents independently selected from the group consisting of alkyl, alkoxycarbonyl, alkylsulfonyl, amino sulfonyl, and 5- to 10-membered monocyclic or bicyclic heteroaryl comprising 1, 2, 3 or 4 heteroatoms independently selected from the group consisting of nitrogen, oxygen, and sulfur, (h) carbamoyl, optionally substituted by 1 or 2 independently selected alkyl, (i) alkylsulfonyl, optionally substituted by a substituent selected from the group consisting of 4- to 8-membered monocyclic aliphatic heterocyclyl comprising 1, 2 or 3 heteroatoms independently selected from the group consisting of nitrogen, oxygen, and sulfur, optionally substituted with hydroxy, and amino, optionally substituted with 1 or 2 independently selected alkyl, (j) 4- to 8-membered monocyclic aliphatic heterocyclyl comprising 1, 2 or 3 heteroatoms independently selected from the group consisting of nitrogen, oxygen, and sulfur, optionally substituted by 1 or 2 oxo, (k) 6- to 10-membered monocyclic or bicyclic aryl, optionally substituted by a substituent selected from the group consisting of alkylsulfonyl and aminosulfonyl, (1) partially hydrogenated 5- to 10-membered monocyclic or bicyclic heteroaryl comprising 1, 2, 3 or 4 heteroatoms independently selected from the group consisting of nitrogen, oxygen, and sulfur, optionally substituted by 1 or 2 substituents independently selected from the group consisting of oxo and hydroxy, and (m) 5- to 10-membered monocyclic or bicyclic heteroaryl comprising 1, 2, 3 or 4 heteroatoms independently selected from the group consisting of nitrogen, oxygen, and sulfur, optionally substituted by a hydroxy; or (7) 5- to 10-membered monocyclic or bicyclic heteroaryl comprising 1, 2, 3 or 4 heteroatoms independently selected from the group consisting of nitrogen, oxygen, and sulfur, optionally substituted with 1, 2 or 3 substituents independently selected from the group consisting of (a) halogen, (b) cyano, (c) hydroxy, (d) alkyl, optionally substituted by 1 or 2 substituents independently selected from the group consisting of halogen, cyano, and hydroxy, (e) alkanoyl, (f) alkoxy, optionally substituted by a 6- to 10-membered monocyclic or bicyclic aryl, (g) amino, optionally substituted by 1 or 2 substituents independently selected from the group consisting of alkyl, alkoxycarbonyl, alkylsulfonyl, aminosulfonyl, and 5- to 10-membered monocyclic or bicyclic heteroaryl comprising 1, 2, 3 or 4 heteroatoms independently selected from the group consisting of nitrogen, oxygen, and sulfur, (h) carbamoyl, optionally substituted by 1 or 2 independently selected alkyl, (i) alkylsulfonyl, optionally substituted by a substituent selected from the group consisting of 4- to 8-membered monocyclic aliphatic heterocyclyl comprising 1, 2 or 3 heteroatoms independently selected from the group consisting of nitrogen, oxygen, and sulfur, optionally substituted with hydroxy, and amino, optionally substituted with 1 or 2 independently selected alkyl, (j) 4- to 8-membered monocyclic aliphatic heterocyclyl comprising 1, 2 or 3 heteroatoms independently selected from the group consisting of nitrogen, oxygen, and sulfur, optionally substituted by 1 or 2 oxo, (k) 6- to 10-membered monocyclic or bicyclic aryl, optionally substituted by a substituent selected from the group consisting of alkylsulfonyl and aminosulfonyl, (1) partially hydrogenated 5- to 10-membered monocyclic or bicyclic heteroaryl comprising 1, 2, 3 or 4 heteroatoms independently selected from the group consisting of nitrogen, oxygen, and sulfur, optionally substituted by 1 or 2 substituents independently selected from the group consisting of oxo and hydroxy, and (m) 5- to 10-membered monocyclic or bicyclic heteroaryl comprising 1, 2, 3 or 4 heteroatoms independently selected from the group consisting of nitrogen, oxygen, and sulfur, optionally substituted by a hydroxy; and $R^4$, $R^5$ and $R^6$ independently represent:
(1) hydrogen;
(2) halogen;
(3) alkyl, optionally substituted with 1 or 2 substituents independently selected from the group consisting of oxo, halogen, cyano, hydroxy, carboxy, alkoxycarbonyl, carbamoyl, alkylsulfonyl, alkylsulfonylamino, alkylsulfonylaminocarbonyl, aminosulfonylaminocarbonyl, and optionally substituted 5- to 10-membered monocyclic or bicyclic heteroaryl comprising 1, 2, 3 or 4 heteroatoms independently selected from the group consisting of nitrogen, oxygen, and sulfur, wherein the carbamoyl and the aminosulfonylaminocarbonyl are optionally and independently substituted with 1 or 2 independently selected alkyl and further wherein the heteroaryl is optionally substituted by a hydroxy;
(4) amino, optionally substituted with 1 or 2 independently selected alkyl, wherein each alkyl is optionally and independently substituted by a carboxy;
(5) cycloalkyl, optionally substituted with 1 or 2 substituents independently selected from the group consisting of oxo, halogen, cyano, hydroxy, alkyl, carboxy, alkoxycarbonyl, optionally substituted carbamoyl, alkylsulfonyl, alkylsulfonylamino, alkylsulfonylaminocarbonyl, optionally substituted aminosulfonylaminocarbonyl, and optionally substituted 5- to 10-membered monocyclic or bicyclic heteroaryl comprising 1, 2, 3 or 4 heteroatoms independently selected from the group consisting of nitrogen, oxygen, and sulfur, wherein the carbamoyl and the aminosulfonylaminocarbonyl are optionally and independently substituted with 1 or 2 independently selected alkyl, and further wherein the heteroaryl is optionally substituted by a hydroxy;
6) 4- to 8-membered monocyclic aliphatic heterocyclyl comprising 1, 2 or 3 heteroatoms independently selected from the group consisting of nitrogen, oxygen, and sulfur, optionally substituted with 1 or 2 substituents independently selected from the group consisting of oxo, halogen, cyano, hydroxy, alkyl, carboxy, alkoxycarbonyl, optionally substituted carbamoyl, alkylsulfonyl, alkylsulfonylamino, alkylsulfonylaminocarbonyl, optionally substituted aminosulfonylaminocarbonyl, and optionally substituted 5- to 10-membered monocyclic or bicyclic heteroaryl comprising 1, 2, 3 or 4 heteroatoms independently selected from the group consisting of nitrogen, oxygen, and sulfur, wherein the carbamoyl and the aminosulfonylaminocarbonyl are optionally and independently substituted with 1 or 2 independently selected alkyl, and further wherein the heteroaryl is optionally substituted by a hydroxy; or
(7) 5- to 10-membered monocyclic or bicyclic heteroaryl comprising 1, 2, 3 or 4 heteroatoms independently selected from the group consisting of nitrogen, oxygen, and sulfur, optionally substituted with 1 or 2 substituents independently selected from the group consisting of oxo, halogen, cyano, hydroxy, alkyl, carboxy, alkoxycarbonyl, optionally substituted carbamoyl, alkylsulfonyl, alkylsulfonylamino, alkylsulfonylaminocarbonyl, optionally substituted aminosulfonylaminocarbonyl, and optionally substituted 5- to 10-membered monocyclic or bicyclic heteroaryl comprising 1, 2, 3 or 4 heteroatoms independently selected from the group consisting of nitrogen, oxygen, and sulfur, wherein the carbamoyl and the aminosulfonylaminocarbonyl are optionally and independently substituted with 1 or 2 independently selected alkyl, and further wherein the heteroaryl is optionally substituted by a hydroxy.

4. The compound according to claim 1, or a pharmaceutically acceptable salt thereof, wherein:
Ring A represents:
(1) phenyl or naphthyl, each optionally substituted with 1, 2 or 3 substituents independently selected from the group consisting of halogen and alkoxy; or
(2) pyrrolyl, furanyl, thienyl, imidazolyl, pyrazolyl, oxazolyl, isoxazolyl, thiazolyl, triazolyl, oxadiazolyl, tetrazolyl, pyridyl, pyridazinyl, pyrimidinyl, pyrazinyl, thiazinyl, triazinyl, indolyl, isoindolyl, quinolyl, isoquinolyl, or benzimidazolyl, each optionally substituted with 1, 2 or 3 substituents independently selected from the group consisting of halogen and alkoxy;

$R^1$ represents:
(1) hydrogen;
(2) alkyl, optionally substituted with 1, 2 or 3 substituents independently selected from the group consisting of (a) halogen, (b) cyano, (c) hydroxy, (d) alkanoyl, (e) alkoxy, optionally substituted by 1 or 2 substituents independently selected from the group consisting of phenyl and naphthyl, (f) amino, optionally substituted by 1 or 2 substituents independently selected from the group consisting of alkyl, alkoxycarbonyl, alkylsulfonyl, aminosulfonyl, pyrrolyl, furanyl, thienyl, imidazolyl, pyrazolyl, oxazolyl, isoxazolyl, thiazolyl, triazolyl, oxadiazolyl, tetrazolyl, pyridyl, pyridazinyl, pyrimidinyl, pyrazinyl, thiazinyl, triazinyl, indolyl, isoindolyl, quinolyl, isoquinolyl, and benzimidazolyl, (g) carbamoyl, optionally substituted by 1 or 2 independently selected alkyl, (h) alkylsulfonyl, optionally substituted by 1 or 2 substituents independently selected from the group consisting of azetidinyl, pyrrolidinyl, piperidinyl, tetrahydrofuranyl, imidazolinyl, thiazolidinyl, isothiazolidinyl, piperazinyl, morpholinyl, thiomorpholinyl, tetrahydropyranyl, homopiperazinyl, homomorpholinyl, 3-azabicyclo hexyl, or octahydropyrrolo pyrrolyl, each optionally substituted with hydroxy, and amino, optionally substituted with 1 or 2 independently selected alkyl, (i) azetidinyl, pyrrolidinyl, piperidinyl, tetrahydrofuranyl, imidazolinyl, thiazolidinyl, isothiazolidinyl, piperazinyl, morpholinyl, thiomorpholinyl, tetrahydropyranyl, homopiperazinyl, homomorpholinyl, 3-azabicyclo hexyl, or octahydropyrrolo pyrrolyl, each optionally substituted by 1 or 2 oxo, (j) phenyl or naphthyl, each optionally substituted by 1 or 2 substituents independently selected from the group consisting of alkylsulfonyl and aminosulfonyl, (k) partially hydrogenated pyrrolyl, furanyl, thienyl, imidazolyl, pyrazolyl, oxazolyl, isoxazolyl, thiazolyl, triazolyl, oxadiazolyl, tetrazolyl, pyridyl, pyridazinyl, pyrimidinyl, pyrazinyl, thiazinyl, triazinyl, indolyl, isoindolyl, quinolyl, isoquinolyl, or benzimidazolyl, each optionally substituted by 1 or 2 substituents independently selected from the group consisting of oxo and hydroxy, and (1) pyrrolyl, furanyl, thienyl, imidazolyl, pyrazolyl, oxazolyl, isoxazolyl, thiazolyl, triazolyl, oxadiazolyl, tetrazolyl, pyridyl, pyridazinyl, pyrimidinyl, pyrazinyl, thiazinyl, triazinyl, indolyl, isoindolyl, quinolyl, isoquinolyl, or benzimidazolyl, each optionally substituted by 1 or 2 hydroxy;

(3) alkanoyl, optionally substituted with 1, 2 or 3 substituents independently selected from the group consisting of (a) halogen, (b) cyano, (c) hydroxy, (d) alkyl, optionally substituted by 1 or 2 substituents independently selected from the group consisting of halogen, cyano, and hydroxy, (e) alkanoyl, (f) alkoxy, optionally substituted by 1 or 2 substituents independently selected from the group consisting of phenyl and naphthyl, (g) amino, optionally substituted by 1 or 2 substituents independently selected from the group consisting of alkyl, alkoxycarbonyl, alkylsulfonyl, aminosulfonyl, pyrrolyl, furanyl, thienyl, imidazolyl, pyrazolyl, oxazolyl, isoxazolyl, thiazolyl, triazolyl, oxadiazolyl, tetrazolyl, pyridyl, pyridazinyl, pyrimidinyl, pyrazinyl, thiazinyl, triazinyl, indolyl, isoindolyl, quinolyl, isoquinolyl, and benzimidazolyl, (h) carbamoyl, optionally substituted by 1 or 2 independently selected alkyl, (i) alkylsulfonyl, optionally substituted by 1 or 2 substituents independently selected from the group consisting of azetidinyl, pyrrolidinyl, piperidinyl, tetrahydrofuranyl, imidazolinyl, thiazolidinyl, isothiazolidinyl, piperazinyl, morpholinyl, thiomorpholinyl, tetrahydropyranyl, homopiperazinyl, homomorpholinyl, 3-azabicyclo [3.1.0]hexyl, or octahydropyrrolo[3,4-c]pyrrolyl, each optionally substituted with hydroxy, and amino, optionally substituted with 1 or 2 independently selected alkyl, (j) azetidinyl, pyrrolidinyl, piperidinyl, tetrahydrofuranyl, imidazolinyl, thiazolidinyl, isothiazolidinyl, piperazinyl, morpholinyl, thiomorpholinyl, tetrahydropyranyl, homopiperazinyl, homomorpholinyl, 3-azabicyclo [3.1.0]hexyl, or octahydropyrrolo[3,4-c]pyrrolyl, optionally substituted by 1 or 2 oxo, (k) phenyl or naphthyl, each optionally substituted by 1 or 2 substituents independently selected from the group consisting of alkylsulfonyl and aminosulfonyl, (1) partially hydrogenated pyrrolyl, furanyl, thienyl, imidazolyl, pyrazolyl, oxazolyl, isoxazolyl, thiazolyl, triazolyl, oxadiazolyl, tetrazolyl, pyridyl, pyridazinyl, pyrimidinyl, pyrazinyl, thiazinyl, triazinyl, indolyl, isoindolyl, quinolyl, isoquinolyl, or benzimidazolyl, each optionally substituted by 1 or 2 substituents independently selected from the group consisting of oxo and hydroxy, and (m) pyrrolyl, furanyl, thienyl, imidazolyl, pyrazolyl, oxazolyl, isoxazolyl, thiazolyl, triazolyl, oxadiazolyl, tetrazolyl, pyridyl, pyridazinyl, pyrimidinyl, pyrazinyl, thiazinyl, triazinyl, indolyl, isoindolyl, quinolyl, isoquinolyl, or benzimidazolyl, each optionally substituted by 1 or 2 hydroxy;

(4) cycloalkyl, optionally substituted with 1, 2 or 3 substituents independently selected from the group consisting of (a) halogen, (b) cyano, (c) hydroxy, (d) alkyl, optionally substituted by 1 or 2 substituents independently selected from the group consisting of halogen, cyano, and hydroxy, (e) alkanoyl, (f) alkoxy, optionally substituted by 1 or 2 substituents independently selected from the group consisting of phenyl and naphthyl, (g) amino, optionally substituted by 1 or 2 substituents independently selected from the group consisting of alkyl, alkoxycarbonyl, alkylsulfonyl, aminosulfonyl, pyrrolyl, furanyl, thienyl, imidazolyl, pyrazolyl, oxazolyl, isoxazolyl, thiazolyl, triazolyl, oxadiazolyl, tetrazolyl, pyridyl, pyridazinyl, pyrimidinyl, pyrazinyl, thiazinyl, triazinyl, indolyl, isoindolyl, quinolyl, isoquinolyl, and benzimidazolyl, (h) carbamoyl, optionally substituted by 1 or 2 independently selected alkyl, (i) alkylsulfonyl, optionally substituted by 1 or 2 substituents independently selected from the group consisting of azetidinyl, pyrrolidinyl, piperidinyl, tetrahydrofuranyl, imidazolinyl, thiazolidinyl, isothiazolidinyl, piperazinyl, morpholinyl, thiomorpholinyl, tetrahydropyranyl, homopiperazinyl, homomorpholinyl, 3-azabicyclo[3.1.0]hexyl, or octahydropyrrolo[3,4-c]pyrrolyl, each optionally substituted with hydroxy, and amino, optionally substituted with 1 or 2 independently selected alkyl, (j) azetidinyl, pyrrolidinyl, piperidinyl, tetrahydrofuranyl, imidazolinyl, thiazolidinyl, isothiazolidinyl, piperazinyl, morpholinyl, thiomorpholinyl, tetrahydropyranyl, homopiperazinyl, homomorpholinyl, 3-azabicyclo [3.1.0]hexyl, or octahydropyrrolo[3,4-c]pyrrolyl, optionally substituted by 1 or 2 oxo, (k) phenyl or naphthyl, each optionally substituted by 1 or 2 substituents independently selected from the group consisting of alkylsulfonyl and aminosulfonyl, (1) partially hydrogenated pyrrolyl, furanyl, thienyl, imidazolyl, pyrazolyl, oxazolyl, isoxazolyl, thiazolyl, triazolyl, oxadiazolyl, tetrazolyl, pyridyl, pyridazinyl, pyrimidinyl, pyrazinyl, thiazinyl, triazinyl, indolyl, isoindolyl, quinolyl, isoquinolyl, or benzimidazolyl, each optionally substituted by 1 or 2 substituents independently selected from the group consisting of oxo and hydroxy, and (m) pyrrolyl, furanyl, thienyl, imidazolyl, pyrazolyl, oxazolyl, isoxazolyl, thiazolyl, triazolyl, oxadiazolyl, tetrazolyl, pyridyl, pyridazinyl, pyrimidinyl, pyrazinyl, thiazinyl, triazinyl, indolyl, isoindolyl, quinolyl, isoquinolyl, or benzimidazolyl, each optionally substituted by 1 or 2 hydroxy;

(5) azetidinyl, pyrrolidinyl, piperidinyl, tetrahydrofuranyl, imidazolinyl, thiazolidinyl, isothiazolidinyl, piperazinyl, morpholinyl, thiomorpholinyl, tetrahydropyranyl, homopiperazinyl, homomorpholinyl, 3-azabicyclo [3.1.0]hexyl, or octahydropyrrolo[3,4-c]pyrrolyl, optionally substituted with 1, 2 or 3 substituents independently selected from the group consisting of (a) halogen, (b) cyano, (c) hydroxy, (d) alkyl, optionally substituted by 1 or 2 substituents independently selected from the group consisting of halogen, cyano, and hydroxy, (e) alkanoyl, (f) alkoxy, optionally substituted by 1 or 2 substituents independently selected from the group consisting of phenyl and naphthyl, (g) amino, optionally substituted by 1 or 2 substituents independently selected from the group consisting of alkyl, alkoxycarbonyl, alkylsulfonyl, aminosulfonyl, pyrrolyl, furanyl, thienyl, imidazolyl, pyrazolyl, oxazolyl, isoxazolyl, thiazolyl, triazolyl, oxadiazolyl, tetrazolyl, pyridyl, pyridazinyl, pyrimidinyl, pyrazinyl, thiazinyl, triazinyl, indolyl, isoindolyl, quinolyl, isoquinolyl, and benzimidazolyl, (h) carbamoyl, optionally substituted by 1 or 2 independently selected alkyl, (i) alkylsulfonyl, optionally substituted by 1 or 2 substituents independently selected from the group consisting of azetidinyl, pyrrolidinyl, piperidinyl, tetrahydrofuranyl, imidazolinyl, thiazolidinyl, isothiazolidinyl, piperazinyl, morpholinyl, thiomorpholinyl, tetrahydropyranyl, homopiperazinyl, homomorpholinyl, 3-azabicyclo[3.1.0]hexyl, or octahydropyrrolo[3,4-c]pyrrolyl, each optionally substituted with hydroxy, and amino, optionally substituted with 1 or 2 independently selected alkyl, (j) azetidinyl, pyrrolidinyl, piperidinyl, tetrahydrofuranyl, imidazolinyl, thiazolidinyl, isothiazolidinyl, piperazinyl, morpholinyl, thiomorpholinyl, tetrahydropyranyl, homopiperazinyl, homomorpholinyl, 3-azabicyclo hexyl, or octahydropyrrolo pyrrolyl, each optionally substituted by 1 or 2 oxo, (k) phenyl or naphthyl, each optionally substituted by 1 or 2 substituents independently selected from the group consisting of alkylsulfonyl and aminosulfonyl, (1) partially hydrogenated pyrrolyl, furanyl, thienyl, imidazolyl, pyrazolyl, oxazolyl, isoxazolyl, thiazolyl, triazolyl, oxadiazolyl, tetrazolyl, pyridyl, pyridazinyl, pyrimidinyl, pyrazinyl, thiazinyl, triazinyl, indolyl, isoindolyl, quinolyl, isoquinolyl, or benzimidazolyl, each optionally substituted by 1 or 2 substituents independently selected from the group consisting of oxo and hydroxy, and (m) pyrrolyl, furanyl, thienyl, imidazolyl, pyrazolyl, oxazolyl, isoxazolyl, thiazolyl, triazolyl, oxadiazolyl, tetrazolyl, pyridyl, pyridazinyl, pyrimidinyl, pyrazinyl, thiazinyl, triazinyl, indolyl, isoindolyl, quinolyl, isoquinolyl, or benzimidazolyl, each optionally substituted by 1 or 2 hydroxy;

(6) phenyl or naphthyl, each optionally substituted with 1, 2 or 3 substituents independently selected from the group consisting of (a) halogen, (b) cyano, (c) hydroxy, (d) alkyl, optionally substituted by 1 or 2 substituents independently selected from the group consisting of halogen, cyano, and hydroxy, (e) alkanoyl, (f) alkoxy, optionally substituted by 1 or 2 substituents independently selected from the group consisting of phenyl and naphthyl, (g) amino, optionally substituted by 1 or 2 substituents independently selected from the group consisting of alkyl, alkoxycarbonyl, alkylsulfonyl, aminosulfonyl, pyrrolyl, furanyl, thienyl, imidazolyl, pyrazolyl, oxazolyl, isoxazolyl, thiazolyl, triazolyl, oxadiazolyl, tetrazolyl, pyridyl, pyridazinyl, pyrimidinyl, pyrazinyl, thiazinyl, triazinyl, indolyl, isoindolyl, quinolyl, isoquinolyl, and benzimidazolyl, (h) carbamoyl, optionally substituted by 1 or 2 independently selected alkyl, (i) alkylsulfonyl, optionally substituted by 1 or 2 substituents independently selected from the group consisting of azetidinyl, pyrrolidinyl, piperidinyl, tetrahydrofuranyl, imidazolinyl, thiazolidinyl, isothiazolidinyl, piperazinyl, morpholinyl, thiomorpholinyl, tetrahydropyranyl, homopiperazinyl, homomorpholinyl, 3-azabicyclo[3.1.0]hexyl, or octahydropyrrolo[3,4-c]pyrrolyl, each optionally substituted with hydroxy, and amino, optionally substituted with 1 or 2 independently selected alkyl, (j) azetidinyl, pyrrolidinyl, piperidinyl, tetrahydrofuranyl, imidazolinyl, thiazolidinyl, isothiazolidinyl, piperazinyl, morpholinyl, thiomorpholinyl, tetrahydropyranyl, homopiperazinyl, homomorpholinyl, 3-azabicyclo [3.1.0]hexyl, or octahydropyrrolo[3,4-c]pyrrolyl, each optionally substituted by 1 or 2 oxo, (k) phenyl or naphthyl, each optionally substituted by 1 or 2 substituents independently selected from the group consisting of alkylsulfonyl and aminosulfonyl, (1) partially hydrogenated pyrrolyl, furanyl, thienyl, imidazolyl, pyrazolyl, oxazolyl, isoxazolyl, thiazolyl, triazolyl, oxadiazolyl, tetrazolyl, pyridyl, pyridazinyl, pyrimidinyl, pyrazinyl, thiazinyl, triazinyl, indolyl, isoindolyl, quinolyl, isoquinolyl, or benzimidazolyl, each optionally substituted by 1 or 2 substituents independently selected from the group consisting of oxo and hydroxy, and (m) pyrrolyl, furanyl, thienyl, imidazolyl, pyrazolyl, oxazolyl, isoxazolyl, thiazolyl, triazolyl, oxadiazolyl, tetrazolyl, pyridyl, pyridazinyl, pyrimidinyl, pyrazinyl, thiazinyl, triazinyl, indolyl, isoindolyl, quinolyl, isoquinolyl, or benzimidazolyl, each optionally substituted by 1 or 2 hydroxy; or (7) pyrrolyl, furanyl, thienyl, imidazolyl, pyrazolyl, oxazolyl, isoxazolyl, thiazolyl, triazolyl, oxadiazolyl, tetrazolyl, pyridyl, pyridazinyl, pyrimidinyl, pyrazinyl, thiazinyl, triazinyl, indolyl, isoindolyl, quinolyl, isoquinolyl, or benzimidazolyl, each optionally substituted with 1, 2 or 3 substituents independently selected from the group consisting of (a) halogen, (b) cyano, (c) hydroxy, (d) alkyl, optionally substituted by 1 or 2 substituents independently selected from the group consisting of halogen, cyano, and hydroxy, (e) alkanoyl, (f) alkoxy, optionally substituted by 1 or 2 substituents independently selected from the group consisting of phenyl and naphthyl, (g) amino, optionally substituted by 1 or 2 substituents independently selected from the group consisting of alkyl, alkoxycarbonyl, alkylsulfonyl, aminosulfonyl, pyrrolyl, furanyl, thienyl, imidazolyl, pyrazolyl, oxazolyl, isoxazolyl, thiazolyl, triazolyl, oxadiazolyl, tetrazolyl, pyridyl, pyridazinyl, pyrimidinyl, pyrazinyl, thiazinyl, triazinyl, indolyl, isoindolyl, quinolyl, isoquinolyl, and benzimidazolyl, (h) carbamoyl, optionally substituted by 1 or 2 independently selected alkyl, (i) alkylsulfonyl, optionally substituted by 1 or 2 substituents independently selected from the group consisting of azetidinyl, pyrrolidinyl, piperidinyl, tetrahydrofuranyl, imidazolinyl, thiazolidinyl, isothiazolidinyl, piperazinyl, morpholinyl, thiomorpholinyl, tetrahydropyranyl, homopiperazinyl, homomorpholinyl, 3-azabicyclo[3.1.0]hexyl, or octahydropyrrolo[3,4-c]pyrrolyl, each optionally substituted with hydroxy, and amino, optionally substituted with 1 or 2 independently selected alkyl, (j) azetidinyl, pyrrolidinyl, piperidinyl, tetrahydrofuranyl, imidazolinyl, thiazolidinyl, isothiazolidinyl, piperazinyl, morpholinyl, thiomorpholinyl, tetrahydropyranyl, homopiperazinyl, homomorpholinyl, 3-azabicyclo hexyl, or octahydropyrrolo pyrrolyl, each optionally substituted by 1 or 2 oxo, (k) phenyl or naphthyl, each optionally substituted by 1 or 2 substituents independently selected from the group consisting of alkylsulfonyl and aminosulfonyl, (l) partially hydrogenated pyrrolyl, furanyl, thienyl, imidazolyl, pyrazolyl, oxazolyl, isoxazolyl, thiazolyl, triazolyl, oxadiazolyl, tetrazolyl, pyridyl, pyridazinyl, pyrimidinyl, pyrazinyl, thiazinyl, triazinyl, indolyl, isoindolyl, quinolyl, isoquinolyl, or benzimidazolyl, each optionally substituted by 1 or 2 substituents independently selected from the group consisting of oxo and hydroxy, and (m) pyrrolyl, furanyl, thienyl, imidazolyl, pyrazolyl, oxazolyl, isoxazolyl, thiazolyl, triazolyl, oxadiazolyl, tetrazolyl, pyridyl, pyridazinyl, pyrimidinyl, pyrazinyl, thiazinyl, triazinyl, indolyl, isoindolyl, quinolyl, isoquinolyl, or benzimidazolyl, each optionally substituted by 1 or 2 hydroxy;

Ring B represents:
(1) cycloalkyl;
(2) phenyl or naphthyl; or
(3) pyrrolyl, furanyl, thienyl, imidazolyl, pyrazolyl, oxazolyl, isoxazolyl, thiazolyl, triazolyl, oxadiazolyl, tetrazolyl, pyridyl, pyridazinyl, pyrimidinyl, pyrazinyl, thiazinyl, triazinyl, indolyl, isoindolyl, quinolyl, isoquinolyl, or benzimidazolyl; and $R^4$, $R^5$ and $R^6$ independently represent:
(1) hydrogen;
2) halogen;
(3) alkyl, optionally substituted with 1 or 2 substituents independently selected from the group consisting of oxo, halogen, cyano, hydroxy, carboxy, alkoxycarbonyl, optionally substituted carbamoyl, alkylsulfonyl, alkylsulfonylamino, alkylsulfonylaminocarbonyl, optionally substituted aminosulfonylaminocarbonyl, and optionally substituted pyrrolyl, furanyl, thienyl, imidazolyl, pyrazolyl, oxazolyl, isoxazolyl, thiazolyl, triazolyl, oxadiazolyl, tetrazolyl, pyridyl, pyridazinyl, pyrimidinyl, pyrazinyl, thiazinyl, triazinyl, indolyl, isoindolyl, quinolyl, isoquinolyl, or benzimidazolyl, wherein the carbamoyl and the aminosulfonylaminocarbonyl are optionally and independently substituted with 1 or 2 independently selected alkyl, and the azetidinyl, pyrrolidinyl, piperidinyl, tetrahydrofuranyl, imidazolinyl, thiazolidinyl, isothiazolidinyl, piperazinyl, morpholinyl, thiomorpholinyl, tetrahydropyranyl, homopiperazinyl, homomorpholinyl, 3-azabicyclo[3.1.0]hexyl, and octahydropyrrolo[3,4-c]pyrrolyl are each optionally substituted by 1 or 2 hydroxy;
(4) amino, optionally substituted with 1 or 2 independently selected alkyl, wherein the alkyl is optionally substituted by 1 or 2 carboxy;
(5) cycloalkyl, optionally substituted with 1 or 2 substituents independently selected from the group consisting of oxo, halogen, cyano, hydroxy, alkyl, carboxy, alkoxycarbonyl, optionally substituted carbamoyl, alkylsulfonyl, alkylsulfonylamino, alkylsulfonylaminocarbonyl, optionally substituted aminosulfonylaminocarbonyl, and optionally substituted pyrrolyl, furanyl, thienyl, imidazolyl, pyrazolyl, oxazolyl, isoxazolyl, thiazolyl, triazolyl, oxadiazolyl, tetrazolyl, pyridyl, pyridazinyl, pyrimidinyl, pyrazinyl, thiazinyl, triazinyl, indolyl, isoindolyl, quinolyl, isoquinolyl, or benzimidazolyl, wherein the carbamoyl and the aminosulfonylaminocarbonyl are optionally and independently substituted with 1 or 2 independently selected alkyl, and the pyrrolyl, furanyl, thienyl, imidazolyl, pyrazolyl, oxazolyl, isoxazolyl, thiazolyl, triazolyl, oxadiazolyl, tetrazolyl, pyridyl, pyridazinyl, pyrimidinyl, pyrazinyl, thiazinyl, triazinyl, indolyl, isoindolyl, quinolyl, isoquinolyl, and benzimidazolyl are each optionally substituted by 1 or 2 hydroxy;
(6) azetidinyl, pyrrolidinyl, piperidinyl, tetrahydrofuranyl, imidazolinyl, thiazolidinyl, isothiazolidinyl, piperazinyl, morpholinyl, thiomorpholinyl, tetrahydropyranyl, homopiperazinyl, homomorpholinyl, 3-azabicyclo[3.1.0]hexyl, or octahydropyrrolo[3,4-c]pyrrolyl, optionally substituted with 1 or 2 substituents independently selected from the group consisting of oxo, halogen, cyano, hydroxy, alkyl, carboxy, alkoxycarbonyl, optionally substituted carbamoyl, alkylsulfonyl, alkylsulfonylamino, alkylsulfonylaminocarbonyl, optionally substituted aminosulfonylaminocarbonyl, and optionally substituted pyrrolyl, furanyl, thienyl, imidazolyl, pyrazolyl, oxazolyl, isoxazolyl, thiazolyl, triazolyl, oxadiazolyl, tetrazolyl, pyridyl, pyridazinyl, pyrimidinyl, pyrazinyl, thiazinyl, triazinyl, indolyl, isoindolyl, quinolyl, isoquinolyl, or benzimidazolyl, wherein the carbamoyl and the aminosulfonylaminocarbonyl are optionally and independently substituted with 1 or 2 independently selected alkyl, and the pyrrolyl, furanyl, thienyl, imidazolyl, pyrazolyl, oxazolyl, isoxazolyl, thiazolyl, triazolyl, oxadiazolyl, tetrazolyl, pyridyl, pyridazinyl, pyrimidinyl, pyrazinyl, thiazinyl, triazinyl, indolyl, isoindolyl, quinolyl, isoquinolyl, or benzimidazolyl are each optionally substituted by 1 or 2 hydroxy; or
(7) pyrrolyl, furanyl, thienyl, imidazolyl, pyrazolyl, oxazolyl, isoxazolyl, thiazolyl, triazolyl, oxadiazolyl, tetrazolyl, pyridyl, pyridazinyl, pyrimidinyl, pyrazinyl, thiazinyl, triazinyl, indolyl, isoindolyl, quinolyl, isoquinolyl, or benzimidazolyl, each optionally substituted with 1 or 2 substituents independently selected from the group consisting of halogen, cyano, hydroxy, alkyl, carboxy, alkoxycarbonyl, optionally substituted carbamoyl, alkylsulfonyl, alkylsulfonylamino, alkylsulfonylaminocarbonyl, optionally substituted aminosulfonylaminocarbonyl, and optionally substituted pyrrolyl, furanyl, thienyl, imidazolyl, pyrazolyl, oxazolyl, isoxazolyl, thiazolyl, triazolyl, oxadiazolyl, tetrazolyl, pyridyl, pyridazinyl, pyrimidinyl, pyrazinyl, thiazinyl, triazinyl, indolyl, isoindolyl, quinolyl, isoquinolyl, or benzimidazolyl, wherein the carbamoyl and the aminosulfonylaminocarbonyl are optionally and independently substituted with 1 or 2 independently selected alkyl, and the pyrrolyl, furanyl, thienyl, imidazolyl, pyrazolyl, oxazolyl, isoxazolyl, thiazolyl, triazolyl, oxadiazolyl, tetrazolyl, pyridyl, pyridazinyl, pyrimidinyl, pyrazinyl, thiazinyl, triazinyl, indolyl, isoindolyl, quinolyl, isoquinolyl, or benzimidazolyl are each optionally substituted by 1 or 2 hydroxy.

5. The compound according to claim 1, or a pharmaceutically acceptable salt thereof, wherein:
Ring A represents:
(1) 6-membered monocyclic aryl, optionally substituted with 1 or 2 substituents independently selected from the group consisting of halogen and alkoxy; or
(2) 5- to 6-membered monocyclic heteroaryl comprising 1 nitrogen atom and optionally 1, 2 or 3 additional heteroatoms independently selected from the group consisting of nitrogen, oxygen, and sulfur, optionally substituted with 1 or 2 halogens;

R¹ represents:
(1) alkyl, optionally substituted with 1 or 2 substituents independently selected from the group consisting of (a) halogen, (b) cyano, (c) hydroxy, (d) alkoxy, optionally substituted by 1 6-membered monocyclic aryl, (e) amino, optionally substituted by 1 or 2 substituents independently selected from the group consisting of alkyl, alkoxycarbonyl, alkylsulfonyl, amino sulfonyl, and 5- to 6-membered monocyclic heteroaryl comprising 1 nitrogen atom and optionally 1, 2 or 3 additional heteroatoms independently selected from the group consisting of nitrogen, oxygen, and sulfur, (f) carbamoyl, optionally substituted by 1 or 2 independently selected alkyl, (g) alkylsulfonyl, optionally substituted by a substituent selected from the group consisting of 4- to 7-membered monocyclic aliphatic heterocyclyl comprising 1 nitrogen atom and optionally 1 additional heteroatom selected from the group consisting of nitrogen, oxygen, and sulfur, optionally substituted with a hydroxy, and amino, optionally substituted with 1 or 2 independently selected alkyl, (h) 4- to 7-membered monocyclic aliphatic heterocyclyl comprising 1 nitrogen atom and optionally 1 additional heteroatom selected from the group consisting of nitrogen, oxygen, and sulfur, optionally substituted by 1 or 2 oxo, (i) 6-membered monocyclic aryl, optionally substituted by a substituent selected from the group consisting of alkylsulfonyl and aminosulfonyl, (j) partially hydrogenated 10-membered bicyclic heteroaryl comprising 1 nitrogen atom and optionally 1, 2 or 3 additional heteroatoms independently selected from the group consisting of nitrogen, oxygen, and sulfur, optionally substituted by 1 or 2 substituents independently selected from the group consisting of oxo and hydroxy, and (k) 5- to 6-membered monocyclic heteroaryl comprising 1 nitrogen atom and optionally 1, 2 or 3 additional heteroatoms independently selected from the group consisting of nitrogen, oxygen, and sulfur, optionally substituted by 1 or 2 hydroxy;
(2) alkanoyl, optionally substituted with a substituent selected from the group consisting of (a) partially hydrogenated 10-membered bicyclic heteroaryl comprising 1 nitrogen atom and optionally 1, 2 or 3 heteroatoms independently selected from the group consisting of nitrogen, oxygen, and sulfur, and (b) 10-membered bicyclic heteroaryl comprising 1 nitrogen atom and optionally 1, 2 or 3 heteroatoms independently selected from the group consisting of nitrogen, oxygen, and sulfur;
(3) cycloalkyl;
(4) 4- to 7-membered monocyclic aliphatic heterocyclyl comprising 1 nitrogen atom and optionally 1 additional heteroatom selected from the group consisting of nitrogen, oxygen, and sulfur, optionally substituted with 1 or 2 substituents independently selected from the group consisting of (a) alkyl, optionally substituted by 1 or 2 substituents independently selected from the group consisting of halogen, cyano, and hydroxy, and (b) alkanoyl; or
5) 5- to 6-membered monocyclic heteroaryl comprising 1 nitrogen atom and optionally 1, 2 or 3 additional heteroatoms independently selected from the group consisting of nitrogen, oxygen, and sulfur, optionally substituted with an alkyl;
Ring B represents:
(1) cycloalkyl;
(2) 6-membered monocyclic aryl; or
(3) 5- to 6-membered monocyclic heteroaryl comprising 1 nitrogen atom and optionally 1, 2 or 3 additional heteroatoms independently selected from the group consisting of nitrogen, oxygen, and sulfur; and
R⁴ represents:
(1) alkyl;
(2) amino, optionally substituted with 1 or 2 independently selected alkyl, wherein each alkyl is optionally substituted by a carboxy;
(3) cycloalkyl, optionally substituted with a carboxy;
(4) 4- to 7-membered monocyclic aliphatic heterocyclyl comprising 1 nitrogen atom and optionally 1 additional heteroatom selected from the group consisting of nitrogen, oxygen, and sulfur, optionally substituted with 1 or 2 substituents independently selected from the group consisting of oxo, halogen, cyano, hydroxy, alkyl, carboxy, alkoxycarbonyl, optionally substituted carbamoyl, alkylsulfonyl, alkylsulfonylamino, alkylsulfonylaminocarbonyl, optionally substituted aminosulfonylaminocarbonyl, and optionally substituted 5- to 6-membered monocyclic heteroaryl comprising 1 nitrogen atom and optionally 1, 2 or 3 additional heteroatoms independently selected from the group consisting of nitrogen, oxygen, and sulfur, wherein the carbamoyl and the aminosulfonylaminocarbonyl are optionally and independently substituted with 1 or 2 independently selected alkyl, and further wherein the heteroaryl is optionally substituted by a hydroxy; or
(5) 5- to 6-membered monocyclic heteroaryl comprising 1 nitrogen atom and optionally 1, 2 or 3 additional heteroatoms independently selected from the group consisting of nitrogen, oxygen, and sulfur, optionally substituted with a 5- to 6-membered monocyclic heteroaryl comprising 1 nitrogen atom and optionally 1, 2 or 3 additional heteroatoms independently selected from the group consisting of nitrogen, oxygen, and sulfur.

6. The compound according to claim 5, or a pharmaceutically acceptable salt thereof, wherein:
Ring A represents:
(1) phenyl, optionally substituted with 1 or 2 substituents independently selected from the group consisting of halogen and alkoxy; or
(2) pyridyl, optionally substituted with 1 or 2 independently selected halogens;
R¹ represents:
(1) alkyl, optionally substituted with 1 or 2 substituents independently selected from the group consisting of (a) halogen, (b) cyano, (c) hydroxy, (d) alkoxy, optionally substituted by 1 phenyl, (e) amino, optionally substituted by 1 or 2 substituents independently selected from the group consisting of alkyl, alkoxycarbonyl, alkylsulfonyl, aminosulfonyl, and pyridyl, (f) carbamoyl, optionally substituted by 1 or 2 independently selected alkyl, (g) alkylsulfonyl, optionally substituted by a substituent selected from the group consisting of pyrrolidinyl, optionally substituted with a hydroxy, and amino, optionally substituted with 1 or 2 independently selected alkyl, (h) piperidinyl, morpholinyl, thiazolidinyl or imidazolidinyl, each optionally substituted by 1 or 2 oxo, (i) phenyl, optionally substituted by a substituent selected from the group consisting of alkylsulfonyl and aminosulfonyl, (j) tetrahydroisoquinolyl, and (k) oxazolyl, oxadiazolyl, triazolyl or pyridyl, each optionally substituted by 1 or 2 hydroxy;
(2) alkanoyl, optionally substituted with a tetrahydroisoquinolyl;

(3) cycloalkyl;
(4) piperidinyl, optionally substituted with 1 or 2 substituents independently selected from the group consisting of (a) alkyl, optionally substituted by 1 or 2 substituents independently selected from the group consisting of halogen, cyano, and hydroxy, and (b) alkanoyl; or
(5) pyridyl, optionally substituted with an alkyl;

Ring B represents:
(1) cycloalkyl;
(2) phenyl; or
(3) pyridyl;

$R^4$ represents:
(1) alkyl;
(2) amino, optionally substituted with 1 or 2 independently selected alkyl, wherein the alkyl is optionally substituted by a carboxy;
(3) cycloalkyl, optionally substituted with a carboxy;
(4) piperidinyl, piperazinyl, morpholinyl or thiomorpholinyl, optionally substituted with 1 or 2 substituents independently selected from the group consisting of oxo, halogen, cyano, hydroxy, alkyl, carboxy, alkoxycarbonyl, optionally substituted carbamoyl, alkylsulfonyl, alkylsulfonylamino, alkylsulfonylaminocarbonyl, optionally substituted aminosulfonylaminocarbonyl, and optionally substituted oxazolyl, oxadiazolyl or tetrazolyl, wherein the carbamoyl and the aminosulfonylaminocarbonyl are optionally and independently substituted with 1 or 2 independently selected alkyl, and the oxazolyl, oxadiazolyl and tetrazolyl are each optionally substituted by a hydroxy; or
(5) pyridyl, optionally substituted with an oxadiazolyl; and $R^5$ and $R^6$ independently represent:
(1) hydrogen;
(2) halogen;
(3) alkyl, optionally substituted with 1 or 2 halogens; or
(4) cycloalkyl.

7. The compound according to claim 5, or a pharmaceutically acceptable salt thereof, wherein:
Ring A represents:
(1) 6-membered monocyclic aryl, optionally substituted with 1 or 2 substituents independently selected from the group consisting of halogen and alkoxy;

$R^1$ represents:
(1) alkyl, optionally substituted with 1 or 2 substituents independently selected from the group consisting of (a) alkoxy, and (b) alkylsulfonyl, optionally substituted by a 4- to 7-membered monocyclic aliphatic heterocyclyl comprising 1 nitrogen atom and optionally 1 additional heteroatom selected from the group consisting of nitrogen, oxygen, and sulfur; or
(2) cycloalkyl;

$R^2$ represents:
(1) halogen;

Ring B represents:
(1) 6-membered monocyclic aryl;

$R^4$ represents:
(1) 4- to 7-membered monocyclic aliphatic heterocyclyl comprising 1 nitrogen atom and optionally 1 additional heteroatom selected from the group consisting of nitrogen, oxygen, and sulfur, optionally substituted with a carboxy; and $R^5$ and $R^6$ independently represent:
(1) hydrogen; or
(2) alkyl, optionally substituted with 1 or 2 halogens.

8. The compound according to claim 7, or a pharmaceutically acceptable salt thereof, wherein:
Ring A represents:
(1) phenyl, optionally substituted with 1 or 2 substituents independently selected from the group consisting of halogen and alkoxy;

$R^1$ represents:
(1) alkyl, optionally substituted with a substituent selected from the group consisting of (a) alkoxy, and (b) alkylsulfonyl, optionally substituted by a pyrrolidinyl; or
(2) cycloalkyl;

Ring B represents:
(1) phenyl; and $R^4$ represents:
(1) piperidinyl, optionally substituted by a carboxy.

9. A pharmaceutical composition comprising a pharmaceutically acceptable carrier and the compound according to claim 1, or a pharmaceutically acceptable salt thereof, as an active ingredient.

10. A method for modulating melanocortin receptor 1 activity in a patient, which comprises administering to the patient in need thereof an effective amount of the pharmaceutical composition according to claim 9.

11. The method according to claim 10, wherein the patient has a disease or symptom of a disease selected from the group consisting of rheumatoid arthritis, gouty arthritis, osteoarthritis, inflammatory bowel disease, systemic sclerosis, psoriasis, fibrosis, protoporphyria, systemic lupus erythematosus, melanoma, skin cancer, vitiligo, alopecia, poliosis, pain, ischemia/reperfusion injury, cerebral inflammatory disease, hepatitis, sepsis/septic shock, nephritis, transplantation, HIV disease exacerbation, vasculitis, uveitis, retinitis pigmentosa, age-related macular degeneration, microbial infection, celiac disease, nephrotic syndrome, and melanoma invasion.

12. The method according to claim 11, wherein the patient has a disease or symptom of a disease selected from the group consisting of systemic sclerosis, psoriasis, protoporphyria, melanoma, skin cancer, vitiligo, alopecia, poliosis, nephrotic syndrome, retinitis pigmentosa, and age-related macular degeneration.

13. The method according to claim 12, wherein the patient has a disease or symptom of a disease selected from the group consisting of systemic sclerosis, protoporphyria, melanoma, vitiligo, nephrotic syndrome, retinitis pigmentosa, and age-related macular degeneration.

14. The method according to claim 13, wherein the protoporphyria is erythropoietic protoporphyria.

15. A method for modulating melanocortin receptor 1 activity in a patient, which comprises administering to the patient in need thereof an effective amount of the compound according to claim 1, or a pharmaceutically acceptable salt thereof.

16. The method according to claim 15, wherein the patient has a disease or symptom of a disease selected from the group consisting of rheumatoid arthritis, gouty arthritis, osteoarthritis, inflammatory bowel disease, systemic sclerosis, psoriasis, fibrosis, protoporphyria, systemic lupus erythematosus, melanoma, skin cancer, vitiligo, alopecia, poliosis, pain, ischemia/reperfusion injury, cerebral inflammatory disease, hepatitis, sepsis/septic shock, nephritis, transplantation, HIV disease exacerbation, vasculitis, uveitis, retinitis pigmentosa, age-related macular degeneration, microbial infection, celiac disease, nephrotic syndrome, and melanoma invasion.

17. A compound selected from the group consisting of:
1-(2-{[2-({[(3R,4R)-4-(2,4-difluorophenyl)-3-fluoro-1-(4-methoxy-4-methylpentyl)pyrrolidin-3-yl]carbonyl}amino)-1H-imidazol-1-yl]methyl}-5-methylphenyl)piperidine-4-carboxylic acid;

1-[2-{[2-({[(3R,4R)-4-(2,4-difluorophenyl)-3-fluoro-1-(pentan-3-yl)pyrrolidin-3-yl]carbonyl}amino)-1H-imidazol-1-yl]methyl}-5-(trifluoromethyl)phenyl]piperidine-4-carboxylic acid;

1-[2-{[2-({[(3R,4R)-1-cyclopentyl-4-(2,4-difluorophenyl)-3-fluoropyrrolidin-3-yl]carbonyl}amino)-1H-imidazol-1-yl]methyl}-5-(trifluoromethyl)phenyl]piperidine-4-carboxylic acid;

1-[2-{[2-({[(3R,4R)-4-(2,4-difluorophenyl)-3-fluoro-1-(4-methoxy-4-methylpentyl)pyrrolidin-3-yl]carbonyl}amino)-1H-imidazol-1-yl]methyl}-5-(trifluoromethyl)phenyl]piperidine-4-carboxylic acid;

1-[2-({2-[({(3R,4R)-4-(2,4-difluorophenyl)-3-fluoro-1-[3-(pyrrolidin-1-ylsulfonyl)propyl]pyrrolidin-3-yl}carbonyl)amino]-1H-imidazol-1-yl}methyl)-5-(trifluoromethyl)phenyl]piperidine-4-carboxylic acid;

1-[2-{[2-({[(3R,4R)-1-tert-butyl-4-(2,4-difluorophenyl)-3-fluoropyrrolidin-3-yl]carbonyl}amino)-1H-imidazol-1-yl]methyl}-5-(trifluoromethyl)phenyl]piperidine-4-carboxylic acid;

1-[2-{[2-({[(3R,4R)-1-tert-butyl-3-fluoro-4-(4-fluorophenyl)pyrrolidin-3-yl]carbonyl}amino)-1H-imidazol-1-yl]methyl}-5-(trifluoromethyl)phenyl]piperidine-4-carboxylic acid;

1-[2-{[2-({[(3R,4R)-1-tert-butyl-3-fluoro-4-(4-fluorophenyl)pyrrolidin-3-yl]carbonyl}amino)-1H-imidazol-1-yl]methyl}-5-(propan-2-yl)phenyl]piperidine-4-carboxylic acid;

1-[2-{[2-({[(3R,4R)-1-tert-butyl-3-fluoro-4-(4-methoxyphenyl)pyrrolidin-3-yl]carbonyl}amino)-1H-imidazol-1-yl]methyl}-5-(trifluoromethyl)phenyl]piperidine-4-carboxylic acid; and 1-[2-{[2-({[(3R,4R)-1-tert-butyl-3-fluoro-4-(4-methoxyphenyl)pyrrolidin-3-yl]carbonyl}amino)-1H-imidazol-1-yl]methyl}-5-(propan-2-yl)phenyl]piperidine-4-carboxylic acid, or a pharmaceutically acceptable salt thereof.

* * * * *